(12) United States Patent
Vujanovic et al.

(10) Patent No.: US 10,104,862 B2
(45) Date of Patent: Oct. 23, 2018

(54) ENDOPHYTIC MICROBIAL SYMBIONTS IN PLANT PRENATAL CARE

(71) Applicant: University Of Saskatchewan, Saskatoon (CA)

(72) Inventors: Vladimir Vujanovic, Saskatoon (CA); James J. Germida, Saskatoon (CA); Michelle Hubbard, Saskatoon (CA)

(73) Assignee: UNIVERSITY OF SASKATCHEWAN, Saskatoon (CA)

( * ) Notice: Subject to any disclaimer, the term of this patent is extended or adjusted under 35 U.S.C. 154(b) by 0 days.

(21) Appl. No.: 14/614,193

(22) Filed: Feb. 4, 2015

(65) Prior Publication Data

US 2015/0230478 A1    Aug. 20, 2015

Related U.S. Application Data

(63) Continuation-in-part of application No. PCT/CA2013/000091, filed on Feb. 5, 2013.

(51) Int. Cl.
*A01H 17/00* (2006.01)
*A01N 63/04* (2006.01)

(52) U.S. Cl.
CPC ............ *A01H 17/00* (2013.01); *A01N 63/04* (2013.01)

(58) Field of Classification Search
CPC ..................................... A01H 17/00
See application file for complete search history.

(56) References Cited

U.S. PATENT DOCUMENTS

| | | |
|---|---|---|
| 4,940,834 A | 7/1990 | Hurley et al. |
| 5,041,290 A | 8/1991 | Gindrat et al. |
| 5,113,619 A | 5/1992 | Leps et al. |
| 5,229,291 A | 1/1993 | Nielsen et al. |
| 5,292,507 A | 3/1994 | Charley |
| 5,415,672 A | 5/1995 | Fahey et al. |
| 5,730,973 A | 3/1998 | Morales et al. |
| 5,919,447 A | 7/1999 | Marrone et al. |
| 5,994,117 A | 11/1999 | Bacon et al. |
| 6,072,107 A | 6/2000 | Latch et al. |
| 6,077,505 A | 6/2000 | Parke et al. |
| 6,337,431 B1 | 1/2002 | Tricoli et al. |
| 6,495,133 B1 | 12/2002 | Xue |
| 6,681,186 B1 | 1/2004 | Denisov et al. |
| 6,689,880 B2 | 2/2004 | Chen et al. |
| 6,823,623 B2 | 11/2004 | Minato et al. |
| 7,037,879 B2 | 5/2006 | Imada et al. |
| 7,084,331 B2 | 8/2006 | Isawa et al. |
| 7,335,816 B2 | 2/2008 | Kraus et al. |
| 7,341,868 B2 | 3/2008 | Chopade et al. |
| 7,485,451 B2 | 2/2009 | VanderGheynst et al. |
| 7,555,990 B2 | 7/2009 | Beaujot |
| 7,632,985 B2 | 12/2009 | Malven et al. |
| 7,763,420 B2 | 7/2010 | Stritzker et al. |
| 7,906,313 B2 | 3/2011 | Henson et al. |
| 7,977,550 B2 | 7/2011 | West et al. |
| 8,143,045 B2 | 3/2012 | Miansnikov et al. |
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,113,636 B2 | 8/2015 | von Maltzahn et al. |
| 9,277,751 B2 | 3/2016 | Sword |
| 9,364,005 B2 | 6/2016 | Mitter et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 | 4/2017 | von Maltzahn et al. |
| 9,687,001 B2 | 6/2017 | Vujanovic et al. |
| 9,756,865 B2 | 9/2017 | Sword |
| 2005/0072047 A1 | 4/2005 | Conkling et al. |
| 2006/0046246 A1 | 3/2006 | Zeng et al. |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1* | 9/2008 | Young .................... A01H 17/00 800/260 |
| 2008/0289060 A1 | 11/2008 | De Beuckeleer et al. |

(Continued)

FOREIGN PATENT DOCUMENTS

| | | |
|---|---|---|
| CA | 1041788 | 11/1978 |
| CA | 1229497 | 11/1987 |

(Continued)

OTHER PUBLICATIONS

Song et al 2010, Acta Agrestia Sinica 18(6): 833-837 (abstract and figures).*
Clay 1987, Oecologia 73: 358-362.*
Hubbard et al, Feb. 9, 2012, Botay 90: 137-149.*
Mao et al 1997, Plant Disease 81(5): 450-454.*
Abdellatif et al 2009, Mycological Research 113: 782-791.*
Yandigeri et al 2012, Plant Growth Regulation 68: 411-420.*
Ashrafuzzaman et al 2009, African Journal of Biotechnology 8(7): 1247-1252.*

(Continued)

*Primary Examiner* — David H Kruse

(74) *Attorney, Agent, or Firm* — Fenwick & West LLP

(57) ABSTRACT

The present disclosure provides compositions comprising novel endophytes capable of promoting germination endophytes that have a symbiotic relationship with plants. The present disclosure further provides methods of improving seed vitality, biotic and abiotic stress resistance, plant health and yield under both stressed and unstressed environmental conditions, comprising inoculating a seed with the novel endophyte strains and cultivating a plant therefrom.

12 Claims, 68 Drawing Sheets

Specification includes a Sequence Listing.

(56) References Cited

U.S. PATENT DOCUMENTS

| | | | |
|---|---|---|---|
| 2009/0155214 A1 | 6/2009 | Isawa et al. | |
| 2010/0064392 A1 | 3/2010 | Yang et al. | |
| 2010/0095396 A1 | 4/2010 | Voeste et al. | |
| 2010/0205690 A1 | 8/2010 | Blasing et al. | |
| 2010/0227357 A1 | 9/2010 | Redman et al. | |
| 2011/0182862 A1 | 7/2011 | Green et al. | |
| 2012/0108431 A1 | 5/2012 | Williams et al. | |
| 2012/0131696 A1 | 5/2012 | Aayal et al. | |
| 2012/0144533 A1* | 6/2012 | Craven | A01N 63/04 800/300 |
| 2012/0149571 A1 | 6/2012 | Kloepper et al. | |
| 2012/0178624 A1 | 7/2012 | Kaminskyj et al. | |
| 2012/0324599 A1 | 12/2012 | Kerns et al. | |
| 2013/0031673 A1 | 1/2013 | Grandlic et al. | |
| 2013/0071425 A1 | 3/2013 | Vidal et al. | |
| 2013/0079225 A1 | 3/2013 | Smith et al. | |
| 2013/0150240 A1 | 6/2013 | Newman et al. | |
| 2013/0233501 A1 | 9/2013 | Van Zyl et al. | |
| 2014/0020136 A1 | 1/2014 | Van Der Wolf et al. | |
| 2014/0109249 A1 | 4/2014 | Turner et al. | |
| 2014/0115731 A1 | 4/2014 | Turner et al. | |
| 2014/0147425 A1 | 5/2014 | Henn et al. | |
| 2014/0342905 A1 | 11/2014 | Bullis et al. | |
| 2015/0020239 A1 | 1/2015 | von Maltzahn et al. | |
| 2015/0033420 A1 | 1/2015 | Rodriguez et al. | |
| 2015/0126365 A1 | 5/2015 | Sword | |
| 2015/0335029 A1 | 11/2015 | Mitter et al. | |
| 2015/0366217 A1 | 12/2015 | Vujanovic et al. | |
| 2015/0373993 A1 | 12/2015 | von Maltzahn et al. | |
| 2016/0150796 A1 | 6/2016 | von Maltzahn et al. | |
| 2016/0174570 A1 | 6/2016 | Vujanovic et al. | |
| 2016/0192662 A1 | 7/2016 | Sword | |
| 2016/0205947 A1 | 7/2016 | Sword | |
| 2016/0235074 A1 | 8/2016 | von Maltzahn et al. | |
| 2016/0255844 A1 | 9/2016 | Mitter et al. | |
| 2016/0286821 A1 | 10/2016 | Sword | |
| 2016/0316760 A1 | 11/2016 | Ambrose et al. | |
| 2016/0316763 A1 | 11/2016 | Sword | |
| 2016/0330976 A1 | 11/2016 | Mitter et al. | |
| 2016/0338360 A1 | 11/2016 | Mitter et al. | |
| 2016/0366892 A1 | 12/2016 | Ambrose et al. | |
| 2017/0020138 A1 | 1/2017 | von Maltzahn et al. | |
| 2017/0164619 A1 | 6/2017 | von Maltzahn et al. | |
| 2017/0164620 A1 | 6/2017 | von Maltzahn et al. | |
| 2017/0215358 A1 | 8/2017 | Franco et al. | |
| 2017/0223967 A1 | 8/2017 | Mitter et al. | |
| 2018/0020677 A1 | 1/2018 | Ambrose et al. | |
| 2018/0092365 A1 | 4/2018 | Sword | |

FOREIGN PATENT DOCUMENTS

| | | |
|---|---|---|
| CA | 2562175 | 1/2013 |
| CN | 1604732 | 4/2005 |
| CN | 101311262 A | 11/2008 |
| CN | 101570738 | 11/2009 |
| CN | 102168022 A | 8/2011 |
| CN | 102010835 B | 4/2012 |
| CN | 102533601 B | 10/2013 |
| CN | 103642725 A | 3/2014 |
| EP | 0192342 | 8/1986 |
| EP | 0223662 | 5/1987 |
| EP | 0378000 | 7/1990 |
| EP | 0494802 | 7/1992 |
| EP | 0818135 | 1/1998 |
| EP | 1935245 | 6/2008 |
| EP | 2676536 | 12/2013 |
| JP | 2009/072168 | 4/2009 |
| KR | 20100114806 A | 10/2010 |
| KR | 101091151 | 12/2011 |
| KR | 20130023491 | 3/2013 |
| WO | WO 1988/09114 | 1/1988 |
| WO | WO 1994/016076 | 7/1994 |
| WO | WO 2000/029607 | 5/2000 |
| WO | WO 2001/083818 | 11/2001 |
| WO | WO 2002/065836 | 8/2002 |
| WO | WO 2005/003328 | 1/2005 |
| WO | WO 2007/021200 | 2/2007 |
| WO | WO 2007/107000 | 9/2007 |
| WO | WO 2008/103422 | 8/2008 |
| WO | WO 2009/012480 A2 | 1/2009 |
| WO | WO 2009/078710 A1 | 6/2009 |
| WO | WO 2009/126473 A1 | 10/2009 |
| WO | WO 2010/109436 | 9/2010 |
| WO | WO 2010/115156 | 10/2010 |
| WO | WO 2011/001127 | 1/2011 |
| WO | WO 2011/082455 | 7/2011 |
| WO | WO 2011/112781 | 9/2011 |
| WO | WO 2011/117351 | 9/2011 |
| WO | WO 2012/034996 | 3/2012 |
| WO | WO 2013/016361 | 1/2013 |
| WO | WO 2012/029112 | 3/2013 |
| WO | WO 2013/090628 | 6/2013 |
| WO | WO 2013/122473 | 8/2013 |
| WO | WO 2013/177615 | 12/2013 |
| WO | WO 2013/190082 | 12/2013 |
| WO | WO 2014/046553 | 3/2014 |
| WO | WO 2014/082950 | 6/2014 |
| WO | WO 2014/121366 | 8/2014 |
| WO | WO 2014/206953 | 12/2014 |
| WO | WO 2014/210372 | 12/2014 |
| WO | WO 2015/035099 | 3/2015 |
| WO | WO 2015/069938 | 5/2015 |
| WO | WO 2015/100431 | 7/2015 |
| WO | WO 2015/100432 | 7/2015 |
| WO | WO 2015/200852 | 12/2015 |
| WO | WO 2015/200902 | 12/2015 |
| WO | WO 2016/109758 | 7/2016 |
| WO | WO 2016/179046 | 11/2016 |
| WO | WO 2016/179047 | 11/2016 |
| WO | WO 2016/200987 | 12/2016 |

OTHER PUBLICATIONS

Tokala et al 2002, Applied andEnvironmental Microbiology 68(5): 2161-2171.*
Schoch et al 2012, Proceedings of the National Academy of Science USA 109(16): 6241-6246.*
Clarridge 2004, Clainical Microbiology Reviews, 17(4): 840-862.*
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
De Souza, J. J., et al., "Terpenoids from Endophytic Fungi," Molecules, 2011, pp. 10604-10618, vol. 16, No. 12.
Emerson, D., et al., Identifying and Characterizing Bacteria in an Era of Genomics and Proteomics, BioScience, 2008, pp. 925-936, vol. 58, No. 10.
Hinton, D. M., et al., "Enterobacter cloacae is an endophytic symbiont of corn," Mycopathologia, 1995, pp. 117-125, vol. 129.
Hubbard, M., et al., "Fungal Endophytes Improve Wheat Seed Germination Under Heat and Drought Stress," Botany, 2012, pp. 137-149, vol. 90.
Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Li, Q., "Agrobacterium tumefaciens Strain TA-AT-10 16S Ribosomal RNA Gene, Partial Sequence: GenBank: KF673157.1," Submitted Sep. 17, 2013.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Mao, W., et al., "Seed Treatment with a Fungal or a Bacterial Antagonist for Reducing Corn Damping-off Caused by Species of Pythium and Fusarium," Plant Disease, 1997, pp. 450-454, vol. 81, No. 5.
Moe, L. A., "Amino Acids in the Rhizosphere: From Plants to Microbes," American Journal of Botany, 2013, pp. 1692-1705, vol. 100, No. 9.

(56) References Cited

OTHER PUBLICATIONS

Petti, C. A., "Detection and Identification of Microorganisms by Gene Amplification and Sequencing," Clinical Infectious Diseases, 2007, pp. 1108-1114, vol. 44.

Tokala, R. T., et al., "Novel Plant-Microbe Rhizosphere Interaction Involving Streptomyces lydicus WYEC108 and the Pea Plant (Pisum sativum)," Applied and Environmental Microbiology, May 2002, pp. 2161-2171, vol. 68, No. 5.

Waller, F., et al., "The Endophytic Fungus Piriformospora indica Reprograms Barley to Salt-Stress Tolerance, Disease Resistance, and Higher Yield," PNAS, 2005, pp. 13386-13391, vol. 102, No. 38.

Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.

You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4. (with English Abstract).

Zuccaro, A., et al., "Endophytic Life Strategies Decoded by Genome and Transcriptome Analyses of the Mutualistic Root Symbiont Piriformospora indica," PLOS Pathogens, 2011, vol. 7, No. 10, e1002290.

PCT International Search Report and Written Opinion, PCT Application No. PCT/US2015/038110, dated Dec. 11, 2015, 36 Pages.

PCT International Search Report and Written Opinion, PCT Application No. PCT/US2015/038187, dated Jan. 22, 2016, 36 Pages.

Baltruschat, H., et al., "Salt tolerance of barley induced by the root enjophyte Piriformospora indica is associated with a strong increase in antioxidants," New Phytologist., 2008, pp. 501-510, vol. 180.

De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.

Fisher, P. J., et al., "Fungal saprobes and pathogens as endophytes of rice (Oryza sativa L.)," New Phytol., 1992, pp. 137-143, vol. 120.

Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.

Redman, R. S., et al., "Thermotolerance Generated by Plant/Fungal Symbiosis," Science, Nov. 2002, vol. 298, 1 Page (with 4 pages of supplemental material).

PCT Invitation to Pay Additional Fees, PCT Application No. PCT/CA2013/000091, dated Mar. 27, 2013, 2 pages.

International Search Report and Written Opinion for PCT/CA2013/000091, dated Sep. 20, 2013, 17 Pages.

International Search Report and Written Opinion for PCT/EP2013/062976, dated Dec. 22, 2014, 9 Pages.

International Search Report, Application No. PCT/US2014/044427, dated Dec. 3, 2014, 9 Pages.

International Search Report and Written Opinion, Application No. PCT/US2014/054160, dated Dec. 9, 2014, 21 Pages.

Invitation to Pay Additional Fees, PCT Application No. PCT/US2014/064411, dated Feb. 5, 2015, 2 Pages.

International Search Report and Written Opinion, International Application No. PCT/US2014/064411, dated Mar. 27, 2015, 15 Pages.

PCT Invitation to Pay Additional Fees, PCT Application No. PCT/US2014/072399, dated Apr. 14, 2015, 2 Pages.

International Search Report and Written Opinion, International Application No. PCT/US2014/072399, dated Jun. 26, 2015, 22 Pages.

Invitation to Pay Additional Fees, PCT Application No. PCT/US2014/072400, dated Apr. 16, 2015, 6 Pages.

International Search Report and Written Opinion, Application No. PCT/US2014/072400, dated Jul. 8, 2015, 21 Pages.

Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.

Abarenkov, K., et al., "The UNITE Database for Molecular Identification of Fungi—Recent Updates and Future Perspectives," New Phytol., 2010, pp. 281-285, vol. 186.

Ahmad, F., et al., "Screening of Free-Living Rhizospheric Bacteria for Their Multiple Plant Growth Promoting Activities," Microbiol Res., 2008, pp. 173-181, vol. 163.

Amann, R., et al., "The Identification of Microorganisms by Fluorescence in Situ Hybridisation," Curr Opin Biotechnol., 2001, pp. 231-236, vol. 12.

Apel, K., et al., "Reactive Oxygen Species: Metabolism, Oxidative Stress, and Signal Transduction," Annu Rev Plant Biol., 2004, pp. 373-399, vol. 55.

Bacon, C.W., et al., "Isolation, In Planta Detection, and Uses of Endophytic Bacteria for Plant Protection," Manual of Environmental Microbiology, 2007, pp. 638-647.

Baker, K.F., et al., "Dynamics of Seed Transmission of Plant Pathogens," Annu Rev Phytopathol., 1966, pp. 311-334, vol. 4.

Block, C.C., et al., "Seed Transmission of Pantoea stewartii in Field and Sweet Corn," Plant Disease, 1998, pp. 775-780, vol. 82.

Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.

Brodie, E.L., et al., "Uncultured Bacterium Clone BANW722 16S Ribosomal RNA Gene, Partial Sequence," NCBI GenBank Accession No. DQ264636, Submitted Oct. 25, 2005.

Bulgarelli, D., et al., "Structure and Functions of the Bacterial Microbiota of Plants," Annu Rev Plant Biol., 2013, pp. 807-838, vol. 64.

Caporaso, J.G., et al., "Ultra-High-Throughput Microbial Community Analysis on the Illumina HiSeq and MiSeq Platforms," ISME J., 2012, pp. 1621-1624, vol. 6.

Castillo, D., et al., "Fungal Entomopathogenic Endophytes: Negative Effects on Cotton Aphid Reproduction in Greenhouse and Field Conditions," Power Point Presentation dated Mar. 23, 2013.

Castillo, D., et al., "Fungal Endophytes: Plant Protective Agents Against Herbivores," Power Point Presentation dated Aug. 4, 2013.

Cavalier-Smith, T., "A Revised Six-Kingdom System of Life," Biol. Rev., 1998, pp. 203-266, vol. 73.

Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.

Chernin, L.S., et al., "Chitinolytic Activity in Chromobacterium violaceum: Substrate Analysis and Regulation by Quorum Sensing," J Bacteriol., 1998, pp. 4435-4441, vol. 180, No. 17.

Clark, E.M., et al., "Improved Histochemical Techniques for the Detection of Acremonium coenophilum in Tall Fescue and Methods of in vitro Culture of the Fungus," J. Microbiol Methods, 1983, pp. 149-155, vol. 1.

Clough, S.J., et al., "Floral Dip: A Simplified Method for Agrobacterium-mediated Transformation of Arabidopsis thaliana," Plant J., 1998, pp. 735-743, vol. 16, No. 6.

Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.

Coombs, J.T., et al., "Isolation and Identification of Actinobacteria from Surface-Sterilized Wheat Roots," Applied and Environmental Microbiology, 2003, pp. 5603-5608, vol. 69, No. 9.

Conn, V.M., "Effect of Microbial Inoculants on the Indigenous Actinobacterial Endophyte Population in the Roots of Wheat as Determined by Terminal Restriction Fragment Length Polymorphism," Applied and Environmental Microbiology, 2004, pp. 6407-6413, vol. 70, No. 11.

Cox, C.D., "Deferration of Laboratory Media and Assays for Ferric and Ferrous Ions," Methods Enzymol., 1994, pp. 315-329, vol. 235.

Craine, J.M., et al., "Global Diversity of Drought Tolerance and Grassland Climate-Change Resilience," Nature Climate Change, 2013, pp. 63-67, vol. 3.

Dalal, J.M., et al., "Utilization of Endophytic Microbes for Induction of Systemic Resistance (ISR) in Soybean (Glycine max (L) Merril) Against Challenge Inoculation with R. solani," Journal of Applied Science and Research, 2014, pp. 70-84, vol. 2, No. 5.

(56) References Cited

OTHER PUBLICATIONS

Danhorn, T., et al., "Biofilm Formation by Plant-Associated Bacteria," Annu Rev Microbiol., 2007, pp. 401-422, vol. 61.
Daniels, R., et al., "Quorum Signal Molecules as Biosurfactants Affecting Swarming in Rhizobium etli," PNAS, 2006, pp. 14965-14970, vol. 103, No. 40.
De Freitas, J.R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.
De Melo Pereira, G. V., et al. "A Multiphasic Approach for the Identification of Endophytic Bacterial in Strawberry Fruit and their Potential for Plant Growth Promotion," Microbial Ecology, 2012, pp. 405-417, vol. 63, No. 2.
Dennis, C., et al., "Antagonistic Properties of Species Groups of Trichoderma," Trans Brit Mycol Soc, 1971, pp. 25-39, vol. 57, No. 1.
Djordjevic, D., et al., "Microtiter Plate Assay for Assessment of Listeria monocytogenes Biofilm Formation," Appl. Environ. Microbiol., 2002, pp. 2950-2958, vol. 68, No. 6.
Don, R.H., et al., "Properties of Six Pesticide Degradation Plasmids Isolated From Alcaligenes Paradoxus and Alcaligenes eutrophus," J Bacteriol., 1981, pp. 681-686, vol. 145, No. 2.
Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012.
Eberhard, A., et al., "Structural Identification of Autoinducer of Photobacterium fischeri Luciferase," Biochem., 1981, pp. 2444-2449, vol. 20.
Edgar, R.C., "Search and Clustering Orders of Magnitude Faster than BLAST," Bioinformatics, 2010, pp. 2460-2461, vol. 26, No. 19.
Edgar, R.C., "UPARSE: Highly Accurate OTU Sequences From Microbial Amplicon Reads," Nat Methods, 2013, pp. 996-998, vol. 10, No. 10.
EK-Ramos, M.J., "Ecology, Distribution and Benefits of Fungal Endophytes Isolated from Cultivated Cotton (*Gossypium hirsutum*) in Texas," Power Point Presentation dated Nov. 7, 2012.
EK-Ramos, M.J., et al., "Spatial and Temporal Variation in Fungal Endophyte Communities Isolated from Cultivated Cotton (*Gossypium hirsutum*)," PLoS ONE, 2013, vol. 8, No. 6, 13 Pages.
EK-Ramos, M.J., et al., "Spatial and Temporal Variation in Fungal Endophyte Communities Isolated from Cultivated Cotton (*Gossypium hirsutum*)," Power Point Presentation dated Jan. 7, 2013.
El-Shanshoury, A.R., "Growth Promotion of Wheat Seedlings by *Streptomyces atroolivaceus*," Journal of Agronomy and Crop Science, 1989, pp. 109-114, vol. 163.
Endre, G., et al., "A Receptor Kinase Gene Regulating Symbiotic Nodule Development," Nature, 2002, pp. 962-966, vol. 417.
Faria, D.C., et al., "Endophytic Bacteria Isolated from Orchid and Their Potential to Promote Plant Growth," World J Microbiol Biotechnol., 2013, pp. 217-221, vol. 29.
Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.
Fiehn, O., et al., "Metabolite Profiling for Plant Functional Genomics," Nature Biotechnol., 2000, pp. 1157-1161, vol. 8.
Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.
Fincher, G.B., "Molecular and Cellular Biology Associated with Endosperm Mobilization in Germinating Cereal Grains," Annu Rev Plant Physiol Plant Mol Biol., 1989, pp. 305-346, vol. 40.
Fisher, P.R., et al., "Isolation and Characterization of the Pesticide-Degrading Plasmid pJP1 from Alcaligenes paradoxus," J Bacteriol., 1978, pp. 798-804, vol. 135, No. 3.
Franco, C., et al., "Actinobacterial Endophytes for Improved Crop Performance," Australasian Plant Pathology, 2007, pp. 524-531, vol. 36.

Fulthorpe, R.R., et al., "Distantly Sampled Soils Carry Few Species in Common," ISME J., 2008, pp. 901-910, vol. 2.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitation of Major Human Cutaneous Bacterial and Fungal Populations," J Clin Microbiol., 2010, pp. 3575-3581, vol. 48, No. 10.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007.
Gilmour, S.J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Gitaitis, R., et al., "The Epidemiology and Management of Seedborne Bacterial Diseases," Annu Rev Phytopathol., 2007, pp. 371-397, vol. 45.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hallman, J., et al., "Bacterial Endophytes in Agricultural Crops," Canadian J Microbiol., 1997, pp. 895-914, vol. 43.
Hardegree, S.P. et al., "Effect of Polyethylene Glycol Exclusion on the Water Potential of Solution-Saturated Filter Paper," Plant Physiol., 1990, pp. 462-466, vol. 92.
Hardoim, P.R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hardoim, P.R., et al., "Dynamics of Seed-Borne Rice Endophytes on Early Plant Growth Stages," PLoS ONE, 2012, vol. 7, No. 2, 13 Pages.
Hepler, P.K., et al., "Polarized Cell Growth in Higher Plants," Annu Rev Cell Dev Biol., 2001, pp. 159-187, vol. 17.
Hiatt, E.E., et al., "Tall Fescue Endophyte Detection: Commerical Immunoblot Test Kit Compared with Microscopic Analysis," Crop Science, 1999, pp. 796-799, vol. 39.
Hibbett, D.S., et al., "A Higher-Level Phylogenetic Classification of the Fungi," Mycol Res., 2007, pp. 509-547, vol. 111.
Hill, N.S., et al., "Endophyte Survival during Seed Storage: Endophyte-Host Interactions and Heritability," Crop Sci., 2009, pp. 1425-1430, vol. 49.
Hill N.S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hung, P.Q., et al., "Isolation and Characterization of Endophytic Bacteria in Soybean (*Glycine* sp.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of the Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.
Johnston-Monje, D., et al., "Conservation and Diversity of Seed Associated Endophytes in *Zea* Across Boundaries of Evolution, Ethnography and Ecology," PLoS ONE, 2011, vol. 6, No. 6, 22 Pages.
Johnston-Monje, D., et al., "Plant and Endophyte Relationships: Nutrient Management," Comprehensive Biotechnol., 2011, pp. 713-727, vol. 4.

(56) References Cited

OTHER PUBLICATIONS

Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.

Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.

Kaga, H., et al., "Rice Seeds as Sources of Endophytic Bacteria," Microbes Environ., 2009, pp. 154-162, vol. 24, No. 2.

Kalns, L., et al., "The Effects of Cotton Fungal Endophytes in the Field on Arthropod Community Structure," Power Point Presentation dated Jan. 7, 2013.

Kang, B.H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.

Kasana, R.C., et al., "A Rapid and Easy Method for the Detection of Microbial Cellulases on Agar Plates Using Gram's Iodine," Curr Microbiol., 2008, pp. 503-507, vol. 57.

Kruger, M., et al., "DNA-Based Species Level Detection of Glomeromycota: One PCR Primer Set for All Arbuscular Mycorrhizal Fungi," New Phytol., 2009, pp. 212-223, vol. 183.

Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

Lanver, D., et al., "Sho1 and Msb2-Related Proteins Regulate Appressorium Development in the Smut Fungus *Ustilago aydis*," Plant Cell, 2010, pp. 2085-2101, vol. 22.

Laus, M.C., et al., "Role of Cellulose Fibrils and Exopolysaccharides of Rhizobium leguminosarum in Attachment to and Infection of Vicia sativa Root Hairs," Mol Plant Microbe Interact., 2005, pp. 533-538, vol. 18, No. 6.

Leonard, C.A., et al., "Random Mutagenesis of the Aspergillus oryzae Genome Results in Fungal Antibacterial Activity," Int J Microbiol., 2013, vol. 2013, Article ID 901697, 6 Pages.

Li, H.M., et al., "Expression of a Novel Chitinase by the Fungal Endophyte in Poa ampla," Mycologia, 2004, pp. 526-536, vol. 96, No. 3.

Liu, M., et al., "A Novel Screening Method for Isolating Exopolysaccharide-Deficient Mutants," Appl Environ Microbiol., 1998, pp. 4600-4602, vol. 64, No. 11.

Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.

Liu, D., et al., "Osmotin Overexpression in Potato Delays Development of Disease Symptoms," Proc Natl Acad Sci USA, 1994, pp. 1888-1892, vol. 91.

Liu, Y., et al., "Study on Diversity of Endophytic Bacterial Communities in Seeds of Hybrid Maize and their Parental Lines," Arch Microbiol., 2012, pp. 1001-1012, vol. 194.

Long, H.H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.

Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.

Lorck, H., "Production of Hydrocyanic Acid by Bacteria," Physiol Plant, 1948, pp. 142-146, vol. 1.

Lugtenberg, B., et al., "Plant-Growth-Promoting Rhizobacteria," Ann. Rev. Microbiol., 2009, pp. 541-556, vol. 63.

Lundberg, D.S., et al., "Defining the Core *Arabidopsis thaliana* Root Microbiome," Nature, 2012, pp. 86-90, vol. 488, No. 7409.

Lundberg, D.S., et al., "Practical Innovations for High-Throughput Amplicon Sequencing," Nat Methods, 2013, pp. 999-1002, vol. 10, No. 10.

Madi, L. et al., "Aggregation in Azospirillum brasilense Cd: Conditions and Factors Involved in Cell-to-Cell Adhesion," Plant Soil, 1989, pp. 89-98, vol. 115.

Mannisto, M.K., et al., "Characterization of Psychrotolerant Heterotrophic Bacteria From Finnish Lapland," Syst Appl Microbiol., 2006, pp. 229-243, vol. 29.

Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.

Manter, D.K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.

Marasco, R., et al., "A Drought Resistance-Promoting Microbiome is Selected by Root System Under Desert Farming," PLoS ONE, 2012, vol. 7, No. 10, 14 Pages.

Marquez, L.M., et al., "A Virus in a Fungus in a Plant: Three-Way Symbiosis Required for Thermal Tolerance," Science, 2007, pp. 513-515, vol. 315.

Mastretta, C., et al., "Endophytic Bacteria from Seeds of Nicotiana Tabacum Can Reduce Cadmium Phytotoxicity," Intl J Phytoremediation, 2009, pp. 251-267, vol. 11.

Mateos, P.F., et al., "Cell-Associated Pectinolytic and Cellulolytic Enzymes in Rhizobium leguminosarum biovar trifolii," Appl Environ Microbiol., 1992, pp. 816-1822, vol. 58, No. 6.

McDonald, D., et al., "An Improved Greengenes Taxonomy with Explicit Ranks for Ecological and Evolutionary Analyses of Bacteria and Archaea," ISME J., 2012, pp. 610-618, vol. 6.

McGuire, K.L., et al., "Digging the New York City Skyline: Soil Fungal Communities in Green Roofs and City Parks," PloS One, 2013, vol. 8, No. 3, 13 Pages.

Medina, P., et al., "Rapid Identification of Gelatin and Casein Hydrolysis Using TCA," J Microbiol Methods, 2007, pp. 391-393, vol. 69.

Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.

Michel, B.E., et al., "The Osmotic Potential of Polyethylene Glycol 6000," Plant Physiol., 1973, pp. 914-916, vol. 51.

Mohiddin, F.A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.

Mousa, W.K., et al., "The Diversity of Anti-Microbial Secondary Metabolites Produced by Fungal Endophytes: An Interdisciplinary Perspective," Front Microbiol., 2013, vol. 4, No. 65, 18 Pages.

Mundt, J.O., et al., "Bacteria Within Ovules and Seeds," Appl Environ Microbiol., 1976, pp. 694-698, vol. 32, No. 5.

Naveed, M., "Maize Endophytes—Diversity, Functionality and Application Potential," University of Natural Resources and Life Sciences, 2013, pp. 1-266 and 81-87; Tables 1-3; Figure 2.

Nejad, P. et al., "Endophytic Bacteria Induce Growth Promotion and Wilt Disease Suppression in Oilseed Rape and Tomato," Biological Control, 2000, pp. 208-215, vol. 18.

Neslon, E.B., "Microbial Dynamics and Interactions in the Spermosphere," Ann. Rev. Phytopathol., 2004, pp. 271-309, vol. 42.

Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.

Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.

Okunishi, S., et al., "Bacterial Flora of Endophytes in the Maturing Seeds of Cultivated Rice (*Oryza sativa*)," Microbes and Environment, 2005, pp. 168-177, vol. 20, No. 3.

Partida-Martinez, L.P., et al., "The Microbe-Free Plant: Fact or Artifact?" Front Plant Sci., 2011, vol. 2, No. 100, 16 Pages.

Pearson, W.R., et al., "Rapid and Sensitive Sequence Comparison With FASTP and FASTA," Methods Enzymol., 2011, pp. 63-98, vol. 183.

Pedraza, R.O., et al., "Azospirillum inoculation and nitrogen fertilization effect on grain yield and on the diversity of endophytic

(56) References Cited

OTHER PUBLICATIONS bacteria in the phyllosphere of rice rainfed crop," European Journal of Soil Biology, 2009, pp. 36-43, vol. 45.
Perez-Fernandez, M.A., et al., "Simulation of Germination of Pioneer Species Along an Experimental Drought Gradient," J Environ Biol., 2006, pp. 669-685, vol. 27, No. 4.
Perez-Miranda, S., et al., "O-CAS, A Fast and Universal Method for Siderophore Detection," J Microbiol Methods, 2007, pp. 127-131, vol. 70.
Phalip, V., et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Pillay, V.K., et al., "Inoculum Density, Temperature, and Genotype Effects on in vitro Growth Promotion and Epiphytic and Endophytic Colonization of Tomato (Lycopersicon esculentum L.) Seedlings Inoculated with a Pseudomonad bacterium," Can J Microbiol., 1997, pp. 354-361, vol. 43.
Powell, W.A., et al., "Evidence of Endophytic Beauveria Bassiana in Seed-Treated Tomato Plants Acting as a Systemic Entomopathogen to Larval Helicoverpa zea (Lepidoptera: Noctuidae)," J. Entomol. Sci., 2009, pp. 391-396, vol. 44, No. 4.
Quadt-Hallmann, A., et al., "Bacterial Endophytes in Cotton: Mechanisms of Entering the Plant," Can J Microbiol., 1997, pp. 577-582, vol. 43.
R Core Team, "R: A Language and Environment for Statistical Computing," R Foundation for Statistical Computing, Vienna, Austria, May 2013, ISBN: 3-900051-07-0. Available online at http://www.R- 25 project.org/, 3604 Pages.
Reiter, B., et al., "Response of Endophytic Bacterial Communities in Potato Plants to Infection with Erwinia carotovora subsp. atroseptica," Appl Environ Microbiol., 2001, pp. 2261-2268, vol. 68, No. 5.
Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001, pp. 11-29, vol. 13.
Rosado, A.S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.
Rosenblueth, A., et al., "Seed Bacterial Endophytes: Common Genera, Seed-to-Seed Variability and Their Possible Role in Plants," Acta Hort., 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in Saccharomyces cerevisiae Using Amine-Reactive Isobaric Tagging Reagents," Mol Cell Proteomics, 2004, pp. 1154-1169, vol. 3, No. 12.
Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Sardi, P., et al., "Isolation of Endophytic Streptomyces Strains from Surface Sterilized Roots," Applied and Environmental Microbiology, 1992, pp. 2691-2693, vol. 58, No. 8.
Sarwar, M., et al., "Tryptophan Dependent Biosynthesis of Auxins in Soil," Plant Soil, 1992, pp. 207-215, vol. 147.
Schmieder, R., et al., "Quality Control and Preprocessing of Metagenomic Datasets," Bioinformatics, 2011, pp. 863-864, vol. 27, No. 6.
Schoch, C.L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.
Schwyn, B. et al., "Universal Chemical Assay for the Detection and Determination of Siderophores," Analytical Biochemistry, 1987, pp. 47-56, vol. 160.
Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.
Singh, AK, et al., "Uncultured Actinomyces sp. Clone EMLACT 80 IV (New) 16S Ribosomal RNA Gene, Partial Sequence," NCBI GenBank Accession No. JQ285908. Submitted Dec. 13, 2011.
Soares, M.M.C.N, et al., "Screening of Bacterial Strains for Pectinolytic Activity: Characterization of the Polygalacturonase Produced by Bacillus SP," Revista de Microbiolgia, 1999, pp. 299-303, vol. 30.
Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.
Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.
Staudt, A.K., et al., "Variations in Exopolysaccharide Production by Rhizobium tropici," Arch Microbiol., 2012, pp. 197-206, vol. 194.
Strobel, G.A., "Endophytes as Sources of Bioactive Products," Microbes and Infection, 2003, pp. 535-544, vol. 5.
Sturz, A.V., et al., "Weeds as a Source of Plant Growth Promoting Rhizobacteria in Agricultural Soils," Can J Microbiol., 2001, pp. 1013-1024, vol. 47, No. 11.
Surette, M. A., et al. "Bacterial Endophytes in Processing Carrots (Oaucus carota L. var. sativus): Their Localization, Population Density, Biodiversity and Their Effects on Plant Growth," Plant and Soil, 2003, pp. 381-390, vol. 253, No. 2.
Suto, M., et al., "Endophytes as Producers of Xylanase," J Biosci Bioeng., 2002, pp. 88-90, vol. 93, No. 1.
Sword, G., "Manipulating Fungal Endophytes to Protect Plants from Insects and Nematodes," Power Point Presentation dated Aug. 7, 2013.
Sword, G., et al., "Manipulating Fungal Endophytes for the Protection of Cotton in the Field," Power Point Presentation dated Jan. 7, 2013.
Sword, G., et al., "Field Trials of Potentially Beneficial Fungal Endophytes in Cotton," Power Point Presentation dated Jan. 7, 2013.
Sword, G., "Fungal Endophytes to Protect Cotton from Insects and Nematodes," Power Point Presentation dated Dec. 7, 2012.
Sword, G., "Natural Enemies—The Forgotten Basis of IPM?," Power Point Presentation dated Sep. 6, 2013.
Taylor, A.G., et al., "Concepts and Technologies of Selected Seed Treatments," Annu. Rev. Phytopathol., 1990, pp. 321-339, vol. 28.
Teather, R.M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Theis, K.R., et al., "Uncultured Bacterium Clone GM2GI8201A64RC 16S Ribosomal RNA Gene, Partial Sequence," NCBI GenBank Accession No. JX051943, Submitted May 14, 2012.
Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M.F., "So What's New in the Field of Plant Cold Acclimation? Lots!," Plant Physiol., 2001, pp. 89-93, vol. 125.
Trotel-Aziz, P., et al., "Characterization of New Bacterial Biocontrol Agents Acinetobacter, Bacillus, Pantoea and Pseudomonas spp. Mediating Grapevine Resistance Against Botrytis cinerea," Environmental and Experimental Botany, 2008, pp. 21-32, vol. 64.

(56) References Cited

OTHER PUBLICATIONS

Truyens, S., et al., "Changes in the Population of Seed Bacteria of Transgenerationally Cd-Exposed *Arabidopsis thaliana*," Plant Biol., 2013, pp. 971-981, vol. 15.
Usadel, B., et al., "The Plant Transcriptome—From Integrating Observations to Models," Front Plant Sci., 2013, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C.U., et al., "Endophytic Establishment as an Unintended Consequence of Biocontrol with Fungal Entomopathogens," Power Point Presentation dated Jan. 7, 2013.
Van Der Lelie, D., et al., "Poplar and its Bacterial Endophytes: Coexistence and Harmony," Critical Rev Plant Sci., 2009, pp. 346-358, vol. 28.
Vining, K., et al., "Methylome Reorganization During in vitro Dedifferentiation and Regeneration of Populus trichocarpa," BMC Plant Biol., 2013, vol. 13, No. 92, 15 Pages.
Virule, E., et al., "Pseudomonas thiveralensis Strain IEHa 16S Ribosomal RNA Fene, Partial Sequence," NCBI GenBank Accession No. GQ169380.1, Submitted May 15, 2009.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Weaver, P.F., et al., "Characterization of Rhodopseudomonas capsulata," Arch Microbiol., 1975, pp. 207-216, vol. 105.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J.F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings," World J Microbiol Biotechnol., 2014, pp. 835-845, vol. 30.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.
Yezerski, A., et al., "The Effects of the Presence of Stored Product Pests on the Microfauna of a Flour Community," Journal of Applied Microbiology, 2005, pp. 507-515, vol. 98.
Zhou, W., et al., "Effects of the Fungal Endophyte *Paecilomyces* sp. in Cotton on the Roo-Knot Nematode *Meloidogyne incognita*," poster dated Jan. 7, 2013.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.
PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Search Report and Written Opinion, PCT Application No. PCT/US2016/030293, dated Aug. 11, 2016, 23 Pages.

European Patent Office, Supplementary Partial European Search Report, European Patent Application No. 13874703.5, dated Jun. 21, 2016, 3 Pages.
Intellectual Property Australia, Examination Report for Australian Patent Application No. 2016202480, dated Apr. 28, 2016, 2 Pages.
New Zealand Intellectual Property Office, First Examination Report, New Zealand Patent Application No. 715728, dated May 10, 2016, 4 Pages.
United States Patent Office, Non-Final Office Action, U.S. Appl. No. 14/964,429, dated Aug. 9, 2016, 6 Pages.
Abdellatif, L., et al., "Endophytic hyphal compartmentalization is required for successful symbiotic Ascomycota association with root cells," Mycological Research, 2009, pp. 782-791, vol. 113.
Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.
Clay, K., "Effects of fungal endophytes on the seed and seedling biology of Lolium perenne and Festuca arundinacea," Oecologia, 1987, pp. 358-362, vol. 73.
Cottyn, B., et al., "Phenotypic and genetic diversity of rice seed-associated bacteria and their role in pathogenicity and biological control," Journal of Applied Microbiology, 2009, pp. 885-897, vol. 107.
Desiro, A., et al., "Detection of a novel intracellular microbiome hosted in arbuscular mycorrhizal fungi," ISME Journal, 2014, pp. 257-270, vol. 8.
Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.
Mei, C., et al., "The Use of Beneficial Microbial Endophytes for Plant Biomass and Stress Tolerance Improvement," Recent Patents on Biotechnology, 2010, pp. 81-95, vol. 4.
Naik, B. S., et al., "Study on the diversity of endophytic communities from rice (*Oryza sativa* L.) and their antagonistic activities in vitro," Microbiological Research, 2009, pp. 290-296, vol. 164.
Orole, O. O., et al., "Bacterial and fungal endophytes associated with grains and roots of maize," Journal of Ecology and the Natural Enviornment, 2011, pp. 298-303, vol. 3, No. 9.
Philrice Batac, Philippine Rice R&D Highlights, 2012, Area-Based R&D Projects, [online][Retrieved Aug. 11, 2016] Retrieved from the Internet <URL:http://www.philrice.gov.ph/2012-rd-highlights/>.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Song, M., et al., "Effects of Neotyphodium Endophyte on Germination of Hordeum brevisubulatum under Temperature and Water Stress Conditions," Acta Agrestia Sinica, 2010, pp. 834-837, vol. 18, No. 6. (English Abstract).
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
Canadian Patent Office, Office Action, Canadian Patent Application No. 2,916,678, dated Feb. 8, 2017, 8 Pages.
European Patent Office, Supplementary European Search Report, European Patent Application No. 13874703.5, dated Oct. 21, 2016, 16 Pages.
European Patent Office, Supplementary European Search Report, European Patent Application No. 14860187.5, dated May 24, 2017, 9 Pages.

(56) References Cited

OTHER PUBLICATIONS

Intellectual Property Australia, Examination Report for Australian Patent Application No. 2014346664, dated Nov. 24, 2016, 3 Pages.
New Zealand Intellectual Property Office, First Examination Report, New Zealand Patent Application No. 715728, dated Dec. 5, 2016, 3 Pages.
United States Patent Office, Non-Final Office Action, U.S. Appl. No. 15/063,350, dated Nov. 10, 2016, 18 Pages.
Buttner, D., et al., "Regulation and secretion of Xanthomonas virulence factors," FEMS Microbiology Reviews, 2010, pp. 107-133, vol. 34, No. 2.
Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.
Darsonval, A., et al., "The Type III Secretion System of *Xanthomonas fuscans* subsp. *fuscans* is involved in the Phyllosphere Colonization Process and in Transmission to Seeds of Susceptible Beans," Applied and Envioronnnental Mirobiology, 2008, pp. 2669-2678, vol. 74, No. 9.
Giraldo, A., et al., "Phylogeny of Sarocladium (Hypocreales)," Persoonia, 2015, pp. 10-24, vol. 34.
Grondona, I., et al., "TUSAL®, a commercial biocontrol formulation based on Trichoderma," Bulletin OILB/SROP, 2004, pp. 285-288, vol. 27, No. 8.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, L.E., "Reduction of Verticillium Wilt Symptoms in Cotton Following Seed Treatment with Trichoderma virens," Proceedings Beltwide Cotton Conferences, 2000, vol. 1. (Abstract).
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Khan, A.L., et al., "Salinity Stress Resistance Offered by Endophytic Fungal Interaction Between Penicillium minioluteum LHL09 and Glycine max. L," J. Microbiol. Biotechnol., 2011, pp. 893-902, vol. 21, No. 9.
Lehman, S.G., "Treat Cotton Seed," Review of Applied Mycology, 1945, 24, 369.
Lehman, S.G., "Treat Cotton Seed," Research and Farming III, Progr. Rept., 1945, 3, 5.
Li, H., et al., "Endophytes and their role in phytoremediation," Fungal Diversity, 2012, pp. 11-18, vol. 54.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.
Trichoderma definition, 2016, [online] [Retrieved on Sep. 16, 2016,] Retrieved from the Internet <URL:en.wikipedia.org/wiki/Trichoderma>.
Wang, B., et al., "Fungal endophytes of native *Gossypium* species in Australia," Mycological Research, 2007, pp. 347-354, vol. 111, No. 3.
Waqas, M., et al., "Endophytic Fungi Produce Gibberellins and Indoleacetic Acid and Promotes Host-Plant Growth during Stress," Molecules, 2012, pp. 10754-10773, vol. 17.
Weindling, "Relation of dosage to control of cotton seedling diseases by seed treatment," Plant Disease Reporter, 1943, 27, 68-70.
PCT International Search Report and Written Opinion, Application No. PCT/AU2014/000360, dated Aug. 5, 2015, 12 Pages.
PCT International Preliminary Report on Patentability, PCT Application No. PCT/US2016/030292, dated Aug. 2, 2017, 23 Pages.
Canadian Patent Office, Office Action, Canadian Patent Application No. CA 2,953,466, dated Dec. 11, 2017, 7 Pages.
Canadian Patent Office, Office Action, Canadian Patent Application No. 2,935,218, dated Jun. 13, 2017, 5 Pages.
Canadian Patent Office, Office Action, Canadian Patent Application No. CA 2,953,697, dated Oct. 12, 2017, 6 Pages.
Canadian Patent Office, Office Action, Canadian Patent Application No. CA 2,952,057, dated Oct. 12, 2017, 4 Pages.
Canadian Patent Office, Office Action, Canadian Patent Application No. CA 2,929,487, dated Dec. 7, 2017, 4 Pages.
Chinese Patent Office, Office Action, Chinese Patent Application No. 201480072142.7, dated Apr. 25, 2017, 14 Pages (with English translation).
Chinese Patent Office, 2nd Office Action for Chinese Patent Application No. CN 201480072142.7, dated Oct. 30, 2017, 13 Pages, (with English translation).
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14874589.6, dated Jul. 11, 2017, 9 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report, European Patent Application No. EP 15812324.0, dated Nov. 2, 2017, 19 Pages.
Intellectual Property Australia, Examination Report for Australian Patent Application No. 2014315191, dated Jul. 15, 2017, 6 Pages.
Intellectual Property Australia, Examination Report for Australian Patent Application No. 2015279600, dated Jul. 21, 2017, 7 Pages.
Intellectual Property Australia, Examination Report for Australian Patent Application No. 2015278238, dated Jul. 24, 2017, 3 Pages.
Intellectual Property Australia, Examination Report No. 1 for Australian Patent Application No. AU 2017254880, dated Nov. 15, 2017, 2 Pages.
New Zealand Intellectual Property Office, First Examination Report, New Zealand Patent Application No. 727449, dated Jun. 8, 2017, 7 Pages.
New Zealand Intellectual Property Office, First Examination Report, New Zealand Patent Application No. 726116, dated Jun. 29, 2017, 2 Pages.
New Zealand Intellectual Property Office, First Examination Report, New Zealand Patent Application No. 726116, dated Sep. 26, 2017, 5 Pages.
New Zealand Intellectual Property Office, First Examination Report, New Zealand Patent Application No. 728495, dated Jul. 12, 2017, 5 Pages.
New Zealand Intellectual Property Office, First Examination Report for New Zealand Patent Application No. NZ 728483, dated Dec. 8, 2017, 2 Pages.
Russian Patent Office, Office Action for Russian Patent Application No. RU 2017127214, dated Nov. 22, 2017, 4 Pages, (with English translation).
Russian Patent Office, Office Action for Russian Patent Application No. RU 2015137613, dated Jun. 7, 2017, 14 Pages (with English translation).
Ukraine Patent Office, Office Action for Ukrainian Patent Application No. a201508515, dated May 19, 2017, 14 Pages (with English translation).

(56) References Cited

OTHER PUBLICATIONS

Abdou, R., et al., "Botryorhodines A-D, antifungal and cytotoxic depsidones from Botryosphaeria rhodina, an endophyte of the medicinal plant *Bidens pilosa*," Phytochemistry, 2010, vol. 71, pp. 110-116.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
Chagas, F., et al., "A Mixed Culture of Endophytic Fungi Increases Production of Antifungal Polyketides," J. Chem Ecol., Oct. 2013, pp. 1335-1342, vol. 39.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
DBGET, "Orthology: K14454," 2005, 2 pages, can be retrieved at <URL.genome.jp/dbget-bin/www_bget?ko:K14454>.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
GenBank: AF034210.1 "Glycine max aspartate aminotransferase glyoxysomal isozyme AAT1 precursor and aspartate aminotransferase cytosolic isozyme AAT2 (AAT) mRNA, complete cds," NCBI, May 26, 1998, 2 Pages, can be retrieved at <URL.ncbi.nlm.nih.gov/nuccore/AF034210>.
GenBank: JN210900.1, "*Enterobacter* sp. WS05 16S ribosomal RNA gene, partial sequence," NCBI, Sep. 24, 2012, 1 Page, can be retrieved at <URL.ncbi.nlm.nih.gov/nuccore/jn210900>.
GenBank: NP_001237541.1, "Aspartate aminotransferase glyoxysomal isozyme AAT1 precursor [Glycine max]," NCBI, Oct. 29, 2016, 2 Pages, can be retrieved at <URL.ncbi.nlm.nih.gov/protein/NP_001237541.1>.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
GenEmbl database, GenEmbl Record No. EU 977189, Jan. 21, 2009, 4 pages, Smith, S.A., et al., "Bioactive endophytes warrant intensified exploration and conservation," PloS ONE 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Kuklinsky-Sobral, J., et al., "Isolation and characterization of soybean-associated bacteria and their potential for plant growth promotion," Environmental Microbiology, 2004, pp. 1244-1251, vol. 6, No. 12.
Le, X.H., et al., "Effects of endophytic *Streptomyces* on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Misk, A., et al., "Biocontrol of chickpea root rot using endophytic actinobacteria", Biocontrol, vol. 56, No. 5, Mar. 12, 2011, pp. 811-822.
Nimnoi, P., et al., "Co-Inoculation of Soybean (*Glycin max*) with Actinomycetes and Bradyrhizobium Japonicum Enhances Plant Growth, Nitrogenase Activity and Plant Nutrition," Journal of Plant Nutrition, 2014, pp. 432-446, vol. 37.
Riken, GI No. GMFL01-01-D03, 2 Pages, [online] [Retrieved on Dec. 18, 2017] Retrieved from the internet <URLspectra.psc.riken.jp/menta.cgi/rsoy/datail?id=GMFL01-01-D03>.
Senthilkumar, M., et al., "Biocontrol Potential of Soybean Bacterial Endophytes Against Charcoal Rot Fungus, *Rhizoctonia batatiola*," Current Microbiology, 2009, vol. 58, pp. 288-293.
Shankar, M., et al., "Root colonization of a rice growth promoting strain of Enterobacter cloacae," Journal of Basic Microbiology, 2011, pp. 523-530, vol. 51.
Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.
Soe, K.M., et al., "Low-Density Co-Inoculation of Myanmar Bradyrhizobium yuanmingense MAS34 and *Streptomyces griseoflavus* P4 to Enhance Symbiosis and Seed Yield in Soybean Varieties," American Journal of Plant Sciences, 2013, pp. 1879-1892, vol. 4.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in Spodoptera litura (Lepidoptera: Noctuidae) Larvae by Endophytic Fungi *Nigrospora oryzae* and *Cladosporium uredinicola*,", Annals of the Entomological Society of America, May 1, 2014, pp. 674-679, vol. 107, No. 3.
Zhang, J., et al: "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50, No. 2, pp. 191-198, GenBank Accession No. JN210900.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Humann, J., et al., "Complete genome of the onion pathogen Enterobacter cloacae EcWSU1," Standard in Genomic Sciences, Dec. 31, 2011, vol. 5, No. 3, pp. 279-286.
Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kim, M., et al., "Towards a taxonomic coherence between average nucleotide identity and 16S rRNA gene sequence similarity for species demarcation of prokaryotes", Int J Systematic Evolutionary Microbial., 2014, vol. 64, pp. 346-351.

(56) References Cited

OTHER PUBLICATIONS

Kumar, S., et al., "MEGA7: Molecular Evolutionary Genetics Analysis version 7.0 for bigger datasets," Molecular Biology and Evolution, Mar. 22, 2016, vol. 33, pp. 1870-1874.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.
Tamura, K., et al., "Estimation of the number of nucleotide substitutions in the control region of mitochondrial DNA in humans and chimpanzees," Molecular Biology and Evolution, 1993, vol. 10, No. 3, pp. 512-526.
Yennamalli, R., et al., "Endoglucanases: insights into thermostability for biofuel applications", Biotech Biofuels, 2013, vol. 6, Issue 136, pp. 1-9.
Adhikari, M., et al., "A New Record of *Pseudeurotium bakeri* from Crop Field Soil in Korea," The Korean Journal of Mycology, 2016, pp. 145-149, vol. 44.
Bensch, K., et al., "Species and ecological diversity within the Cladosporium cladosporioides complex (Davidiellaceae, Capnodiales)," Studies in Mycology, 2010, pp. 1-94, vol. 67.
Labeda, D.P., et al., "Phylogenetic study of the species within the family Streptomycetaceae," Antonie van Leeuwenhoek, 2012, vol. 101, pp. 73-104, Springer.
Op De Beeck, M., et al., "Comparison and Validation of Some ITS Primer Pairs Useful for Fungal Metabarcoding Studies," PLOS ONE, Jun. 2014, vol. 9, Issue 6, e97629, pp. 1-11.
Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.
Verkley, G., et al., "*Paraconiothyrium*, a new genus to accommodate the mycoparasite *Coniothyrium minitans*, anamorphs of Paraphaeosphaeria, and four new species," Studies in Mycology, 2004, pp. 323-335, vol. 50.
Visagie, C.M., et al., "Identification and nomenclature of the genus *Penicillium*," Studies in Mycology, Jun. 2014, pp. 343-371, vol. 78.
PCT Invitation to Pay Additional Fees, PCT App. No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT Invitation to Pay Additional Fees, PCT App. No. PCT/ US2017/064292, dated Mar. 6, 2018, 15 Pages.
PCT International Search Report and Written Opinion, PCT Application No. PCT/USS2017/068255, dated Mar. 19, 2018, 14 Pages.
European Patent Office, Communication Pursuant to Article 94(3) EPC for European Patent Application No. EP 14748326.7, dated Feb. 15, 2018, 7 Pages.
European Patent Office, Supplementary European Search Report for European Patent Application No. EP 15810847.2, dated Feb. 28, 2018, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
Intellectual Property Australia, Examination Report No. 1 for Australian Patent Application No. AU 2017201009, dated Apr. 4, 2018, 3 Pages.
New Zealand Intellectual Property Office, Further Examination Report, New Zealand Patent Application No. 726116, dated Feb. 27, 2018, 6 Pages.
Ukraine Patent Office, Office Action for Ukrainian Patent Application No. a201508515, dated Feb. 20, 2018, 9 Pages.
Office Action for Israel Patent Application No. IL 255682, dated Mar. 15, 2018, 2 Pages (Translation).
Office Action for Israel Patent Application No. IL 255684, dated Mar. 19, 2018, 2 Pages (Translation).
Office Action for Israel Patent Application No. IL 255685, dated Mar. 20, 2018, 2 Pages (Translation).
Office Action for Israel Patent Application No. IL 255688, dated Mar. 22, 2018, 2 Pages (Translation).
Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.
Abou-Shanab, R.A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Amatuzzi, R.F., et al., "Universldade Federal Do Parana," Jan. 1, 2014, 52 Pages. (With English Abstract).
Amatuzzi, R.F., et al., "Potential of endophytic fungi as biocontrol agents of Duponchelia fovealis (Zeller) (Lepidoptera:Crambidae," Brazilian Journal of Biology, Nov. 9, 2017, 7 Pages.
Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.
NCBI GenBank: CP000653.1 "*Enterobacter* sp. 638, complete genome" Jan. 28, 2014, 5 Pages, Can be retrieved at <URL.ncbi.nlm.nih.gov/nuccore/CP000653.1>.
NCBI GenBank: CP000653.1, ASM1632v1 "*Enterobacter* sp. 638, complete genome" Apr. 18, 2007, 2 Pages, Can be retrieved at <URL.ncbi.nlm.nih.gov/assembly/GCA_000016325.1>.
NCBI GenBank: EU340965.1 "*Enterobacter* sp. 638 16S ribosomal RNA gene, partial sequence" Jan. 30, 2009, 1 Page, Can be retrieved at <URL.ncbi.nlm.nih.gov/nuccore/EU340965.1>.
NCBI GenBank: EBI accession No. EM STD:JQ759988, "*Dothideomycetes* sp. genotype 226 isolate FL0175 internal transcribed spacer 1, partial sequence; 5.8S ribosomal RNA gene and internal transcribed spacer 2, complete sequence; and 28S ribosomal RNA gene, partial sequence," May 17, 2012, 1 Page.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 1 Page.
Database Geneseq Database accession No. BAP97938 "Pantoea dispersa strain KACC91642P 16S rDNA sequence, Seq ID 1." Aug. 15, 2013, 1 Page.
Hamayun, M., et al., "Cladosporium sphaerospermum as a new plant growth-promoting endophyte from the roots of *Glycine max* (L.) Merr," World Journal of Microbiology and Biotechnology, Kluwer Academic Publishers, DO, vol. 25, No. 4, Feb. 15, 2009 (Feb. 15, 2009), pp. 627-632.
Klaubauf, S., et al., "Molecular diversity of fungal communities in agricultural soils from Lower Austria," Fungal Diversity, Aug. 13, 2010, pp. 65-75, vol. 44, No. 1.
Knapp, D., et al., "Inter- and intraspecific functional diversity of fungal root endophytes of semiarid sandy grasslands," Acta Microbiologica et Immunologica Hungarica, Nov. 2017, vol. 64, Issue Supplement 1, pp. 1-101.
Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.
Kusari, S., et al. "Chemical ecology of endophytic fungi: origins of secondary metabolites," Cell Press, Chem & Biol, vol. 19, pp. 792-798, 2012.
Mandyam, K., et al., "Mutualism-parasitism paradigm synthesized from results of root-endophyte models", Frontiers in Microbiology, vol. 5, Jan. 12, 2015, pp. 1-14.
Rae, R., et al., "A subset of naturally isolated Bacillus strains show extreme virulence to the free-living nematodes *Caenorhabditis elegans* and *Pristionchus pacificus*", Environmental Microbiology, vol. 12, No. 11, 2010, pp. 3007-3021.

(56) References Cited

OTHER PUBLICATIONS

Sam Ways, M.J., et al., "Assessment of the Fungus *Cladosporium oxyspoum* (Berk. and Curt.) As a Potential BioControl Agent Against Certain Homoptera," Elsevier Science Publishers B.V., Jan. 1, 1986, pp. 231-239.

Saunders, M., et al., "Host-Synthesized Secondary Compounds Influence the In Vitro Interactions between Fungal Endophytes of Maize", Applied and Environmental Microbiology, vol. 74, No. 1, Nov. 9, 2007, pp. 136-142.

Shiraishi, A., et al., "Nodulation in black locust by the ammaproteobacteria *Pseudomonas* sp. and the Betaproteobacteria *Burkholderia* sp", Systematic and Applied Microbiology, 2010, vol. 33, pp. 269-274.

Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, vol. 46, pp. 381-387.

Taghavi, S., et al., "Genome Sequence of the Plant Growth promoting Endophytic Bacterium *Enterobacter* sp. 638", PLoS Genet., May 2010, vol. 6, Issue 5, e1000943, pp. 1-15.

U'Ren, J.M., et al., "Host and geographic structure of endophytic and endolichenic fungi at the continental scale," American Journal of Botany, May 1, 2012, pp. 898-914, vol. 99, No. 5.

Valencia, E., et al., "Mini-review: Brazilian fungi diversity for biomass degradation," Fungal Genetics and Biology, 2013, pp. 9-18, vol. 60.

Vujanovic, V., et al., "Viability Testing of Orchid Seed and the Promotion of Colouration and Germination," Annals of Botany, Mar. 17, 2000, vol. 86, pp. 79-86.

Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.

Vujanovic, V., et al., "Mycovitality—a new concept of plant biotechnology," Canadian Journal Plant Pathol, 2007, vol. 29, p. 451.

Vujanovic, V., et al., "Seed endosymbiosis: a vital relationship in providing prenatal care to plants," Can. J. Plant Sci., NRC Research Press, Feb. 6, 2017, pp. 972-981, vol. 97.

Youssef, Y.A., et al., "Production of Plant Growth Substances by Rhizosphere Myoflora of Broad Bean and Cotton," Biologia Plantarum, 1975, pp. 175-181, vol. 17, No. 3.

\* cited by examiner

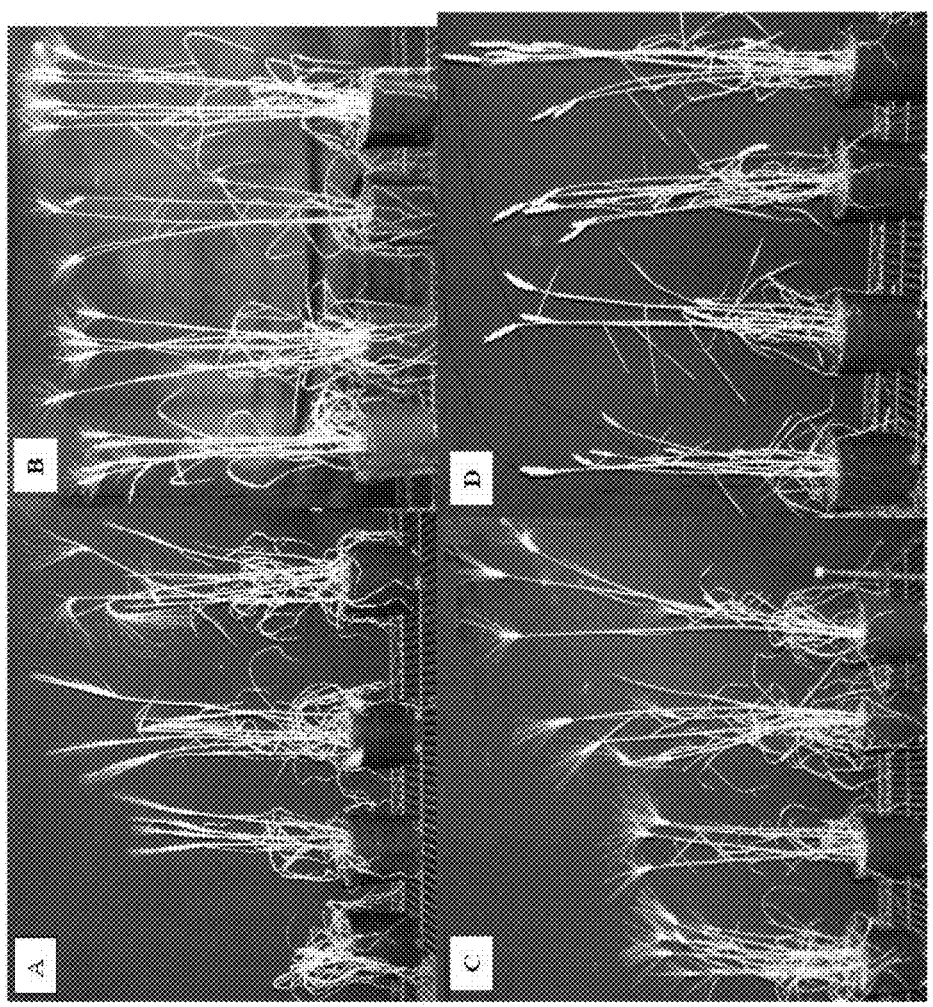

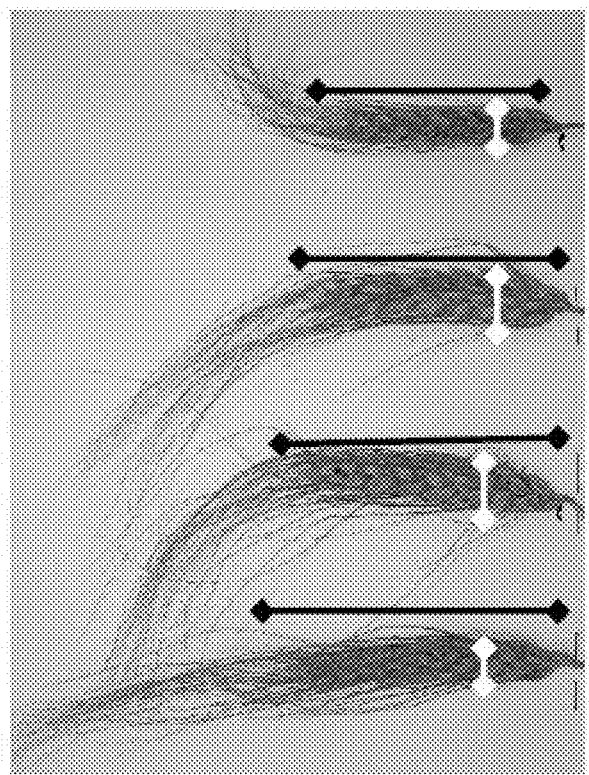
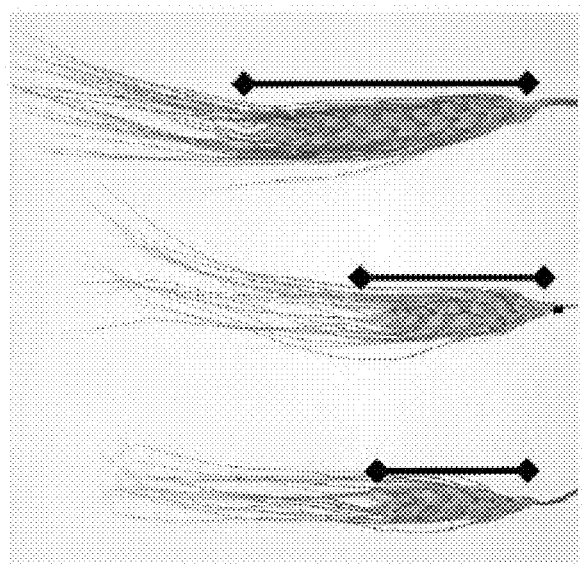
FIG. 42

ENDOPHYTIC MICROBIAL SYMBIONTS IN PLANT PRENATAL CARE

CROSS REFERENCE TO RELATED APPLICATIONS

This application is a continuation-in-part of co-pending International Application No. PCT/CA2013/000091, filed Feb. 5, 2013, which is herein incorporated in its entirety by reference

SEQUENCE LISTING

The instant application contains a Sequence Listing which has been submitted via EFS-Web and is hereby incorporated by reference in its entirety. Said ASCII copy, created on Feb. 4, 2015, is named 28761US_sequencelisting.txt, and is 9,382 bytes in size.

FIELD

The present disclosure relates to synthetic preparations comprising a seed and a composition, where the composition comprises fungal and bacterial endophytes of plants that enhance seed vitality and/or plant health, conferring general improvements in the plant's agricultural traits, under normal and stressed conditions.

BACKGROUND

Fungi and bacteria are ubiquitous microorganisms. Endophyte is the term first coined by de Bary [1866] defining those microbes that colonize asymptomatically plant tissues [Stone et al., 2000]. The existence of endophytes has been known for more than one century [Freeman 1904] and it seems that each individual host, among the 300,000 plant species, inhabits several to hundreds of endophytes [Tan and Zou, 2001]. Endophytes are microbial organisms mostly symbiotically or mutualistically associated with living tissues of plant hosts. Many are capable of conferring plant tolerance to abiotic stressors or can be used by the plant for defense against pathogenic fungi and bacteria [Singh et al. 2011]. Some of these microorganisms have proven useful for very small subsets of agriculture (e.g., forage grass growth), forestry and horticulture sectors, as well as plant production of medicinally important compounds. However, no commercial endophyte seed coating products are used in the world's largest crops including corn, wheat, rice, and barley, and such endophyte approaches have suffered from high variability, inconsistent colonization, low performance across multiple crop cultivars, and the inability to confer benefits to elite crop varieties under field conditions.

Endophytes largely determine plant cell and whole plant genome regulation, including the plant's vital cycles: (i) seed pre- and post-germination events (mycovitalism) [Vujanovic and Vujanovic 2007], (ii) plant nutrient uptake and growth-promoting mechanisms (mycoheterotrophism) [Smith and Read 2008], and (iii) plant environmental stress tolerance and induced systemic resistance against diseases and pests (mycosymbionticism) [Wallin 1927; Margulis, 1991]. They could play a major role in plant biomass production, $CO_2$ sequestration, and/or yield and therefore be significant players in regulating the ecosphere, ensuring plant health and food security. In addition, they can be important sentinels (bioindicators) of environmental changes, as alterations in the structure and biomass of endophytic communities can herald changes not only in pathways of nutrient (N, P, K), energy transfer in food-webs and biogeochemical cycles but also in UV-B, heat, drought or salt tolerance influencing the overall plant ecosystem establishment and stability. Despite their abundance and likely importance in all terrestrial ecosystems, nearly nothing about the composition of endophytes in seeds or spermosphere, their interactions, or their common response to environmental changes is known.

While the spermosphere represents a rapidly changing and microbiologically dynamic zone of soil surrounding a germinating seed [Nelson, 2004], the rhizosphere is a microbiologically active zone of the bulk soil surrounding the plant's roots [Smith and Read 2008]. The rhizosphere supports mycoheterotrophy or a plant-mycorrhiza symbiotic relationship. The spermosphere, on the other hand, promotes mycovitality or an endophytic fungi relationship with the plant seeds—enhancing seed vigour, energy and uniformity of germination that could be fairly predicted. Fungal endophytes are distinct from mycorrhizae in that they can colonize not only roots, but also other plant organs including seeds [Vujanovic et al. 2000; Hubbard et al. 2011]. They belong to the multicellular phyla Ascomycota and Basidiomycota and form colonization symbiotic structures different from those produced by unicellular or cenocytic phylum Glomeromycota, known as vesicular-arbuscular mycorrhizal symbiosis [Abdellatif et al. 2009]. Endophytic bacteria have been also found in virtually every plant studied, where they colonize an ecological niche similar to that of fungi, such as the internal healthy tissues. Although most bacterial endophytes appear to originate from the rhizosphere or phyllosphere; some may be transmitted through the seed [Ryan et al. 2008].

Seed germination is a vital phenophase to plants' survival and reproduction in either optimal or stressful environmental conditions. Microbial endophytic colonization at the seed state is especially critical because of the role of the seed as a generative organ in regeneration and dispersion of flowering plants [Baskin and Baskin 2004] and the role of mycobionts and symbiotically associated bacteria (bactobionts) as potential drivers of seedling recruitment in natural—undisturbed, disturbed and polluted—habitats [Mühlmann and Peintner 2000; Adriaensen et al. 2006; White and Torres 2010]. Thus, developing methods by which seedling emergence can be enhanced and protected under the limitations of disease pressure, heat or drought is precious. The use of endophytic symbionts is a promising method by which seed germination can be enhanced [Vujanovic et al. 2000; Vujanovic and Vujanovic 2006; Vujanovic and Vujanovic 2007]. The methods and compositions described herein overcome these and other limitations of the prior art. It was hypothesized that plant stress hardiness can be conferred via a mycobiont-seed relationship known as mycovitality—a phenomenon that had been reserved for Orchidaceae [Vujanovic 2008] and via bactovitality which refers to a form of bactosymbiosis, using different endophytic strains with variety of activities.

SUMMARY

The synthetic preparations and compositions described herein can benefit plant hosts, for example, but not limited to, wheat, barley, corn, soybeans, alfalfa, rice, cotton, pulses, canola, vegetables, sugarbeet, sugarcane, trees, shrubs or grasses. The benefit may come from bactovitality, mycovitality and mycoheterotrophy, and enhance tolerance to environmental stresses, as demonstrated herein. Prenatal care in agriculture is more than just seed or germinant vitality, health or vigour. It also determines what to expect before and during the germination process, seedling establishment, and, later crop productivity or yield.

Several parameters of symbiotic efficacy (dormancy breakdown, germination, growth and yield) were assessed using efficient endophytic Saskatchewan Microbial Collection and Database (SMCD) strain(s)-crop(s) interaction(s) under in vitro, phytotron, greenhouse and field conditions. The synthetic preparations and compositions described herein have effects on germination, which can be assessed by measuring percent of germination, energy of germination and hydrothermal time required for germination, for example.

Also tested was the endophyte's capacity to confer seed vitality. For both fungal and bacterial endosymbionts, improved seed vitality can increase tolerance for abiotic and biotic stresses in plants that have progressed beyond the seedling stage to the plant's maturity via mycoheterotrophy. The synthetic preparations and compositions described herein can improve plant traits such as increased yield, faster seedling establishment, faster growth, increased drought tolerance, increased heat tolerance, increased cold tolerance, increased salt tolerance, increased tolerance to pests and diseases, for example increased tolerance to *Fusarium* infection and to *Puccinia* infection, increased biomass, increased root length, increased fresh weight of seedlings, increased plant vigour, nitrogen stress tolerance, enhanced *Rhizobium* activity, enhanced nodulation frequency or early flowering time.

The synthetic preparations and compositions described herein can also modulate the expression of genes involved in plant growth, genes associated with systemic acquired resistance, or genes involved in protection from oxidative stress. These genes may be involved in phytohormone production, for example gibberellin (GA) biosynthesis or breakdown, abscisic acid (ABA) biosynthesis or breakdown, NO production or breakdown, superoxide detoxification, or could be positive or negative regulators of these pathways. The genes associated with systemic acquired resistance may be redox-regulated transcription factors, for example those in the MYB family. Non-limiting examples of such genes include ent-kaurenoic (KAO), repression of shoot growth (RSG), NCED, ABA 8'-hydroxylase, GA3-oxidase 2, 14-3-3 or nitric oxide (NO) genes and/or stress resistance superoxide dismutase (SOD), manganese SOD (MnSOD), proline (Pro), Myb1 and Myb2.

In certain embodiments, the present disclosure provides a synthetic preparation comprising an agricultural plant seed and a composition comprising an endophyte capable of promoting germination and an agriculturally-acceptable carrier, wherein an agricultural plant grown from the seed has an altered trait as compared to a control agricultural plant. In certain embodiments, the endophyte capable of promoting germination is a coleorhiza-activating endophyte and the agricultural plant seed is a monocot seed. In some embodiments, the composition is disposed on an exterior surface of the agricultural seed in an amount effective to colonize the cortical cells of an agricultural plant grown from the seed and to produce the altered trait, wherein the altered trait is an improved functional trait selected from the group consisting of increased yield, faster seedling establishment, faster growth, increased drought tolerance, increased heat tolerance, increased cold tolerance, increased salt tolerance, increased tolerance to *Fusarium* infection, increased tolerance to *Puccinia* infection, increased biomass, increased root length, increased fresh weight of seedlings, increased plant vigor, nitrogen stress tolerance, enhanced *Rhizobium* activity, enhanced nodulation frequency, and early flowering time. In some embodiments, the composition is disposed on an exterior surface of the agricultural seed in an amount effective to colonize at least 1% of the cortical cells of an agricultural plant grown from the seed. In other embodiments, the composition is disposed on an exterior surface of the agricultural seed in an amount effective to cause a population of seeds inoculated with said composition to have greater germination rate, faster dormancy breakdown, increased energy of germination, increased seed germination vigor or increased seed vitality than a population of control agricultural seeds. In some embodiments, the composition is disposed on an exterior surface of the agricultural seed in an amount effective to cause a population of seeds inoculated with said composition to reach 50% germination faster than a population of control agricultural seeds.

In some embodiments, the endophytes are a selected from the group consisting of a spore-forming endophyte, a facultative endophyte, a filamentous endophyte, an endophyte capable of living within another endophyte, an endophyte capable of forming hyphal coils within the plant, an endophyte capable of forming microvesicles within the plant, an endophyte capable of forming micro-arbuscules within the plant, an endophyte capable of forming hyphal knots within the plant, an endophyte capable of forming Hartig-like nets within the plant, and an endophyte capable of forming symbiosomes within the plant. In some embodiments, the endophyte is in the form of at least one of conidia, chlamydospore, and mycelia.

In other embodiments, the composition is disposed on an exterior surface of the agricultural seed in an amount effective to colonize the cortical cells of an agricultural plant grown from the seed and to produce the altered trait, wherein the altered trait is altered gene expression, wherein the gene is selected from the group consisting of a gene involved in plant growth, an acquired resistance gene, and a gene involved in protection from oxidative stress. In some embodiments, the gene is involved in phytohormone production. In other embodiments, the gene is a redox-regulated transcription factor. In yet other embodiments, the gene involved in superoxide detoxification or in NO production or breakdown.

In some embodiments, the agricultural plant seed is selected from the group consisting of corn, soy, wheat, cotton, rice, canola, barley and pulses. In some embodiments, a population comprising at least 10 synthetic preparations is disposed within a packaging material.

Further provided herein is a seed comprising an endophyte or culture disclosed herein. In one embodiment, the seed is coated with the endophyte. In another embodiment, the seed is cultured or planted near the endophyte such that the endophyte is able to colonize the seed. In one embodiment, the seed planted near the endophyte is up to 4 cm away from the endophyte.

The endophytes used to inoculate the seeds may be selected from the group consisting of a spore-forming endophyte, a facultative endophyte, a filamentous endophyte, and an endophyte capable of living within another endophyte. In some embodiments, the endophyte is capable of forming certain structures in the plant, where the structures are selected from the group consisting of hyphal coils, Hartig-like nets, microvesicles, micro-arbuscules, hyphal knots, and symbiosomes. In some embodiments, the endophyte is in the form of at least one of conidia, chlamydospore, and mycelia. In other embodiments, the fungus or bacteria is capable of being part of a plant-fungus symbiotic system or plant-bacteria symbiotic system that produces altered levels of phytohormones or anti-oxidants, as compared to a plant that is not in symbiosis. In other embodiments, the plant-fungus symbiotic system or plant-bacterium symbiotic system has anti-aging and/or anti-senescence effects, as compared to a plant or plant organ that is not in symbiosis. In other embodiments, the plant-fungus symbiotic system or plant-bacteria symbiotic system has increased protection against pathogens, as compared to a plant that is not in symbiosis. In some embodiments, The present disclosure also provides methods for improving seed vitality and enhancing plant health and yield under normal and stressed conditions. Accordingly, there is provided a method of improving seed vitality, plant health and/or plant yield comprising inoculating a seed with an endophyte or culture disclosed herein or a combination or mixture thereof or with a composition disclosed herein. In some embodiments, the seed is cultivated into a first generation plant.

In certain embodiments, provided herein are methods of altering a trait in an agricultural plant seed or an agricultural plant grown from said seed, where the methods comprise inoculating the seed with a composition comprising endophytes capable of promoting germination and an agriculturally-acceptable carrier, where the endophyte replicates within at least one plant tissue and colonizes the cortical cells of said plant. In some embodiments, the endophyte colonizes at least 1% of the cortical cells of said agricultural plant.

In some embodiments, the trait altered by using the method is an improved functional trait selected from the group consisting of increased yield, faster seedling establishment, faster growth, increased drought tolerance, increased heat tolerance, increased cold tolerance, increased salt tolerance, increased tolerance to *Fusarium* infection, increased tolerance to *Puccinia* infection, increased biomass, increased root length, increased fresh weight of seedlings, increased plant vigor, nitrogen stress tolerance, enhanced *Rhizobium* activity, enhanced nodulation frequency, and early flowering time. In other embodiments, the altered trait is a seed trait selected from the group consisting a greater germination rate, faster dormancy breakdown, increased energy of germination, increased seed germination vigor or increased seed vitality than a population of control agricultural seeds. In other embodiments, the altered trait is reaching 50% germination faster than a population of control agricultural seeds. In other embodiments, the altered trait is altered gene expression, where the gene is selected from the group consisting of a gene involved in plant growth, an acquired resistance gene, and a gene involved in protection from oxidative stress.

In some embodiments, the endophytes used in the method are a selected from the group consisting of a spore-forming endophyte, a facultative endophyte, a filamentous endophyte, an endophyte capable of living within another endophyte, an endophyte capable of forming hyphal coils within the plant, an endophyte capable of forming microvesicles within the plant, an endophyte capable of forming micro-arbuscules within the plant, an endophyte capable of forming hyphal knots within the plant, an endophyte capable of forming Hartig-like nets within the plant, and an endophyte capable of forming symbiosomes within the plant. In some embodiments, the endophyte is in the form of at least one of conidia, chlamydospore, and mycelia.

In some embodiments, the endophyte is a fungus of subphylum Pezizomycotina. In some embodiments, the endophyte is a fungus of class Leotiomycetes, Dothideomycetes, Sordariomycetes, or Eurotiomycetes. In some embodiments, the endophyte is of order Helotiales, Capnodides, Pleosporales, Hypocreales, or Eurotiales. In some embodiments, the composition comprises an agriculturally-acceptable carrier and a spore-forming, filamentous bacterial endophyte of phylum Actinobacteria. In some embodiments, the endophyte is a bacteria of order actinomycetales.

In some embodiments, the present disclosure provides a composition comprising a carrier and an endophyte of *Paraconiothyrium* sp. strain deposited as IDAC 081111-03 or comprising a DNA sequence with at least 97% identity to SEQ ID NO:5; an endophyte of *Pseudoeurotium* sp. strain deposited as IDAC 081111-02 or comprising a DNA sequence with at least 97% identity to SEQ ID NO:4; an endophyte of *Penicillium* sp. strain deposited as IDAC 081111-01 or comprising a DNA sequence with at least 97% identity to SEQ ID NO:3; an endophyte of *Cladosporium* sp. strain deposited as IDAC 200312-06 or comprising a DNA sequence with at least 97% identity to SEQ ID NO:1; an endophyte of *Sarocladium* sp. strain deposited as IDAC 200312-05 or comprising a DNA sequence with at least 97% identity to SEQ ID NO:2; and/or an endophyte of *Streptomyces* sp. strain deposited as IDAC 081111-06 or comprising a DNA sequence with at least 97% sequence identity to SEQ ID NO:6. In certain embodiments, the endophyte of *Paraconiothyrium* sp. strain comprises a DNA sequence with at least 98% identity to SEQ ID NO:5; the endophyte of *Pseudoeurotium* sp. strain comprises a DNA sequence with at least 98% identity to SEQ ID NO:4; the endophyte of *Penicillium* sp. strain comprises a DNA sequence with at least 98% identity to SEQ ID NO:3; the endophyte of *Cladosporium* sp. strain comprises a DNA sequence with at least 98% identity to SEQ ID NO:1; the endophyte of *Sarocladium* sp. strain comprises a DNA sequence with at least 98% identity to SEQ ID NO:2; and the endophyte of *Streptomyces* sp. strain comprises a DNA sequence with at least 98% sequence identity to SEQ ID NO:6. In certain embodiments, the endophyte of *Paraconiothyrium* sp. strain comprises a DNA sequence with at least 99% identity to SEQ ID NO:5; the endophyte of *Pseudoeurotium* sp. strain comprises a DNA sequence with at least 99% identity to SEQ ID NO:4; the endophyte of *Penicillium* sp. strain comprises a DNA sequence with at least 99% identity to SEQ ID NO:3; the endophyte of *Cladosporium* sp. strain comprises a DNA sequence with at least 99% identity to SEQ ID NO:1; the endophyte of *Sarocladium* sp. strain comprises a DNA sequence with at least 99% identity to SEQ ID NO:2; and the endophyte of *Streptomyces* sp. strain comprises a DNA sequence with at least 99% sequence identity to SEQ ID NO:6. In certain embodiments, the endophyte of *Paraconiothyrium* sp. strain comprises a DNA sequence of SEQ ID NO:5; the endophyte of *Pseudoeurotium* sp. strain comprises a DNA sequence of SEQ ID NO:4; the endophyte of *Penicillium* sp. strain comprises a DNA sequence of SEQ ID NO:3; the endophyte of *Cladosporium* sp. strain comprises a DNA sequence of SEQ ID NO:1; the endophyte of *Sarocladium* sp. strain comprises a DNA sequence of SEQ ID NO:2; and the endophyte of *Streptomyces* sp. strain comprises a DNA sequence of SEQ ID NO:6.

In another aspect, there is provided a method of improving plant health and/or plant yield comprising treating plant propagation material or a plant with an endophyte or culture disclosed herein or a combination or mixture thereof or a composition disclosed herein. In some embodiments, the plant propagation material is cultivated into a first generation plant or the plant is allowed to grow.

In an embodiment, the plant propagation material is any plant generative/sexual (seed, generative bud or flower) and vegetative/asexual (stem, cutting, root, bulb, rhizome, tuber, vegetative bud, or leaf) part that has the ability to be cultivated into a new plant.

In an embodiment, the methods enhance landscape development and remediation. Accordingly, in one embodiment, there is provided a method of reducing soil contamination comprising treating plant propagation material or a plant with an endophyte or culture disclosed herein or a combination or mixture thereof or a composition disclosed herein; and cultivating the plant propagation material into a first generation plant or allowing the plant to grow. In one embodiment, the soil contaminant is hydrocarbons, petroleum or other chemicals, salts, or metals, such as lead, cadmium or radioisotopes.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description and respective drawings and drawing legends.

BRIEF DESCRIPTION OF THE DRAWINGS

The disclosure will now be described in relation to the drawings in which:

FIG. 22 shows (A) Barley-six row AC Metcalfe, from left to the right: Drought (E−), Drought and SMCD 2206 (E+), Control (E−), Control and SMCD 2206 (E+); (B) Wheat-Unity cultivar, from left to the right: Drought (E−), Drought and SMCD 2215 (E+), Control (E−), Control and SMCD 2215 (E+); (C) Wheat-Verona cultivar, from left to the right: Drought (E−), Drought and SMCD 2215 (E+), Control (E−), Control and SMCD 2215 (E+); and (D) *Durum* wheat-TEAL, from left to the right: Drought (E−), Drought and SMCD 2210 (E+), Control (E−), Control and SMCD 2210 (E+).

FIG. 42 shows comparison of TEAL spike sizes in wheat in the presence of pathogen (negative control) and without presence of pathogen (positive control). Left Figure—from left to right: i) plant+F.gr, ii) plant+F.av, and (iii) plant; Right Figure—from left to right: i) plant; ii) plant+endophyte; iii) plant+endophyte+F. av; and iv) plant+endophyte+F.gr.

Figure 57:
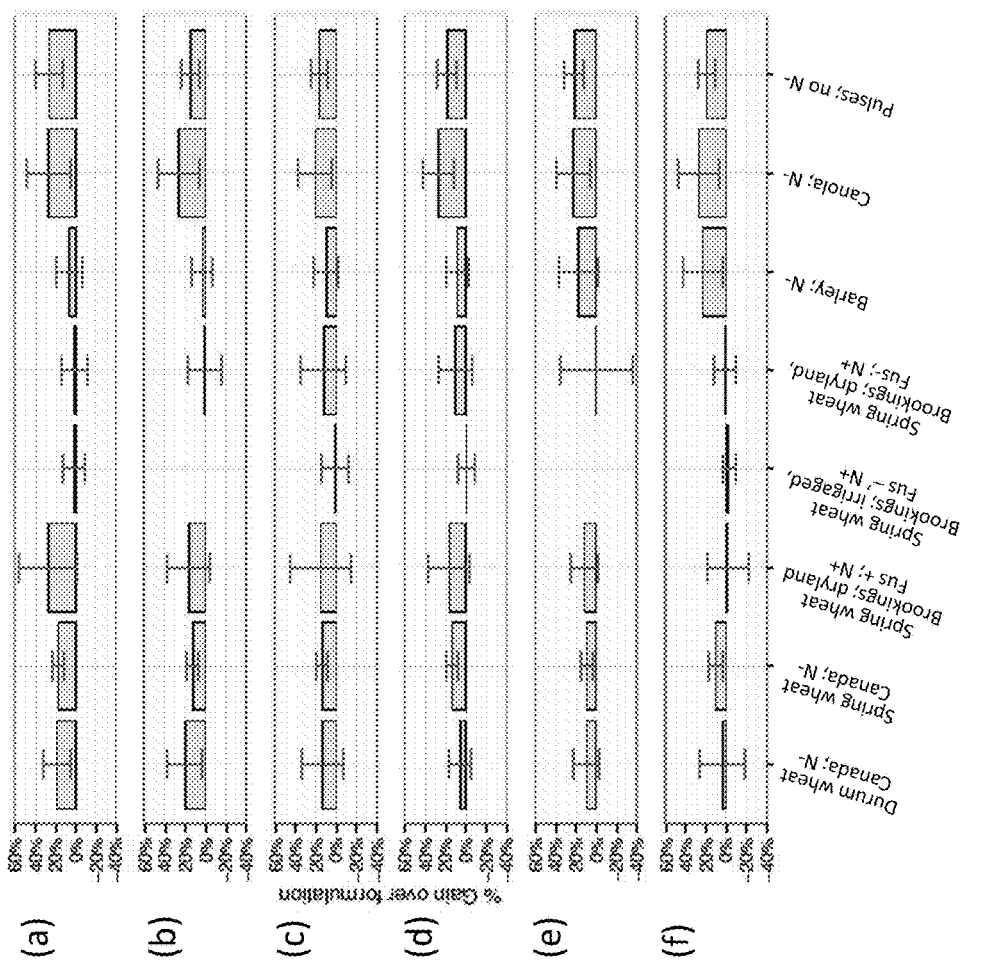

FIG. 57 shows aggregated yield data for *durum* wheat, spring wheat, barley, canola, and pulses (chickpea, pea, and lentil). 95% confidence intervals for the respective formulation and crop are shown. The data are presented as percentage gain over the abiotic formulation control for each combination of crop, field trial and condition (irrigated or dryland). (a) refers to SMCD 2215, (b) refers to SMCD 2210, (c) refers to SMCD 2204, (d) refers to SMCD 2206, (e) refers to SMCD 2208, and (f) refers to SMCD 2204F. Data shown is from n=4 independent replicate plots for all Canadian sites and n=6 plots for Brookings, S. Dak. As above, the notation "Fus−" indicates that there was no visible occurrence of *Fusarium* Head Blight (*Fusarium graminearum*) in that specific field and "Fus+" indicates that there was clear evidence of *Fusarium* Head Blight (*Fusarium graminearum*) occurrence. N− indicates that there was no nitrogen fertilizer applied to the field and N+ indicates that nitrogen fertilizer was applied at agriculturally relevant rates.

Figure 58:
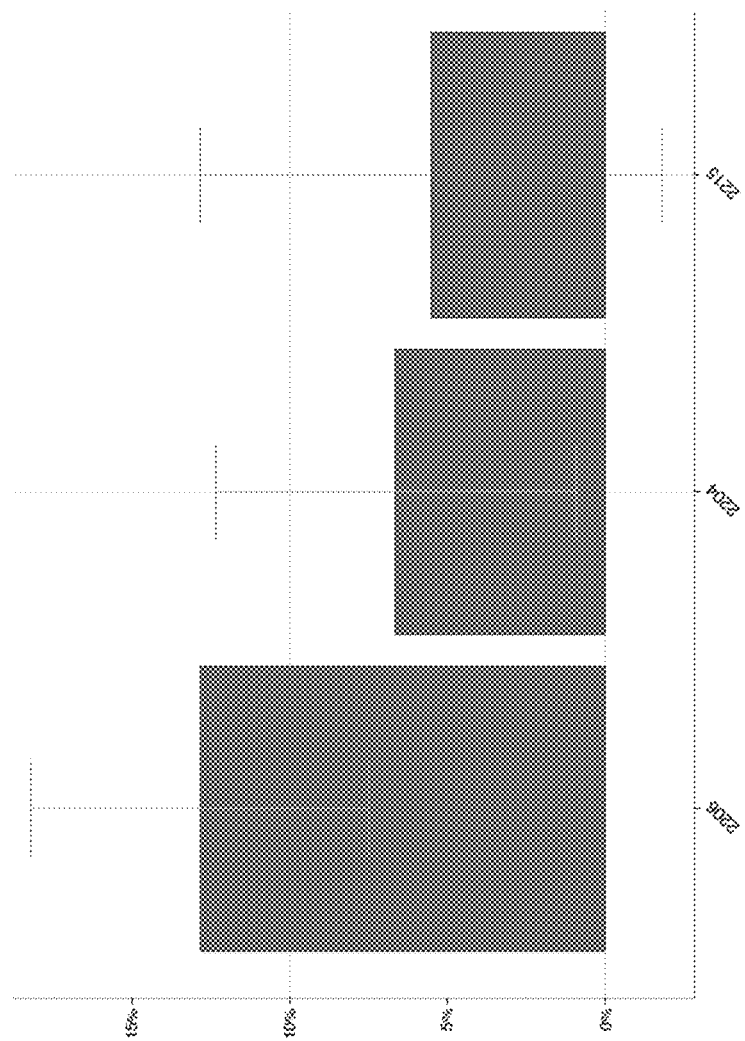

FIG. 58 shows the aggregated ear weight data from the corn field trial in Brookings, S. Dak. 95% confidence intervals for the respective formulation is shown. The data is presented as percentage gain over the abiotic formulation control. "2206" refers SMCD 2206, "2204" refers to SMCD 2204, and "2215" refers to SMCD 2215.

Figure 59:
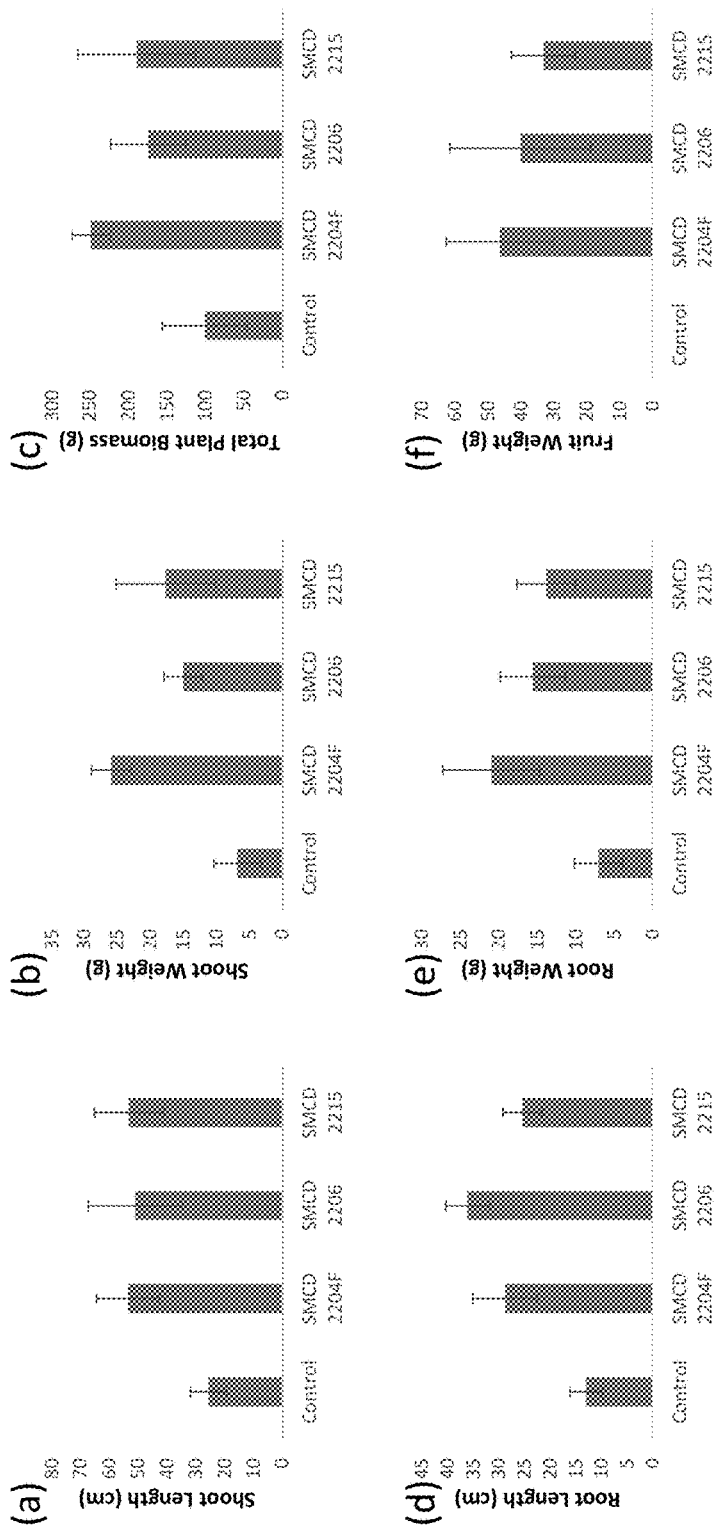

FIG. 59 shows data from greenhouse trials of tomato inoculated with the described microbial compositions: (a) shoot length, (b) shoot weight, (c) total plant biomass, (d) root length, (e) root weight, and (f) tomato fruit weight under drought conditions. Data shown is from n=3 independent replicate plants±one standard deviation.

Figure 60:
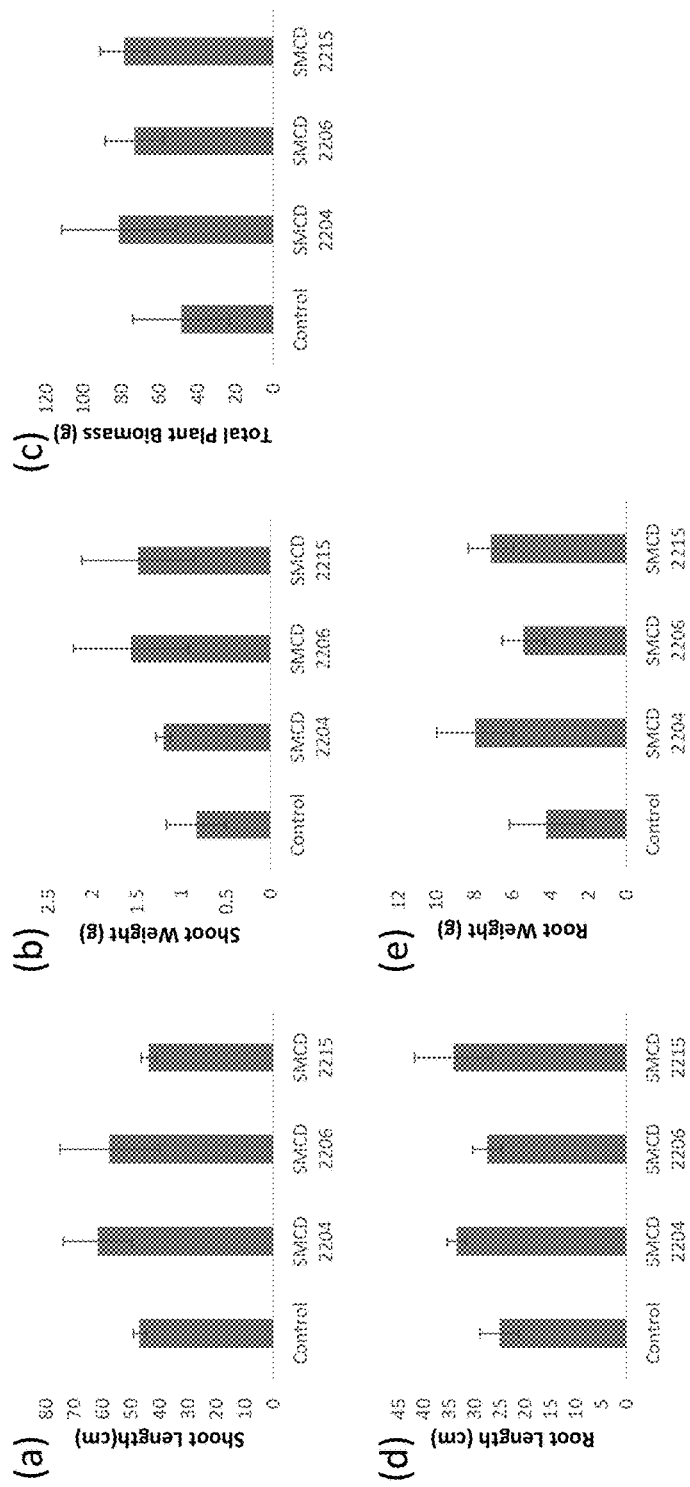

FIG. 60 shows data from greenhouse trials of alfalfa treated with the described microbial compositions: (a) shoot length, (b) shoot weight, (c) total plant biomass, (d) root length, and (e) root weight under drought conditions. Data shown is from n=3 independent replicate plants±one standard deviation.

Figure 61:
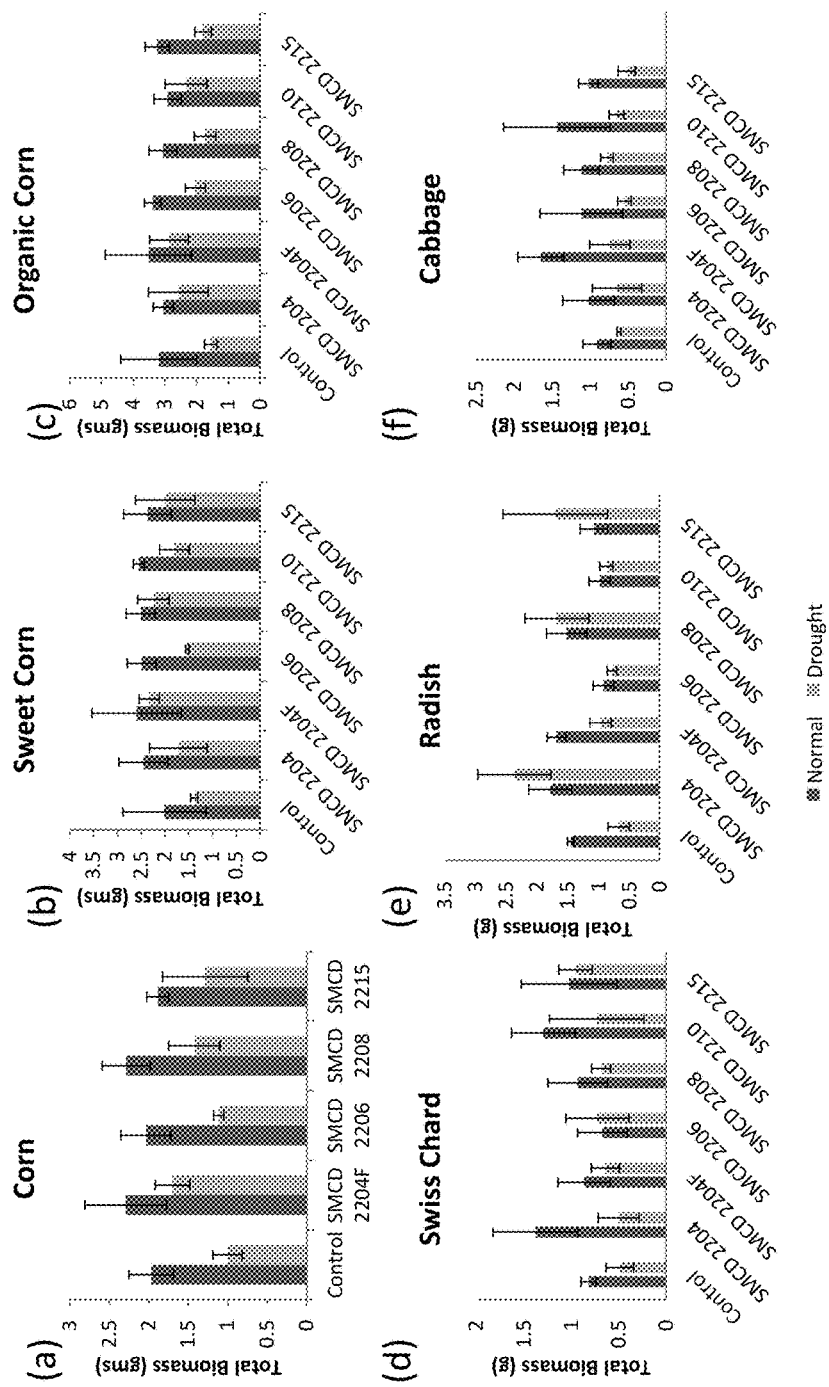

FIG. 61 shows data from greenhouse trials comparing normal (dark gray) and drought (light gray) water conditions for: (a) corn, (b) sweet corn, (c) organic corn, (d) swiss chard, (e) radish, and (f) cabbage. Data shown is total biomass from n=3 independent replicate plants±one standard deviation.

Figure 62:
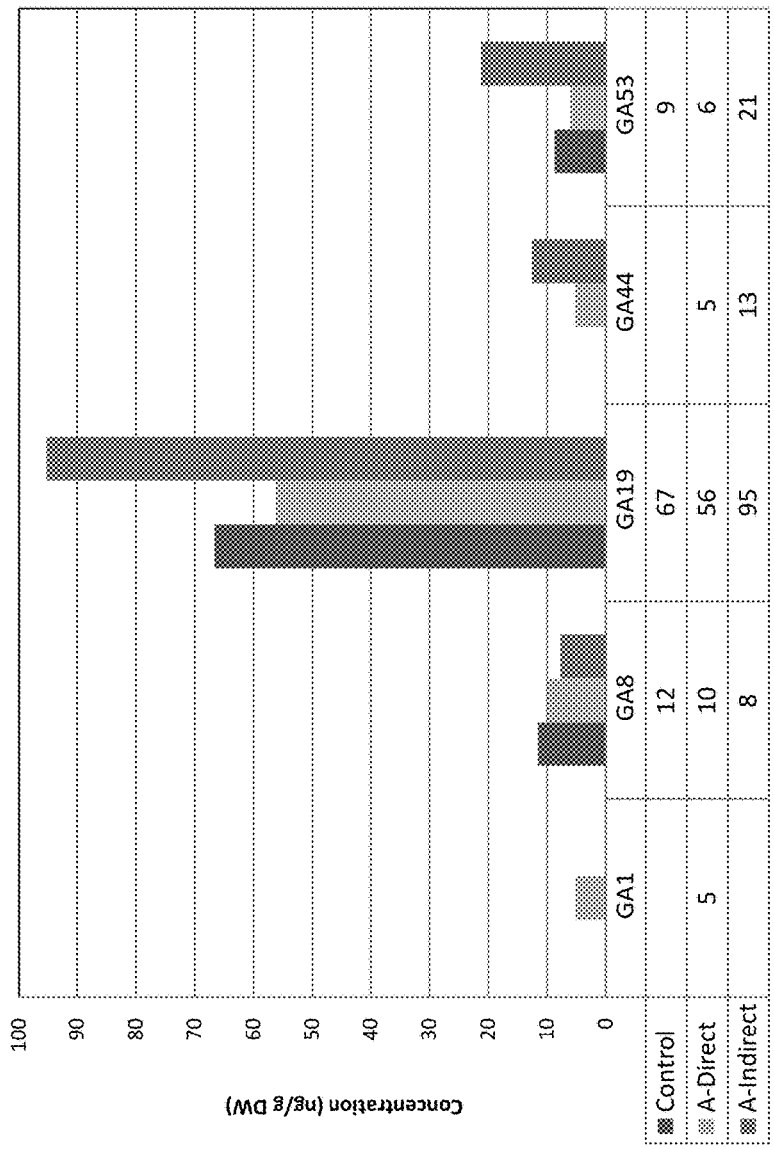

FIG. 62 shows gibberellin production data from wheat (CDC Avonlea) in seedling studies. "Control" refers to the formulation control wherein SMCD 2206 was not added, "A-Direct" refers to direct application of SMCD 2206 to the seedling, and "A-Indirect" refers to the indirect application of SMCD 2206 to the seedling through a small-molecule permeable membrane. See Table 12 for abbreviation of molecules. Data shown is average concentration in ng per gram dry tissue weight from n=3 independent replicates.

Figure 63:
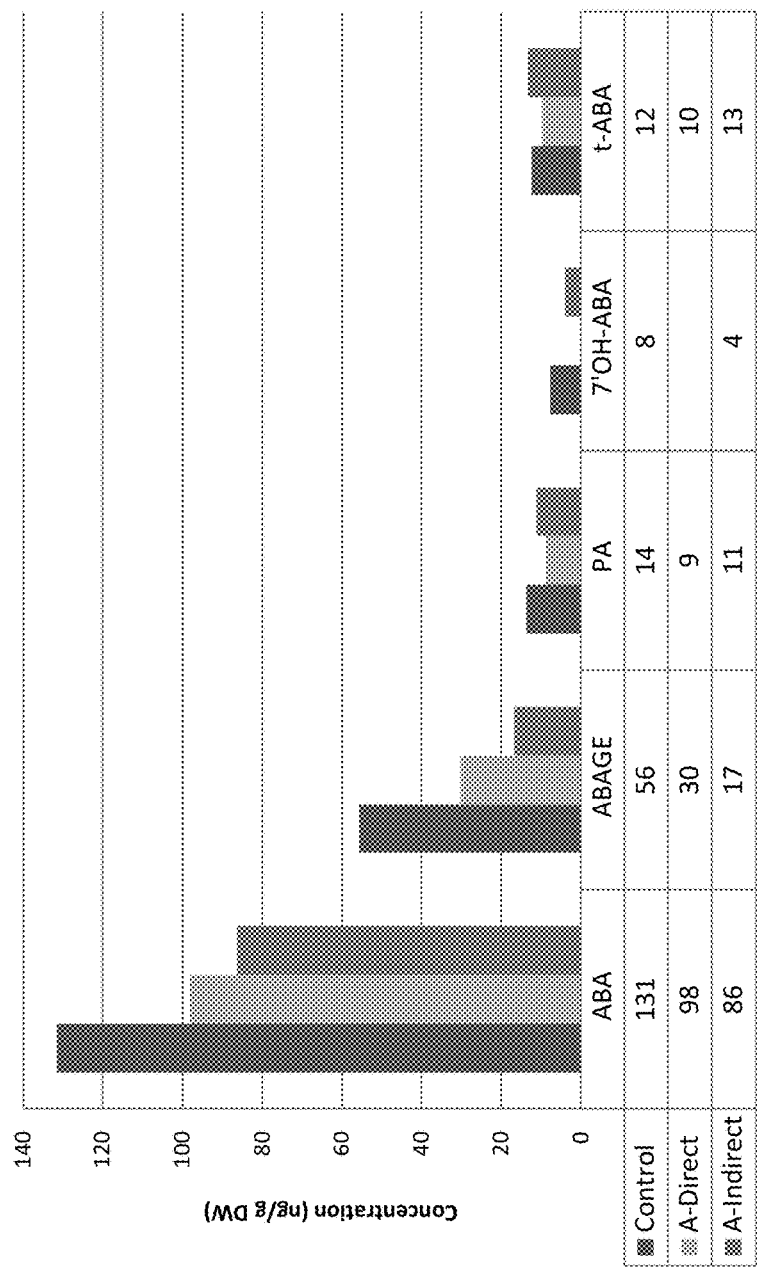

FIG. 63 shows ABA metabolite production data from wheat (CDC Avonlea) in seedling studies. "Control" refers to the formulation control wherein SMCD 2206 was not added, "A-Direct" refers to direct application of SMCD 2206 to the seedling, and "A-Indirect" refers to the indirect application of SMCD 2206 to the seedling through a small-molecule permeable membrane. See Table 13 for abbreviation of the names of the molecules. Data shown is average concentration in ng per gram dry tissue weight from n=3 independent replicates.

Figure 64:
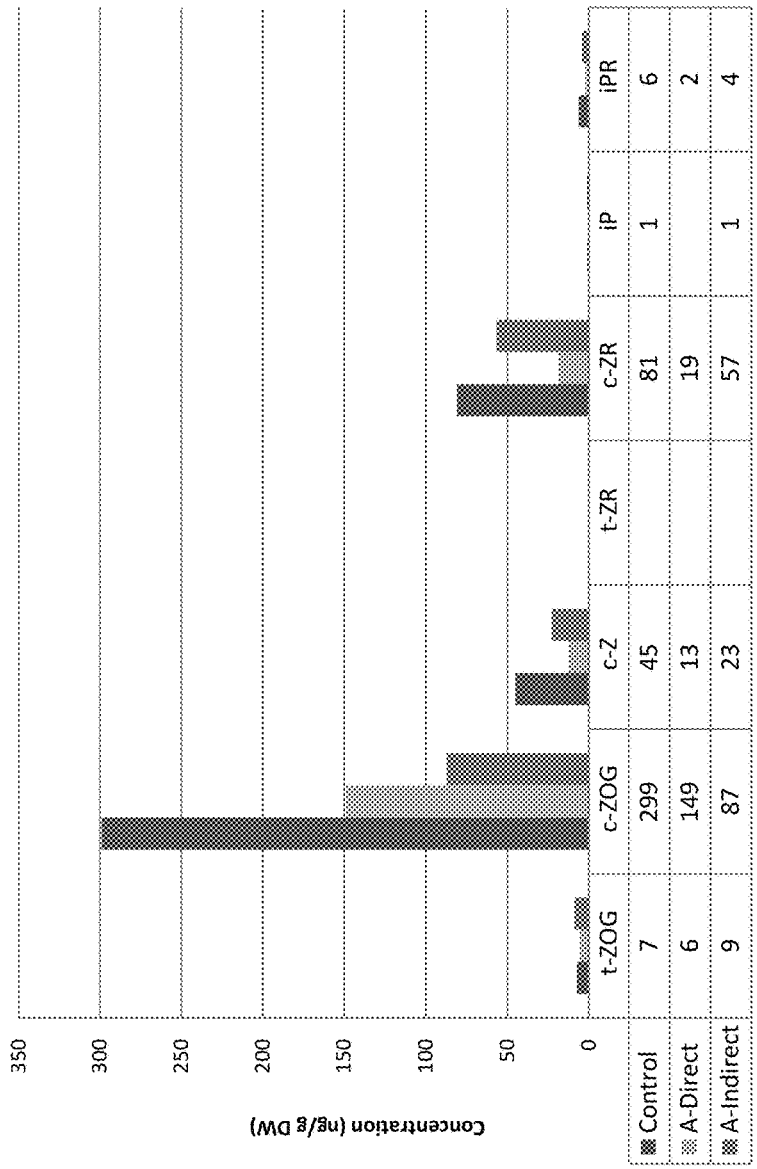

FIG. 64 shows cytokinin production data from wheat (CDC Avonlea) in seedling studies. "Control" refers to the formulation control wherein SMCD 2206 was not added, "A-Direct" refers to direct application of SMCD 2206 to the seedling, and "A-Indirect" refers to the indirect application of SMCD 2206 to the seedling through a small-molecule permeable membrane. See Table 14 for abbreviation of molecules. Data shown is average concentration in ng per gram dry tissue weight from n=3 independent replicates.

Figure 65:
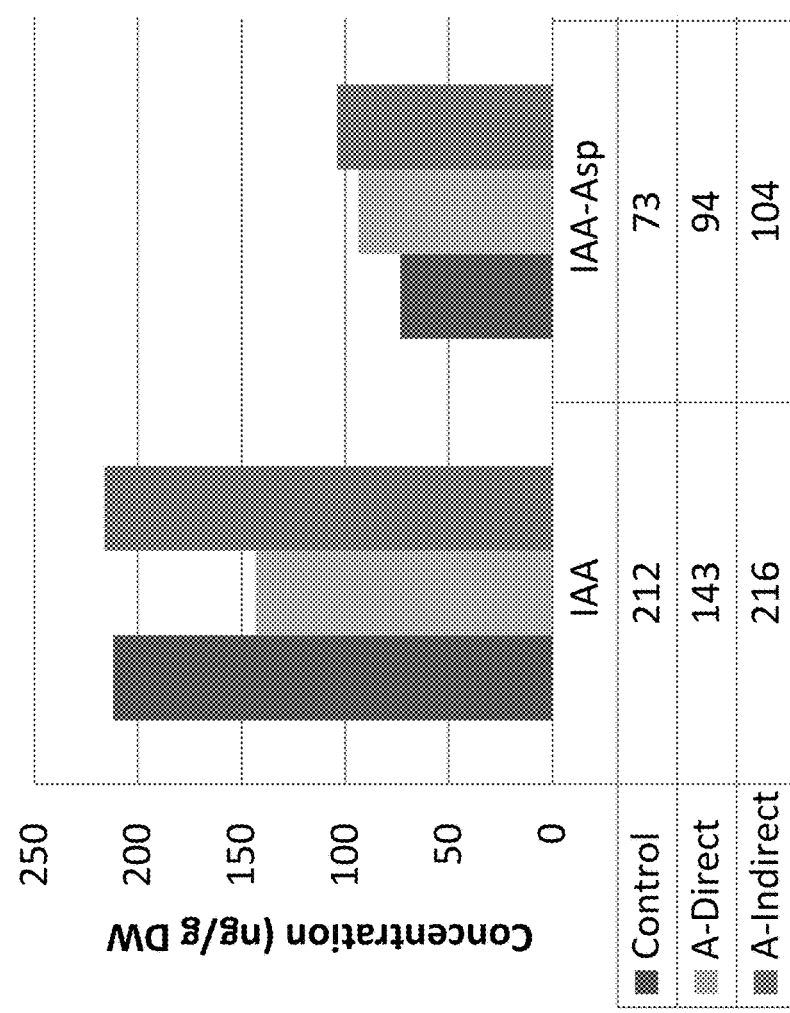

FIG. 65 shows auxin production data from wheat (CDC Avonlea) in seedling studies. "Control" refers to the formulation control wherein SMCD 2206 was not added, "A-Direct" refers to direct application of SMCD 2206 to the seedling, and "A-Indirect" refers to the indirect application of SMCD 2206 to the seedling through a small-molecule permeable membrane. Auxins were represented by the biologically active indole acetic acid IAA and its conjugate with aspartic acid IAA-Asp. Data shown is average concentration in ng per gram dry tissue weight from n=3 independent replicates.

Figure 66:
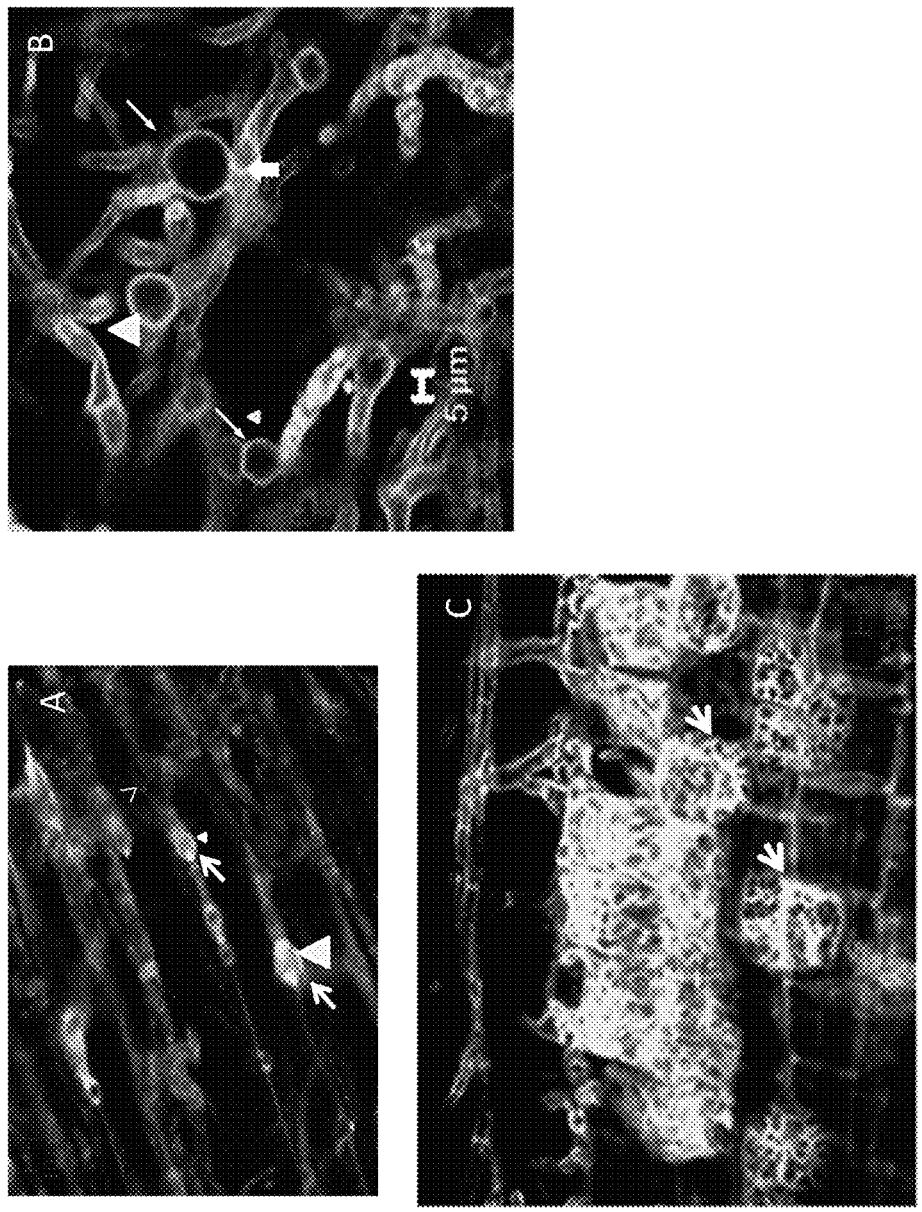

FIG. 66 shows symbiosomes in root of wheat germinant visualized with lactofuchsin staining and fluorescence microscopy. A type I symbiosome, which is composed of an intercellular microvesiculoid compartment formed between two plant cell membranes (arrows), a perivesiculoid membrane (large triangle) and a partially fragmented outer vesiculoid membrane (small triangle), is shown in A. A type II symbiosome, which is composed of an intracellular vesiculoid compartment (arrows), a perivesiculoid membrane (large triangle) and a partially fragmented outer vesiculoid membrane (small triangle), is shown in B. Also shown in B is a vesiculophore (filled arrow). The symbiosomes shown in A and B are both of vesicle form. Shown in C are symbiosomes of knot form (type I—lower arrow; type II— upper arrow).

DEFINITIONS

The term "mycovitality" as used herein refers to the plant-fungus symbiosis that exists between the seeds and the fungi, which helps maintain the seeds' capacity to live and develop, and leads to germination. In some embodiments, mycovitality may be characterized by a change in levels of certain phytohormones within the plant-fungus symbiotic system. In some embodiments, this change may be associated with a change in the levels of abscisic acid (ABA), gibberellins (GA), auxins (IAA), and/or cytokinins. In other embodiments, mycovitality may be characterized by a change in expression of the genes involved in gibberellin (GA) biosynthesis or breakdown or in abscisic acid (ABA) biosynthesis or breakdown, or in positive or negative regulation of these pathways within the plant-fungus symbiotic system. In certain embodiments, the levels of expression of the gibberellin (GA) biosynthetic genes, such as GA3-oxidase 2, RSG, KAO, and 14-3-3 genes may be increased. In other embodiments, the levels of expression of the genes that are regulated by GAs, such as ent-kaurenoic (KAO) and repression of shoot growth (RSG), are increased. In other embodiments, the levels of expression of the GA degradation genes or negative regulators of the GA biosynthesis pathway, for example 14-3-3 genes, are decreased. In still other embodiments, mycovitality may be characterized by decreased levels of expression of the genes involved in the ABA biosynthesis pathway, for example the NCED gene, within the plant-fungus symbiotic system. In other embodiments, the expression of the genes involved in the ABA catabolic pathway, for example the 8'-hydroxylase gene, are increased. In some embodiments, mycovitality may be characterized by altered levels of nitric oxide (NO) within the plant-fungus symbiotic system, for example as a result of a change in the expression of certain genes involved in NO production or breakdown. In yet other embodiments, mycovitality may be characterized by protection of the plant-fungus symbiotic system from oxidative stress. In some embodiments, mycovitality is characterized by increased levels of expression of the genes involved in superoxide detoxification within the plant-fungus symbiotic system. In some embodiments, the genes associated with superoxide detoxification encode superoxide dismutase (SOD) or manganese SOD (MnSOD), and in other cases the levels of the amino acid proline (Pro) are elevated. In some embodiments, mycovitality is characterized by an increase in the levels of activity of the genes associated with systemic acquired disease resistance, such as redox-regulated transcription factors, for example those in the MYB family. In some embodiments, the genes in the MYB family are Myb1 and Myb2.

The term "bactovitality" as used herein refers to the plant-bacterium symbiosis that exists between the seeds and the bacteria, which helps maintain the seeds' capacity to live and develop, and leads to germination. In some embodiments, bactovitality may be characterized by a change in levels of certain phytohormones within the plant-bacterium symbiotic system. In some embodiments, this change may be associated with a change in the levels of abscisic acid (ABA), gibberellins (GA), auxins (IAA), and/or cytokinins. In other embodiments, bactovitality may be characterized by a change in expression of the genes involved in gibberellin (GA) biosynthesis or breakdown or in abscisic acid (ABA) biosynthesis or breakdown, or in positive or negative regulation of these pathways within the plant-bacteria symbiotic system. In certain embodiments, the levels of expression of the gibberellin (GA) biosynthetic genes, such as GA3-oxidase 2, RSG, KAO, and 14-3-3 genes may be increased. In other embodiments, the levels of expression of the genes that are regulated by GAs, such as ent-kaurenoic (KAO) and repression of shoot growth (RSG), are increased. In other embodiments, the levels of expression of the GA degradation genes or negative regulators of the GA biosynthesis pathway, for example 14-3-3 genes, are decreased. In still other embodiments, bactovitality may be characterized by decreased levels of expression of the genes involved in the ABA biosynthesis pathway, for example the NCED gene, within the plant-bacterium symbiotic system. In other embodiments, the expression of the genes involved in the ABA catabolic pathway, for example the 8'-hydroxylase gene, are increased. In some embodiments, bactovitality may be characterized by altered levels of nitric oxide (NO) within the plant-bacterium symbiotic system, for example as a result of a change in the expression of certain genes involved in NO production or breakdown. In yet other embodiments, bactovitality may be characterized by protection of the plant-bacterium symbiotic system from oxidative stress. In some embodiments, bactovitality is characterized by increased levels of expression of the genes involved in superoxide detoxification within the plant-bacterium symbiotic system. In some embodiments, the genes associated with superoxide detoxification encode superoxide dismutase (SOD) or manganese SOD (MnSOD), and in other cases the levels of the amino acid proline (Pro) are elevated. In some embodiments, bactovitality is characterized by an increase in the levels of activity of the genes associated with systemic acquired disease resistance, such as redox-regulated transcription factors, for example those in the MYB family. In some embodiments, the genes in the MYB family are Myb1 and Myb2.

"Cold stratification" as used herein refers to the process of pretreating seeds to simulate the natural winter conditions during which, amongst many physiological changes, the seed coat is softened up by frost and weathering action, leading to dormancy breakdown. "Biological stratification" as used herein refers to the process of treating seeds with biological components to release seed dormancy and thereby promoting germination. In some embodiments, the biological components may be endophytes. Therefore, as compared to cold stratification, in which an abiotic stimulation is used, biological stratification uses a biotic stimulation. As for cold stratification, biological stratification may increase the rate of germination in seeds. In both cases, the progress of stratification and dormancy breakdown may be associated with an increase in levels of GA and a decrease in levels of ABA. In certain embodiments, the levels of expression of gibberellin (GA) biosynthetic genes, such as GA3-oxidase 2 and 14-3-3 genes, are increased. In other embodiments, the levels of expression of the genes that are regulated by GAs, such as ent-kaurenoic (KAO) and repression of shoot growth (RSG), are increased. In other embodiments, the levels of expression of GA degradation genes or negative regulators of the GA biosynthesis pathway, for example 14-3-3 genes, are decreased. In still other embodiments, the levels of expression of the genes involved in the ABA biosynthesis pathway, for example the NCED gene, are decreased. In other embodiments, the expression of genes involved in the ABA catabolic pathway, for example the 8'-hydroxylase gene, is increased.

"Anti-aging" or "anti-senescence" as used herein refers to a process within a seed or plant that protects the seed or plant from aging and senescence or that results in delayed aging or senescence of the seed or plant. In some embodiments, the anti-aging or anti-senescence effects of endophytes are characterized by increased levels of nitric oxide (NO) within the plant-fungus or plant-bacterium symbiotic system, for example as a result of a change in the expression of certain genes involved in NO production or breakdown. In certain embodiments, the anti-aging or anti-senescence effects of endophytes may be characterized by a change in levels of certain phytohormones within the plant-fungus or plant-bacterium symbiotic system. In some embodiments, this change may be associated with decreased by levels of abscisic acid (ABA), increased levels of gibberellins (GA) or increased levels of auxins. In some embodiments, mycovitality may be characterized by a change in expression of the genes involved in gibberellin (GA) biosynthesis or breakdown or in abscisic acid (ABA) biosynthesis or breakdown, or in positive or negative regulation of these pathways within the plant-fungus or plant-bacterium symbiotic system. In certain embodiments, the levels of expression of the gibberellin (GA) biosynthetic genes, such as GA3-oxidase 2, RSG, KAO, and 14-3-3 genes may be increased. In other embodiments, the levels of expression of the genes that are regulated by GAs, such as ent-kaurenoic (KAO) and repression of shoot growth (RSG), are increased. In other embodiments, the levels of expression of the GA degradation genes or negative regulators of the GA biosynthesis pathway, for example 14-3-3 genes, are decreased. In still other embodiments, the anti-aging or anti-senescence effects of endophytes may be characterized by decreased levels of expression of the genes involved in the ABA biosynthesis pathway, for example the NCED gene, within the plant-fungus or plant-bacterium symbiotic system. In other embodiments, the expression of the genes involved in the ABA catabolic pathway, for example the 8'-hydroxylase gene, are increased.

As used herein, "symbiosome" or "symbiotic organs" refers to the new compartment that is formed within the plant cell when bacteria or fungi colonize the plant. In type I symbiosomes, the new structure is an intercellular microvesiculoid compartment formed between two plant cell membranes. A "microvesiculoid" compartment is a structure that has the form of a microvesicle. In type II symbiosomes, the new compartment is localized intracellularly and can be described as an intracellular structure in the form of a vesicle, or "intracellular vesiculoid compartment." Both types of symbiosomes are further characterized by the presence of a "perivesiculoid membrane," which is the plasma membrane that surrounds the vesicles, and a partially fragmented "outer vesiculoid membrane," which is an outer membrane in the form of a vesicle. In this context, a symbiosome is not limited to the structure that is formed during nitrogen fixation.

"Mycoheterotrophy" as used herein refers to a symbiotic relationship between a plant and a fungus that allows the plant to obtain water, minerals, and carbohydrates more efficiently. In this context, the plant may be any plant, even a fully photosynthetic plant, that may derive a benefit via its association with the fungus.

As used herein, the term "microarbuscule" refers to intracellular, multiarbuscular, microsized (~10 um), bush-like haustorial structures.

The term "vitality," as used herein means the capacity to live and develop.

The term "hydrothermal time" refers to parameters of water, temperature and time by which seed germination can be described under various environmental conditions. The parameters enable germination strategies to be compared in different environments and to assess the effects of endophytes on germination relative to other variables.

In some embodiments, the endophyte is chosen from the group consisting of a spore-forming endophyte, a facultative endophyte, a filamentous endophyte, and an endophyte capable of living within another endophyte. In some embodiments, the endophyte is capable of forming certain structures in the plant, where the structures are selected from the group consisting of hyphal coils, Hartig-like nets, microvesicles, micro-arbuscules, hyphal knots, and symbiosomes. In some embodiments, the endophyte is in the form of at least one of conidia, chlamydospore, and mycelia. In other embodiments, the fungus or bacteria is capable of being part of a plant-fungus symbiotic system or plant-bacteria symbiotic system that produces altered levels of phytohormones or anti-oxidants, as compared to a plant that is not in symbiosis. In other embodiments, the plant-fungus symbiotic system or plant-bacterium symbiotic system has anti-aging and/or anti-senescence effects, as compared to a plant or plant organ that is not in symbiosis. In other embodiments, the plant-fungus symbiotic system or plant-bacteria symbiotic system has increased protection against pathogens, as compared to a plant that is not in symbiosis.

A "spore" or a population of "spores" refers to bacterial or fungal structures that are more resilient to environmental influences such as heat and bacteriocidal agents and fungicides than vegetative forms of the same bacteria or fungi. Spores are typically capable of germination and out-growth giving rise to vegetative forms of the species. Bacteria and fungi that are "capable of forming spores" or "spore-forming endophytes" are those bacteria and fungi containing the genes and other necessary abilities to produce spores under suitable environmental conditions.

The term "filamentous fungi" as used herein are fungi that form hyphae, and includes taxa that have both filamentous and yeast-like stages in their life cycle.

The term "facultative endophytes" as used herein are endophytes capable of surviving in the soil, on the plant surface, inside a plant and/or on artificial nutrients. Facultative endophytes may also have the capacity to survive inside a variety of different plant species.

The term "endophyte capable of living within another endophyte" as used herein refers to an endophytic bacterium or fungus that can live within another endophyte. Such endophytic bacteria may also be able to live autonomously in the soil, on the plant surface, inside a plant and/or on artificial nutrients.

The term "endophyte capable of promoting germination" as used herein refers to endophytes that have the capacity to colonize a seed or part of a seed and alter the seed's physiology such that the seed or a population of seeds shows a faster dormancy breakdown, greater germination rate, earlier germination, increased energy of germination, greater rate of germination, greater uniformity of germination, including greater uniformity of rate of germination and greater uniformity of timing of germination, and/or increased vigor and energy of germination. In some embodiments, the endophyte capable of promoting germination is an endophyte that is capable of activating the coleorhiza of a monocot seed, and can be called a "coleorhiza-activating endophyte".

The term "agricultural plant" means a plant that is typically used in agriculture. The agricultural plant may be a monocot or dicot plant, and may be planted for the production of an agricultural product, for example grain, food, fiber, etc. The plant may be a cereal plant. The term "plant" as used herein refers to a member of the Plantae Kingdom and includes all stages of the plant life cycle, including without limitation, seeds, and includes all plant parts. The plant can be selected from, but not limited to, the following list:

Food crops: Cereals including Maize/corn (*Zea mays*), Sorghum (Sorghum spp.), Millet (*Panicum miliaceum, P. sumatrense*), Rice (*Oryza sativa* indica, *Oryza sativa japonica*), Wheat (*Triticum sativa*), Barley (*Hordeum vulgare*), Rye (*Secale cereale*), Triticale (*Triticum×Secale*), Oats (*Avena fatua*);

leafy vegetables (brassicaceous plants such as cabbages, broccoli, bok Choy, rocket; salad greens such as spinach, cress, lettuce);

fruiting and flowering vegetables (e.g. avocado, sweet corn, artichokes, curcubits e.g. squash, cucumbers, melons, courgettes, pumpkins; solononaceous vegetables/fruits e.g. tomatoes, eggplant, capsicums);

podded vegetables (groundnuts, peas, beans, lentils, chickpea, okra);

bulbed and stem vegetables (asparagus, celery, *Allium* crops e.g garlic, onions, leeks);

roots and tuberous vegetables (carrots, beet, bamboo shoots, cassava, yams, ginger, Jerusalem artichoke, parsnips, radishes, potatoes, sweet potatoes, taro, turnip, wasabi);

sugar crops including sugar beet (*Beta vulgaris*), sugar cane (*Saccharum officinarum*);

crops grown for the production of non-alcoholic beverages and stimulants (coffee, black, herbal and green teas, cocoa, tobacco);

fruit crops such as true berry fruits (e.g. kiwifruit, grape, currants, gooseberry, guava, feijoa, pomegranate), citrus fruits (e.g. oranges, lemons, limes, grapefruit), epigynous fruits (e.g. bananas, cranberries, blueberries), aggregate fruit (blackberry, raspberry, boysenberry), multiple fruits (e.g. pineapple, fig), stone fruit crops (e.g. apricot, peach, cherry, plum), pip-fruit (e.g. apples, pears) and others such as strawberries, sunflower seeds;

culinary and medicinal herbs e.g. rosemary, basil, bay laurel, coriander, mint, dill, *Hypericum*, foxglove, alovera, rosehips);

crop plants producing spices e.g. black pepper, cumin cinnamon, nutmeg, ginger, cloves, saffron, cardamom, mace, paprika, masalas, star anise;

crops grown for the production of nuts and oils e.g. almonds and walnuts,

Brazil nut, cashew nuts, coconuts, chestnut, macadamia nut, pistachio nuts; peanuts, pecan nuts, soybean, cotton, olives, sunflower, sesame, lupin species and brassicaeous crops (e.g. canola/oilseed rape); and, crops grown for production of beers, wines and other alcoholic beverages e.g grapes, hops;

edible fungi e.g. white mushrooms, Shiitake and oyster mushrooms;

Plants Used in Pastoral Agriculture:

legumes: *Trifolium* species, *Medicago* species, and *Lotus* species; White clover (*T. repens*); Red clover (*T. pratense*); Caucasian clover (*T. ambigum*); subterranean clover (*T. subterraneum*); Alfalfa/Lucerne (*Medicago sativum*); annual medics; barrel medic; black medic; Sainfoin (*Onobrychis viciifolia*); Birdsfoot trefoil (*Lotus corniculatus*); Greater Birdsfoot trefoil (*Lotus pedunculatus*);

Forage and Amenity grasses: Temperate grasses such as *Lolium* species; *Festuca* species; *Agrostis* spp., Perennial ryegrass (*Lolium perenne*); hybrid ryegrass (*Lolium hybridum*); annual ryegrass (*Lolium multiflorum*), tall fescue (*Festuca arundinacea*); meadow fescue (*Festuca pratensis*); red fescue (*Festuca rubra*); *Festuca ovina*; Festuloliums (*Lolium×Festuca* crosses); Cocksfoot (*Dactylis glomerata*); Kentucky bluegrass *Poa pratensis; Poa palustris; Poa nemoralis; Poa trivialis; Poa* compresa; *Bromus* species; *Phalaris* (*Phleum* species); *Arrhenatherum elatius; Agropyron* species; *Avena* strigosa; *Setaria* italic;

Tropical grasses such as: *Phalaris* species; *Brachiaria* species; *Eragrostis* species; *Panicum* species; Bahai grass (*Paspalum notatum*); *Brachypodium* species; and, Grasses used for biofuel production such as Switchgrass (*Panicum virgatum*) and *Miscanthus* species;

Fiber Crops:

hemp, jute, coconut, sisal, flax (*Linum* spp.), New Zealand flax (*Phormium* spp.); plantation and natural forest species harvested for paper and engineered wood fiber products such as coniferous and broadleafed forest species;

Tree and Shrub Species Used in Plantation Forestry and Bio Fuel Crops:

Pine (*Pinus* species); Fir (*Pseudotsuga* species); Spruce (*Picea* species); Cypress (*Cupressus* species); Wattle (*Acacia* species); Alder (*Alnus* species); Oak species (*Quercus* species); Redwood (*Sequoiadendron* species); willow (*Salix* species); birch (*Betula* species); Cedar (*Cedurus* species); Ash (*Fraxinus* species); Larch (*Larix* species); *Eucalyptus* species; Bamboo (*Bambuseae* species) and Poplars (*Populus* species).

Plants Grown for Conversion to Energy, Biofuels or Industrial Products by Extractive, Biological, Physical or Biochemical Treatment: Oil-producing plants such as oil palm, jatropha, linseed;

Latex-producing plants such as the Para Rubber tree, *Hevea brasiliensis* and the Panama Rubber Tree *Castilla elastica;* plants used as direct or indirect feedstocks for the production of biofuels i.e. after chemical, physical (e.g. thermal or catalytic) or biochemical (e.g. enzymatic pre-treatment) or biological (e.g. microbial fermentation) transformation during the production of biofuels, industrial solvents or chemical products e.g. ethanol or butanol, propane diols, or other fuel or industrial material including sugar crops (e.g. beet, sugar cane), starch-producing crops (e.g. C3 and C4 cereal crops and tuberous crops), cellulosic crops such as forest trees (e.g. Pines, Eucalypts) and Graminaceous and Poaceous plants such as bamboo, switch grass, *miscanthus;* crops used in energy, biofuel or industrial chemical production by gasification and/or microbial or catalytic conversion of the gas to biofuels or other industrial raw materials such as solvents or plastics, with or without the production of biochar (e.g. biomass crops such as coniferous, eucalypt, tropical or broadleaf forest trees, graminaceous and poaceous crops such as bamboo, switch grass, *miscanthus*, sugar cane, or hemp or softwoods such as poplars, willows; and, biomass crops used in the production of biochar;

Crops Producing Natural Products Useful for the Pharmaceutical, Agricultural Nutraceutical and Cosmeceutical Industries:

crops producing pharmaceutical precursors or compounds or nutraceutical and cosmeceutical compounds and materials for example, star anise (shikimic acid), Japanese knotweed (resveratrol), kiwifruit (soluble fiber, proteolytic enzymes);

Floricultural, Ornamental and Amenity Plants Grown for their Aesthetic or Environmental Properties: Flowers such as roses, tulips, chrysanthemums;

Ornamental shrubs such as *Buxus*, Hebe, Rosa, *Rhododendron, Hedera;*

Amenity plants such as *Platanus*, Choisya, Escallonia, *Euphorbia*, Carex;

Mosses such as sphagnum moss; and

Plants Grown for Bioremediation:

*Helianthus, Brassica, Salix, Populus*, and *Eucalyptus*.

A "host plant" includes any plant, particularly an agricultural plant, which an endophytic microbe such as an endophyte capable of promoting germinations can colonize. As used herein, a microbe is said to "colonize" a plant or seed when it can be stably detected within the plant or seed over a period time, such as one or more days, weeks, months or years. In other words, a colonizing microbe is not transiently associated with the plant or seed.

As used herein, an "agricultural seed" is a seed used to grow a plant typically used in agriculture (an "agricultural plant"). The seed may be of a monocot or dicot plant, and may be planted for the production of an agricultural product, for example grain, food, fiber, etc. The seed may be of a cereal plant. As used herein, an agricultural seed is a seed that is prepared for planting, for example, in farms for growing.

As used herein, a "control agricultural plant" or "control seed" is an agricultural plant or seed of the same species, strain, or cultivar to which a treatment, formulation, composition or endophyte preparation as described herein is not administered/contacted. A control agricultural plant or control seed, therefore, is identical to the treated plant or seed with the exception of the presence of the endophyte and can serve as a control for detecting the effects of the endophyte that is conferred to the plant.

A "population" of plants or seeds, as used herein, can refer to a plurality of plants or seeds that were subjected to the same inoculation methods described herein, or a plurality of plants or seeds that are progeny of a plant or group of seeds that were subjected to the inoculation methods. In addition, a population of plants can be a group of plants that are grown from coated seeds. The plants or seeds within a population will typically be of the same species, and will also typically share a common genetic derivation.

The term "endophyte" as used herein refers to a fungal or bacterial organism that can live symbiotically in a plant and is also referred to herein as "endosymbiont". A fungal endophyte may be in the form of a spore, hypha, or mycelia. A bacterial endophyte may be a cell or group of cells. The term "endophyte" as used herein includes progeny of the strains recited herein.

In some cases, the present invention contemplates the use of microbes that are "compatible" with agricultural chemicals, for example, a fungicide, an anti-bacterial compound, or any other agent widely used in agricultural which has the effect of killing or otherwise interfering with optimal growth of microbes. As used herein, a microbe is "compatible" with an agricultural chemical when the microbe is modified, such as by genetic modification, e.g., contains a transgene that confers resistance to an herbicide, or is adapted to grow in, or otherwise survive, the concentration of the agricultural chemical used in agriculture. For example, a microbe disposed on the surface of a seed is compatible with the fungicide metalaxyl if it is able to survive the concentrations that are applied on the seed surface.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

In some embodiments, the invention uses microbes that are heterologous to a seed or plant in making synthetic combinations or agricultural formulations. A microbe is considered heterologous to the seed or plant if the seed or seedling that is unmodified (e.g., a seed or seedling that is not treated with a population of endophytes capable of promoting germination described herein) does not contain detectable levels of the microbe. For example, the invention contemplates the synthetic combinations of seeds or seedlings of agricultural plants and an endophytic microbe population (e.g., an endophyte capable of promoting germination), in which the microbe population is "heterologously disposed" on the exterior surface of or within a tissue of the agricultural seed or seedling in an amount effective to colonize the plant. A microbe is considered "heterologously disposed" on the surface or within a plant (or tissue) when the microbe is applied or disposed on the plant in a number that is not found on that plant before application of the microbe. For example, population of endophytes capable of promoting germination that is disposed on an exterior surface or within the seed can be an endophyte that may be associated with the mature plant, but is not found on the surface of or within the seed. As such, a microbe is deemed heterologously disposed when applied on the plant that either does not naturally have the microbe on its surface or within the particular tissue to which the microbe is disposed, or does not naturally have the microbe on its surface or within the particular tissue in the number that is being applied. The term "exogenous" can be used interchangeably with "heterologous."

The phrase "inoculating a seed" as used herein refers to applying, infecting, co-planting, spraying, immersing, dusting, dipping or coating the seed with the endophyte. Techniques for inoculating the seed are known in the art, for example, as disclosed by Hynes and Boyetchko (2006, Soil Biology & Biochemistry 38: 845-84). In an embodiment, inoculation comprises foliar application or soil application of the endophyte or combination thereof with any solid or liquid carrier at any growing stage of the plant.

The term "enhancing seed vitality" as used herein refers to plant prenatal care improving the ability of the seed to germinate and produce a plant under normal and/or stressed conditions and includes, without limitation, any one or more of the following: breaking dormancy, providing seed stratification, increasing seed germination, modulating gene expression, decreasing time to reach energy of germination, protecting against biotic stresses, protecting against abiotic stresses, reducing hydrothermal time required for germination, increasing seed germination vigour, increasing seed germination efficacy, increasing uniformity of seed germination, ameliorating drought/heat tolerance efficacy, increasing the weight of seedlings, and increasing the yield of seedlings. Drought/Heat Tolerance Efficiency (DTE/THE) is the term opposed (antonym) to susceptibility.

Energy of germination is defined as 50% of germination, relative to the number of seeds tested. The seed germination vigour shows the difference between total percentage of germinating treated seeds and germinating untreated seeds. The hydrothermal time postulates that an individual seed begins to germinate when the sum of both temperatures and water potential are sufficiently accumulated over a period of time allowing germination. Germination efficacy is defined as the percentage of treated seeds germinating after a set time period after planting, relative to the number of seeds tested in an untreated control. Biological stratification is defined as releasing seed dormancy by a symbiont in promoting germination. Uniformity of seed germination represents the maximum percentage of seed germination within a minimal time of incubation.

The terms "decreased", "fewer", "slower" and "increased" "faster" "enhanced" "greater" as used herein refers to a decrease or increase in a characteristic of the endophyte treated seed or resulting plant compared to an untreated seed or resulting plant. For example, a decrease in a characteristic may be at least 1%, at least 2%, at least 3%, at least 4%, at least 5%, at least 10%, at least 15%, at least 20%, at least 25%, at least 30%, at least 35%, at least 40%, at least 45%, at least 50%, at least 75%, at least 100%, or at least 200% or more lower than the untreated control and an increase may be at least 1%, at least 2%, at least 3%, at least 4%, at least 5%, at least 10%, at least 15%, at least 20%, at least 25%, at least 30%, at least 35%, at least 40%, at least 45%, at least 50%, at least 75%, at least 100%, or at least 200% or more higher than the untreated control.

The term "increased yield" refers to increased seed weight, seed size, seed number per plant, seed number per unit area (i.e. seeds, or weight of seeds, per acre), bushels per acre, tons per acre, kilo per hectare, increased grain yield, increased dry weight of grain, increased seed weight, increased dry weight of wheat spikes and increased biomass. "Biomass" means the total mass or weight (fresh or dry), at a given time, of a plant tissue, plant tissues, an entire plant, or population of plants. Biomass is usually given as weight per unit area. Increased biomass includes without limitation increased pod biomass, stem biomass, and root biomass.

In certain embodiments, the plant is cultivated under abiotic or biotic stressed conditions. The term "abiotic stress" as used herein refers to a non-living stress that typically affects seed vitality and plant health and includes, without limitation, heat, drought, nitrogen, cold, salt and osmotic stress. In one embodiment, the abiotic stress is heat stress. In another embodiment, the abiotic stress is drought stress, osmotic stress or salt stress. The term "biotic stress" as used herein refers to a living stress that typically affects seed vitality and plant health, and includes without limitation, insect infestation, nematode infestation, bacterial infection, fungal infection, oomycete infection, protozoal infection, viral infection, and herbivore grazing, or any combination thereof. In one embodiment, the biotic stress is a *Fusarium* infection.

As used herein an "agriculturally compatible carrier" refers to any material, other than water, which can be added to a seed or a seedling without causing or having an adverse effect on the seed (e.g., reducing seed germination) or the plant that grows from the seed, or the like.

The term "plant propagation material" as used herein refers to any plant generative/sexual and vegetative/asexual part that has the ability to be cultivated into a new plant. In an embodiment, the plant propagation material is generative seed, generative bud or flower, and vegetative stem, cutting, root, bulb, rhizome, tuber, vegetative bud, or leaf parts.

In some cases, the present invention contemplates the use of microbes (e.g., endophytes) that are "compatible" with agricultural chemicals, for example, a fungicide, an antibacterial compound, or any other agent widely used in agriculture that has the effect of killing or otherwise interfering with optimal growth of microbes. As used herein, a microbe such as a seed bacterial endophyte is "compatible" with an agricultural chemical when the microbe is modified, such as by genetic modification, e.g., contains a transgene that confers resistance to an herbicide, or is adapted to grow in, or otherwise survive, the concentration of the agricultural chemical used in agriculture. For example, a microbe disposed on the surface of a seed is compatible with the fungicide metalaxyl if it is able to survive the concentrations that are applied on the seed surface.

The term "phytoremediation" as used herein refers to the use of plants for removal, reduction or neutralization of substances, wastes or hazardous material from a site so as to prevent or minimize any adverse effects on the environment. The term "phytoreclamation" as used herein refers to the use of plants for reconverting disturbed land to its former or other productive uses.

DETAILED DESCRIPTION

The present invention identifies a small, unique family of endophytes that can be placed into synthetic combination with a variety of plant hosts and work synergistically with the plant hosts to exhibit a surprising number of altered and improved biological processes.

Plants across the Angiosperms have many features in common that emanate from having evolved from a common ancestor. This is true for the many systems that control growth and development and also tolerance to abiotic and biotic stresses. Plants have co-evolved with endosymbionts and in consequence these latter organisms, fungi and bacteria, can possess features that enable them to interact with plants. It is well accepted that microorganisms can be classified on the basis of their taxonomy or cladistics groupings, as well as based on key morphological, functional, and ecological roles. Here, by screening hundreds of synthetic associations between endophytes and plants, we discovered a family of endophytes based on their ability to interact with a variety of plant species to create agricultural value. These endophytes possess systems that enable them to physically and chemically interact with a broad range of agricultural plants bred by man, including monocots and dicots, endorsing the conclusion that when living together with the plant they interact intimately with the conserved genetic and physiological properties of plant species. Our classification based on studies involving a large range of agricultural plants distinguishes the chosen endophytes from those endophytes that interact with only some classes of plant species. Endophytes classified in this way can include fungi and bacteria and the classification highlights that the fungi and bacteria have informational systems in common. The informational systems programming the plant-endophyte interactions are complex and comprise signaling systems, multiple networks and pathways that underpin growth of many types of plant cells and organs as well as endophyte cells. They are thus best described by the outcomes of the plant-endophyte interactions.

The endophyte class described herein provides the unique ability to confer mycovitalism to a large number of diverse plant hosts, as well as to confer stress tolerance and increased yield. Specifically, this endophyte class is able to, when coated onto the outside of a seed or placed in its proximity, increase expression of key genes related to seed germination, vigor, and stress tolerance. The endophytes are then able to penetrate the cortical layer of the seed and plant in order to enter the plant's internal tissues and replicate within at least one tissue in the host and establish symbiotic organs comprising microstructures that allow intimate communication between the endophyte and the plant's intra- and/or intercellular spaces. These endophytes further act in symbiosis with the host to improve stress tolerance of the seedling and adult plant and to increase yield.

Germination of mature, dry seeds is a process that is conserved across angiosperms, being regulated by water, temperature, the hormones gibberellic acid, abscisic acid and ethylene, amongst other vital molecules, and involves changes to cell walls, breakdown of food reserves and their conversion to new molecules and structures that define root and shoot growth. The group of endophytes revealed here is readily characterized by its ability to stimulate seed germination or make germination more uniform when any of its members are present as a synthetic preparation that physically interacts with a seed from monocot or dicot plants. In other embodiments, the group of endophytes is recognized as capable of altering plant flowering time and/or increasing tolerance to biotic and abiotic stresses and many other traits. All of these features support the conclusion that members of this group of endophytes can be physically complexed with monocot and dicot seeds to achieve multiple agricultural benefits due to their particular informational systems that interact with those conserved in plants.

This family of endophytes represents a surprising discovery in their ability to engage in synthetic associations with plants, leading to a number of altered physiological processes across the lifespan of the plant-endophyte composite association. Notably, the synthetic associations between this small family of endophytes and both monocot and dicot plants are characterized by the activation of multiple plant genes and hormones during seed germination, seedling development, and responses to environmental and biotic stresses.

Novel Compositions and Seeds

Accordingly, the present disclosure provides a composition comprising at least one endophyte capable of promoting germination or comprising a combination or mixture thereof, and an agriculturally-acceptable carrier. In some embodiments, the at least one endophyte capable of promoting germination are coleorhiza-activing endophytes. In some embodiments, a synthetic preparation is made using the composition and an agricultural plant seed. In some cases, plants are inoculated with at least one endophyte that is heterologous to the inoculated agricultural plant seed or the agricultural plant grown from the agricultural seed. In some embodiments, the at least one endophyte capable of promoting germination are disposed on the surface or within a tissue of the agricultural seed or seedling. In some embodiments, a plant grown from a seed inoculated with this composition has an improved functional trait as compared to a control plant. In some embodiments, the improved functional trait is resistance to biotic or abiotic stress. In some embodiments, the improved functional trait is selected from the group consisting of increased yield, faster seedling establishment, faster growth, increased photosynthetic rate, increased carbon dioxide assimilation rate, increased drought tolerance, increased heat tolerance, increased cold tolerance, increased salt tolerance, increased tolerance to pests and diseases, increased biomass, increased root and/or shoot length or weight, increased fresh weight of seedlings, increased seed or fruit number, increased plant vigour, nitrogen stress tolerance, enhanced *Rhizobium* activity, enhanced nodulation frequency, early flowering time, or any combination thereof. In some embodiments, the increased tolerance to disease is increased tolerance to *Fusarium* infection, increased tolerance to *Septoria* infection, and/or increased tolerance to *Puccinia* infection. In some embodiments, yield is measured on a population of plants grown in the field and is calculated via combine harvesting or measuring ear weight. For all altered traits, the change can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant. In some embodiments, the improved trait is heritable by progeny of the agricultural plant grown from the seed.

In some embodiments, the agricultural seed is a seed of a monocot plant. In some embodiments, the agricultural seed is a seed of a cereal plant. In some embodiments, the agricultural seed is a seed of a corn, wheat, barley, rice, sorghum, millet, oats, rye or triticale. In some embodiments, the agricultural seed is a seed of a dicot plant. In some embodiments, the agricultural seed is a seed of cotton, canola, soybean or a pulse.

In some embodiments, a synthetic preparation is made comprising a canola seed and a composition comprising at least one endophyte capable of promoting germination and an agriculturally-acceptable carrier, and a canola plant grown from the seed flowers earlier as compared to a control canola plant. In some embodiments, a synthetic preparation is made comprising a tomato, alfalfa, corn, swiss chard, radish, or cabbage seed and a composition comprising at least one endophyte capable of promoting germination and an agriculturally-acceptable carrier, and a tomato, alfalfa, corn, swiss chard, radish, or cabbage plant grown under drought conditions from the seed has higher biomass as compared to a control plant grown under drought conditions.

In some embodiments, the composition is disposed on an exterior surface of the agricultural seed in an amount effective to colonize at least 0.1%, at least 1%, at least 2%, at least 3%, at least 4%, at least 5%, at least 10%, at least 20%, at least 30%, at least 40%, at least 50%, at least 60%, at least 70% or at least 80% of cortical cells of a plant grown from the seed.

In some embodiments, the composition comprises a carrier and at least one endophyte chosen from the group consisting of a spore-forming endophyte, a facultative endophyte, a filamentous endophyte, and an endophyte capable of living within another endophyte. In some embodiments, the at least one endophyte is capable of forming certain structures in the plant, where the structures are selected from the group consisting of hyphal coils, Hartig-like nets, microvesicles, micro-arbuscules, hyphal knots, and symbiosomes. In some embodiments, the at least one endophyte is in the form of at least one of conidia, chlamydospore, and mycelia. In other embodiments, the fungus or bacteria is capable of being part of a plant-fungus symbiotic system or plant-bacteria symbiotic system that produces altered levels of phytohormones or anti-oxidants, as compared to a plant that is not in symbiosis. In other embodiments, the plant-fungus symbiotic system or plant-bacterium symbiotic system has anti-aging and/or anti-senescence effects, as compared to a plant or plant organ that is not in symbiosis. In other embodiments, the plant-fungus symbiotic system or plant-bacteria symbiotic system has increased protection against pathogens, as compared to a plant that is not in symbiosis.

In some embodiments, the at least one endophyte is a fungus of subphylum Pezizomycotina. In some embodiments, the at least one endophyte is a fungus of class Leotiomycetes, Dothideomycetes, Sordariomycetes, or Eurotiomycetes. In some embodiments, the at least one endophyte is of order Helotiales, Capnodides, Pleosporales, Hypocreales, or Eurotiales. In some embodiments, the at least one endophyte is selected from one of the following families: Acarosporaceae, Adelococcaceae, Agyriaceae, Aigialaceae, Ajellomycetaceae, Amniculicolaceae, Amorphothecaceae, Amphisphaeriaceae, Amplistromataceae, Anamylopsoraceae, Annulatascaceae, Anteagloniaceae, Antennulariellaceae, Aphanopsidaceae, Apiosporaceae, Apiosporaceae, Arachnomycetaceae, Arctomiaceae, Armatellaceae, Arthoniaceae, Arthopyreniaceae, Arthrodermataceae, Arthrorhaphidaceae, Ascobolaceae, Ascocorticiaceae, Ascodesmidaceae, Ascodichaenaceae, Ascosphaeraceae, Asterinaceae, Aulographaceae, Australiascaceae, Baeomycetaceae, Bambusicolaceae, Batistiaceae, Bertiaceae, Biatorellaceae, Biatriosporaceae, Bionectriaceae, Boliniaceae, Brigantiaeeaceae, Bulgariaceae, Byssolomataceae, Caliciaceae, Caloscyphaceae, Calosphaeriaceae, Calycidiaceae, Candelariaceae, Capnodiaceae, Carbomycetaceae, Carbonicolaceae, Catabotrydaceae, Catillariaceae, Celotheliaceae, Cephalothecaceae, Ceratocystidaceae, Ceratomycetaceae, Ceratostomataceae, Chadefaudiellaceae, Chaetomiaceae, Chaetosphaerellaceae, Chaetosphaeriaceae, Chaetosphaeriaceae, Chaetothyriaceae, Chorioactidaceae, Chrysotrichaceae, Cladoniaceae, Cladosporiaceae, Clavicipitaceae, Clypeosphaeriaceae, Coccocarpiaceae, Coccodiniaceae, Coccoideaceae, Coccotremataceae, Coenogoniaceae, Collemataceae, Coniocessiaceae, Coniochaetaceae, Coniocybaceae, Coniothyriaceae, Cordycipitaceae, Coronophoraceae, Coryneliaceae, Corynesporascaceae, Crocyniaceae, Cryphonectriaceae, Cryptomycetaceae, Cucurbitariaceae, Cudoniaceae, Cyphellophoraceae, Cyttariaceae, Dactylosporaceae, Davidiellaceae, Delitschiaceae, Dermateaceae, Diademaceae, Diaporthaceae, Diatrypaceae, Didymellaceae, Didymosphaeriaceae, Discinaceae, Dissoconiaceae, Dothideaceae, Dothidotthiaceae, Dothioraceae, Ectolechiaceae, Elaphomycetaceae, Elixiaceae, Elsinoaceae, Eremascaceae, Eremithallaceae, Erysiphaceae, Euceratomycetaceae, Extremaceae, Fissurinaceae, Fuscideaceae, Geoglossaceae, Glaziellaceae, Gloeoheppiaceae, Glomerellaceae, Glomerellaceae, Gnomoniaceae, Gomphillaceae, Gondwanamycetaceae, Graphidaceae, Graphostromataceae, Gyalectaceae, Gymnoascaceae, Gypsoplacaceae, Haematommataceae, Halojulellaceae, Halosphaeriaceae, Halotthiaceae, Harknessiaceae, Helminthosphaeriaceae, Helotiaceae, Helvellaceae, Hemiphacidiaceae, Heppiaceae, Herpomycetaceae, Herpotrichiellaceae, Hyaloscyphaceae, Hymeneliaceae, Hypocreaceae, Hyponectriaceae, Hypsostromataceae, Icmadophilaceae, Jobellisiaceae, Juncigenaceae, Karstenellaceae, Kathistaceae, Koerberiaceae, Koralionastetaceae, Laboulbeniaceae, Lachnaceae, Lasiosphaeriaceae, Lecanoraceae, Lecideaceae, Lentitheciaceae, Leotiaceae, Leprocaulaceae, Leptosphaeriaceae, Letrouitiaceae, Lichinaceae, Lindgomycetaceae, Lobariaceae, Lophiostomataceae, Lophiotremataceae, Loramycetaceae, Lulworthiaceae, Lyrommataceae, Magnaporthaceae, Malmideaceae, Massariaceae, Massarinaceae, Megalariaceae, Megalosporaceae, Megasporaceae, Melanconidaceae, Melanommataceae, Melaspileaceae, Meliolaceae, Metacapnodiaceae, Microascaceae, Miltideaceae, Monascaceae, Monoblastiaceae, Montagnulaceae, Morchellaceae, Morosphaeriaceae, Mycoblastaceae, Mycocaliciaceae, Mycosphaerellaceae, Myeloconidaceae, Myriangiaceae, Myxotrichaceae, Nannizziopsidaceae, Nectriaceae, Nephromataceae, Niessliaceae, Nitschkiaceae, Obryzaceae, Ochrolechiaceae, Odontotremataceae, Onygenaceae, Ophiocordycipitaceae, Ophioparmaceae, Ophiostomataceae, Orbiliaceae, Pachyascaceae, Pannariaceae, Pannariaceae, Papulosaceae, Parmeliaceae, Parmulariaceae, Peltigeraceae, Peltulaceae, Pertusariaceae, Pezizaceae, Phacidiaceae, Phaeochoraceae, Phaeococcomycetaceae, Phaeosphaeriaceae, Phaeotrichaceae, Phaneromycetaceae, Phlyctidaceae, Phyllachoraceae, Physciaceae, Piedraiaceae, Pilocarpaceae, Placynthiaceae, Platystomaceae, Plectosphaerellaceae, Pleomassariaceae, Pleosporaceae, Pleurostomataceae, Porinaceae, Porpidiaceae, Protothelenellaceae, Pseudoplagiostomataceae, Pseudovalsaceae, Psoraceae, Pycnoraceae, Pyrenulaceae, Pyronemataceae, Pyxidiophoraceae, Ramalinaceae, Requienellaceae, Reticulascaceae, Rhizinaceae, Rhizocarpaceae, Rhynchostomataceae, Rhytismataceae, Roccellaceae, Roccellographaceae, Ropalosporaceae, Roussoellaceae, Rutstroemiaceae, Sagiolechiaceae, Salsugineaceae, Sarcoscyphaceae, Sarcosomataceae, Sarrameanaceae, Schaereriaceae, Schizoparmaceae, Schizoparmeaceae, Sclerotiniaceae, Scoliciosporaceae, Scortechiniaceae, Shiraiaceae, Sordariaceae, Spathulosporaceae, Sphaerophoraceae, Sphinctrinaceae, Sporastatiaceae, Sporormiaceae, Stereocaulaceae, Stictidaceae, Strigulaceae, Sydowiellaceae, Sympoventuriaceae, Teichosporaceae, Teloschistaceae, Teratosphaeriaceae, Testudinaceae, Tetraplosphaeriaceae, Thelebolaceae, Thelenellaceae, Thelocarpaceae, Thermoascaceae, Thyridariaceae, Thyridiaceae, Thyridiaceae, Togniniaceae, Trapeliaceae, Trematosphaeriaceae, Trichocomaceae, Trichomeriaceae, Trichosphaeriaceae, Tuberaceae, Tubeufiaceae, Umbilicariaceae, Vahliellaceae, Valsaceae, Venturiaceae, Verrucariaceae, Vezdaeaceae, Vialaeaceae, Vibrisseaceae, Xanthopyreniaceae, Xylariaceae, Xylonomycetaceae, and Zopfiaceae.

In some embodiments, the composition comprises an agriculturally-acceptable carrier and at least one spore-forming, filamentous bacterial endophyte of phylum Actinobacteria. In some embodiments, the at least one endophyte is a bacteria of order actinomycetales. In some embodiments, the at least one endophyte is selected from one of the following families: Actinomycetaceae, Actinopolysporineae, Catenulisporineae, Corynebacterineae, Frankineae, Glycomycineae, Kineosporiineae, Micrococcineae, Micromonosporineae, Propionibacterineae, Pseudonocardineae, Streptomycineae, and Streptosporangineae.

In some embodiments, the present disclosure provides a composition comprising a carrier and an endophyte of *Paraconiothyrium* sp. strain deposited as IDAC 081111-03 or comprising a DNA sequence with at least 97% identity to SEQ ID NO:5; an endophyte of *Pseudoeurotium* sp. strain deposited as IDAC 081111-02 or comprising a DNA sequence with at least 97% identity to SEQ ID NO:4; an endophyte of *Penicillium* sp. strain deposited as IDAC 081111-01 or comprising a DNA sequence with at least 97% identity to SEQ ID NO:3; an endophyte of *Cladosporium* sp. strain deposited as IDAC 200312-06 or comprising a DNA sequence with at least 97% identity to SEQ ID NO:1; an endophyte of *Sarocladium* sp. strain deposited as IDAC 200312-05 or comprising a DNA sequence with at least 97% identity to SEQ ID NO:2; and/or an endophyte of *Streptomyces* sp. strain deposited as IDAC 081111-06 or comprising a DNA sequence with at least 97% sequence identity to SEQ ID NO:6. In certain embodiments, the endophyte of *Paraconiothyrium* sp. strain comprises a DNA sequence with at least 98% identity to SEQ ID NO:5; the endophyte of *Pseudoeurotium* sp. strain comprises a DNA sequence with at least 98% identity to SEQ ID NO:4; the endophyte of *Penicillium* sp. strain comprises a DNA sequence with at least 98% identity to SEQ ID NO:3; the endophyte of *Cladosporium* sp. strain comprises a DNA sequence with at least 98% identity to SEQ ID NO:1; the endophyte of *Sarocladium* sp. strain comprises a DNA sequence with at least 98% identity to SEQ ID NO:2; and the endophyte of *Streptomyces* sp. strain comprises a DNA sequence with at least 98% sequence identity to SEQ ID NO:6. In certain embodiments, the endophyte of *Paraconiothyrium* sp. strain comprises a DNA sequence with at least 99% identity to SEQ ID NO:5; the endophyte of *Pseudoeurotium* sp. strain comprises a DNA sequence with at least 99% identity to SEQ ID NO:4; the endophyte of *Penicillium* sp. strain comprises a DNA sequence with at least 99% identity to SEQ ID NO:3; the endophyte of *Cladosporium* sp. strain comprises a DNA sequence with at least 99% identity to SEQ ID NO:1; the endophyte of *Sarocladium* sp. strain comprises a DNA sequence with at least 99% identity to SEQ ID NO:2; and the endophyte of *Streptomyces* sp. strain comprises a DNA sequence with at least 99% sequence identity to SEQ ID NO:6. In certain embodiments, the endophyte of *Paraconiothyrium* sp. strain comprises a DNA sequence of SEQ ID NO:5; the endophyte of *Pseudoeurotium* sp. strain comprises a DNA sequence of SEQ ID NO:4; the endophyte of *Penicillium* sp. strain comprises a DNA sequence of SEQ ID NO:3; the endophyte of *Cladosporium* sp. strain comprises a DNA sequence of SEQ ID NO:1; the endophyte of *Sarocladium* sp. strain comprises a DNA sequence of SEQ ID NO:2; and the endophyte of *Streptomyces* sp. strain comprises a DNA sequence of SEQ ID NO:6.

In some embodiments, the present disclosure provides a synthetic preparation comprising an agricultural plant seed and a composition comprising endophytes capable of promoting germination and an agriculturally-acceptable carrier, wherein the synthetic preparation has altered gene expression in a plant grown from a seed inoculated with said composition, as compared to a control plant. In some embodiments, the composition is disposed on an exterior surface of an agricultural seed in an amount effective to colonize the cortical cells of an agricultural plant grown from the seed and to alter the expression of genes involved in plant growth, genes associated with systemic acquired resistance, or genes involved in protection from oxidative stress. In some embodiments, these genes may be involved in phytohormone production, for example in gibberellin (GA) biosynthesis or breakdown, abscisic acid (ABA) biosynthesis or breakdown, NO production or breakdown, superoxide detoxification, or are positive or negative regulators of these pathways. In other embodiments, the genes associated with systemic acquired resistance are redox-regulated transcription factors. In still other embodiments, the redox-regulated transcription factors belong to the MYB family of genes. In some embodiments, the gene with altered expression is selected from the group consisting of P5CS, SOD, MnSOD, GA3-oxidase 2, 14-3-3, NCED2, ABA8'OH1, RSG, KAO, Myb1 and Myb2. In some embodiments, the change in gene expression can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant. In some embodiments, said composition is disposed on an exterior surface of an agricultural seed in an amount effective to colonize at least 0.1%, at least 1%, at least 2%, at least 3%, at least 4%, at least 5%, at least 10%, at least 20%, at least 30%, at least 40%, at least 50%, at least 60%, at least 70%, or at least 80% of the cortical cells of an agricultural plant grown from the seed and to alter the expression of genes involved in plant growth, genes associated with systemic acquired resistance, or genes involved in protection from oxidative stress.

In some embodiments, the present disclosure provides a composition comprising at least one endophyte capable of promoting germination and an agriculturally-acceptable carrier, wherein said composition is disposed on an exterior surface of an agricultural seed in an amount effective to cause a population of seeds inoculated with said composition to have a faster dormancy breakdown, greater germination rate, earlier germination, increased energy of germination, greater rate of germination, greater uniformity of germination, including greater uniformity of rate of germination and greater uniformity of timing of germination, and/or increased energy of germination as compared to a population of control seeds. In some embodiments, the composition is disposed on the surface or within a tissue of an agricultural seed or seedling in an amount effective to cause a population of seeds inoculated with said composition to reach 50% germination faster than a population of control seeds or to cause increased NO accumulation in a plant grown from a seed inoculated with said composition, as compared to a control plant. In other embodiments, the composition is disposed on an exterior surface of an agricultural seed an in an amount effective to cause altered levels of phytohormones to be produced in an agricultural plant grown from the seed, as compared to a control agricultural plant. In some embodiments, the phytohormones that are altered are gibberellins, abscisic acid, or cytokinins. In further embodiments, the gibberellins may be gibberellin 1, 19, 44 or 53. In still further embodiments, the cytokinin may be zeatin. For all these altered traits (a faster dormancy breakdown, greater germination rate, earlier germination, increased energy of germination, greater rate of germination, greater uniformity of germination, including greater uniformity of rate of germination and greater uniformity of timing of germination, increased energy of germination, 50% germination, increased NO accumulation, and altered levels of phytohormones), the change can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant.

In some embodiments, the present disclosure provides a composition comprising at least one endophyte and a carrier, wherein said composition is capable of colonizing at least 0.1%, at least 1%, at least 2%, at least 3%, at least 4%, at least 5%, at least 10%, at least 20%, at least 30%, at least 40%, at least 50% at least 60%, at least 70%, or at least 80% of cortex cells of a plant grown from a seed inoculated with said composition and wherein said plant has an improved trait as compared to a control plant. In certain embodiments, the plant grown from seed inoculated with the composition has an improved trait selected from the group consisting of increased yield, faster seedling establishment, faster growth, increased drought tolerance, increased heat tolerance, increased cold tolerance, increased salt tolerance, increased tolerance to *Fusarium* infection, increased biomass, increased root length, increased fresh weight of seedlings, increased plant vigour, nitrogen stress tolerance, enhanced *Rhizobium* activity, enhanced nodulation frequency and early flowering time compared to a control plant.

In another embodiment, the synthetic preparations and compositions described herein comprise two or more (e.g., 3 or more, 4 or more, 5 or more, 6 or more, 7 or more, 8 or more, 9 or more, 10 or more, 15 or more, 20 or more, 25 or more, or greater than 25) different endophytes capable of promoting germination, e.g., obtained from different families or different genera of fungi or bacteria, or from the same genera but different species of fungi or bacteria. In embodiments in which two or more endophytes capable of promoting germination are used, each of the endophytes capable of promoting germination can have different properties or activities, confer different beneficial traits, or colonize different parts of a plant (e.g., leaves, stems, flowers, fruits, seeds, or roots). For example, one endophyte capable of promoting germination can colonize a first tissue and a second endophyte capable of promoting germination can colonize a tissue that differs from the first tissue. Alternatively, each of the endophytes capable of promoting germination can have similar properties or activities, confer similar beneficial traits, or colonize different parts of a plant.

The synthetic combination or preparation of the present invention contemplates the presence of an endophyte on the surface of the seed of the first plant. In one embodiment, the seed of the first plant is coated with at least 10 CFU of the endophyte per seed, for example, at least 20 CFU, at least 50 CFU, at least 100 CFU, at least 200 CFU, at least 300 CFU, at least 500 CFU, at least 1,000 CFU, at least 3,000 CFU, at least 10,000 CFU, or at least 30,000 CFU or more per seed. In another embodiment, the seed is coated with at least 10, for example, at least 20, at least 50, at least 100, at least 200, at least 300, at least 500, at least 1,000, at least 3,000, at least 10,000, at least 30,000, at least 100,000, at least 300,000, at least 1,000,000 or more of the endophyte as determined by the number of copies of a particular endophyte gene detected, for example, by quantitative PCR.

Further provided herein is a seed inoculated with any of the compositions described herein. In one embodiment, the seed is inoculated by soil-based inoculation. In another embodiment, the seed is coated with an endophyte or culture thereof. In yet another embodiment, the seed is sprayed, injected, inoculated, grafted, coated or treated with the endophyte or culture thereof. In an embodiment, the seed is planted near an endophyte. In one embodiment, the seed planted near the endophyte is about 4 cm away from the endophyte.

In another aspect, the invention provides a population of at least 10 synthetic preparations, each synthetic preparation comprising an agricultural plant seed and a composition comprising at least one endophyte capable of promoting germination and an agriculturally-acceptable carrier, where the population is comprised within a packaging material. The packaging material can be selected from a bag, box, bin, envelope, carton, or container. In an embodiment, the synthetic preparation can be disposed within a package and is shelf stable. In another embodiment, the invention features an agricultural product that includes a predetermined number of seeds or a predetermined weight of seeds. In an embodiment, the bag or container contains at least 1000 seeds, wherein the packaging material optionally comprises a dessicant, and wherein the synthetic preparation optionally comprises an anti-fungal agent.

In yet another aspect, the invention features an article of manufacture that includes packaging material; one or more plant seeds within the packaging material, and at least one species of endophytes capable of promoting germination associated with the seeds. The article can include two or more species of endophytes capable of promoting germination.

In another aspect, the invention features an agricultural product that includes a predetermined number of seeds or a predetermined weight of seeds. In an embodiment, the bag or container contains at least 1000 seeds of a synthetic preparation produced by the step of inoculating a plurality of plant seeds with a formulation comprising a fungal or bacterial population at a concentration of at least 1 CFU per agricultural plant seed, wherein at least 10% of the CFUs present in the formulation are one or more endophytes capable of promoting germination, under conditions such that the formulation is associated with the surface of the seeds in a manner effective for the endophytes capable of promoting germination to confer a benefit to the seeds or to a crop comprising a plurality of agricultural plants produced from the seeds. The endophytes capable of promoting germination can be present in a concentration of from about $10^2$ to about $10^5$ CFU/ml or from about $10^5$ to about $10^8$ CFU/seed. The formulation can be a liquid and the fungal or bacterial concentration can be from about $10^3$ to about $10^{11}$ CFU/ml. The formulation can be a gel or powder and the fungal or bacterial concentration can be from about $10^3$ to about $10^{11}$ CFU/gm.

In some cases, the endophytic microbe can be modified. For example, the endophytic microbe can be genetically modified by introduction of a transgene that stably integrates into its genome. In another embodiment, the endophytic microbe can be modified to harbor a plasmid or episome containing a transgene. In still another embodiment, the microbe can be modified by repeated passaging under selective conditions.

The microbe can be modified to exhibit altered characteristics. In one embodiment, the endophytic microbe is modified to exhibit increased compatibility with chemicals commonly used in agriculture. Agricultural plants are often treated with a vast array of agrichemicals, including fungicides, biocides (anti-bacterial and anti-fungal agents), herbicides, insecticides, nematicides, rodenticides, fertilizers, and other agents. Many such agents can affect the ability of an endophytic microbe to grow, divide, and/or otherwise confer beneficial traits to the plant.

In some cases, it can be important for the microbe to be compatible with agrichemicals, particularly those with fungicidal or antibacterial properties, in order to persist in the plant although, as mentioned earlier, there are many such fungicidal or antibacterial agents that do not penetrate the plant, at least at a concentration sufficient to interfere with the microbe. Therefore, where a systemic fungicide or antibacterial agent is used in the plant, compatibility of the microbe to be inoculated with such agents will be an important criterion.

In one embodiment, spontaneous isolates of microbes that are compatible with agrichemicals can be used to inoculate the plants according to the methods described herein. For example, fungal microbes which are compatible with agriculturally employed fungicides can be isolated by plating a culture of the microbes on a petri dish containing an effective concentration of the fungicide, and isolating colonies of the microbe that are compatible with the fungicide. In another embodiment, a microbe that is compatible with a fungicide is used for the methods described herein. For example, the endophyte can be compatible with at least one of the fungicides selected from the group consisting of: 2-(thiocyanatomethylthio)-benzothiazole, 2-phenylphenol, 8-hydroxyquinoline sulfate, ametoctradin, amisulbrom, antimycin, Ampelomyces quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyroquilon, quinoclamine, quinoxyfen, quintozene, Reynoutria *sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, 5-fluorocytosine and profungicides thereof, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamide, IK-1140

In still another embodiment, an endophyte that is compatible with an antibacterial compound is used for the methods described herein. For example, the endophyte can be compatible with at least one of the antibiotics selected from the group consisting of: Amikacin, Gentamicin, Kanamycin, Neomycin, Netilmicin, Tobramycin, Paromomycin, Spectinomycin, Geldanamycin, Herbimycin, Rifaximin, streptomycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin (Rifampin in US), Rifabutin, Rifapentine, Streptomycin, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, and Trimethoprim. Fungicide compatible microbes can also be isolated by selection on liquid medium. The culture of microbes can be plated on petri dishes without any forms of mutagenesis; alternatively, the microbes can be mutagenized using any means known in the art. For example, microbial cultures can be exposed to UV light, gamma-irradiation, or a chemical mutagen such as ethylmethanesulfonate (EMS) prior to selection on fungicide containing media. Finally, where the mechanism of action of a particular fungicide is known, the target gene can be specifically mutated (either by gene deletion, gene replacement, site-directed mutagenesis, etc.) to generate a microbe that is resilient against that particular fungicide. It is noted that the above-described methods can be used to isolate fungi that are compatible with both fungistatic and fungicidal compounds.

It will also be appreciated by one skilled in the art that a plant may be exposed to multiple types of fungicides or antibacterial compounds, either simultaneously or in succession, for example at different stages of plant growth. Where the target plant is likely to be exposed to multiple fungicidal and/or antibacterial agents, a microbe that is compatible with many or all of these agrichemicals can be used to inoculate the plant. A microbe that is compatible with several fungicidal agents can be isolated, for example, by serial selection. A microbe that is compatible with the first fungicidal agent is isolated as described above (with or without prior mutagenesis). A culture of the resulting microbe can then be selected for the ability to grow on liquid or solid media containing the second antifungal compound (again, with or without prior mutagenesis). Colonies isolated from the second selection are then tested to confirm its compatibility to both antifungal compounds.

Likewise, bacterial microbes that are compatible to biocides (including herbicides such as glyphosate or antibacterial compounds, whether bacteriostatic or bactericidal) that are agriculturally employed can be isolated using methods similar to those described for isolating fungicide compatible microbes. In one embodiment, mutagenesis of the microbial population can be performed prior to selection with an antibacterial agent. In another embodiment, selection is performed on the microbial population without prior mutagenesis. In still another embodiment, serial selection is performed on a microbe: the microbe is first selected for compatibility to a first antibacterial agent. The isolated compatible microbe is then cultured and selected for compatibility to the second antibacterial agent. Any colony thus isolated is tested for compatibility to each, or both antibacterial agents to confirm compatibility with these two agents.

The selection process described above can be repeated to identify isolates of the microbe that are compatible with a multitude of antifungal or antibacterial agents. Candidate isolates can be tested to ensure that the selection for agrichemical compatibility did not result in loss of a desired microbial bioactivity. Isolates of the microbe that are compatible with commonly employed fungicides can be selected as described above. The resulting compatible microbe can be compared with the parental microbe on plants in its ability to promote germination.

Methods

Further provided herein are methods of enhancing seed vitality, plant health and/or yield comprising inoculating a seed with an endophyte or culture disclosed herein or a combination or mixture thereof or with a composition disclosed herein. In some embodiments, a first generation plant is cultivated from the seed.

In one aspect, the invention provides a method of altering a trait in an agricultural plant seed or an agricultural plant grown from said seed, said method comprising inoculating said seed with a composition comprising endophytes capable of promoting germination and an agriculturally-acceptable carrier, wherein the endophyte replicates within at least one plant tissue and colonizes the cortical cells of said plant. In one embodiment, the endophyte capable of promoting germination is a coleorhiza-activating endophyte, and the seed is a monocot seed. In another embodiment, the endophyte capable of promoting germination is heterologous to the seed.

In some embodiments, the endophytes are a selected from the group consisting of a spore-forming endophyte, a facultative endophyte, a filamentous endophyte, and an endophyte capable of living within another endophyte. In some embodiments, the endophyte is capable of forming certain structures in the plant, where the structures are selected from the group consisting of hyphal coils, Hartig-like nets, microvesicles, micro-arbuscules, hyphal knots, and symbiosomes. In some embodiments, the endophyte is in the form of at least one of conidia, chlamydospore, and mycelia. In other embodiments, the fungus or bacteria is capable of being part of a plant-fungus symbiotic system or plant-bacteria symbiotic system that produces altered levels of phytohormones or anti-oxidants, as compared to a plant that is not in symbiosis. In other embodiments, the plant-fungus symbiotic system or plant-bacterium symbiotic system has anti-aging and/or anti-senescence effects, as compared to a plant or plant organ that is not in symbiosis. In other embodiments, the plant-fungus symbiotic system or plant-bacteria symbiotic system has increased protection against pathogens, as compared to a plant that is not in symbiosis. In other aspects, the endophyte colonizes at least 0.1%, at least 1%, at least 2%, at least 3%, at least 4%, at least 5%, at least 10%, at least 20%, at least 30%, at least 40%, at least 50%, at least 60%, at least 70%, or at least 80% of the cortical cells of said agricultural plant.

In yet another aspect, the invention provides a method of altering a trait in an agricultural plant seed or an agricultural plant grown from said seed, said method comprising inoculating said seed with a composition comprising endophytes capable of promoting germination and an agriculturally-acceptable carrier, wherein the altered trait is an improved functional trait selected from the group consisting of increased yield, faster seedling establishment, faster growth, increased drought tolerance, increased heat tolerance, increased cold tolerance, increased salt tolerance, increased tolerance to pests and diseases, increased biomass, increased root and/or shoot length or weight, increased fresh weight of seedlings, increased seed or fruit number, increased plant vigour, nitrogen stress tolerance, enhanced *Rhizobium* activity, enhanced nodulation frequency, early flowering time, or any combination thereof. In some embodiments, the increased tolerance to disease is increased tolerance to *Fusarium* infection, increased tolerance to *Septoria* infection, increased tolerance to *Puccinia* infection. In some embodiments, yield is measured on a population of plants grown in the field and is calculated via combine harvesting or measuring ear weight. In another aspect, the altered trait is a seed trait selected from the group consisting a greater germination rate, faster dormancy breakdown, increased energy of germination, increased seed germination vigor or increased seed vitality. In yet another embodiment, the altered trait is altered gene expression, wherein the gene is selected from the group consisting of a gene involved in gibberellin production, a gene involved in abscisic acid production, a gene involved in plant growth, an acquired resistance gene, and a gene involved in protection from oxidative stress. In some embodiments, the genes may be involved in phytohormone production. In some embodiments, the phytohormone is altered in the plant-fungus or plant-bacterial symbiotic system. In some embodiments, the method further comprises planting the agricultural plant seed. In another embodiment, the method further comprises selecting a plant seed or plant that has the altered trait. For all altered traits, the change can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant.

In one embodiment, the invention provides methods of improving the 50% germination rate of a population of seeds comprising inoculating said population of seeds with a composition as described herein. In one embodiment, the method is a method of improving the 50% germination rate of a population of seeds and of improving a trait in plants grown from the seeds, comprising inoculating said population of seeds with a composition as described herein. In one embodiment, the improved trait is selected from the group consisting of increased yield, faster seedling establishment, faster growth, increased drought tolerance, increased heat tolerance, increased cold tolerance, increased salt tolerance, increased tolerance to pests and diseases, increased biomass, increased root and/or shoot length or weight, increased fresh weight of seedlings, increased seed or fruit number, increased plant vigour, nitrogen stress tolerance, enhanced *Rhizobium* activity, enhanced nodulation frequency, early flowering time, or any combination thereof. In some embodiments, the increased tolerance to disease is increased tolerance to *Fusarium* infection, increased tolerance to *Septoria* infection, increased tolerance to *Puccinia* infection. In some embodiments, yield is measured on a population of plants grown in the field and is calculated via combine harvesting or measuring ear weight. For all altered traits, the change can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant. In some embodiments, the method further comprises planting the agricultural plant seed. In another embodiment, the method further comprises selecting a plant seed or plant that has the altered trait.

In one embodiment, the method is a method of improving the 50% germination rate of a population of seeds and altering the gene expression in a plant grown from the seeds, comprising inoculating said population of seeds with a composition as described herein. In some embodiments, the gene is altered in the plant-fungus or plant-bacterial symbiotic system. In some embodiments, the gene with altered expression is a gene involved in plant growth, an acquired resistance gene, and a gene involved in protection from oxidative stress. In some embodiments, these genes may be involved in phytohormone production, such as those involved in GA biosynthesis or breakdown, abscisic acid (ABA) biosynthesis or breakdown, NO production or breakdown, superoxide detoxification, or are positive or negative regulators of these pathways. In other embodiments, the genes associated with systemic acquired resistance are redox-regulated transcription factors. In still other embodiments, the redox-regulated transcription factors belong to the MYB family of genes. In some embodiments, the gene with altered expression is selected from the group consisting of P5CS, SOD, MnSOD, GA3-oxidase 2, 14-3-3, NCED2, ABA8'OH1, RSG, KAO, Myb1 and Myb2. In some embodiments, the change in gene expression can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant. In some embodiments, the method further comprises planting the agricultural plant seed. In another embodiment, the method further comprises selecting a plant seed or plant that has the altered trait.

In one embodiment, a method of improving the 50% germination rate of a population of seeds and providing at least 0.1%, at least 1%, at least 2%, at least 3%, at least 4%, at least 5%, at least 10%, at least 20%, at least 30%, at least 40%, at least 50%, at least 60%, at least 70%, or at least 80% colonization in cortex cells of plants grown from the seeds is provided.

In one embodiment, methods of obtaining at least 0.1%, at least 1%, at least 2%, at least 3%, at least 4%, at least 5%, at least 10%, at least 20%, at least 30%, at least 40%, at least 50%, at least 60%, at least 70%, or at least 80% endophyte colonization in the cortex cells of a plant and of improving a trait in the plant are disclosed, comprising inoculating the seed of said plant with a composition as described herein. In one embodiment, the improved trait is selected from the group consisting of increased yield, faster seedling establishment, faster growth, increased drought tolerance, increased heat tolerance, increased cold tolerance, increased salt tolerance, increased tolerance to pests and diseases, increased biomass, increased root and/or shoot length or weight, increased fresh weight of seedlings, increased seed or fruit number, increased plant vigour, nitrogen stress tolerance, enhanced *Rhizobium* activity, enhanced nodulation frequency, early flowering time, or any combination thereof. In some embodiments, the increased tolerance to disease is increased tolerance to *Fusarium* infection, increased tolerance to *Septoria* infection, increased tolerance to *Puccinia* infection. In some embodiments, yield is measured on a population of plants grown in the field and is calculated via combine harvesting or measuring ear weight. For all altered traits, the change can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant.

In one embodiment, the method is a method of increasing the germination rate, speeding up dormancy breakdown, increasing the energy of germination, increasing the germination vigour, speeding up germination, increasing the energy of germination, producing greater uniformity of germination, including greater uniformity of rate of germination and greater uniformity of timing of germination, or increasing the vitality of a seed, comprising inoculating seeds or a population of seeds with a composition as described herein. In some embodiments, the method further comprises planting the agricultural plant seed.

In one embodiment, the invention provides a method of releasing a seed from dormancy, said method comprising inoculating said seed with a composition comprising endophytes capable of promoting germination and an agriculturally-acceptable carrier. In some embodiments, the endophytes capable of promoting germination are coleorhiza-activating endophytes.

In one embodiment, the invention provides a method of improving the 50% germination rate of a population of seeds and increasing NO accumulation in a plant grown from the seeds, comprising inoculating seeds with a composition as described herein. In some embodiments, the method further comprises planting the agricultural plant seed.

In another embodiment, a method of altering a trait in an agricultural plant seed or an agricultural plant grown from said seed is disclosed, comprising obtaining a synthetic preparation comprising an agricultural plant seed and a composition comprising endophytes capable of promoting germination and an agriculturally-acceptable carrier and planting the synthetic preparation. In some embodiments, the method further comprises planting the agricultural plant seed. In another embodiment, the method further comprises selecting a plant seed or plant that has the altered trait.

In another embodiment, the invention provides a method for treating seeds comprising contacting the surface of an agricultural plant seed with a formulation comprising a microbial population that comprises an endophyte capable of promoting germination that is heterologous to the seed, wherein the endophyte capable of promoting germination is present in the formulation in an amount effective to alter the level of at least one gene within the seed, seedlings derived from the seed or agricultural plants derived from the seed. In some embodiments, the gene with altered expression is a gene involved in phytohormone production, an acquired resistance gene, and a gene involved in protection from oxidative stress. In some embodiments, these genes are those involved in GA biosynthesis or breakdown, abscisic acid (ABA) biosynthesis or breakdown, NO production or breakdown, superoxide detoxification, or are positive or negative regulators of these pathways. In other embodiments, the genes associated with systemic acquired resistance are redox-regulated transcription factors. In still other embodiments, the redox-regulated transcription factors belong to the MYB family of genes. In some embodiments, the gene with altered expression is selected from the group consisting of P5CS, SOD, MnSOD, GA3-oxidase 2, 14-3-3, NCED2, ABA8'OH1, RSG, KAO, Myb1 and Myb2.

In another embodiment, the invention provides a method for treating seeds comprising contacting the surface of an agricultural plant seed with a formulation comprising a microbial population that comprises an endophyte capable of promoting germination that is heterologous to the seed, wherein the endophyte capable of promoting germination is present in the formulation in an amount effective to alter the level of at least one phytohormone within the seed, seedlings derived from the seed or agricultural plants derived from the seed. In some embodiments, the phytohormones that are altered are gibberellins, abscisic acid, or cytokinins. In further embodiments, the gibberellins may be gibberellin 1, 19, 44 or 53. In still further embodiments, the cytokinin may be zeatin. For these altered phytohormone levels, the change can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant.

In another embodiment, the invention provides a method for treating seeds comprising contacting the surface of an agricultural plant seed with a formulation comprising a microbial population that comprises an endophyte capable of promoting germination that is heterologous to the seed, wherein the endophyte capable of promoting germination is present in the formulation in an amount effective to improve a trait in the seed or a plant grown from the seed. In some embodiments, the improved trait is selected from the group consisting of increased yield, faster seedling establishment, faster growth, increased drought tolerance, increased heat tolerance, increased cold tolerance, increased salt tolerance, increased tolerance to pests and diseases, increased biomass, increased root and/or shoot length or weight, increased fresh weight of seedlings, increased seed or fruit number, increased plant vigour, nitrogen stress tolerance, enhanced *Rhizobium* activity, enhanced nodulation frequency, early flowering time, or any combination thereof. In some embodiments, the increased tolerance to disease is increased tolerance to *Fusarium* infection, increased tolerance to *Septoria* infection, increased tolerance to *Puccinia* infection. In some embodiments, yield is measured on a population of plants grown in the field and is calculated via combine harvesting or measuring ear weight. For all altered traits, the change can be at least 1%, for example at least 2%, at least 3%, at least 4%, at least 5%, at least 10%, at least 20%, at least 30%, at least 40%, at least 50%, at least 60%, at least 75%, at least 100%, or more, when compared with a control agricultural seed or plant. In some embodiments, the method further comprises planting the agricultural plant seed. In another embodiment, the method further comprises selecting a plant seed or plant that has the altered trait.

In another aspect, there is provided a method of improving plant health and/or plant yield comprising treating plant propagation material or a plant with a composition disclosed herein; and cultivating the plant propagation material into a first generation plant or allowing the plant to grow.

In another embodiment, the methods reduce the effects of stress, such as heat, drought and/or biotic stress.

In an embodiment, the methods enhance landscape development and remediation.

Accordingly, in one embodiment, there is provided a method of phytoremediation or phytoreclamation of a contaminated site comprising treating plant propagation material or a plant with a composition disclosed herein, and cultivating the plant propagation material into a first generation plant or allowing the plant to grow; thereby remediating or reclaiming the site.

In one embodiment, the site is soil, such as at a landfill. In an embodiment, the substances, wastes or hazardous materials comprise hydrocarbons, petroleum or other chemicals, salts, or metals, such as lead, cadmium or radioisotopes.

Formulations/Seed coating compositions

The purified endophytes described herein can be formulated using an agriculturally compatible carrier. The formulation useful for these embodiments generally typically include at least one member selected from the group consisting of a tackifier, a microbial stabilizer, a fungicide, an antibacterial agent, an herbicide, a nematicide, an insecticide, a plant growth regulator, a rodenticide, a dessicant, and a nutrient.

In some cases, the purified bacterial or fungal population is mixed with an agriculturally compatible carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the purified bacterial or fungal population (see, for example, U.S. Pat. No. 7,485,451, which is incorporated herein by reference in its entirety). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant parts, sugar cane bagasse, hulls or stalks from grain processing, ground plant material or wood from building site refuse, sawdust or small fibers from recycling of paper, fabric, or wood. Other suitable formulations will be known to those skilled in the art.

In one embodiment, the formulation can include a tackifier or adherent. Such agents are useful for combining the bacterial or fungal population of the invention with carriers that can contain other compounds (e.g., control agents that are not biologic), to yield a coating composition. Such compositions help create coatings around the plant or seed to maintain contact between the microbe and other agents with the plant or plant part. In one embodiment, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788, each of which is incorporated herein by reference in its entirety.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the bacterial or fungal population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non-reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%.

In some cases, it is advantageous for the formulation to contain agents such as a fungicide, an antibacterial agent, an herbicide, a nematicide, an insecticide, a plant growth regulator, a rodenticide, or a nutrient. Such agents are ideally compatible with the agricultural seed or seedling onto which the formulation is applied (e.g., it should not be deleterious to the growth or health of the plant). Furthermore, the agent is ideally one that does not cause safety concerns for human, animal or industrial use (e.g., no safety issues, or the compound is sufficiently labile that the commodity plant product derived from the plant contains negligible amounts of the compound).

In the liquid form, for example, solutions or suspensions, the bacterial or fungal endophytic populations of the present invention can be mixed or suspended in water or in aqueous solutions. Suitable liquid diluents or carriers include water, aqueous solutions, petroleum distillates, or other liquid carriers.

Solid compositions can be prepared by dispersing the bacterial or fungal endophytic populations of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

In one particular embodiment, the formulation is ideally suited for coating of the endophytic microbial population onto seeds. The bacterial or fungal endophytic populations described in the present invention are capable of conferring many fitness benefits to the host plants. The ability to confer such benefits by coating the bacterial or fungal populations on the surface of seeds has many potential advantages, particularly when used in a commercial (agricultural) scale.

The bacterial or fungal endophytic populations herein can be combined with one or more of the agents described above to yield a formulation suitable for combining with an agricultural seed or seedling. The bacterial or fungal population can be obtained from growth in culture, for example, using a synthetic growth medium. In addition, the microbe can be cultured on solid media, for example on petri dishes, scraped off and suspended into the preparation. Microbes at different growth phases can be used. For example, microbes at lag phase, early-log phase, mid-log phase, late-log phase, stationary phase, early death phase, or death phase can be used.

The formulations comprising the bacterial or fungal endophytic population of the present invention typically contains between about 0.1 to 95% by weight, for example, between about 1% and 90%, between about 3% and 75%, between about 5% and 60%, or between about 10% and 50% in wet weight of the bacterial or fungal population of the present invention. It is preferred that the formulation contains at least about $10^3$ CFU per ml of formulation, for example, at least about $10^4$, at least about $10^5$, at least about $10^6$, at least $10^7$ CFU, at least $10^8$ CFU per ml of formulation.

Populations of Seeds

In another aspect, the invention provides for a substantially uniform population of seeds comprising a plurality of seeds comprising the population of endophytes capable of promoting germination, as described herein above. Substantial uniformity can be determined in many ways. In some cases, at least 10%, for example, at least 20%, at least 30%, at least 40%, at least 50%, at least 60%, at least 70%, at least 75%, at least 80%, at least 90%, at least 95% or more of the seeds in the population, contain the endophytic population in an amount effective to colonize the plant disposed on the surface of the seeds. In other cases, at least 10%, for example, at least 20%, at least 30%, at least 40%, at least 50%, at least 60%, at least 70%, at least 75%, at least 80%, at least 90%, at least 95% or more of the seeds in the population, contain at least 1, at least 10, or at least 100 CFU on the seed surface or per gram of seed, for example, at least 200 CFU, at least 300 CFU, at least 1,000 CFU, at least 3,000 CFU, at least 10,000 CFU, at least 30,000 CFU, at least 100,000 CFU, at least 300,000 CFU, or at least 1,000,000 CFU per seed or more.

In a particular embodiment, the population of seeds is packaged in a bag or container suitable for commercial sale. Such a bag contains a unit weight or count of the seeds comprising the bacterial or fungal endophytic population as described herein, and further comprises a label. In one embodiment, the bag or container contains a predetermined number of seeds. In an embodiment, the bag or container contains at least 1,000 seeds, for example, at least 5,000 seeds, at least 10,000 seeds, at least 20,000 seeds, at least 30,000 seeds, at least 50,000 seeds, at least 70,000 seeds, at least 80,000 seeds, at least 90,000 seeds or more. In another embodiment, the bag or container can comprise a discrete weight of seeds, for example, at least 1 lb, at least 2 lbs, at least 5 lbs, at least 10 lbs, at least 30 lbs, at least 50 lbs, at least 70 lbs or more. The bag or container may comprise a label describing the seeds and/or said bacterial or fungal endophytic population. The label can contain additional information, for example, the information selected from the group consisting of: net weight, lot number, geographic origin of the seeds, test date, germination rate, inert matter content, and/or the amount of noxious weeds, if any. Suitable containers or packages include those traditionally used in plant seed commercialization. The invention also contemplates other containers with more sophisticated storage capabilities (e.g., with microbiologically tight wrappings or with gas- or water-proof containments).

In some cases, a sub-population of seeds comprising the bacterial or fungal endophytic population is further selected on the basis of increased uniformity, for example, on the basis of uniformity of microbial population. For example, individual seeds of pools collected from individual cobs, individual plants, individual plots (representing plants inoculated on the same day) or individual fields can be tested for uniformity of microbial density, and only those pools meeting specifications (e.g., at least 80% of tested seeds have minimum density, as determined by quantitative methods described elsewhere) are combined to provide the agricultural seed sub-population.

The methods described herein can also comprise a validating step. The validating step can entail, for example, growing some seeds collected from the inoculated plants into mature agricultural plants, and testing those individual plants for uniformity. Such validating step can be performed on individual seeds collected from cobs, individual plants, individual plots (representing plants inoculated on the same day) or individual fields, and tested as described above to identify pools meeting the required specifications.

In some embodiments, methods described herein include planting a synthetic combination described herein. Suitable planters include an air seeder and/or fertilizer apparatus used in agricultural operations to apply particulate materials including one or more of the following, seed, fertilizer and/or inoculants, into soil during the planting operation. Seeder/fertilizer devices can include a tool bar having ground-engaging openers thereon, behind which is towed a wheeled cart that includes one or more containment tanks or bins and associated metering means to respectively contain and meter therefrom particulate materials. See, e.g., U.S. Pat. No. 7,555,990.

In certain embodiments, a composition described herein may be in the form of a liquid, a slurry, a solid, or a powder (wettable powder or dry powder). In another embodiment, a composition may be in the form of a seed coating. Compositions in liquid, slurry, or powder (e.g., wettable powder) form may be suitable for coating seeds. When used to coat seeds, the composition may be applied to the seeds and allowed to dry. In embodiments wherein the composition is a powder (e.g., a wettable powder), a liquid, such as water, may need to be added to the powder before application to a seed.

In still another embodiment, the methods can include introducing into the soil an inoculum of one or more of the endophyte populations described herein. Such methods can include introducing into the soil one or more of the compositions described herein. The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In one embodiment, seeds may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed. Systems and apparati for performing these processes are commercially available from numerous suppliers, e.g., Bayer CropScience (Gustafson).

In another embodiment, the treatment entails coating seeds. One such process involves coating the inside wall of a round container with the composition(s) described herein, adding seeds, then rotating the container to cause the seeds to contact the wall and the composition(s), a process known in the art as "container coating". Seeds can be coated by combinations of coating methods. Soaking typically entails using liquid forms of the compositions described. For example, seeds can be soaked for about 1 minute to about 24 hours (e.g., for at least 1 min, at least 5 min, at least 10 min, at least 20 min, at least 40 min, at least 80 min, at least 3 hr, at least 6 hr, at least 12 hr, or at least 24 hr).

Increased Uniformity in Populations of Plants/Agricultural Fields

A major focus of crop improvement efforts has been to select varieties with traits that give, in addition to the highest return, the greatest homogeneity and uniformity. While inbreeding can yield plants with substantial genetic identity, heterogeneity with respect to plant height, flowering time, and time to seed, remain impediments to obtaining a homogeneous field of plants. The inevitable plant-to-plant variability is caused by a multitude of factors, including uneven environmental conditions and management practices. Another possible source of variability can, in some cases, be due to the heterogeneity of the microbial population inhabiting the plants. By providing bacterial or fungal endophytic populations onto seeds and seedlings, the resulting plants generated by germinating the seeds and seedlings have a more consistent microbial composition, and thus are expected to yield a more uniform population of plants.

Therefore, in another aspect, the invention provides a substantially uniform population of plants. The population can include at least 100 plants, for example, at least 300 plants, at least 1,000 plants, at least 3,000 plants, at least 10,000 plants, at least 30,000 plants, at least 100,000 plants or more. The plants are grown from the seeds comprising the bacterial and/or fungal endophytic population as described herein. The increased uniformity of the plants can be measured in a number of different ways.

In one embodiment, there is an increased uniformity with respect to the microbes within the plant population. For example, in one embodiment, a substantial portion of the population of plants, for example at least 10%, at least 20%, at least 30%, at least 40%, at least 50%, at least 60%, at least 70%, at least 75%, at least 80%, at least 90%, at least 95% or more of the seeds or plants in a population, contains a threshold number of the bacterial or fungal endophytic population. The threshold number can be at least 10 CFU, at least 100 CFU, for example at least 300 CFU, at least 1,000 CFU, at least 3,000 CFU, at least 10,000 CFU, at least 30,000 CFU, at least 100,000 CFU or more, in the plant or a part of the plant. Alternatively, in a substantial portion of the population of plants, for example, in at least 1%, at least 10%, at least 20%, at least 30%, at least 40%, at least 50%, at least 60%, at least 70%, at least 75%, at least 80%, at least 90%, at least 95% or more of the plants in the population, the bacterial or fungal endophyte population that is provided to the seed or seedling represents at least 0.1%, at least 1%, at least 5%, at least 10%, at least 20%, at least 30%, at least 40%, at least 50%, at least 60%, at least 70%, at least 80%, at least 90%, at least 95%, at least 99%, or 100% of the total microbe population in the plant/seed.

In one embodiment, there is increased genetic uniformity of a substantial proportion or all detectable microbes within the taxa, genus, or species of the microbe relative to an uninoculated control. This increased uniformity can be a result of the microbe being of monoclonal origin or otherwise deriving from a microbial population comprising a more uniform genome sequence and plasmid repertoire than would be present in the microbial population a plant that derives its microbial community largely via assimilation of diverse soil symbionts.

In another embodiment, there is an increased uniformity with respect to a physiological parameter of the plants within the population. In some cases, there can be an increased uniformity in the height of the plants when compared with a population of reference agricultural plants grown under the same conditions. For example, there can be a reduction in the standard deviation in the height of the plants in the population of at least 5%, for example, at least 10%, at least 15%, at least 20%, at least 30%, at least 40%, at least 50%, at least 60% or more, when compared with a population of reference agricultural plants grown under the same conditions. In other cases, there can be a reduction in the standard deviation in the flowering time of the plants in the population of at least 5%, for example, at least 10%, at least 15%, at least 20%, at least 30%, at least 40%, at least 50%, at least 60% or more, when compared with a population of reference agricultural plants grown under the same conditions.

Decreased Uniformity in Populations of Plants/Agricultural Fields

In certain circumstances, decreased uniformity in a population can be desirable. For example, plants within a population that are not all at the same developmental stage may not all be negatively affected by a biotic or an abiotic stress event, and as a result, the population as a whole may show a beneficial trait such as increased yield. As another example, a lack of uniformity may allow for the selection of plants/seeds with a trait that is not present in the other members of the population. Therefore, in another embodiment, there is a decreased uniformity with respect to a physiological parameter of the plants within the population. In some cases, there can be a decreased uniformity in the height of the plants when compared with a population of reference agricultural plants grown under the same conditions. For example, there can be an increase in the standard deviation in the height of the plants in the population of at least 5%, for example, at least 10%, at least 15%, at least 20%, at least 30%, at least 40%, at least 50%, at least 60% or more, when compared with a population of reference agricultural plants grown under the same conditions. In other cases, there can be an increase intracellular vesiculoid in the standard deviation in the flowering time of the plants in the population of at least 5%, for example, at least 10%, at least 15%, at least 20%, at least 30%, at least 40%, at least 50%, at least 60% or more, when compared with a population of reference agricultural plants grown under the same conditions.

Commodity Plant Product

The present invention provides a commodity plant product, as well as methods for producing a commodity plant product, that is derived from a plant of the present invention. As used herein, a "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, paper, tea, coffee, silage, crushed of whole grain, and any other food for human or animal consumption; and biomasses and fuel products; and raw material in industry. Industrial uses of oils derived from the agricultural plants described herein include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat. Commodity plant products also include industrial compounds, such as a wide variety of resins used in the formulation of adhesives, films, plastics, paints, coatings and foams. The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Dormancy and germination depend on several processes and factors. To ensure seedling establishment and success, it is important to control the underlying processes or conditions. The role of plant genetics, hormones, and different seed tissues have been relatively well studied. The present examples study the endophyte-plant seed relationship, transitting into a root symbiotic stage towards plant maturation.

Example 1

Taxonomy and Physical Properties of the Endophytes

The endophytes used in the synthetic compositions described herein have been deposited as follows: International Depositary Authority of Canada—IDAC (original strains deposited—IDAC, National Microbiology Laboratory, Public Health Agency of Canada, 1015 Arlington Street, Winnipeg, Manitoba, Canada, R3E 3R2; receipts and viability in Appendix A) and Saskatchewan Microbial Collection and Database—SMCD (copies of strains deposited) International Depository Authority of Canada—IDAC (original strains deposited) and Saskatchewan Microbial Collection and Database—SMCD (copies of strains deposited), (see FIGS. 1-6 and Table 1). Strains:

(a) IDAC 081111-06=SMCD 2215;
(b) IDAC 081111-03=SMCD 2210;
(c) IDAC 081111-02=SMCD 2208;
(d) IDAC 081111-01=SMCD 2206;
(e) IDAC 200312-06=SMCD 2204; and
(f) IDAC 200312-05=SMCD 2204F.

SMCD 2215 strain was originally isolated as an endophytic bacterium of *Phyalocephala sensu lato* plant endophytic SMCD fungus. Classification according to Labeda et al. [2012]. This phylogenetic study examines almost all described species (615 taxa) within the family Streptomycetaceae based on 16S rDNA gene sequences and illustrates the species diversity within this family, which is observed to contain 130 statistically supported clades. The present 16S rDNA sequence data confirm that *Streptomyces* sp. strain SMCD 2215 can be assigned to a separate unknown Glade according to Labeda et al [2012] but separate species from *Streptomyces lividans*. Within a plant, it is capable of forming intercellular hyphae-like filaments and intracellular individual spore-like cells.

SMCD2204 is a filamentous, spore-forming facultative endophyte. Within a plant, it is capable of forming hyphal coils, microvesicles, microarbuscules, hyphal knots and intracellular or Hartig net-like structures. SMCD2204 is a fungus that is capable of being part of a plant-fungus symbiont that produces altered levels of phytohormones, and/or altered levels of anti-oxidants, as compared to a plant that is not in symbiosis. This endophyte is also capable of being part of a plant-fungus symbiont that shows decreased aging and/or senescence, and/or increased protection against pathogens, as compared to a plant or plant organ that is not in symbiosis.

SMCD2204F is filamentous, spore-forming facultative endophyte that is capable of living within another endophyte. It is capable of forming hyphal coils and intracellular or Hartig net-like structures within a plant. This endophyte is also capable of being part of a plant-fungus symbiont that shows decreased aging and/or senescence, as compared to a plant or plant organ that is not in symbiosis.

SMCD2206 is a filamentous, spore-forming facultative endophyte. Within a plant, it is capable of forming hyphal coils, microvesicles, microarbuscules, and hyphal knots. SMCD2204 is a fungus that is capable of being part of a plant-fungus symbiont that produces altered levels of phytohormones, and/or altered levels of anti-oxidants, as compared to a plant that is not in symbiosis. This endophyte is also capable of being part of a plant-fungus symbiont that shows decreased aging and/or senescence, and/or increased protection against pathogens, as compared to a plant or plant organ that is not in symbiosis.

SMCD2208 is a spore-forming facultative endophyte.

SMCD2210 is a facultative, spore-forming endophyte that is capable of living within another endophyte. Within a plant, it is capable of forming hyphal coils and microvesicles. SMCD2210 is a fungus that is capable of being part of a plant-fungus symbiont that produces altered levels of phytohormones, and/or altered levels of anti-oxidants, as compared to a plant that is not in symbiosis. This endophyte is also capable of being part of a plant-fungus symbiont that shows decreased aging and/or senescence, and/or increased protection against pathogens, as compared to a plant or plant organ that is not in symbiosis.

SMCD2215 is also a facultative, spore-forming endophyte that is capable of living within another endophyte. It is capable of forming hyphal coils and intracellular or Hartig net-like structures within a plant. SMCD2215 is a bacterium that is capable of being part of a plant-fungus symbiont that produces altered levels of phytohormones, and/or altered levels of anti-oxidants, as compared to a plant that is not in symbiosis. This endophyte is also capable of being part of a plant-fungus symbiont that shows decreased aging and/or senescence, and/or increased protection against pathogens, as compared to a plant or plant organ that is not in symbiosis.

Example 2

Symbiotic Microbe-Plant Association and Level of Compatibility

Figure 1:
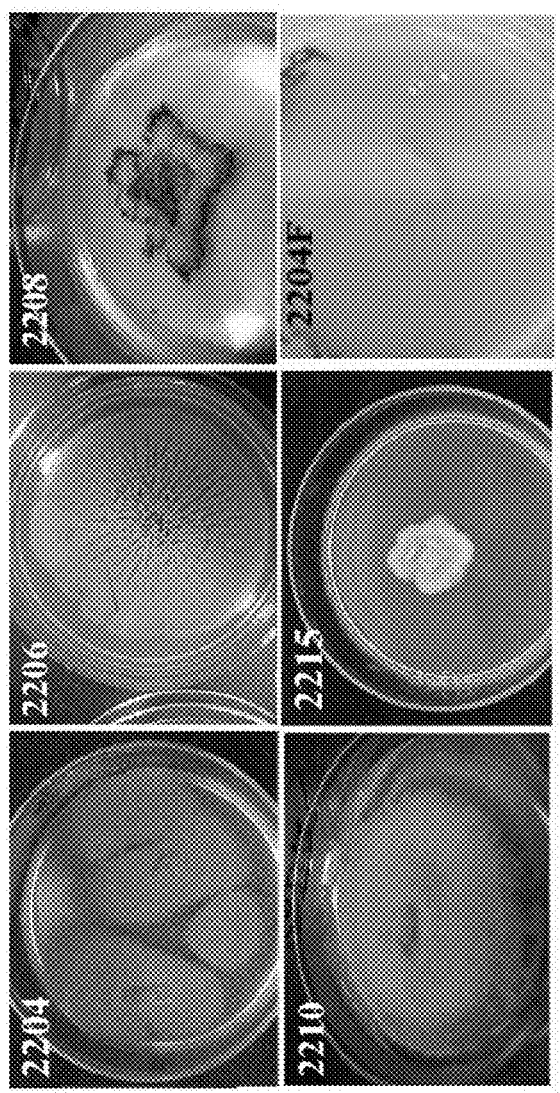
FIG. 1 shows the phenotypic appearance of the endophytic fungal strains SMCD 2204, 2004F, 2206, 2208, and 2210 and bacterial strain SMCD 2215; after 10 days of growth on PDA at 21° C.
Figure 2A:
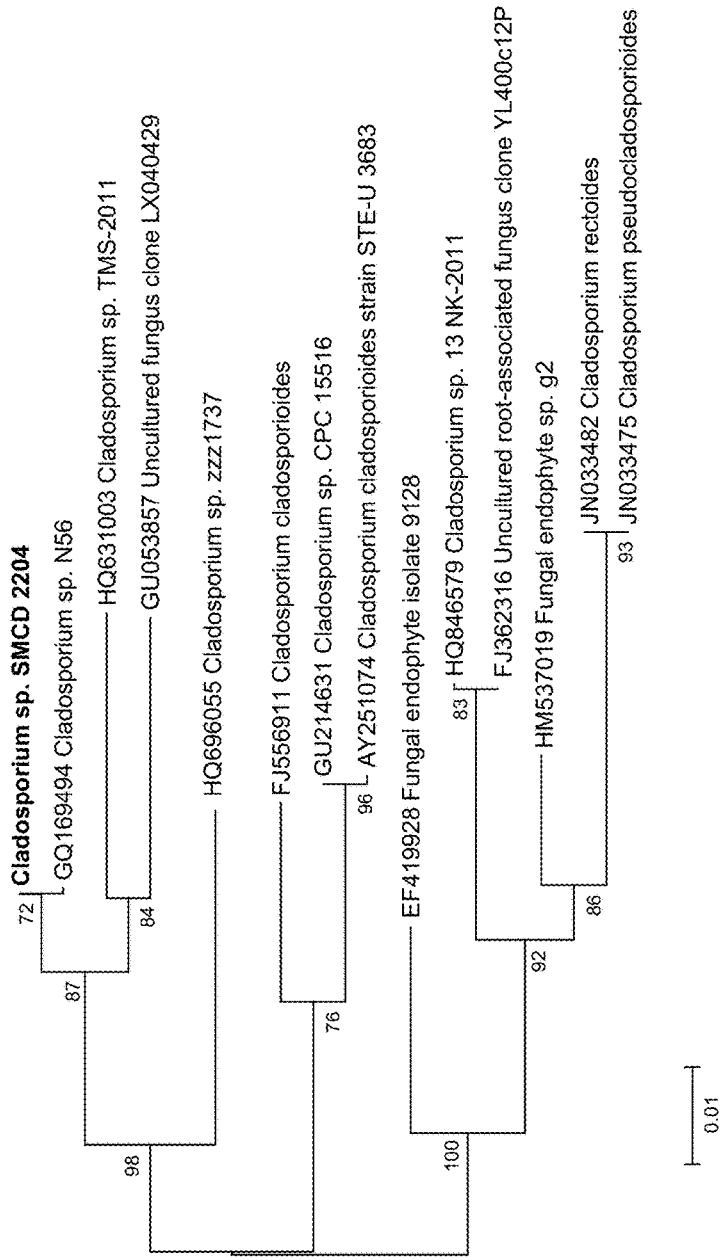
FIG. 2A shows the inferred neighbour-joining phylogenetic tree of the *Cladosporium* sp. SMCD 2204 based on ITS rDNA. Numbers at nodes indicate bootstrap support values for 1000 replicates; only values that were >70% are given. Bar indicates 0.01 nucleotide substitutions per site (nucleotide position).
Figure 2B:
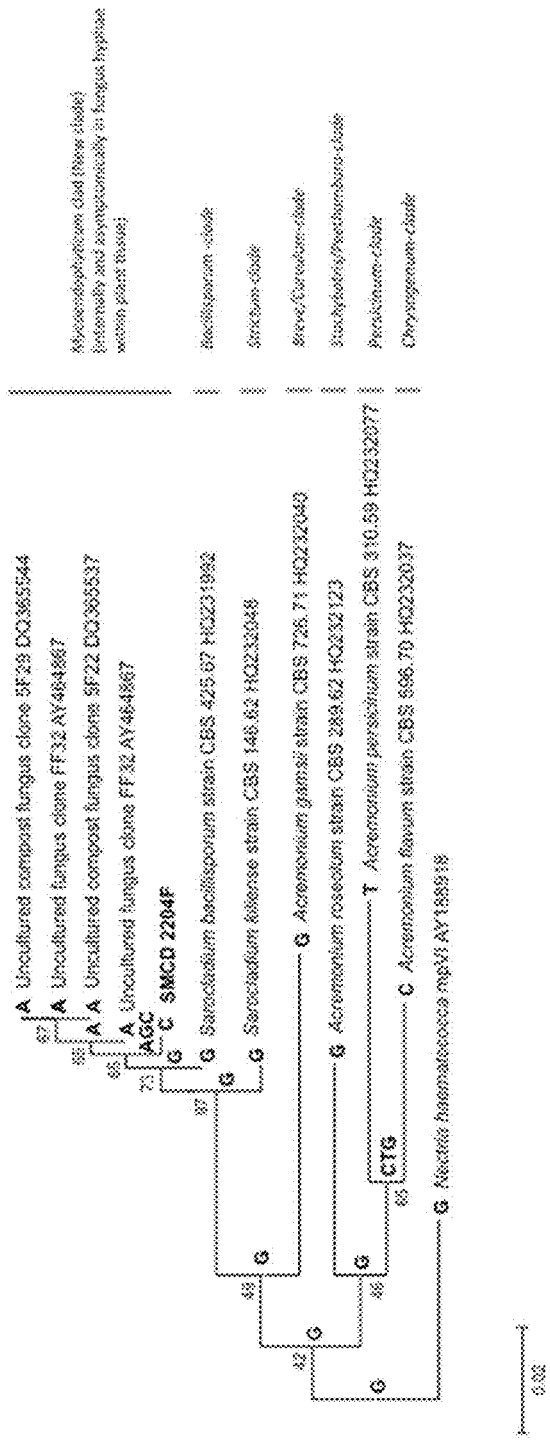
FIG. 2B shows the inferred neighbour-joining phylogenetic tree of the *Sarocladium* sp. SMCD 2204F based on the sequence of the large subunit of the nuclear ribosomal RNA gene (LSU). Numbers at nodes indicate bootstrap support values for 1000 replicates. Only values that were >70% are given. Bar indicates 0.01 nucleotide substitutions per site (nucleotide position).
Figure 3:
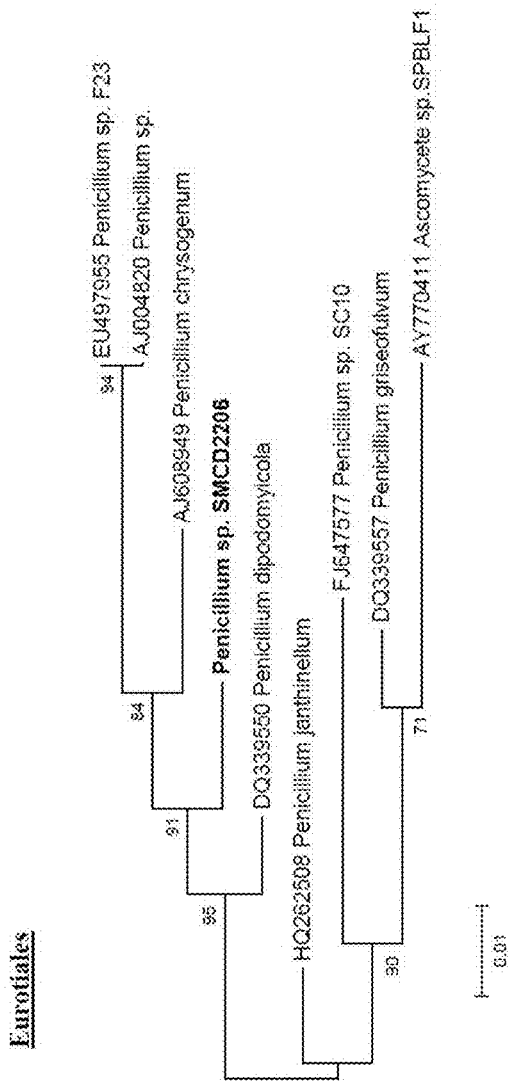
FIG. 3 shows the inferred neighbour-joining phylogenetic tree of the *Penicillium* sp. SMCD 2206 based on ITS rDNA. Numbers at nodes indicate bootstrap support values for 1000 replicates; only values that were >70% are given. Bar indicates 0.01 nucleotide substitutions per site (nucleotide position).
Figure 4:
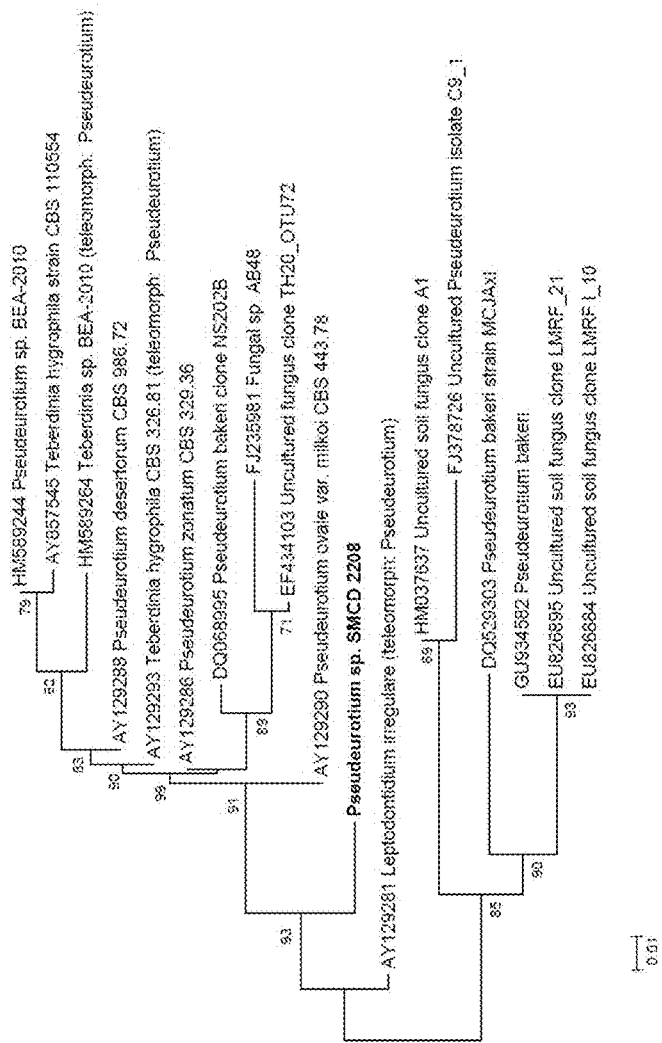
FIG. 4 shows the inferred neighbour-joining phylogenetic tree of the *Pseudoeurotium* sp. SMCD 2208 based on ITS rDNA. Numbers at nodes indicate bootstrap support values for 1000 replicates; only values that were >70% are given. Bar indicates 0.01 nucleotide substitutions per site (nucleotide position).
Figure 5:
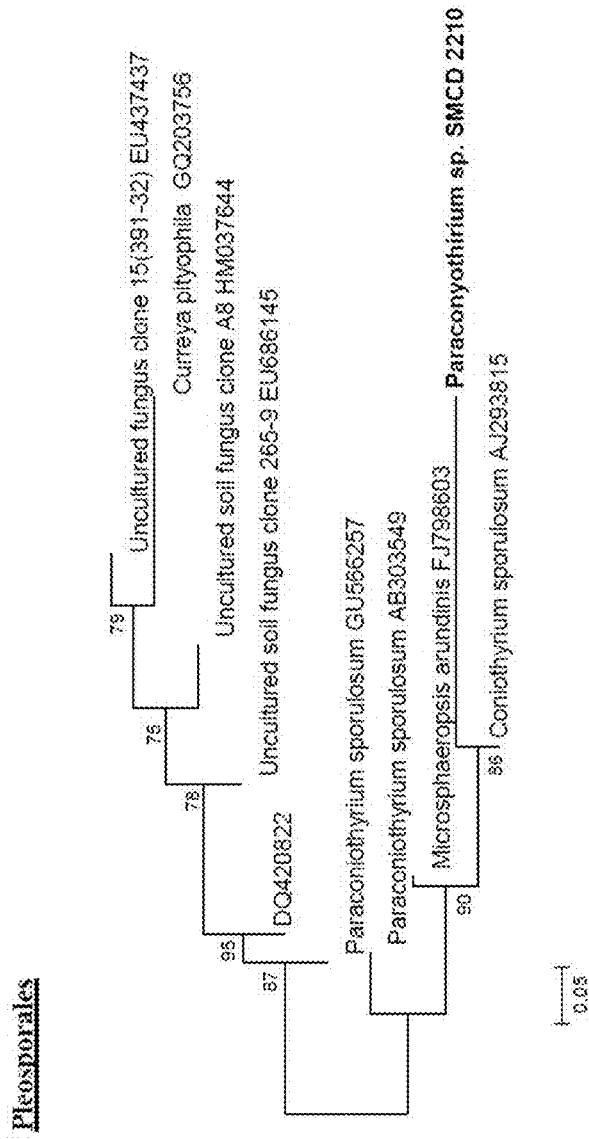
FIG. 5 shows the inferred neighbour-joining phylogenetic tree of the *Coniothyrium* strain SMCD 2210 based on ITS rDNA. Numbers at nodes indicate bootstrap support values for 1000 replicates; only values that were >70% are given. Bar indicates 0.05 nucleotide substitutions per site (nucleotide position).
Figure 6:
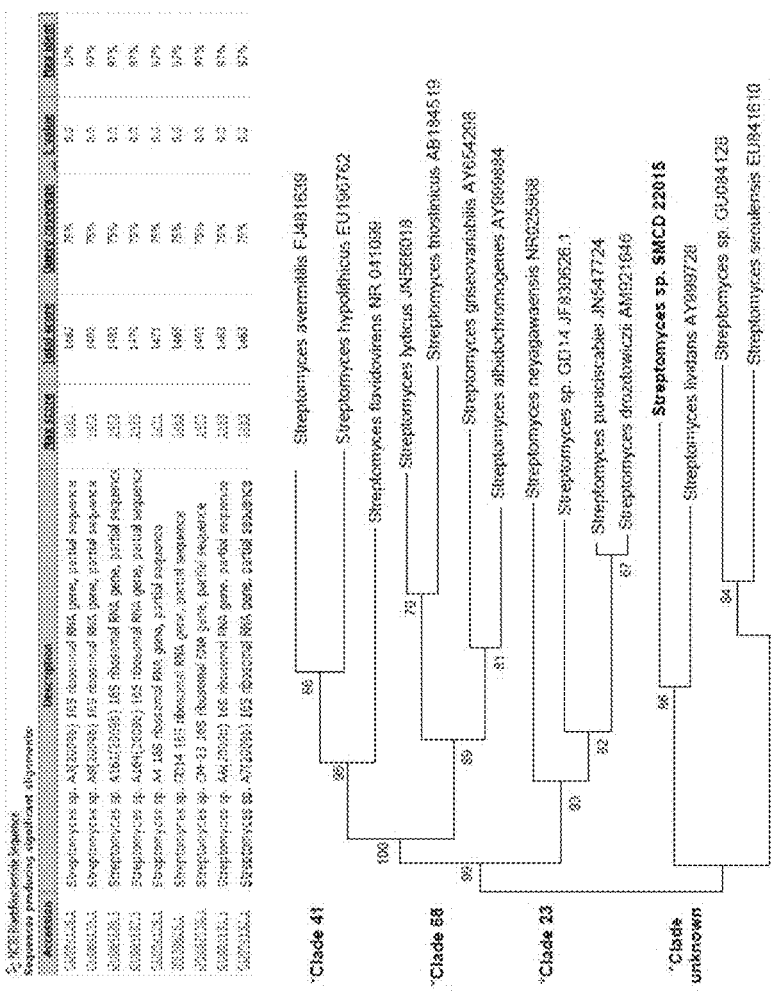
FIG. 6 shows the inferred neighbour-joining phylogenetic tree of the *Streptomyces* sp strain SMCD 2215 based on 16S rDNA. Numbers at nodes indicate bootstrap support values for 1000 replicates; only values that were >60% are given. Bar indicates 0.05 nucleotide substitutions per site (nucleotide position).
Figure 7:
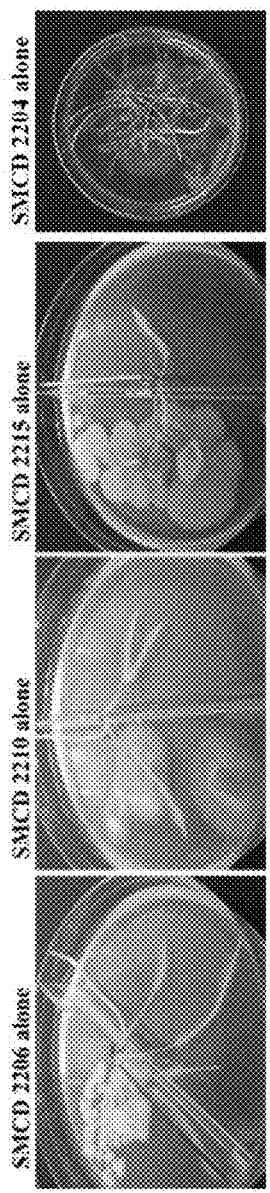
FIG. 7 shows left compartments of split plates (plant with microbial partner): healthy phenotypic appearance of wheat when the root is grown in contact with the microbial mats; and right-compartments of split plates (plant without microbial partner): massive formation of root hairs of wheat due to the plant-fungus association made in the left compartments of the split plates.

The level of microbe-plant compatibility was assessed using a slightly modified method of Abdellatif et al. [2009]. In a bicompartmental agar 10 cm plate without nutrients (FIG. 7), the plant's health and the formation of root hairs—the absorbants of water and minerals—were characterized in co-culture, with and without microbial partners. In FIG. 7, the left compartment of each split plate shows a culture with the microbial partner, and the right compartment of each split plate shows a culture without the microbial partner. The experiment was repeated twice in three replicates.

As shown in the left compartment of each split plate, healthy plant tissue formed even when the plant roots were grown directly on the dense microbial mats. The biomass of root hairs is enhanced to about twice as much compared to the right compartment of each split plate where the microbial partner is absent (see left compartments).

Figure 8:
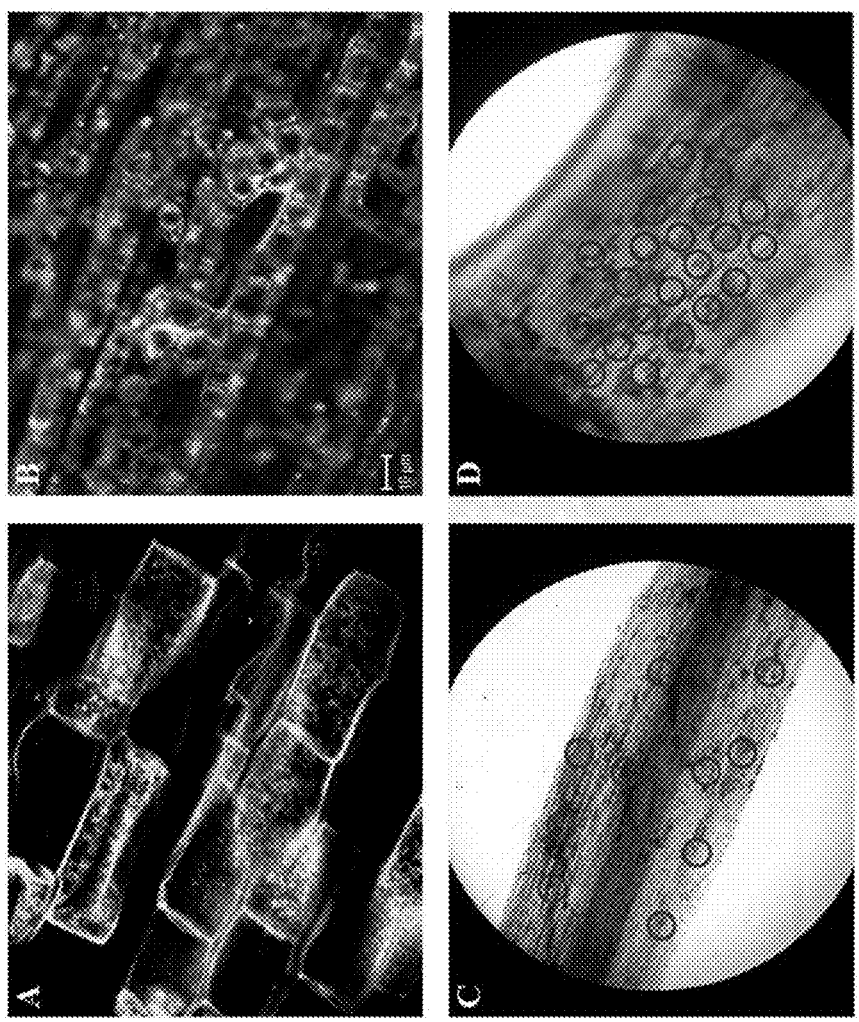
FIGS. 8 (A) and (C) shows SMCD2206 discontinuous colonization of wheat root (epidermis and cortex) tissue compared to (B) and (D) which shows pathogenic *Fusarium graminearum*'s uniform/continual cell colonization of wheat root including vascular cylinder.

The plant efficacy to establish symbiotic association is dependent on the type of endophyte distribution within the root endodermis. Typical endophytic root colonization is discontinuous and partial with a lower number of occupied cells<50% (Table 2) compared to the colonization of fungal pathogens which is characterized by a uniform/continual (frequency: 60-80%) colonization of cells (FIG. 8).

Figure 9:
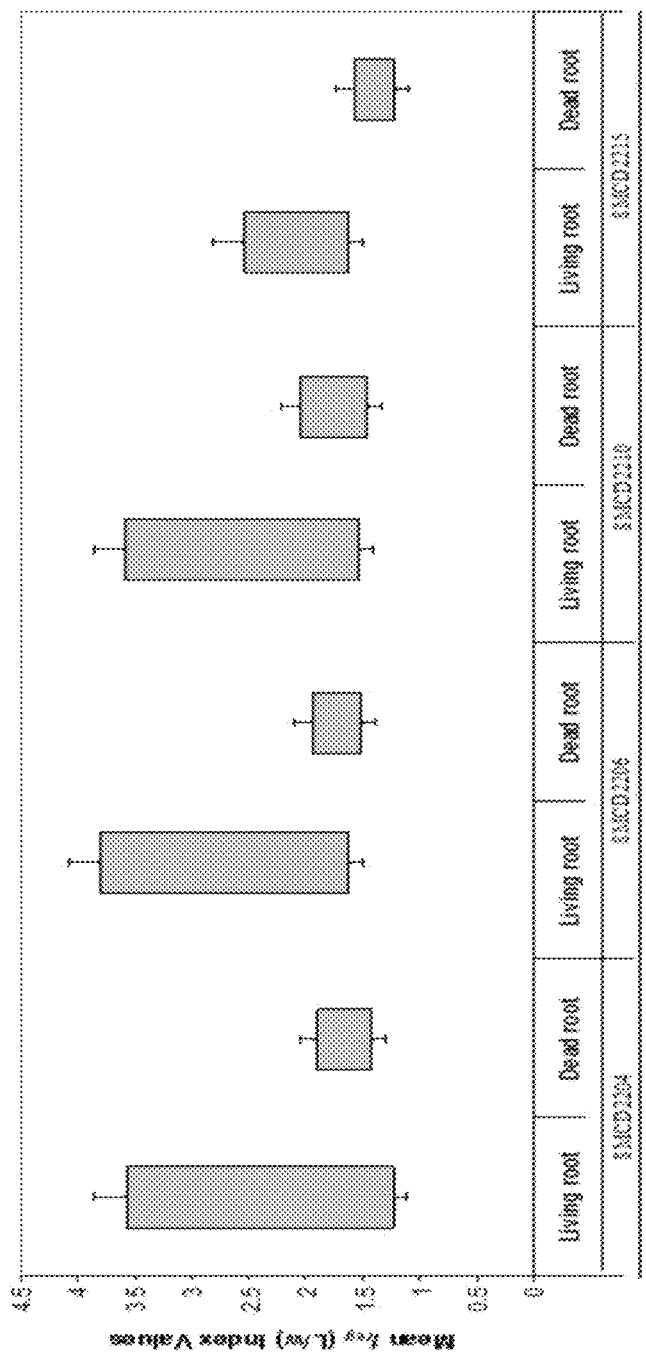
FIG. 9 shows Ireg index—level of deviation (irregularity) in endophyte (SMCDs) cell form.
Figure 10:
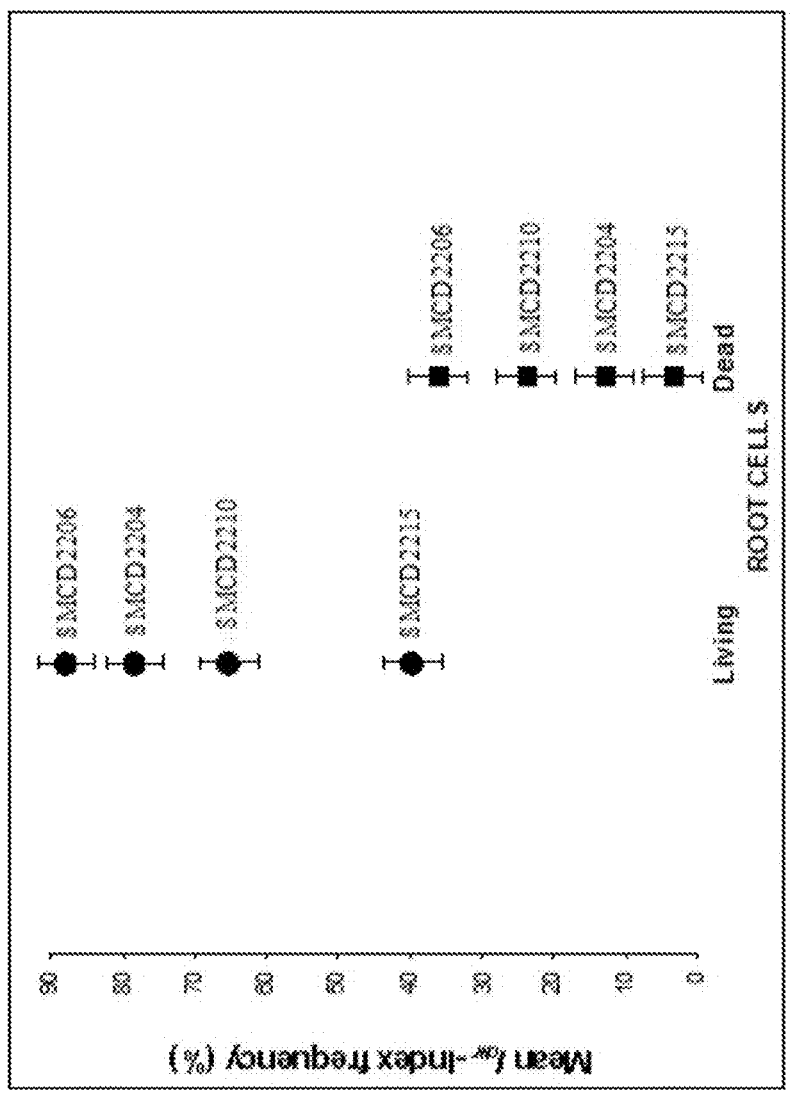
FIG. 10 shows Idir index—level of direction changes when colonizing living plant-host cell.

An endophyte's performance should not only be assessed by measuring biomass production, because what underlies the visibly increased yield is the endophyte's efficiency in colonizing the plant. This can be assessed by characterizing their association with plant cells, tissues, or organs (i.e. seed and radicles) using mathematical Indices which have been developed [Abdellatif et al. 2009] and applied in this study (FIG. 9 and FIG. 10).

These Indices are based on the following observations: Endophytic symbionts show different radicle (root)-colonization patterns (regularity or level of deviation in endophyte cell form-Ireg and direction-Idir when colonizing living cell) compared to dead radicle-cell (which usually remain colonized by true saprophytes).

High Ireg and Idir index values determine mutualistic (beneficial) plant-symbiont relationships. In conclusion, the results show that the symbiotic microbe-plant association is characterised by a high level of compatibility between the two partners, leading to an equilibrated (<50% of colonized cortex cells) and discontinuous root colonisation by the microbial endophytes measured using mathematical indices [Abdellatif et al. 2009]. This mutualistic partnership is further characterised by the direct effect of endophytic microbes on plant healthy growth (bacto- and mycodependency) when the plant is challenged to use the microbial partners as the only source of nutrients or energy for growth. In addition, the enhancement of the root hairs biomass by the endophytes was observed and measured even in roots in distal compartments of split plates where microbial partners were absent, indicating a possible systemic plant growth promoting function of the endophytes.

Example 3

Symbiotic Organs of Endophytes on Wheat

Figure 11:
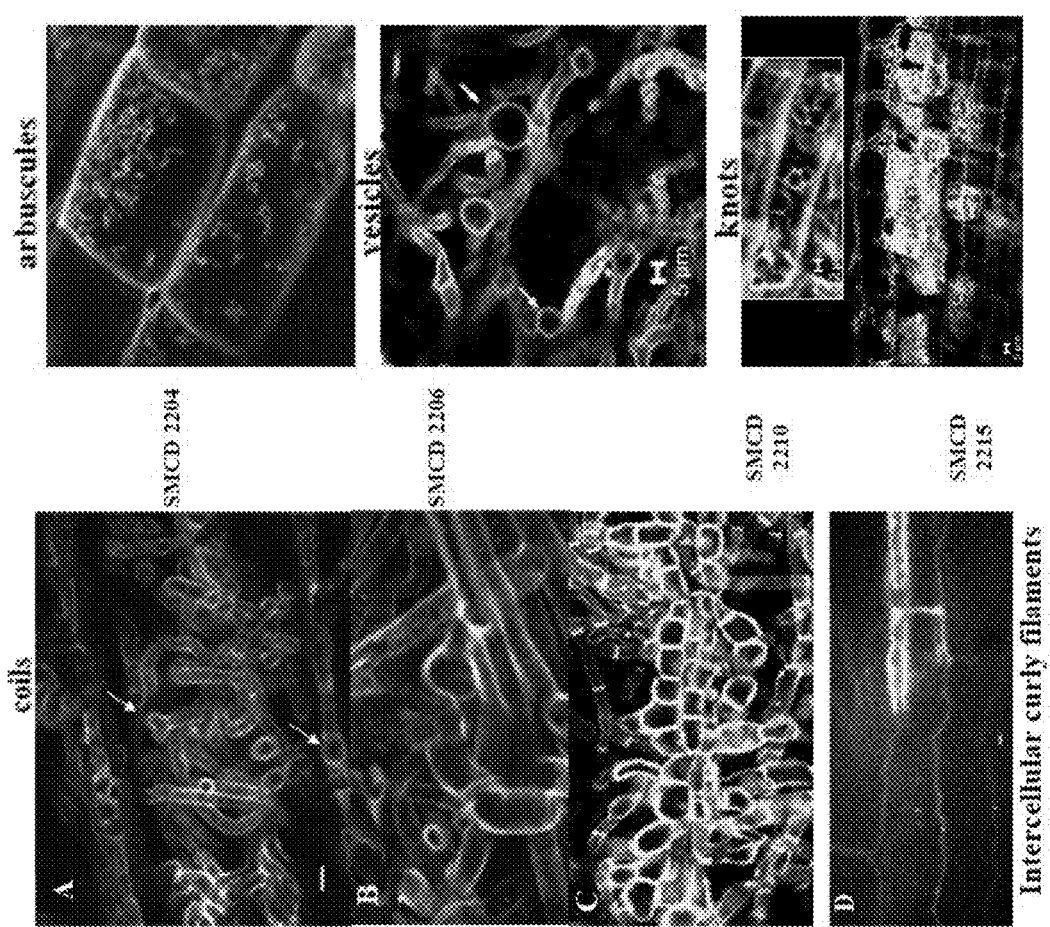
FIG. 11 shows endophytic hyphae in root of wheat germinant (A—SMCD 2204; B—SMCD 2206; C—SMCD 2210; and D—SMCD-2215) visualized with lactofuchsin staining and fluorescence microscopy. Symbiotic structures/organs: (D) SMCD 2215 bacterial endophyte mostly formed curly intercellular filaments, whereas endophytic fungi (Figures to the right) produced: SMCD 2204 intracellular coils and arbuscules, SMCD 2206 intracellular vesicules, and SMCD 2110 intracellular knots.

Each taxonomical group of endophytes establishes a unique type of mycovitalism, consequently forming different symbiotic organs. Characterization of the mycovitalism was done using Abdellatif et al. [2009] methodology, consisting of in vitro seed and microbe co-cultures assessing an early stage of the microbe-plant symbiotic association. The diversity of microbial symbiotic organs formed by SMCD 2204, 2206, 2210, and 2215 on wheat germinants is shown in FIG. 11.

In summary, the results show differential types of symbiotic organs formed in wheat root by each endophyte likely related to their different symbiotic functions. An equilibrated colonization abundance, patchy colonization patterns, increased hypha septation in living root cells, as well as formation of arbuscules, knots, coils and vesicles—putative symbiotic functional organs—may indicate local specialization within the fungal endophytes to promote plant mycovitality and mycoheterotrophy. Bactovitality is mostly characterized by *Streptomyces* intercellular curly filaments.

FIG. 66 shows symbiosomes formed in wheat root. The symbiosome is the new compartment that is formed in the plant cell when bacteria or fungi enter it. Symbiosomes can be classified into two types: I and II. Both types are composed of a perivesiculoid membrane and a partially fragmented outer vesiculoid membrane. Type I symbiosomes are additionally composed of an intercellular microvesiculoid compartment formed between two plant cell membranes, while type II symbiosomes are additionally composed of an intracellular vesiculoid compartment. Both types can be seed in the form of vesicles (A and B) and knots (C).

Figure 12:
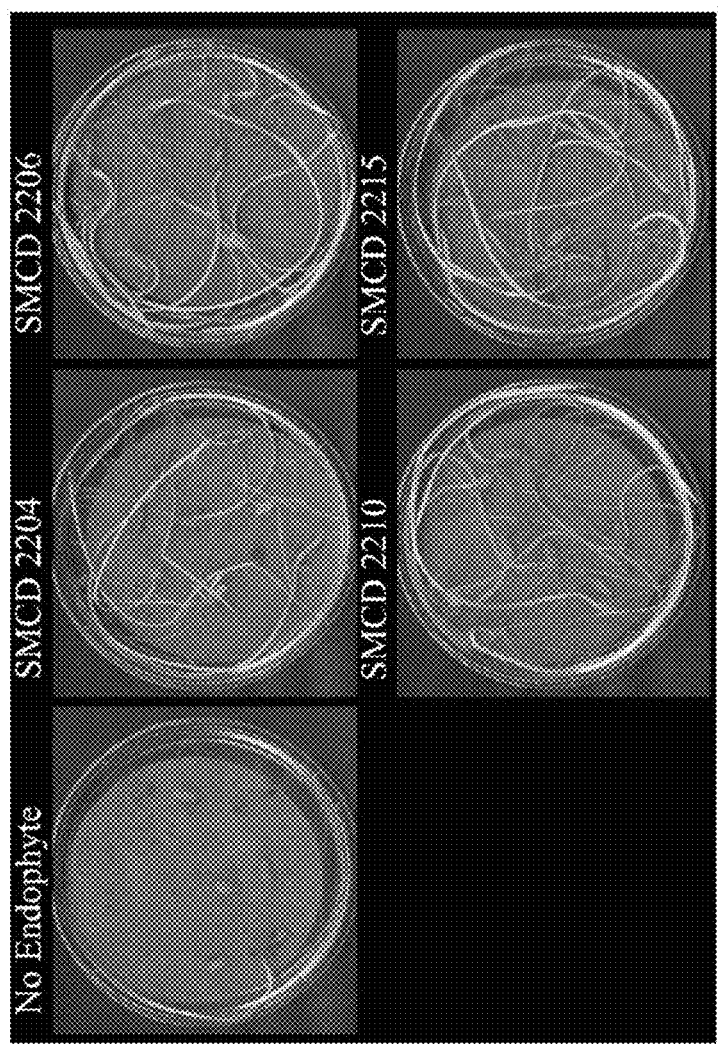
FIG. 12 shows the appearance of symbiotic germinating wheat seedlings after 10 days on moist filter paper at 21° C.
Figure 13:
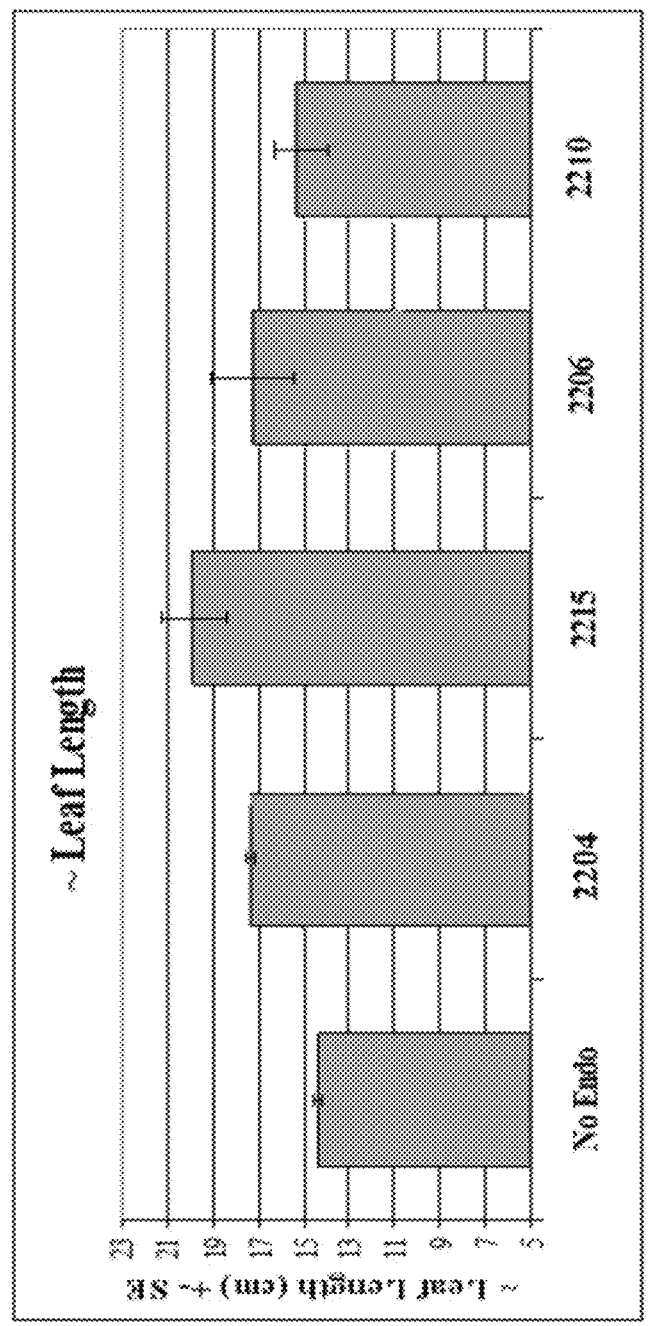
FIG. 13 shows leaf length of germinating wheat seedlings after 10 days at moisture filter paper at 21° C.

Symbiosis at the seed level resulted in increased wheat germinants after 10 days of co-innoculation (FIG. 12 and FIG. 13).

Example 4

Endophytes Improve Wheat Seed Germination Under Heat and Drought Stress

Seed germination is a critical life stage for plant survival and timely seedling establishment especially in stressful environments. It was hypothesized that endophytes would improve wheat seed germination under heat and drought stress. The hydrothermal time (HTT) model of germination is a conceptual model useful for predicting the timing and energy of germination (EG) under a given set of conditions. The HTT and EG are applied to determine if one or more compatible endophytes enhance heat or drought tolerance in wheat. Endophytes tested dramatically increased the percent of germination, improved EG and HTT values, and diminished wheat susceptibility to heat and drought as measured by fresh weight of seedlings. When colonised by the most effective endophyte, the values of the parameters tested in wheat seeds exposed to heat stress resembled those of unstressed seeds.

Materials and Methods

Hydrothermal Time Model of Germination and Energy of Germination

The hydrothermal time (HTT) model [Gummerson 1986] postulates that an individual seed begins to germinate when two conditions are met. First, the sum of daily temperatures, above a minimum cardinal value ($T_{min}$), accumulated over a period of time, must pass a threshold value ($\theta_T$), measured in degree days. Second, the seed must accumulate sufficient water potential ($\theta_H$) per degree-day. Thus, HTT ($\theta_{HT}$) can be expressed as:

$$\theta_{HT}=(\theta_H)(\theta_T).\qquad\text{(Equation 1)}$$

According to Köchy and Tielborger [2007], $$\theta_T=(T_{substrate}-T_{min})t\qquad\text{(Equation 2)}$$

with t representing the time elapsed in days, and $$\theta_H=\psi_{substrate}-\psi_{min}\qquad\text{(Equation 3)}$$

in a constant environment assuming that $T_{substrate}$ is equal to or less than the optimal temperature for seed germination. In Equation 3, $\psi_{substrate}$ and $\psi_{min}$ represent the water potential of the substrate and the minimum water potential at which germination is possible, in MPa, respectively. Consistent with Bradford [2002], equations 2 and 3 can be substituted into equation 1 to yield:

$$\theta_{HT}=(\psi_{substrate}-\psi_{min})(T_{substrate}-T_{min})t\qquad\text{(Equation 4)}.$$

However, in the present study, the temperature exceeds the optimal temperature for the germination of wheat [reviewed by McMaster (2009)], necessitating the consideration of a maximum temperature ($T_{max}$) above which germination cannot occur. Thus, equation 2 was modified to:

$$\theta_T=\sqrt{[(T_{substrate}-T_{min})(|T_{substrate}-T_{max}|)]}t\qquad\text{(Equation 5)}$$

where $T_{min}\leq T_{substrate}\leq T_{max}$. If equation 5 is substituted for 2 in equation 4, the following results:

$$\theta_{HT}=(\psi_{substrate}-\psi_{min})\sqrt{[(T_{substrate}-T_{min})(|T_{substrate}-T_{max}|)]}t\qquad\text{(Equation 6)}$$

where $T_{min}\leq T_{substrate}\leq T_{max}$.

Energy of germination (EG) can be defined in several ways, including the percentage of seeds germinating after a set time period after planting, relative to the number of seeds tested [Ruan et al. 2002; Dong-dong et al. 2009], or 50% of germination attained [Allen 1958]. In order to integrate EG with the HTT model of germination the latter definition was used, meaning that EG is equal to t in Equation 2.

Estimation of Parameters

The estimation of $T_{min}$ and $T_{max}$ for wheat was based on both information available in the literature and the present inventors' own observations. McMaster [2009] summarizes data originating from Friend et al. [1962], Cao and Moss [1989], and Jame et al. [1998] indicating the existence of a curvilinear relationship between wheat development rate and temperature. Since germination and development of wheat does not take place below 0° C. or above 40° C., $T_{min}$ and $T_{max}$ were assigned the values of 0° C. and 40° C., respectively.

The parameter $\psi_{min}$ was estimated in vitro by germinating wheat seeds grown on potato dextrose agar (PDA; Difco) media containing a range of polyethylene glycol (PEG) 8000 concentrations (Amresco Inc.). The water activity ($a_w$) of PDA alone and PDA containing 8%, 12% and 16% PEG was measured using the AquaLab 4TE, Series 4 Quick Start, Decagon Devices. Water activity was converted to water potential (ψ) using the relationship adapted from Bloom and Richard [2002]:

$$\Psi=[(RT)\ln(a_w)]/V \quad \text{(Equation 7)}$$

where R is the universal gas constant (8.314 J mol$^{-1}$ K$^{-1}$), T is the temperature in °K, and V is the partial molar volume of water (18 mL/mol). For unit conversions, 1 J/mL=1 MPa=10 bar. Water potential is zero for a free water surface or a saturated medium; all other values are negative.

The water activities of PDA and PDA containing 8%, 12% and 16% PEG were 0.9974, 0.9890, 0.9863, and 0.9825, respectively. These values are equivalent to −0.35, −1.51, −1.88, and −2.41 MPa, respectively and are consistent with those reported in the literature [Leone et al. 1994].

Plant and Fungal Material

Figure 14:
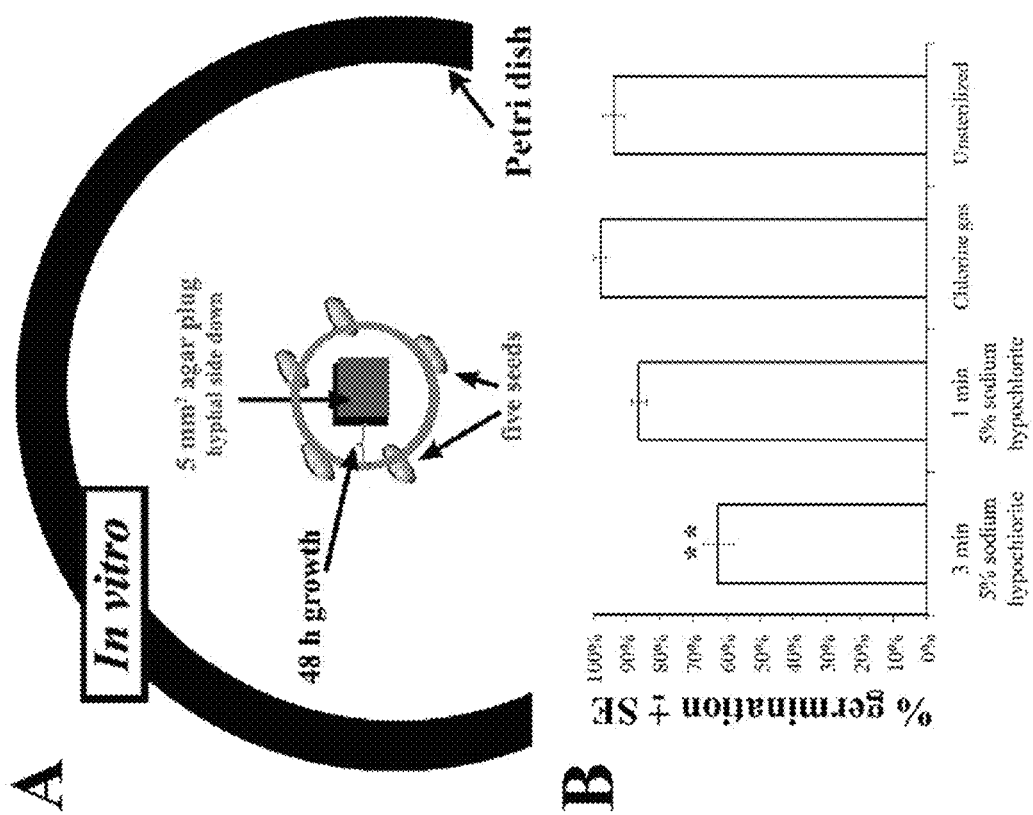
FIG. 14 shows an in vitro inoculation method (A). A 5 mm$^2$ agar plug, cut from the margin of the parent colony, was placed hyphal side down in the centre of a 60 mm Petri dish containing potato dextrose agar (PDA) media. Next, five surface-sterilized seeds were placed a distance equivalent to 48 h hyphal growth from the agar plug and germinated in the dark. The impact of three seed surface sterilization methods on seed germination (B). Bars labeled with one or two asterisks (*) are significantly, or highly significantly, different from the same endophyte grown under control conditions ($p \leq 0.05$ or $p \leq 0.01$, respectively; ANOVA, followed by post-hoc LSD test). Error bars represent standard error of the mean (SE).

The plant material used was the *durum* wheat cultivar AC Avonlea, which has low resistance to environmental stressors [SaskSeed guide 2008]. The seeds used in the first round of experiments were produced by Paterson Grain in 2008, under field conditions, and not certified to be free of microbes. Seeds used in the second set of experiments were produced by the Agriculture and Agri-Food Canada (AAFC) Seed Increase Unit Research Farm in 2006 under greenhouse conditions, and were certified to be free of microbes. Wheat seeds were surface-sterilized with 95% ethanol for 10 s, rinsed in sterile distilled water for 10 s, submerged for either 3 min (first round of experiments involving seeds not certified to be free of microbes) or 1 min (second round of experiments using seeds certified to be microbe-free) in 5% sodium hypochlorite (Javex), rinsed three times in sterile distilled water and PDA for germination [Abdellatif et al. 2009]. A third seed sterilization method, involving a 3 hr exposure to chlorine gas (produced by combining 25 mL 6% sodium hypochlorite with 1.0 mL concentrated hydrochloric acid in a beaker) in a closed plastic box placed in a fumehood [Rivero et al. 2011] was also tested. The percent germination of seeds subjected to each sterilization protocol and placed on PDA for three days is shown in FIG. 14B. Only the 3 min submersion in sodium hypochlorite resulted in a significant decrease in germination (p≤0.01). Seed surface sterilization was intended to eliminate microbes which could compete with the endophytes being investigated. In addition, microbes present on the surface of the seeds could overgrow the plate and emerging seedling, inhibiting plant growth. All seeds used in the study were determined to be free from microorganisms after sterilization, based on the absence of unintended microbial growth on the plate.

Four endophytic Ascomycota mitosporic fungal isolates (classified according to Kiffer and Morelet [2000]): SMCD 2204, SMCD 2206, SMCD 2208, and SMCD 2210, plus the Actinomycetes filamentous gram positive bacterial isolate SMCD 2215; compatible with *Triticum turgidum* L. [Abdellatif et al. 2009] were used in this study. Endophytes were grown on PDA for at least three days at room temperature in darkness prior to experimental use.

Endophytes as Free-Living Organisms

Agar plugs (5 mm$^2$) cut from the margins of the parent colony were placed in the centre of a 90-mm Petri dish containing either PDA alone or amended with 8% PEG (drought). The Petri dish was sealed with parafilm (Pechiney Plastic Packaging) to maintain sterility and placed in a bench-top incubator (Precision Thermo Scientific, model 3522) at either 23° C., or under heat stress, 36° C., in darkness. The diameter of the colony was measured at 24, 48, 72, 96 h, and five and six days. The changes in diameter were used to calculate colony growth rate. The growth of a minimum of three replicates per isolate was measured.

Endophytes Ability to Confer Heat and Drought Tolerance to Wheat

Each isolate was applied individually to wheat seeds prior to germination according to the method described in Abdellatif et al. [2010] and shown in FIG. 14A. Briefly, five surface-sterilized seeds were placed at a distance equivalent to 48-h hyphal growth from a 5 mm$^2$-agar plug, placed hyphal side down in the centre of a 60-mm Petri dish. For slow growing isolates, the agar plug of endophyte colony was placed in the Petri dish one to four days prior to the introduction of the seeds. The seedlings were germinated for one week under abiotic stress and control conditions.

Drought stress was induced using PDA containing 8% PEG. Heat stress was induced in a bench-top incubator in darkness; the temperature was gradually raised by 2° C. every 2 h from 28° C. to 36° C. In the initial round of experiments, percent germination at three days and fresh weight at one week was assessed. Each experiment consisted of six Petri plates and was repeated, independently, three times. In subsequent experiments, percent germination was assessed every 24 hrs for seven days. Each experiment consisted of 10 Petri plates and was repeated either twice (heat and drought stress combined) or three times (heat stress, drought stress and control conditions).

The stable internal colonization of wheat roots by the intended endophytes was confirmed by re-isolation of the endophytic organism from roots which had been surface sterilized to remove an external microbial growth using a procedure modified from Larran et al. [2002]. Root fragments (~0.5 cm) were surface sterilized in 95% ethanol for 10 s, rinsed in sterile distilled water for 10 s, submerged for 20 s in 5% sodium hypochlorite (Javex), rinsed three times in sterile distilled water and placed on PDA in a 60 mm diameter Petri dish. The Petri dish was sealed with parafilm and incubated in the dark at room temperature for four to seven days prior examination.

Statistical Analysis

The colony growth rates of free-living endophytic organisms grown under heat or drought stress were compared to those of the same organism grown under control conditions using analysis of variance (ANOVA) followed by post-hoc Fischer's' least significant difference (LSD) test. Percent germination data was subjected to arcsine transformation prior to statistical analysis [McDonald 2009]. Statistical differences between percent germination after both three and seven days, and fresh weight at seven days were assessed using a single factor ANOVA to compare all treatments. Subsequently, a post-hoc LSD test was used to evaluate the significance of differences between the no endophyte control and seeds treated with each mycobiont. The level of statistical significance associated with differences between the EG and HTT required to reach 50% germination of endophyte-colonized and control seeds were assessed by evaluating the EG for each of the three independent replicates of the experiment. The resulting data were subjected to an ANOVA and post-hoc LSD analysis. P-values less than 0.05 and 0.01 were considered to be significant and highly significant, respectively. Statistical tests were run with SPSS Inc. 2011.

Results

Within each section, the results are organised according to the type of stress: heat, drought, heat and drought, or no stress. Within each stress, the results dealing with plant material are presented according to the germinant and/or seedling traits measured: percent germination at three and seven days, fresh weight at seven days, EG and HTT.

Free-Living Endophytes

Figure 15:
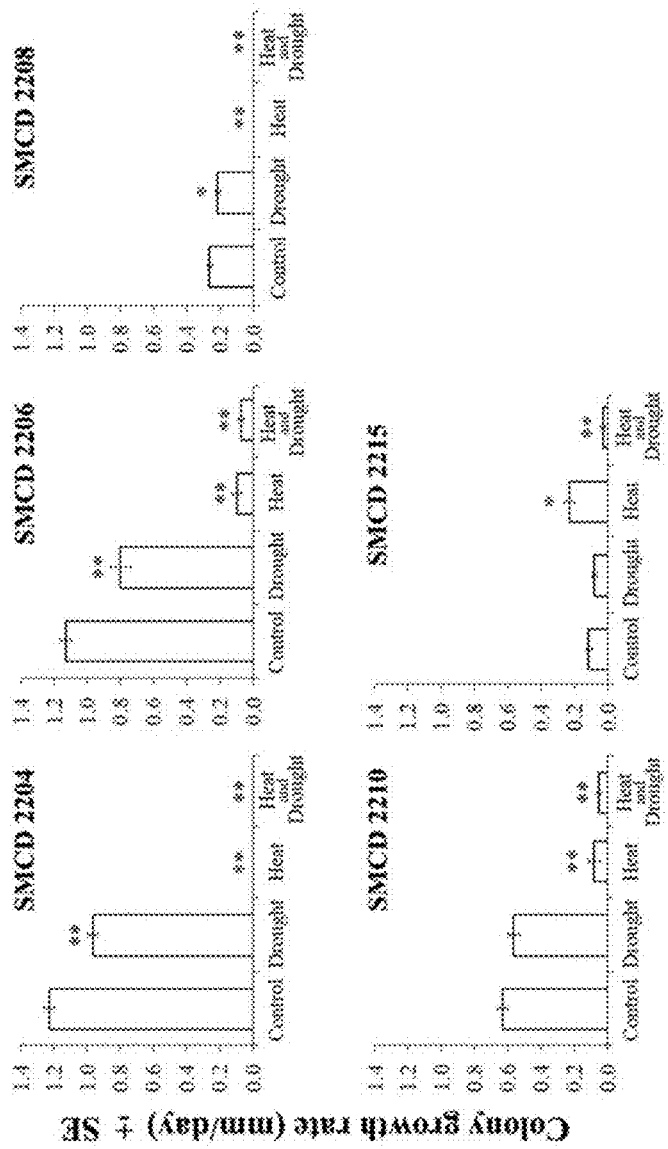
FIG. 15 shows growth rates of free-living endophytes SMCD 2204, 2206, 2208, 2210, and 2215 in vitro on potato dextrose agar (PDA) under heat stress (36° C.), drought (8% polyethylene glycol (PEG) 8000) stress and control conditions for five days and simultaneous heat (36° C.) and drought (8% PEG) for six days. Bars labeled with one or two asterisks (*) are significantly, or highly significantly, different from the same endophyte grown under control conditions ($p \leq 0.05$ or $p \leq 0.01$, respectively; ANOVA, followed by post-hoc LSD test). Error bars represent standard error of the mean (SE).

The phenotypes of SMCD 2206, 2210 and 2215 were not altered by heat (36° C.), while SMCD 2204 and 2208 did not grow at 36° C. The colony growth rates of SMCD 2206 and 2210 were reduced by 36° C. as compared to non-stressed conditions (p 0.01), while the growth rate of SMCD 2215 at 36° C. was increased (p≤0.05) (FIG. 15). At 36° C. SMCD 2215 grew the most rapidly, followed in decreasing order by 2206 and 2210 (FIG. 15).

The morphology of SMCD 2204, 2206, 2208 and 2215 was not appreciably altered by drought (8% PEG). However, when SMCD 2210 was exposed to drought, this organism lost its "woolly" appearance and instead acquired a "shiny" or "slimy" appearance. The colony growth rates of SMCD 2204, 2206, and 2208 were reduced by drought (p≤0.01, p≤0.01, and p≤0.05 respectively), while the rate of colony growth of all other endophytes remained unchanged (FIG. 15). When drought stress was applied, SMCD 2204 grew at the highest rate followed in decreasing order by 2206, 2210, 2208 and 2215 (FIG. 15).

When challenged by 36° C. heat and drought (8% PEG) simultaneously, SMCD 2204, and 2208 failed to grow, while SMCD 2206, 2210 and 2215 grew at a significantly slower rate than under control conditions (p≤0.01) (FIG. 15). In control conditions, SMCD 2204 grew the fastest, followed in decreasing order by SMCD 2206, 2210, 2208 and 2215 (FIG. 15).

Response of Endophyte-Colonized Wheat to Heat

Figure 16:
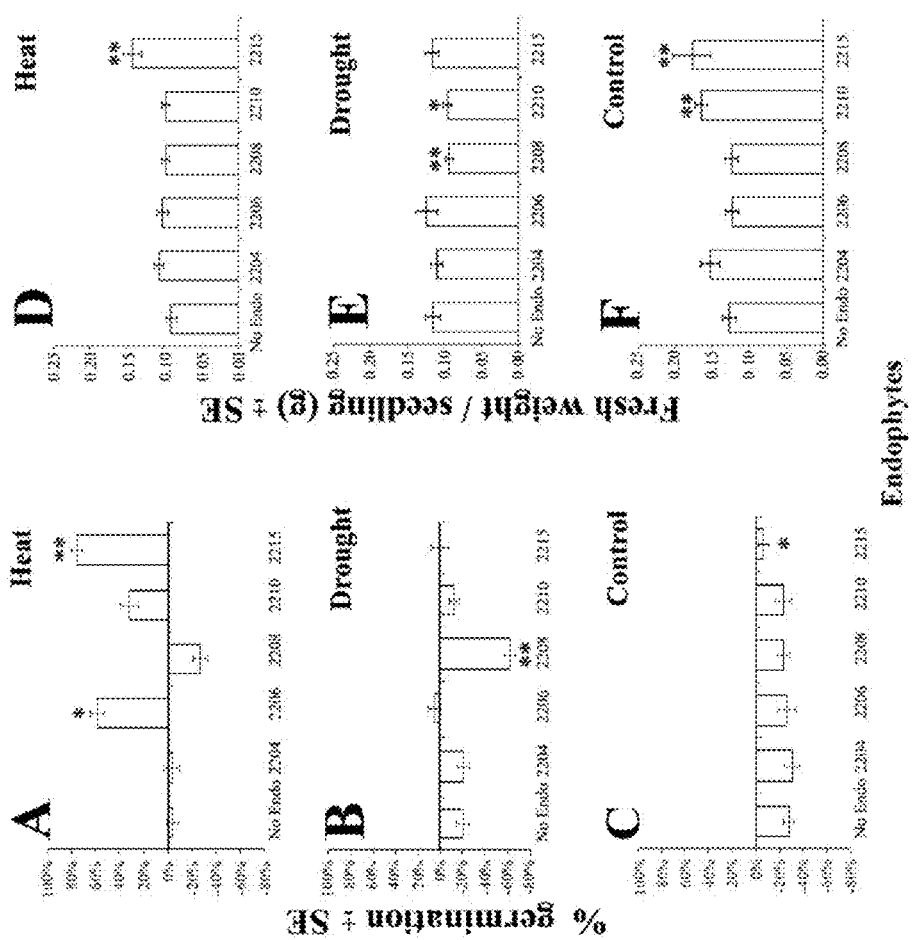
FIG. 16 shows percent germination and fresh weight of seedlings from initial experiments in which seeds were surface sterilized in 5% sodium hypochlorite for 3 min. Percent germination of wheat seeds in vitro after three days on potato dextrose agar (PDA) under heat stress (36° C.), drought stress (8% polyethylene glycol (PEG) 8000) and control conditions (A, B and C) with the y axis normalized to percent germination obtained under the same conditions by seeds surface sterilized in 5% sodium hypochlorite for 1 min. Fresh weight of seedlings in vitro at seven days on PDA under heat stress, drought stress and control conditions (D, E and F). Bars labeled with one (*) or two asterisks (**) are significantly, or highly significantly, different from the no endophyte control (p≤0.05 or p≤0.01, respectively; ANOVA, followed by post-hoc LSD test). Error bars represent the standard error of the mean (SE).
Figure 17:
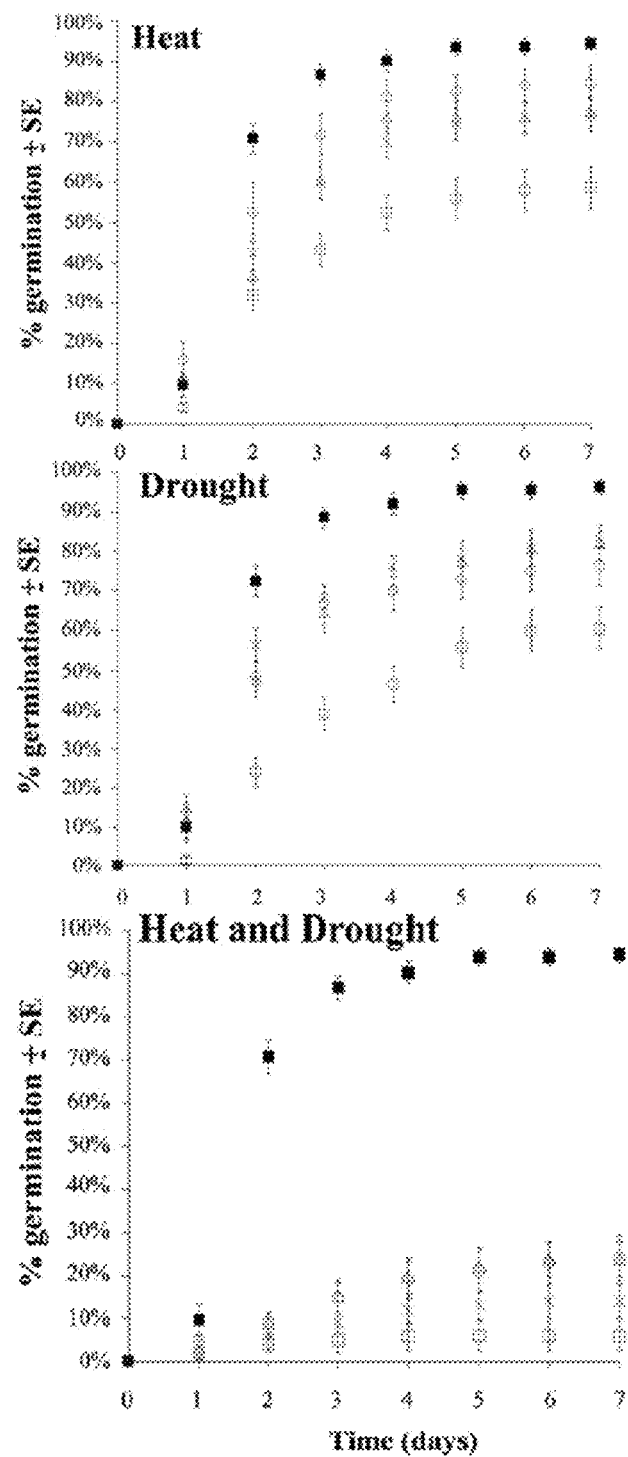
FIG. 17 shows percent germination over time of wheat seeds co-cultured with the endophytes most effective at conferring abiotic stress tolerance (SMCD 2206, 2210 and 2215) compared to uncolonized, unstressed seeds (positive control) and uncolonized, stressed seeds (negative control). Energy of germination (EG) is related to the time, in days (x axis) at which 50% germination (y axis) is reached. The symbols "■", "x", "○", "∆", and "□" represent the positive control, SMCD 2206 treated seeds, SMCD 2210 treated seeds, SMCD 2215 treated seeds and the negative control, respectively. Heat and drought treatments correspond to 36° C. and 8% polyethylene glycol (PEG) 8000, respectively. Error bars represent the standard error of the mean (SE). Note: The seeds used in EG determination were from the second round of experiments, and hence sterilized in 5% sodium hypochlorite for one minute, rather than three.

At 36° C., colonization by SMCD 2206 and 2215 increased germination after three days (p≤0.05 and p≤0.01, respectively; FIG. 16A), whereas SMCD 2204, 2208 and 2210 did not alter this parameter (p≥0.1; FIG. 16A). After seven days, 63% and 56% of seeds germinated in co-culture with SMCD 2204 and 2208, respectively. These values were not statistically different (p>0.1) from the 59% germination achieved by the uncolonized control. In contrast, the endosymbionts SMCD 2206, 2210 and 2215 promoted germination after seven days (p≤0.01; FIG. 17).

When subjected to 36° C., the fresh weight of wheat seedlings was stable in co-culture with SMCD 2204, 2206, 2208, and 2210, while SMCD 2215 significantly increased this parameter (p≤0.01 respectively; FIG. 16D).

The EG for wheat seeds co-cultured at 36° C. with fungal endophyte SMCD 2210 (p≤0.05; Table 3, FIG. 17) improved compared to endophyte-free seeds. However, SMCD 2204, 2206, 2208 and 2215 did not alter EG (p>0.1; Table 3) relative to the control. SMCD 2210 augmented the EG to the greatest extent, followed by SMCD 2206 and 2215 (Table 3). SMCD 2210 reduced the time required for 50% of seeds to germinate to a mere two days.

Figure 18:
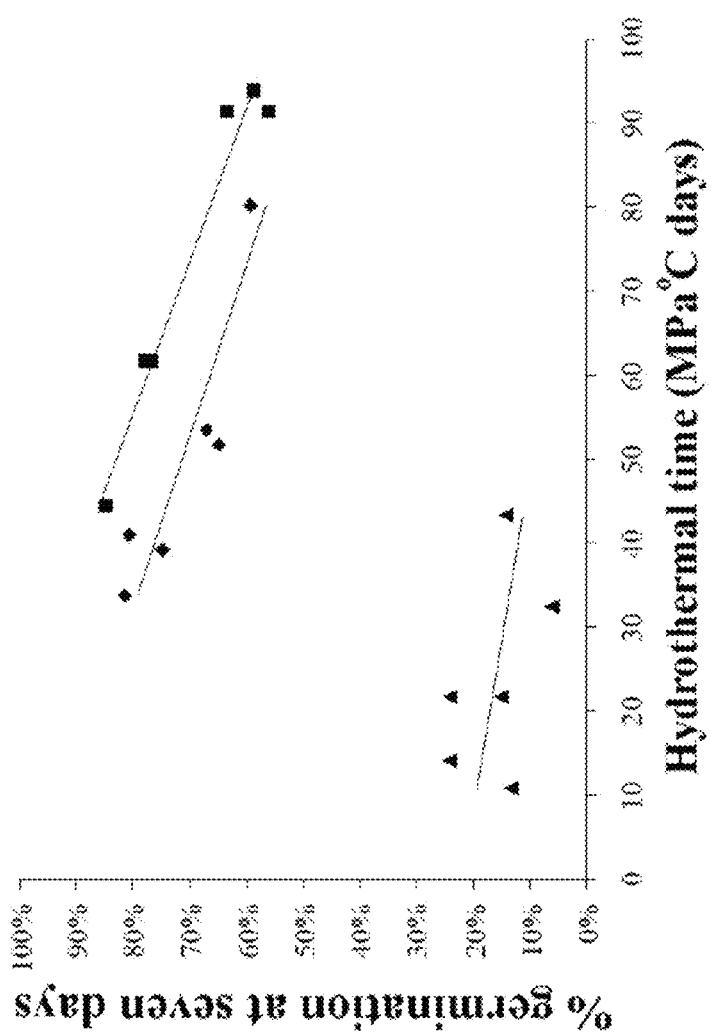
FIG. 18 shows the relationship between hydrothermal time (HTT) required to achieve 50% germination for heat and drought alone and 5% germination for heat and drought combined (x axis) and percent germination attained after seven days (y axis). Germination after seven days and HTT were based on the results of the second round of experiments. The symbols "■", "♦" and "▲" represent seeds exposed to heat (36° C.), drought (8% polyethylene glycol (PEG) 8000) or both heat and drought stress, respectively. The R-squared values associated with the trendlines are 0.96, 0.80 and 0.18 for seeds exposed to heat, drought or both heat and drought stress, respectively. Note: The seeds used to determine percent germination at seven days and HTT were from the second round of experiments, and hence treated with 5% sodium hypochlorite for one minute, rather than three.

When exposed to heat stress, the HTT required for germination was reduced for wheat seeds colonized by SMCD 2210 (p≤0.05; Table 3), but not any of the other endophytes tested (p>0.1; Table 3). Endophyte-free wheat seeds needed 50 MPa ° C. days more than seeds colonized by SMCD 2210 (the most effective endophyte tested) to achieve 50% germination (Table 3). There was a clear, negative, linear correlation between the HTT necessary for 50% germination and the percent germination after seven days under heat stress (FIG. 18).

Response of Endophyte-Colonized Wheat to Drought

When subjected to drought stress for three days, a diminished percentage of wheat seeds germinated in co-culture with SMCD 2208, compared to endophyte-free seeds (p≤0.01; FIG. 16B), while SMCD 2204, 2206, 2210, and 2215 did not alter this trait (p>0.1; FIG. 16B). After seven days, treatment with SMCD 2206, 2210 and 2215 led to an increase in seed germination (p≤0.01, p≤0.05, and p≤0.01, respectively; FIG. 17). In contrast, 65 and 67% of seeds co-cultured with SMCD 2204 and 2208 had germinated after seven days. Neither of these values differed statistically from the 59% of uncolonized seeds that germinated under the same conditions (p>0.1). Under drought conditions, SMCD 2208 and 2210 decreased fresh weight after seven days (p≤0.05 and p≤0.01. respectively; FIG. 16E). None of the other mycobionts altered this parameter (p>0.1; FIG. 16E).

The EG decreased for wheat seeds co-cultured in drought conditions with all endophytes tested, as compared to endophyte-free seeds (0.05≤p≤0.1 for SMCD 2204 and 2208 and p≤0.05 for 2206, 2210 and 2215; Table 3). SMCD 2206 improved the EG to the greatest extent, decreasing the time elapsed before 50% germination was achieved after 2.6 days (Table 3; FIG. 17).

The HTT required for germination was reduced for wheat seeds treated with all endophytes tested under drought stress (Table 3). While uncolonized seeds needed 80 MPa ° C. days to achieve 50% germination, seeds colonized by endophyte SMCD 2206 (the most effective endophyte tested) required only 34 MPa ° C. days, representing a drop of 46 MPa ° C. days (Table 3). There was a visible, negative, linear correlation between the HTT required for 50% germination and the percent germination at seven days under drought stress (FIG. 18). However, the $R^2$ value associated with this linear relationship was smaller than for the correlation found under heat stress. The ranges of HTTs needed to achieve 50% germination differ between heat and drought stress, with values between 34 and 44 MPa ° C. days and 80 and 94 MPa ° C. days being unique to seeds exposed to drought and heat stress, respectively (FIG. 18; Table 3). The ranges of percent germination after seven days are similar between seeds exposed to drought and those subjected to heat, though the germination levels of heat-stressed seeds cover a slightly larger range (FIG. 18).

Response of Endophyte-Colonized Wheat to Drought and Heat in Combination

Very few wheat seeds germinated when exposed to drought (8% PEG) and heat stress (36° C.) simultaneously (FIG. 17). Colonization by endophytes SMCD 2210 and 2215 increased the percent germination after seven days (p≤0.01; FIG. 17). On the other hand, SMCD 2204, 2206 and 2208 failed to improve this trait (p>0.1). Seeds co-cultured with SMCD 2215 (the most beneficial microorganism tested for this parameter) reached 24% germination, four times the level attained by their endophyte-free counterparts (FIG. 17).

Because neither uncolonized seeds nor those colonized by any of the endophytes reached 50% germination within seven days, EG could not be determined and HTT was calculated for 5%, rather than 50%, germination. The time required to reach 5% germination ranged from 24 h to four days. None of the endophytes tested decreased the time required to attain 5% germination or HTT values (p>0.1). Overall, the HTT needed to reach 5% germination varied from 11 to 43 MPa ° C. days ($HTT_{mean}=23.9$) (FIG. 18; Table 3).

The range of HTT values for seeds subjected to both heat and drought stress were unique, as compared to the HTT values when either heat or drought was applied alone. There was a negative, linear relationship between HTT required and the percent germination under combined heat and drought stress. However, the $R^2$ value associated with this linear relationship was smaller than for the correlation found when either heat or drought stress was applied individually (FIG. 18).

Response of Endophyte-Colonized Wheat to Control Conditions

Under non-stressed conditions, SMCD 2215 significantly increased seed germination compared to uncolonized seeds after three days (p≤0.01) (FIG. 16C). SMCD 2206, 2208 and 2210 positively impacted, whereas SMCD 2204 did not alter percent of germination. In unstressed conditions, SMCD 2204, 2210 and 2215 increased the fresh weight of wheat seedlings after seven days (p≤0.05 and p≤0.01, respectively). Furthermore, SMCD 2206 and 2208 showed no impact on the fresh weight as compared to uncolonized seedlings (FIG. 16F).

In control conditions, EG and HTT parameters were slightly improved by SMCD 2206 and 2215 endosymbionts (Table 3). Relatively little alteration in EG and HTT parameters was measured associated with non-stressed wheat seeds in co-culture with different isolates.

Example 5

Figure 19:
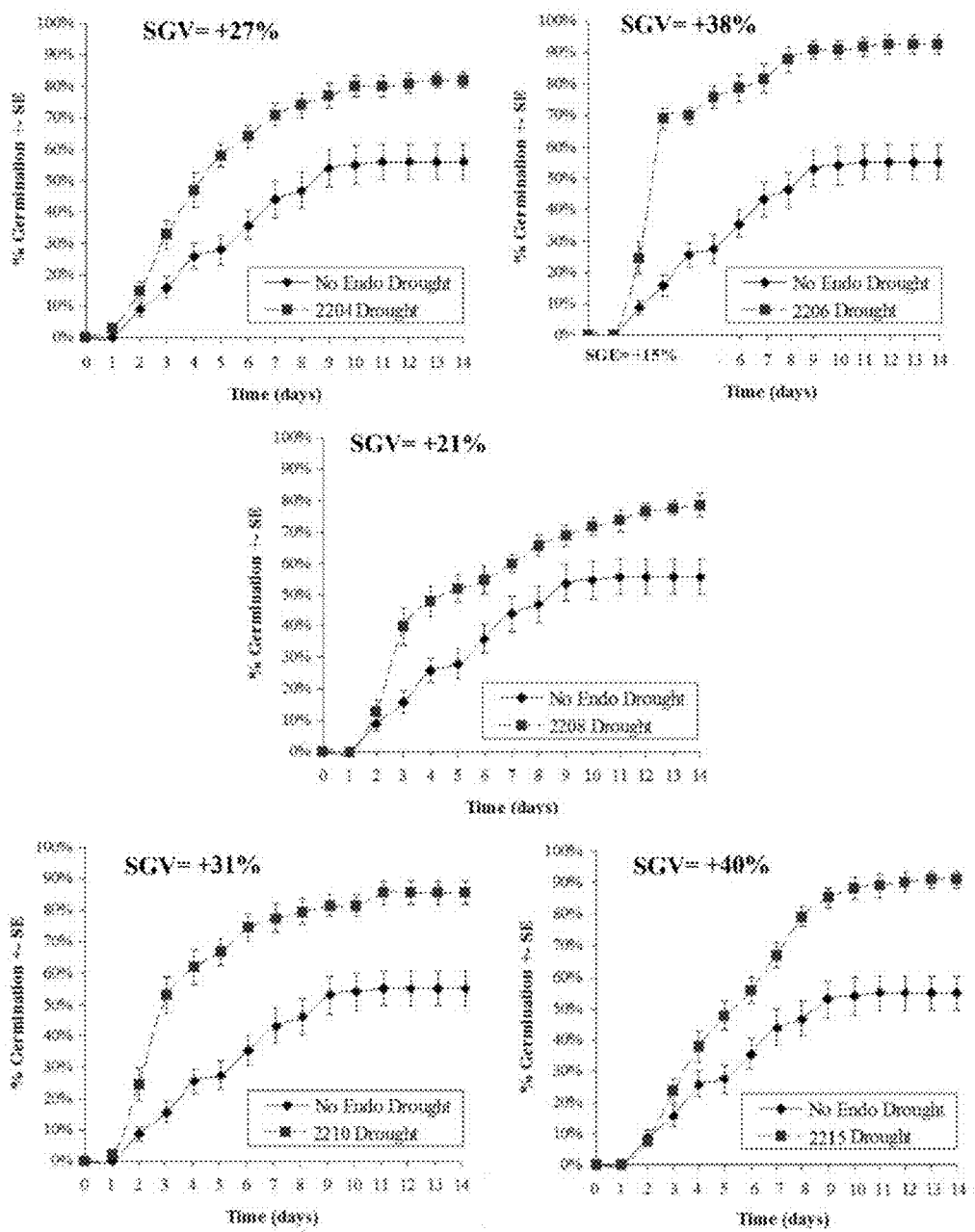
FIG. 19 shows seeds treated or inoculated with SMCD strains demonstrate improvement in all tested seed germination parameters including seed germination vigour (SGV) efficacy.
Figure 20:
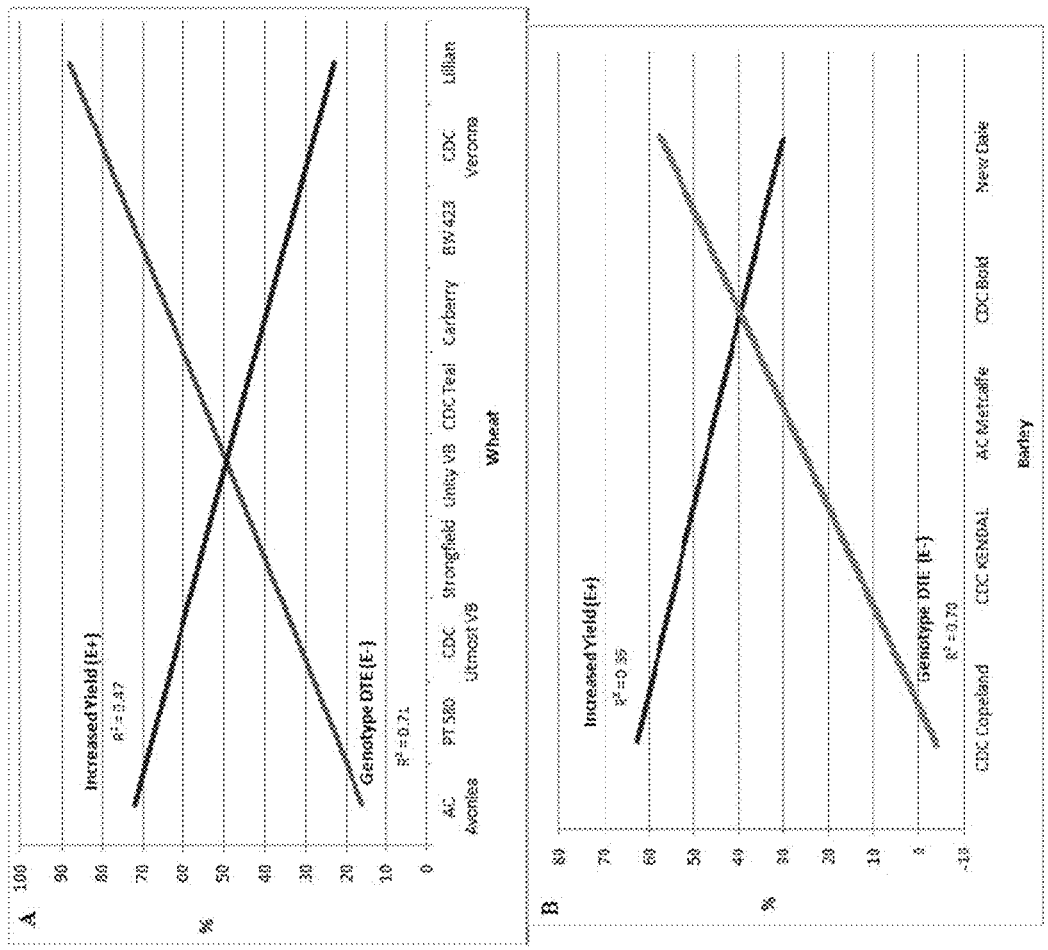
FIG. 20 shows the relationship between drought tolerance efficiency (DTE) values in wheat (A) and barley (B) cultivars without (E−) and with (E+) endophytes, based on the average effect of symbiosis using all tested SMCD isolates, on yield exposed to drought stress in greenhouse.
Figure 21A:
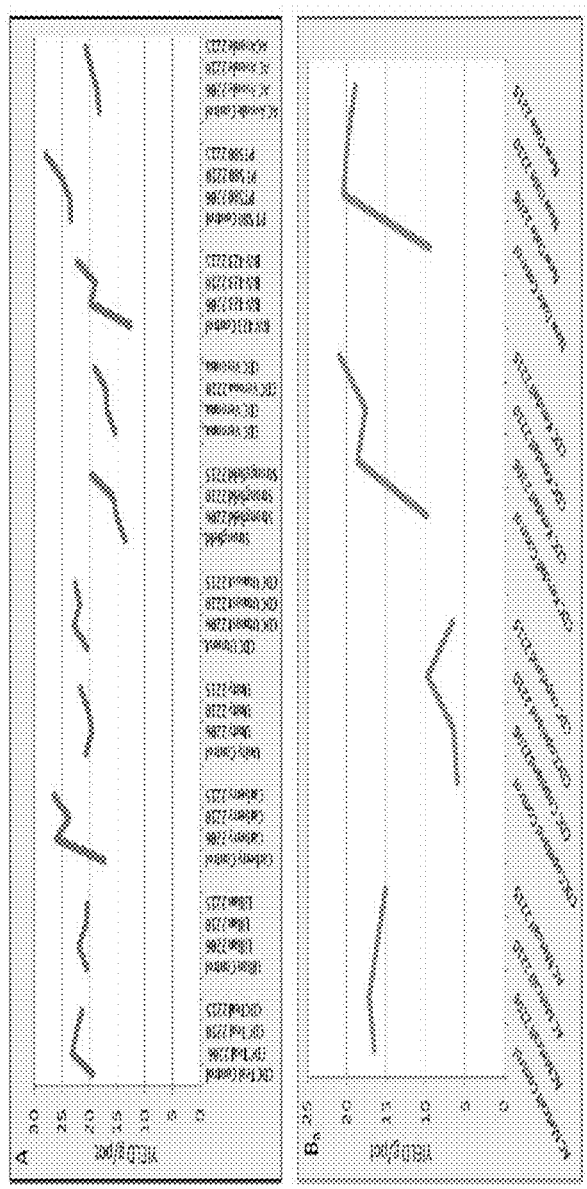
FIG. 21A shows endophytic (E+) inoculants (SMCD 2206, SMCD 2210, and SMCD 2215) improve kernel yield in wheat genotypes compared to control (E−) treatment (yield g/3 pots).
Figure 21B:
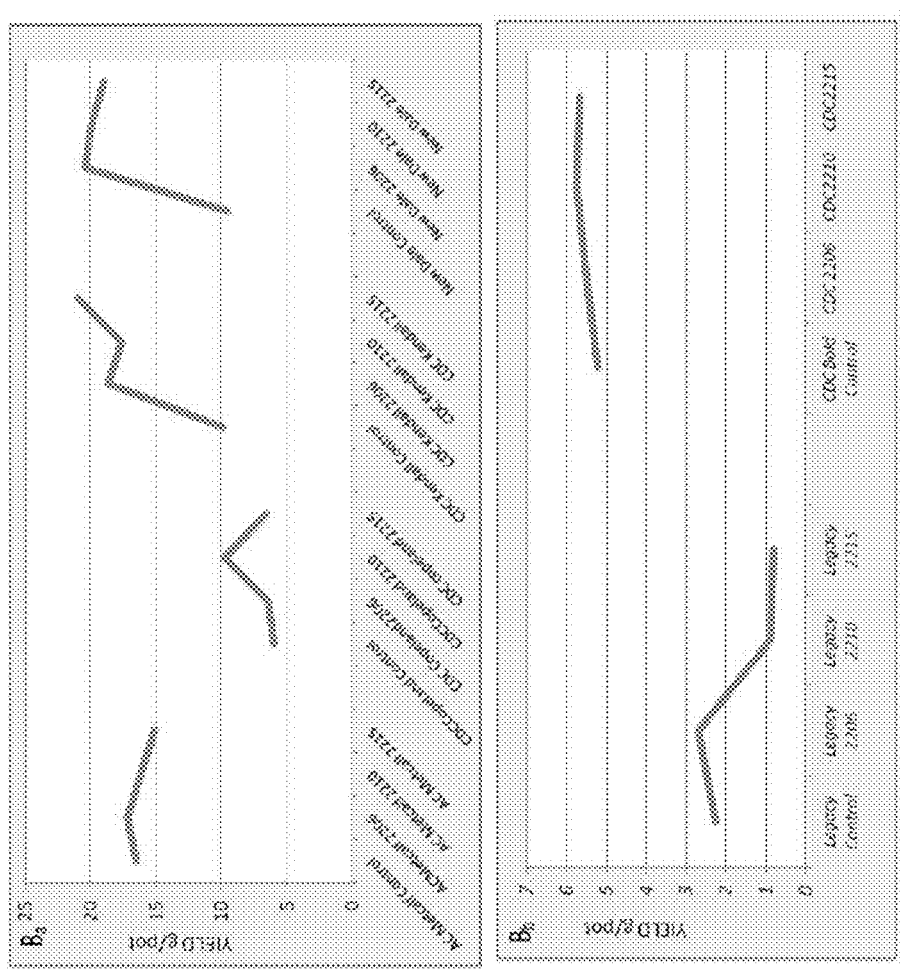
FIG. 21B shows endophytic inoculants (SMCD 2206, SMCD 2210, and SMCD 2215) improve kernel yield in two row barley ($B_a$) and six row barley ($B_b$) genotypes (kernel yield: 3plants/pot).

Endophytes Enhance Yield of Wheat and Barley Genotypes Under Severe Drought Stress Summary:

Due to climate change and population growth, the development of techniques increasing agriculture crop tolerance in stressful environments is critical. Inoculation with three symbiotic endophytes, indigenous to the Canadian prairies, increases wheat and barley resistance to heat or drought stress, as well as grain yield and seed weight. The use of such fungal and bacterial endophytes in the field has the potential to increase the seed germination vigour (SGV=difference between total percentage of E− germinating seeds and E+germinating seeds) (FIG. 19, FIGS. 20A and B), and to enhance yield in stress-prone conditions (Table 4; FIGS. 21 A, Ba, and Bb). Evidence supports that SMCD strains increase seed-vitality and plant vigour (FIG. 22A-D). Overall results demonstrate that the prenatal care of seed using endophytic microbes, particularly SMCD strains, ensures superior crop yield of wheat and barley genotypes through physiological improvements.

Materials and Methods

Seeds of the wheat and barley cultivars were produced at University of Saskatchewan experimental plots and Crop Science Field Laboratory (Saskatoon). Visually healthy seeds were surface sterilized in 95% ethanol for 10 s, rinsed in sterile distilled water for 10 s, submerged for 1 min in 5% sodium hypochlorite (Javex) and then rinsed three times in sterile distilled water.

The endophytic isolates used in this study were originally isolated from the roots of *durum* wheat *Triticum turgidum* L. grown at field sites in Saskatchewan, Canada [Vujanovic 2007b]: SMCD 2204, 2206, 2208, 2210, 2215. All endophytic isolates are culturable on potato dextrose agar (PDA; Difco) in the absence of a host plant. Isolates were grown on PDA for three days at room temperature (23° C.) in darkness prior to experimental use.

The experiment inoculations were done in pots. Each of the endophytic isolates was applied to cereal (wheat and barley) seeds prior to germination according to the method described in Abdellatif et al. [2010]. Briefly, five surface-sterilized seeds were positioned at a distance equivalent to 48 h hyphal growth from a 5 mm² agar plug, placed hyphal side down in the centre of a 2 L plastic pot filled with 300 grams (dry weight) of autoclaved, field capacity Sunshine mix 4 potting soil. The seeds and agar plug were then covered with a 3.5-4.0 cm layer of Sunshine mix 4. Five seeds were planted per pot and there were twelve pots per treatment. Pots containing plants were placed in a greenhouse for drought stress and control treatments. The pots were arranged in a randomized block design.

Drought stress was induced from May to September when night-day maximum temperatures in the greenhouse ranged from 18 to 26° C. On sunny days, natural sunlight provided irradiation, while on cloudy or winter days with a shorter photoperiod, 1000 watt high pressure sodium light bulbs, suspended from the ceiling roughly 2 m above the plants, supplemented sunlight. In the first experiment, drought stressed and control (well watered) plants were grown at 25% soil water content by weight and 100% water retention capacity, respectively. During the experiment control plants were watered to 100% water retention capacity three times per week, while drought stressed plants were water to 100% water retention capacity weekly. This drought regime was adopted in order to mimic the natural cycle of drought that can occur during the growing season in North American prairies [Chipanshi et al. 2006].

Mature spikes were collected and dry kernels weighed on a Mettler Toledo PG802-S balance in laboratory.

Results and Discussion

Increased Wheat Seed Germination Vigour (SGV)

Under in vitro control conditions, SMCD (2204, 2206, 2208, 2210, 2215) treated wheat seeds germinated consistently faster, more uniformly, and with much higher SGE (seed germination efficacy). The SGV of seeds inoculated with SMCD (E+) was 15% to 40% greater compared to untreated (E−) seeds (FIG. 19), demonstrating SMCD's efficacy in controlling seed dormacy and enhancing seed vigor. Positive effects of SMCD strains on yield of wheat and barley genotypes under severe drought were also demonstrated.

Barley genotypes generally show higher drought susceptibility (low DTE (Drought Tolerance Efficacy) values) and lower yield performance than wheat (Table 4), possibly due to the extreme drought conditions in the greenhouse more fitting to wheat. In particular, CDC Kendall-two row barley, without endophyte (E−), shows high susceptibility to drought stress compared to other barley genotypes. However, the endophyte treatments (E+) demonstrate a remarkable positive effect on yield of all genotypes (Table 4). Conferred resistance ranges from low drought resistant CDC Kendall to highly resistant New Dale genotypes, whereas conferred resistance to wheat was consistently high.

During the maturity stage of wheat and barley, SMCD endophytes dramatically increase the genotypes drought tolerance parameters such as DTE efficacy and yield. SMCD application on Avonlea, the most drought susceptible wheat cultivar detected (DTE=16.1), resulted in a high increase in yield (77%) under drought conditions compared to control or standard watering. Carberry profited the most from endophytes under control or normal conditions, whereas CDC Utmost VB and BW 423 performed equally well under both dry and control conditions.

In conclusion, combining drought resistant genotypes with compatible endophytic SMCD 2206, SMCD 2210, and SMCD 2215 microbial symbionts maximizes plant drought resistance, an important aspect in ensuring food security. Without wishing to be bound by theory, this suggests that the most drought susceptible (low DTE values) wheat (FIG.

19A) and barley (FIG. 19B) cultivars will gain the most from the symbiotic association when exposed to the drought stress.

The only exception seemed to be the six row barley genotype Legacy showing an extremely low DTE=1.1. Although it responded positively to the endophyte presence with increased yield of 26.9% under control conditions, it ameliorated yield only for 5% in symbiosis under stress. Thus, this cultivar was excluded from the barley model presented in FIG. 19B.

Effect of Individual SMCD Strains on Wheat and Barley Productivity

Individual SMCD strains positively affect the average kernel yield of each genotype, although the actual magnitude varies by genotype-strain combination. FIG. 21 presents results obtained under drought conditions in the greenhouse (FIG. 21: A—Wheat; $B_a$—Barley (two row), and $B_b$—Barley (six row)).

Early seed contact with compatible SMCD isolates is a prerequisite for protecting crop against drought, resulting in a higher yield or production of kernels. SMCD 2206 generally confers the highest degree of improvement for most genotypes. However, strain-cultivar specificity ensures highest improvements on an individual basis, e.g. Wheat-PT580 and Barley-CDC Copeland prefer SMCD 2210; whereas Wheat-BW423 and PT580, as well as CDC Kendall show higher performance and drought resistance when inoculated with SMCD 2215.

Results highlight the importance of mycovitalism in stress-challenged wheat and barley seeds, assisting breeders in the making of highly productive cultivars capable of withstanding drought conditions significantly better than any cultivar alone (FIG. 22: A-D). Upon demonstrated performance of SMCD strains in fields, producers will have green symbiotic products to secure crop yield, and the agro-business will benefit from a guaranteed level of positive crop outcomes independent of fluctuations in environmental conditions.

Example 6

Phytotron Heat Stress Experiment on Pulses

This experiment was conducted under phytotron conditions. All seed varieties were inoculated with endophytes (SMCD 2204F, SMCD 2206, SMCD 2210, and SMCD 2215) and without endophytes in pots containing the soil mix. Details about the approaches used for endophyte inoculation on plant are described above under Example 5. Pots containing plants for heat stress were placed in a phytotron Conviron PGR15 growth chamber (Controlled Environments Ltd.) using a randomized block design. A temperature of about 33° C. was selected for heat stress. Plants were exposed to this temperature for 8 h, after which time the plants were exposed to a temperature of 21° C. for 16 h up to 10 days. After heat shock, temperatures were changed to 16° C. for 8 h and 21° C. for 16 h.

Results

Figure 23:
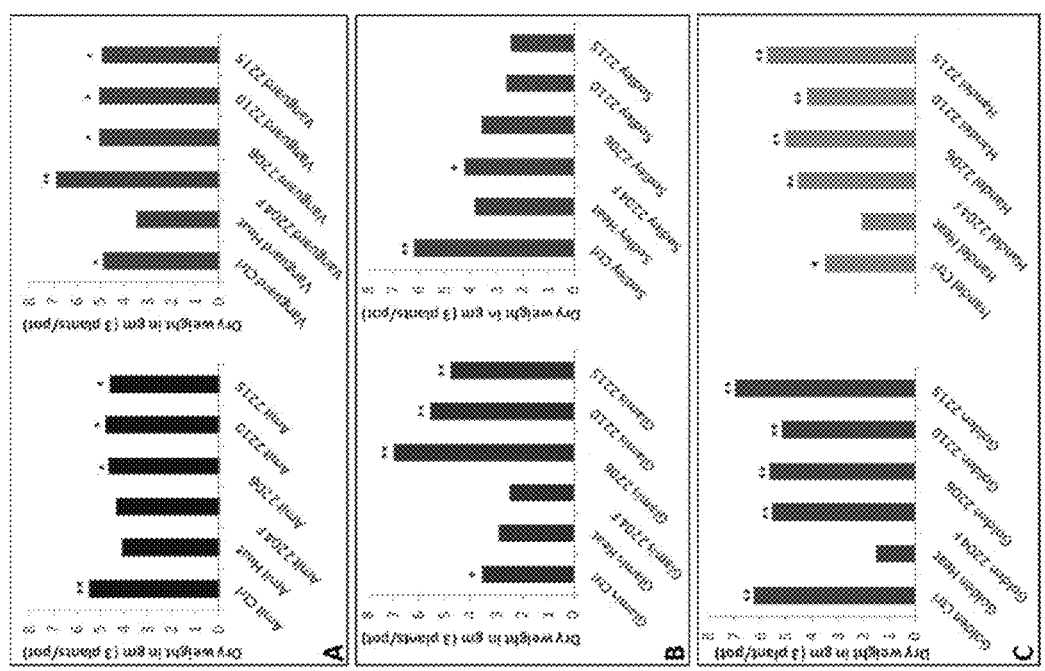
FIG. 23 shows stem dry weight of (A) chickpeas, (B) lentils, and (C) peas in symbiosis with SMCD endophytes (E+) under heat stress phytotron conditions. Bars labeled with one (*) or two asterisks (**) are significantly, or highly significantly, different from the no endophyte stressed control (p≤0.05 or p≤0.01, respectively; ANOVA, followed by post-hoc LSD test).
Figure 24:
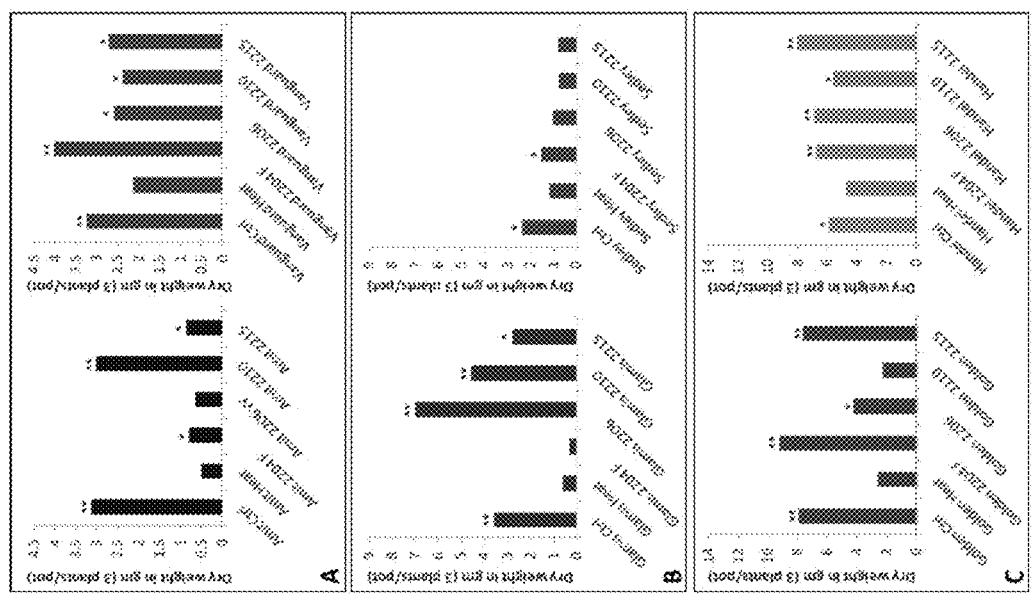
FIG. 24 shows pods dry weight of of (A) chickpeas, (B) lentils, and (C) peas in symbiosis with SMCD endophytes (E+) under heat stress phytotron conditions. Bars labeled with one (*) or two asterisks (**) are significantly, or highly significantly, different from the no endophyte stressed control (p≤0.05 or p≤0.01, respectively; ANOVA, followed by post-hoc LSD test).
Figure 25:
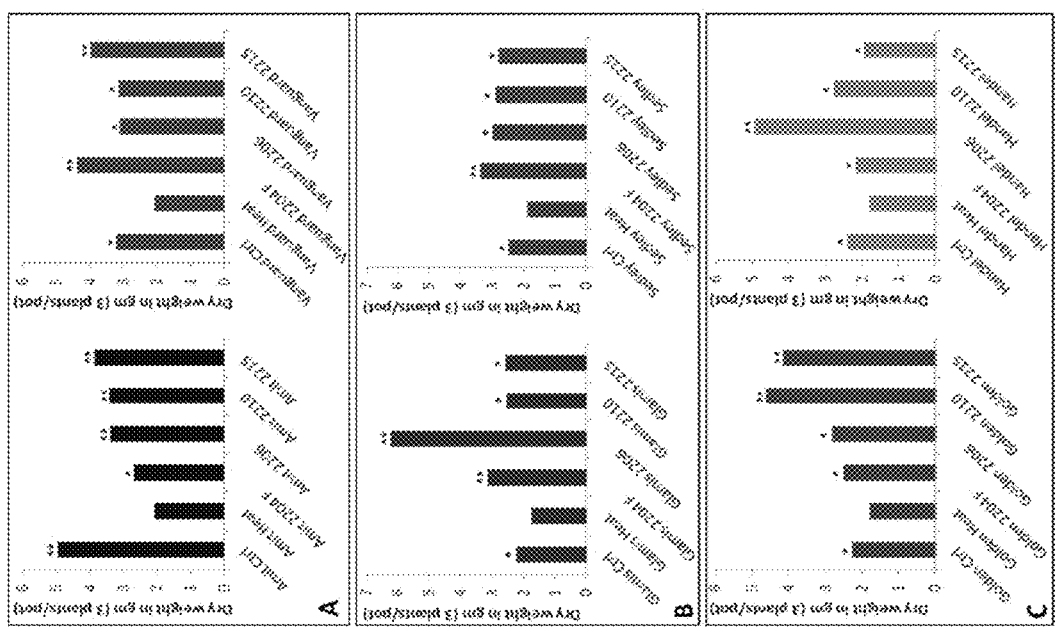
FIG. 25 shows roots dry weight of (A) chickpeas, (B) lentils, and (C) peas in symbiosis with SMCD endophytes (E+) under heat stress phytotron conditions. Bars labeled with one (*) or two asterisks (**) are significantly, or highly significantly, different from the no endophyte stressed control (p≤0.05 or p≤0.01, respectively; ANOVA, followed by post-hoc LSD test).

In summary, the results show that the efficacy of each tested endophyte in conferring heat stress tolerance is related to the particular plant genotype or host variety (A—chickpea, B—lentil, and C—pea), and that the improvement in the biomass is associated to a particular plant organ as each organ: pod (FIG. 23), stem (FIG. 24) and root (FIG. 25), is differentially impacted by heat stress.

SMCD 2215 mostly enhanced the biomass of the stem and pod in pea, and the biomass of root in chickpea. SMCD 2206 increased the biomass of the stem and pod in lentil, and the biomass of root in chickpea, pea, and lentil. SMCD 2210 mostly improved the biomass of the stem and pod in chickpea, and the biomass of root in pea. SMCD 2204F improved the biomass of pods in most of the tested crops (chickpea, pea, and lentil). The best performer endophyte-crop genotype combination (E+) showed an improvement of about 300% in the biomass of pod, stem, and root compared to no endophyte (E−) heat stressed control.

Stem:

The following endophytes showed the best response to heat stress: Chickpea: Amit: SMCD 2210. Vanguard: SMCD 2204F; Pea: Golden: SMCD 2215. Handel: SMCD 2215; and Lentil: Glamis: SMCD 2206. Sedley: SMCD 2206.

Pods:

The following endophytes showed the best response to heat stress: Chickpea: Amit: SMCD 2210. Vanguard: SMCD 2204F; Pea: Golden: SMCD 2204F. Handel: SMCD 2215; Lentil: Glamis: SMCD 2206. Sedley: SMCD 2204F.

Root:

The following endophytes showed the best response to heat stress: Chickpea: Amit: SMCD 2215. Vanguard: SMCD 2206; SMCD 2215; Pea: Golden: SMCD 2210; SMCD2215. Handel: SMCD 2206; Lentil: Glamis: SMCD 2206; Sedley: SMCD 2204F.

Example 7

Greenhouse Drought Stress Experiment on Pulses

Six seed varieties [Amit, Vanguard (chickpeas), Golden, Handel (peas) and Glamis, Sedley (lentils)] and endophytes SMCD 2204, SMCD 2204F, SMCD 2206, SMCD 2210, and SMCD 2215 were used in this study. These experiments were conducted in the greenhouse. After sowing the seed and inoculating endophytes, pots were allowed to stay without water for 14 days to mimic severe drought as proposed by Charlton et. al. [2008] and as per the methodology and conditions outlined by Gan et al. [2004].

Results

Figure 26:
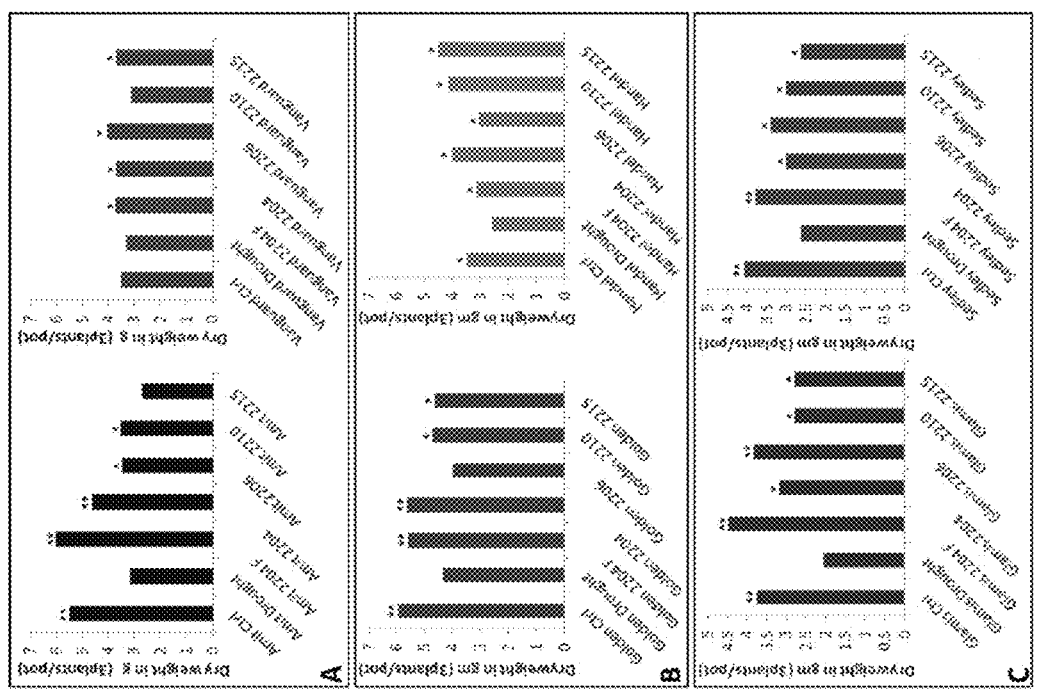
FIG. 26 shows stem dry weight of (A) chickpeas, (B) peas, and (C) lentils under drought stress in a greenhouse. Bars labeled with one (*) or two asterisks (**) are significantly, or highly significantly, different from the no endophyte (E−) stressed control (p≤0.05 or p≤0.01, respectively; ANOVA, followed by post-hoc LSD test).
Figure 27:
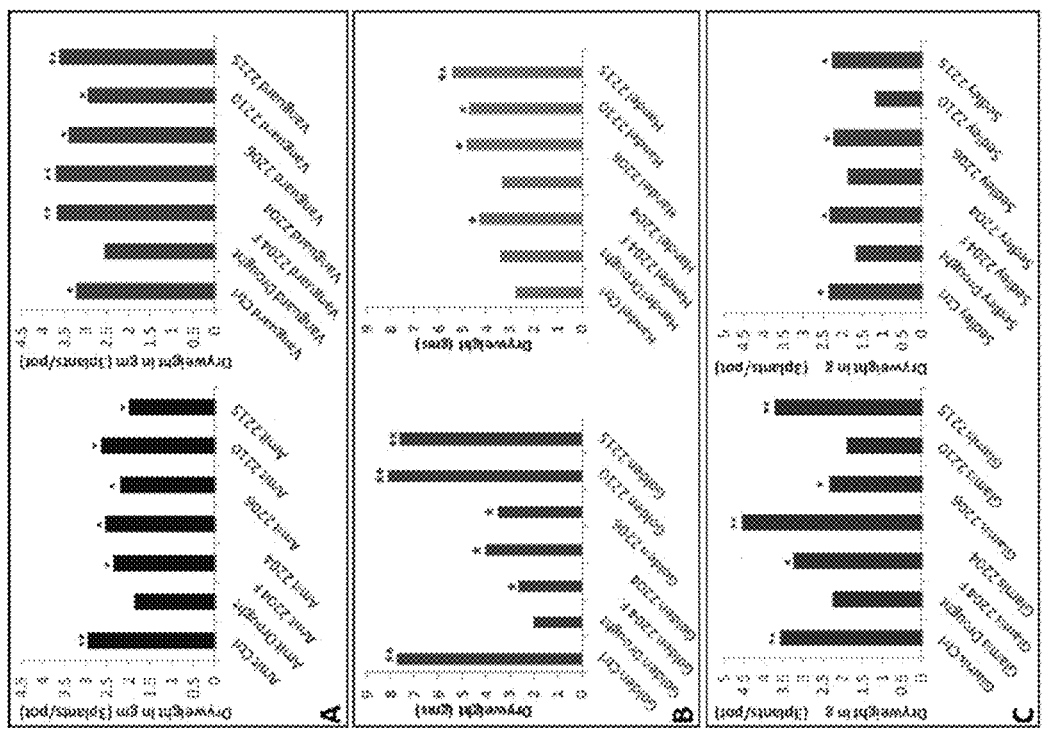
FIG. 27 shows dry weights of (A) chickpeas, (B) peas, and (C) lentils pods in association with an endophyte (E+) under drought stress in the greenhouse. Bars labeled with one (*) or two asterisks (**) are significantly different from the no endophyte (E−) stressed control (p≤0.05 or p≤0.01, respectively; ANOVA, followed by post-hoc LSD test).
Figure 28:
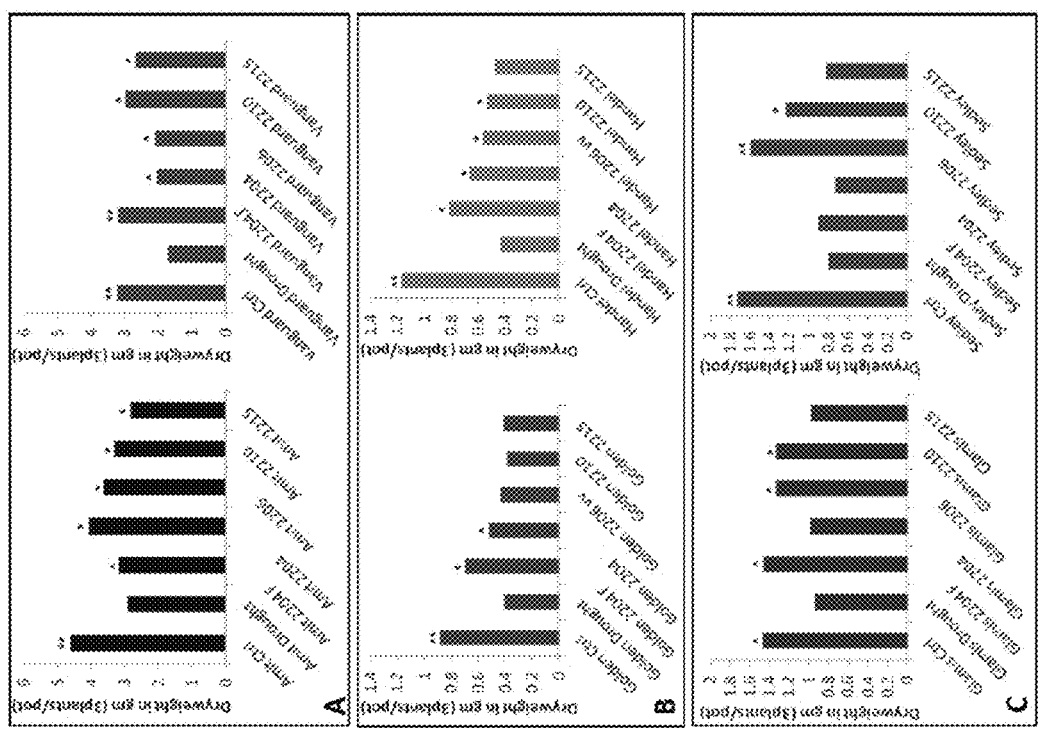
FIG. 28 shows roots dry weight of (A) chickpeas, (B) peas, and (C) lentils under drought stress in the greenhouse. Bars labeled with one (*) or two asterisks (**) are significantly, or highly significantly, different from no endophyte (E−) stressed control (p≤0.05 or p≤0.01, respectively; ANOVA, followed by post-hoc LSD test).

In summary, the results show that each SMCD strain positively affects several agricultural parameters on pod production or yield (FIG. 27), and biomass of stem (FIG. 26) and root (FIG. 28) in chickpea (A), pea (B), lentil (C) and under drought stress. Overall, crop genotypes colonised by the symbiotic endophyte (E+) became more resistant to drought vs. heat stress. The level of efficacy of the tested endophytes in conferring drought tolerance varied with the particular plant organ: the pod yield was highly improved in Glamis by SMCD 2204, in Vanguard by SMCD 2204F, in Sedley by SMCD 2206, in Golden by SMCD 2210, and in Handel by SMCD 2215.

Stem:

The following endophytes showed the best response to drought stress: Chickpea: Amit: SMCD 2204F, Vanguard: SMCD 2206; Pea: Golden: SMCD 2204, Handel: SMCD 2204; SMCD 2210; SMCD 2215; Lentil: Glamis: SMCD 2204F; SMCD 2206. Sedley: SMCD 2204F; SMCD 2206.

Pods:

The following endophytes showed the best response to drought stress: Chickpea: Amit: SMCD 2204; SMCD 2210. Vanguard: SMCD 2204; SMCD 2206; SMCD 2215; Pea: Golden: SMCD 2210; SMCD2215. Handel: SMCD 2204F; SMCD 2206; SMCD 2215; Lentil: Glamis: SMCD 2204F; SMCD 2206. Sedley: SMCD 2210; SMCD2215.

Root:

The following endophytes showed the best response to drought stress: Chickpea: Amit: SMCD 2204; SMCD 2215. Vanguard: SMCD 2204F; SMCD 2206; Pea: Golden: SMCD 2204F; SMCD2215. Handel: SMCD 2204F; Lentil: Glamis: SMCD 2204F; SMCD 2206; SMCD 2210. Sedley: SMCD 2206; SMCD 2210.

Example 8

Figure 29:
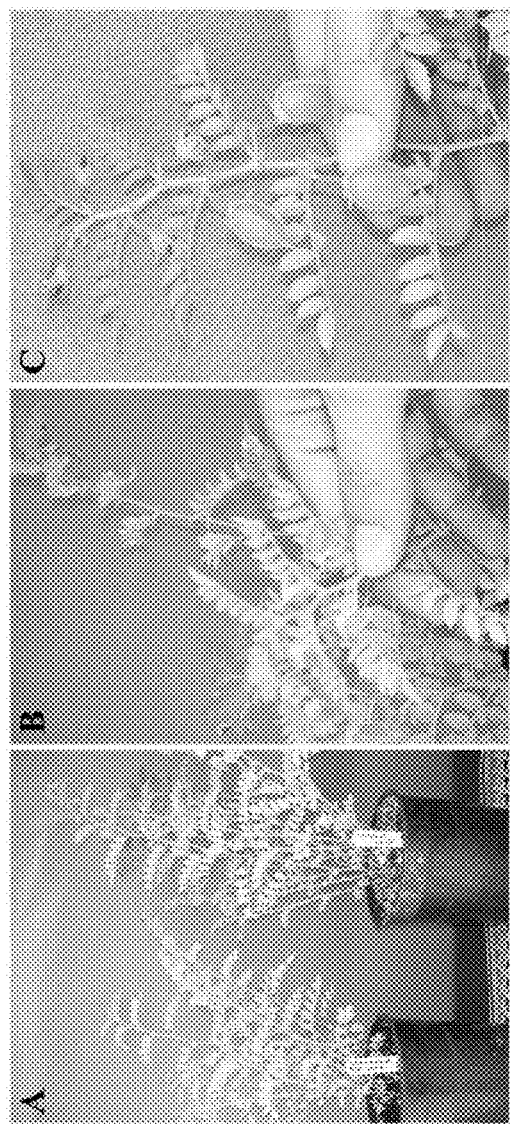
FIG. 29 shows (A) Chickpea Vanguard flowering plants bearing pods under drought stress in a greenhouse—left plant is non-symbiotic (E−) and right plant is symbiotic with strain SMCD 2215 (E+); (B) and (C), Chickpea Vanguard plants bearing pods under drought stress in a greenhouse—(B) non-symbiotic and (C) symbiotic with SMCD 2215.
Figure 30:
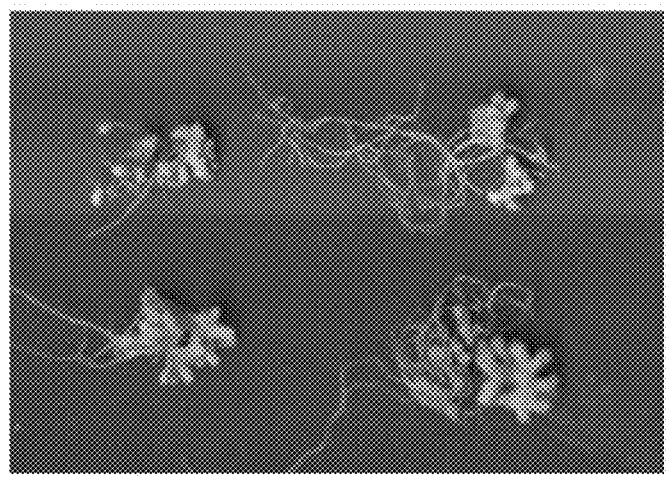
FIG. 30 shows root nodulation of pea varieties under heat stress in a phytotron: Hendel (Above) and Golden (Below) inoculated (left) and uninoculated (right) with SMCD 2215. Note: in all samples natural infection with *Rhizobium* sp. from pea seeds has been observed.

*Streptomyces* sp. SMCD 2215 Increases *Rhizobium* Activity and Nodulation Frequency in Peas Under Heat Stress As was recently observed for another *Streptomyces* species, *S. lydicus* WYEC10 [Tokala et al. 2002], the *Streptomyces* sp. nov. SMCD2215 colonizes the roots of young pea seedlings from seeds produced from plants grown under control conditions. It specifically enhances plant flowering and pod yield (FIG. 29), and root nodulation by *Rhizobium* sp. (FIG. 30), a native endophytic colonizer of pea seeds discovered in this study (Table 5). Vegetative hyphae of *Streptomyces* sp. nov. SMCD2215 colonize the cells of emerging nodules as discovered by culture plate (PDA), fluorescence microscopy (Carl Zeiss Axioskop 2) and PCR (BioRad) amplification methods [Schrey and Tarkka 2008]

Example 9

Endophytes Confer Abiotic Stress Tolerance to Pulses Via Enhanced Seed Viability Pulse crops refer to a group of more than sixty different grain legume crops grown around the world. The seeds of pulse crops are important to human nutrition. The chief constraints to pulse production are biotic and abiotic stresses such as drought, heat, cold and salinity. Recent research suggests that endophytic microbe-plant interactions are an instrumental determinant of plant adaptation.

This study hypothesizes that endophytes increase the rapidity and uniformity of seed germination under optimal and stress conditions in-vitro. The aim was, firstly, to measure the intrinsic symbiotic capacity of endophytes to trigger germination; and, secondly, to measure the efficiency of the compatible endophytes in conferring heat and drought resistance to pulses genotypes.

Material and Methods

Two varieties of pulses, Glamis (lentil) and Handel (pea), were co-cultured with compatible SMCD 2206 and SMCD 2215, fungal and bacterial symbiotic strains, respectively. The endophytic strains' ability to confer stress tolerance to Glamis (FIG. 31) and Handel (FIG. 32) genotypes were tested during in-vitro seed germination modelling drought (6% PEG) and heat (33° C.) environments.

Seeds were surface sterilized with 95% ethanol for 20s, rinsed twice in sterile distilled water for 10s followed by 2 min in 3% sodium hypochlorite (Javex). Finally, seeds were rinsed in sterile distilled water 4 times. Seeds were inoculated on PDA media with and without endophytes in the dark at room temperature [Abdellatif et al. 2009]. Microbial organisms were grown on PDA for at least three days at room temperature in darkness prior to experimental use. The endophytic ability to confer plant stress resistance was assessed using the energy of germination, which is meant to capture the temporal nature of germination and which is defined as the number of days required to reach 50% of germinating seeds.

Results

The present study demonstrates the differential capacity of fungal or bacterial endophytes to confer drought and heat resistance in pulses specific to a fungal or bacterial strain-plant genotype-abiotic stress combination. This study used molecular and proteomic analyses to better understand the mechanism by which endophytes confer symbiotic stress resistance to pulses.

Figure 31:
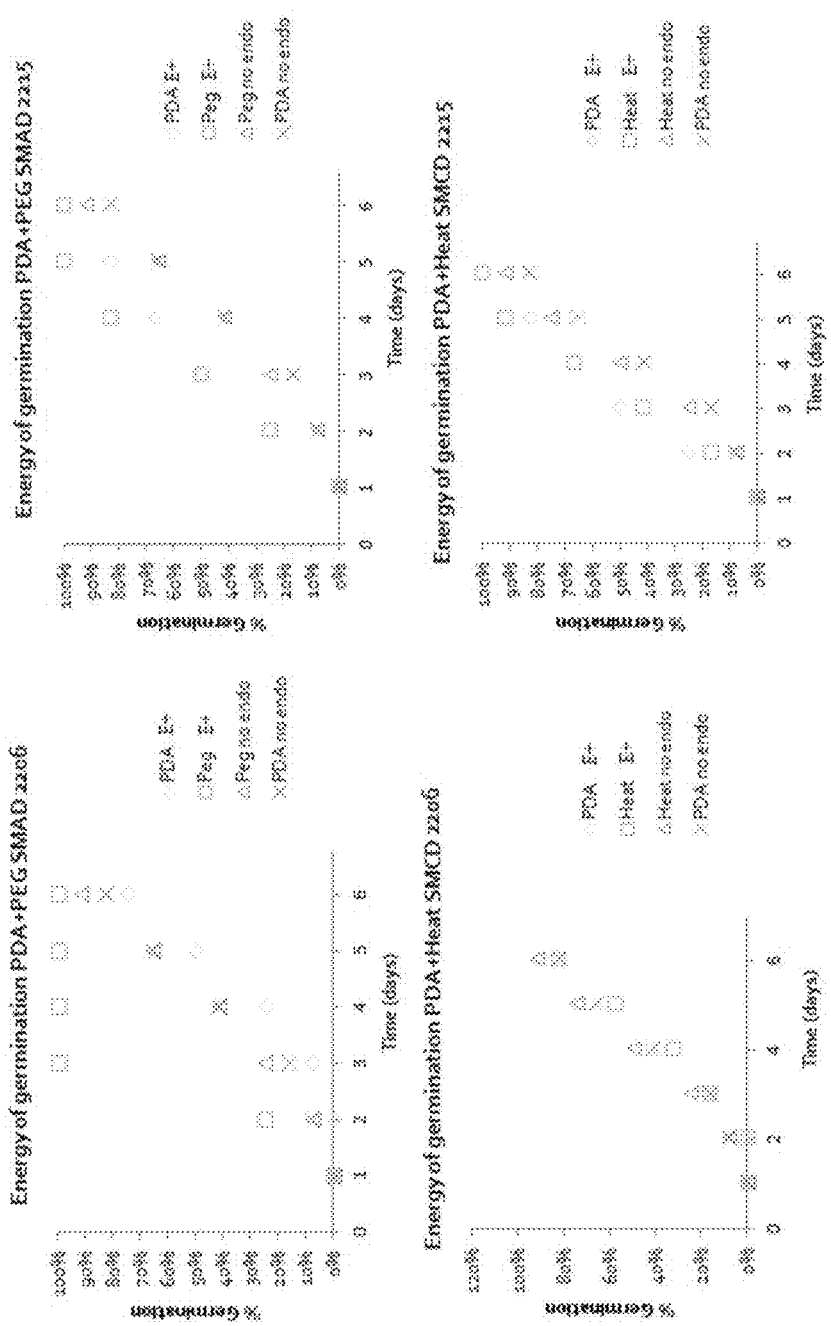
FIG. 31 shows SMCD2206 and SMCD 2215 considerably increase energy of seed germination (≥50%) in Glamis (lentil) as a function of time under heat and drought in vitro.
Figure 32:
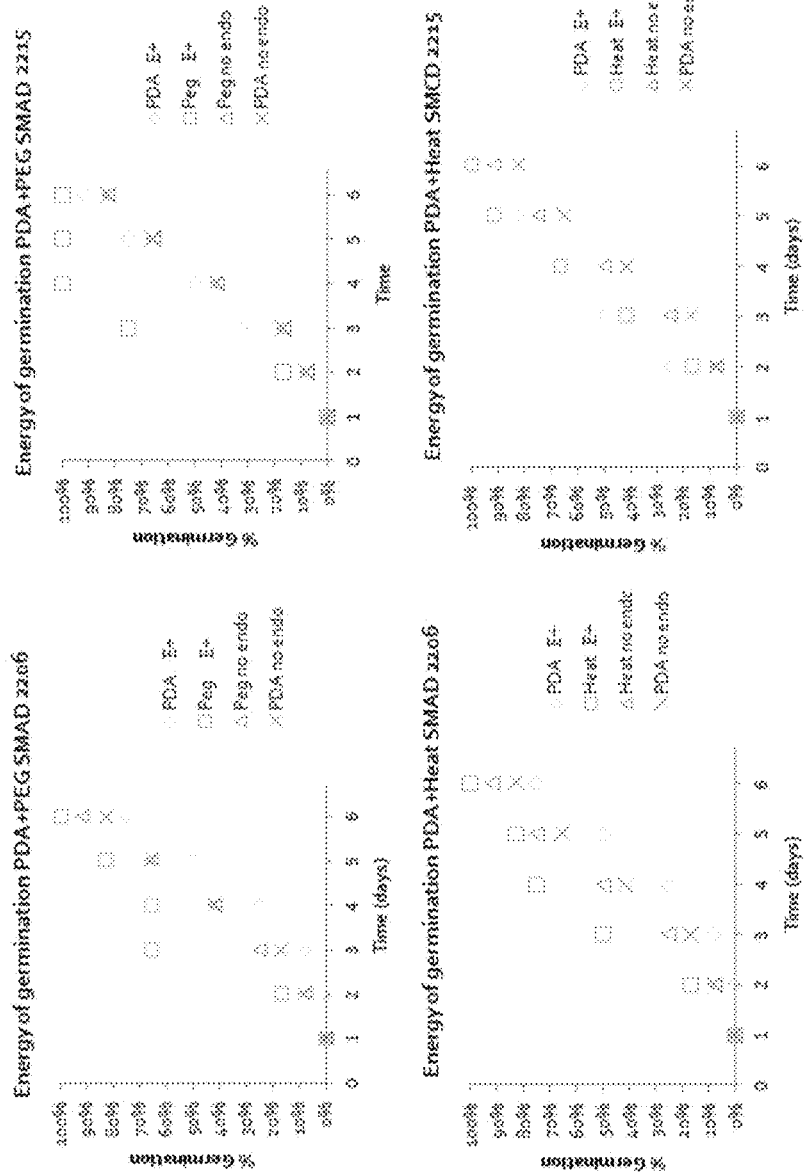
FIG. 32 shows SMCD2206 and SMCD 2215 considerably increase energy of seed germination (≥50%) in Handel (pea) as a function of time under heat and drought in vitro.

SMCD strains significantly increased the frequency of pulse seed germination under standard in-vitro conditions (FIGS. 31 and 32). Under stressful conditions, both endophytes (SMCD 2206 and SMCD 2215) increased the frequency of germination when compared to non-colonized seeds. Frequency of germination was from 70-100% in symbiotic treatments and 60-80% germination in the control, meaning that the tested endophytes have the potential to increase seed germination vigour (SGV) by >15%. The highest frequency of germination (100%) was observed in Glamis (lentil) associated with both SMCD 2206 and SMCD 2215 under drought stress vs. heat stress. When co-inoculated with SMCD strains, the energy of germination (>50% germinating seeds) in Glamis was achieved in 2 days under drought and in 3 days under heat conditions. Similar results were achieved in Handel (pea), except that this genotype has inherently a higher ability to support heat shock than Glamis (lentil).

Example 10

Endophytes Enhance Yield of Flax and Canola Genotypes Under Severe Drought Stress in Greenhouse Experiment The aim of this study was to use three randomly selected isolates (SMCD 2206, SMCD 2210 and SMCD 2215 and to expand the efficiency test on flax and canola yield production under drought stress.

Material and Methods

The experimental design, flax (Bethun and Sorel) and canola (1768S) seed manipulation, endophytic inoculant (SMCD 2206, SMCD 2210 and SMCD 2215) application, drought conditions, and yield assessment are as detailed under Example 5 with small modifications. Briefly, control plants were watered to 100% water retention capacity three times per week, while drought stressed plants were watered to 100% water retention capacity weekly. This drought regime was adopted in order to mimic the natural cycle of drought that can occur during the Canadian prairie growing season in which no precipitation falls for seven consecutive days, or more.

Results and Discussion

Figure 33:
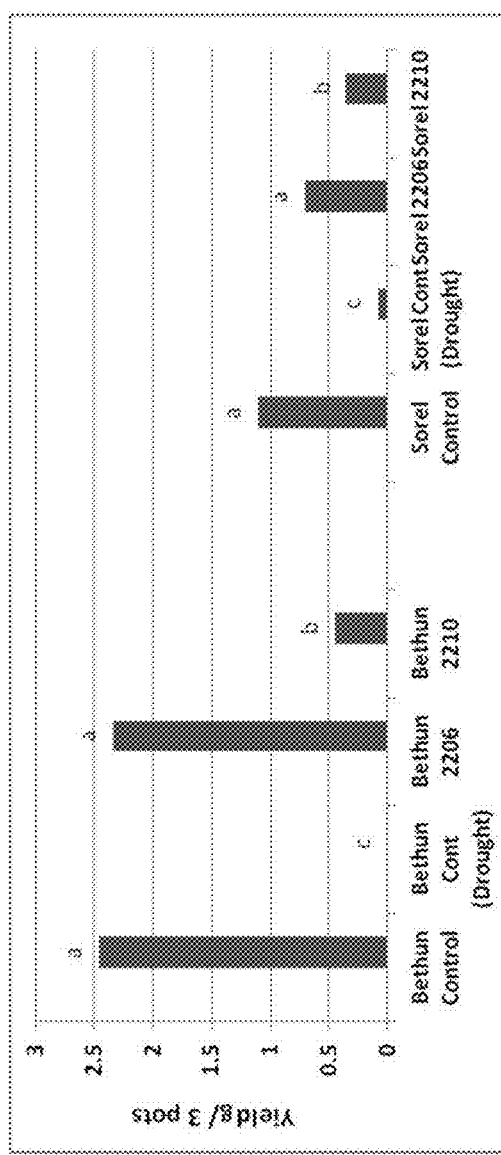
FIG. 33 shows endophytic inoculants (SMCD 2206 and SMCD 2210) improve flax yield under drought conditions in a greenhouse. Different letters above the bars indicate statistically significant differences between samples (p≤0.05, Kruskal-Wallis test).
Figure 34:
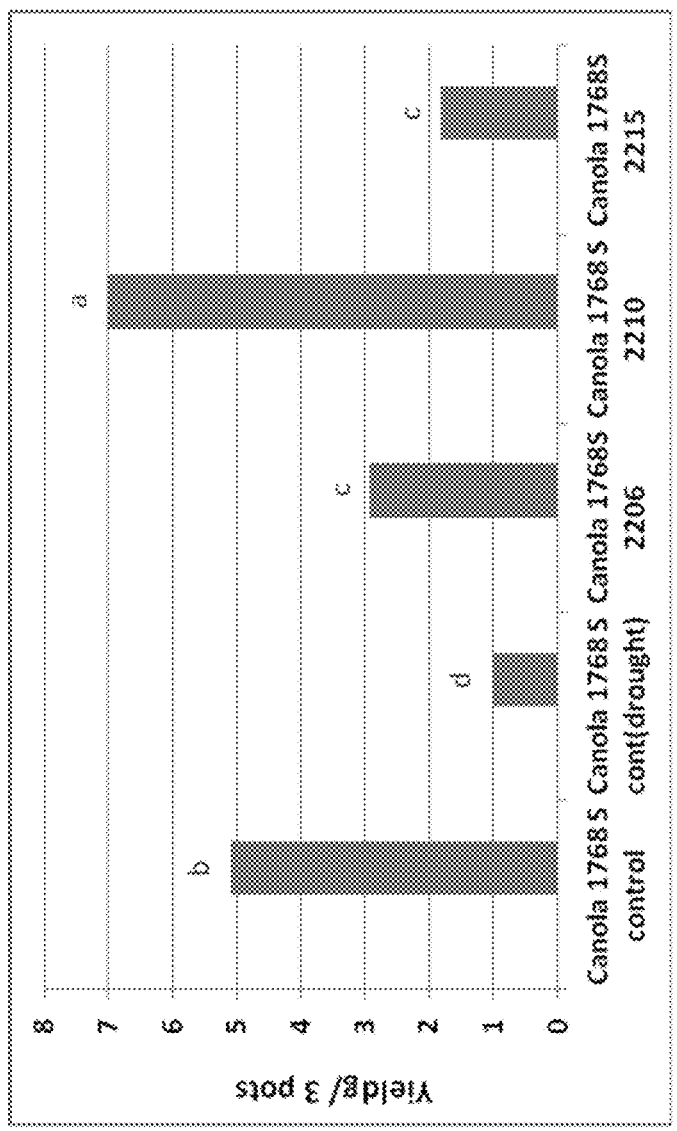
FIG. 34 shows endophytic inoculants (SMCD 2206, SMCD 2210, and SMCD 2215) improve canola yield under drought conditions in a greenhouse. Different letters above the bars indicate statistically significant differences between samples (p≤0.05, Kruskal-Wallis test).

Severe drought conditions compromised non-symbiotic flax yield, while endophytic inoculants SMCD 2206 and SMCD 2210 dramatically improved flax yield in these same conditions. In particular, under drought conditions, SMCD 2206 maintains a nearly 100% yield in Bethun while SMCD 2210 provides a 50% yield compared to the unstressed control in the greenhouse (FIG. 33). In terms of canola, an improved yield was registered in combination with SMCD 2210 (>100%), followed by SMCD 2206 (~50%) and SMCD 2215 (~30%) compared with unstressed control (FIG. 34).

Figure 35:
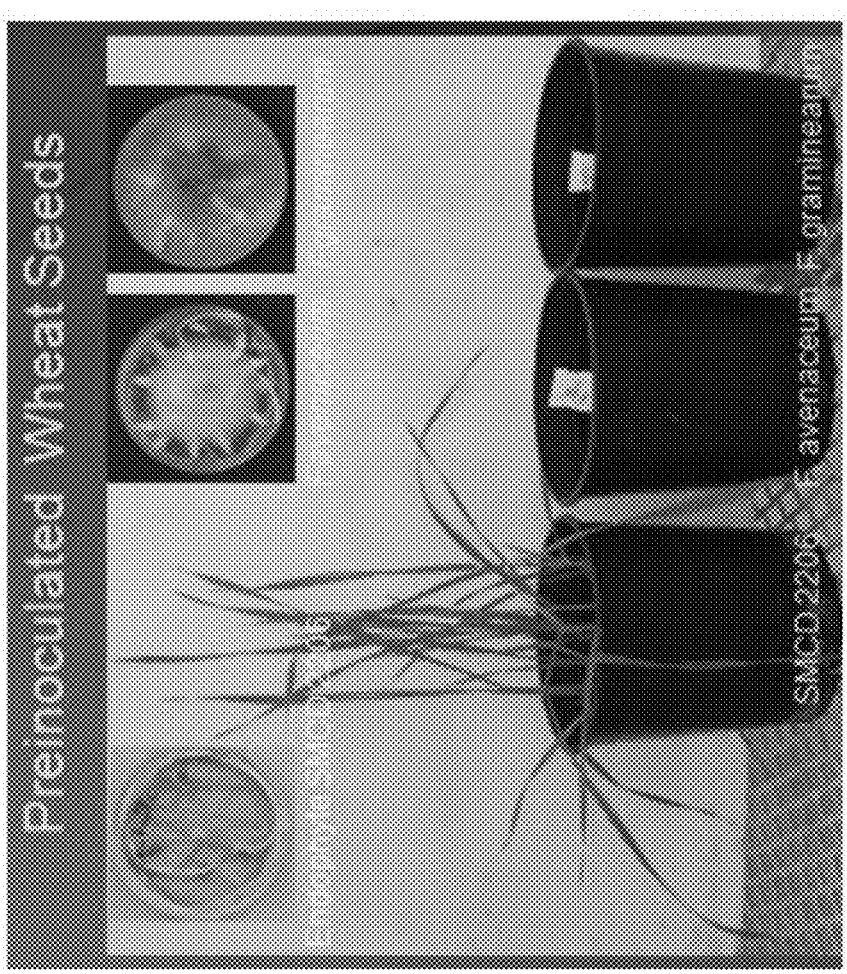
FIG. 35 shows the survival of wheat seeds pre-inoculated in-vitro (plates in above row) and wheat seedlings pre-inoculated in greenhouse (pots in below row) with endophytic SMCD 2206-showing healthy plant growth, and with pathogenic *Fusarium avenaceum* and *Fusarium graminearum*—showing disease symptoms and death of plants.
Figure 36:
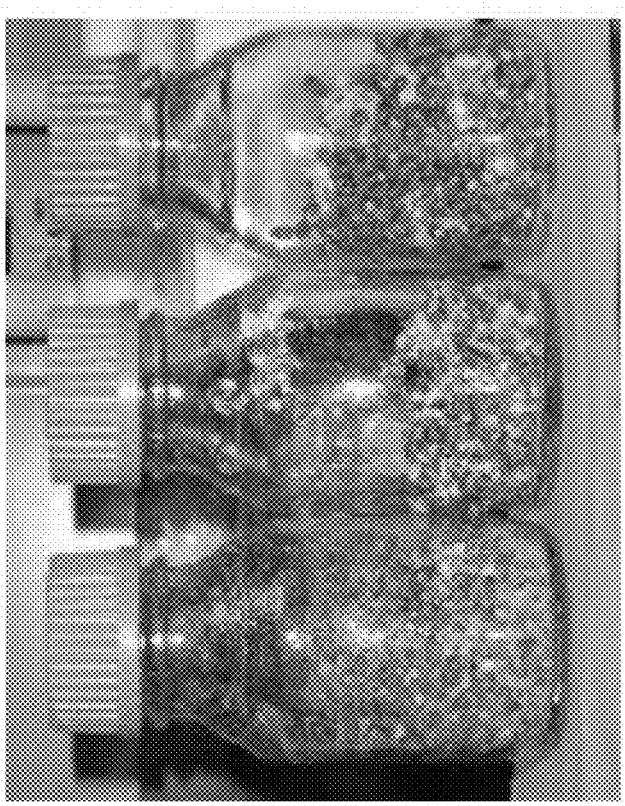
FIG. 36 shows *Fusarium* inoculants produced on wheat kernels.
Figure 37:
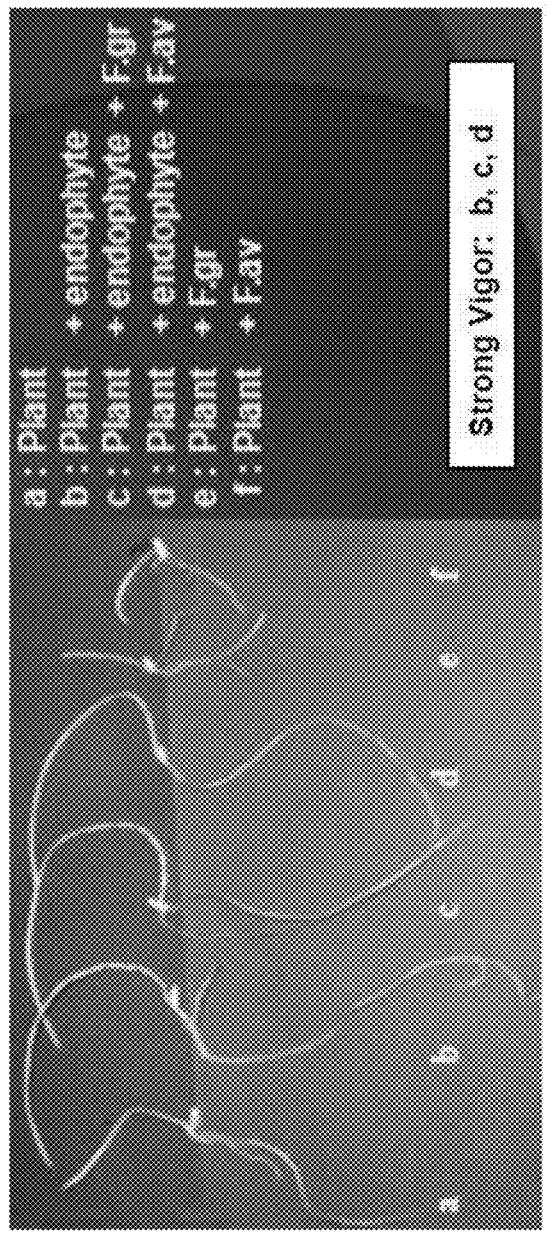
FIG. 37 shows that post-emergence damping-off has been prevented by SMCD 2206 endophyte in wheat in the greenhouse.

The bioprotection capacity was also tested in greenhouse against *Fusarium avenaceum* and *F. graminearum*. Autoclaved seeds were infected by Fusaria inoculants in darkness for 7 days at 25° C. (FIGS. 35-36), and were inoculated by endophytes produced on petri plates as described by Abdellatif et al. [2009].

Mixed pot soil was inoculated with twenty seeds bearing *Fusarium*. The composition of mixed soil was 55-65% Canadian Sphagnum Peat Moss, Perlite, and Limestone mixed with sand. Standard greenhouse conditions were 8 h day light interchanged with a 16 h photoperiod (1000 lux) regime under a relative humidity of 70% and a constant temperature of 25° C.±2° C.

Plants treatments were as follows:
T1: Untreated plants (control)
T2: Plant+endophyte
T3: Plant+pathogen, *Fusarium avenaceum*
T4: Plant+pathogen, *Fusarium graminearum*
T5: Plant+endophyte fungus+*Fusarium avenaceum*
T6: Plant+endophyte+*Fusarium graminearum*

Each treatment was replicated in three pots, and seedlings were watered three times a week under controlled conditions. The endophyte-root colonisation was tested using a fluorescence microscope to distinguish symbiotic vs. pathogenic endophyte-wheat relationships [Abdellatif et al. 2009].

Figure 38:
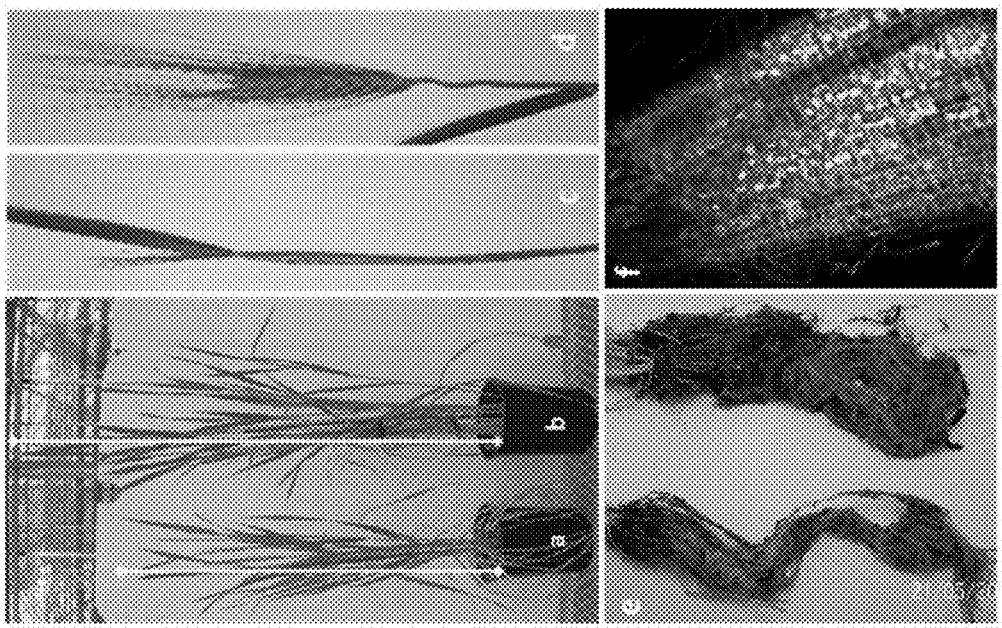
FIG. 38 shows wheat biomass (aerial a-d and root e-f) improved in the presence of SMCD 2206 endophyte compared to untreated plants. (a) control plant (E−), (b) inoculated plant (E+), (c) control flowering plant, (d) inoculated flowering plant, (e) control plant (E−, left) compared to SMCD 2206 inoculated plant (E+, right), and (f) fluorescent microscopy of SMCD 2206 wheat root-colonization (E+).
Figure 39:
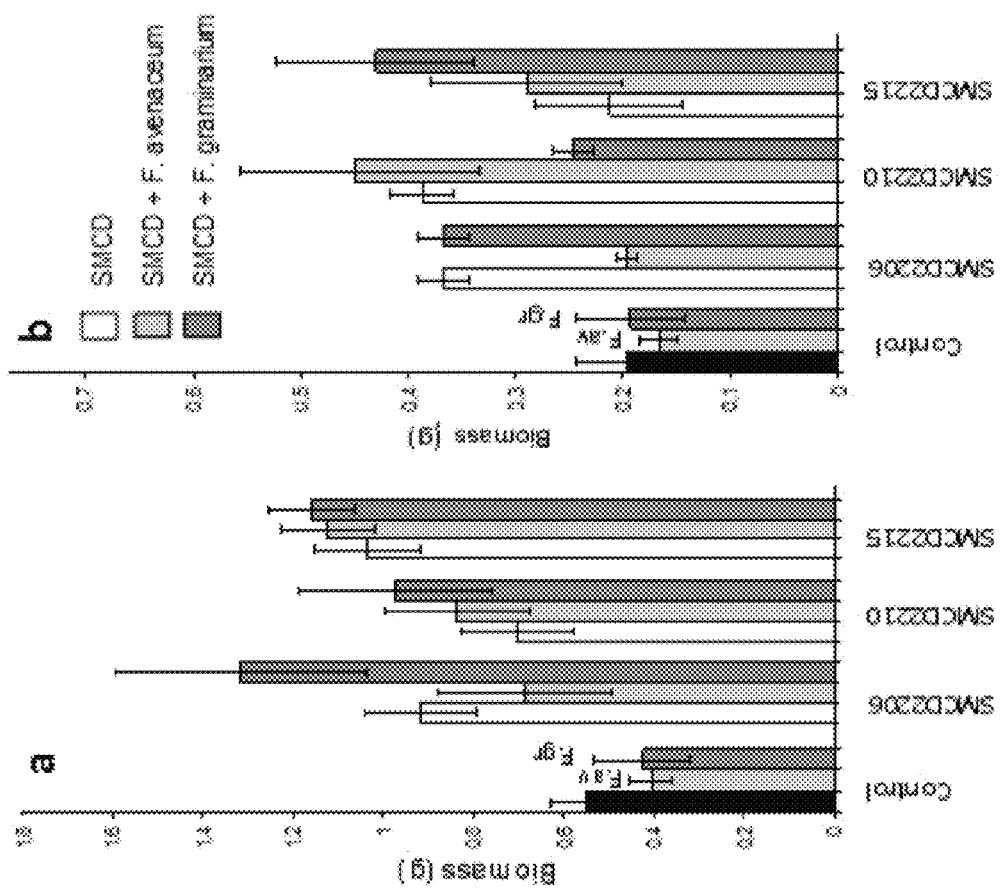
FIG. 39 shows aerial plant biomass/plant (left) and underground (root) biomass/plant (right) in control (E−) and SMCD inoculated wheat plants (E+) against *F. graminearum* and *F. avenaceum*. Vertical error bars on data points represent the standard error of the mean.
Figure 40:
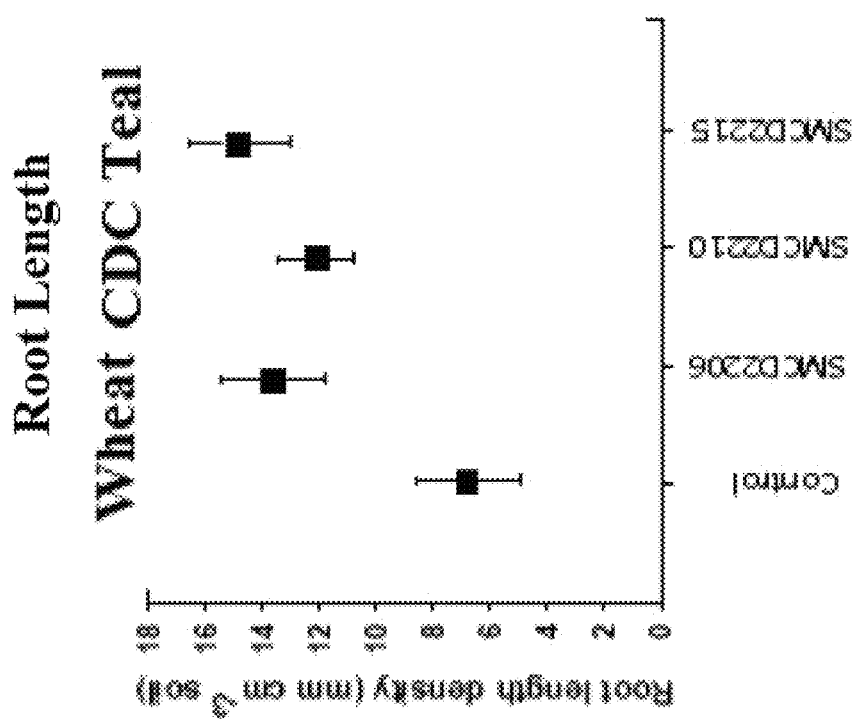
FIG. 40 shows root length in control plant (CDC Teal) without SMCD endophyte compared to inoculated wheat plant with SMCD strains. Bars on data points represent the standard error of the mean.

FIGS. 37-40 show the positive effect of endophytes on wheat post-emergency seedling resistance (FIG. 37), foliage and root biomass (FIG. 38 and FIG. 39), and flowering/anthesis stage and spikes (FIG. 38, FIG. 39, and FIG. 40). All tested endophytes induced well-developed foliage compared to control, as well as well-developed flowers in the presence of endophytes.

To confirm the ability of the endophytes to stimulate mature plant growth in the presence of *Fusarium* pathogens, the performance of the flowering stage bearing the spikes we assessed as a more advanced growth stage.

Figure 41:
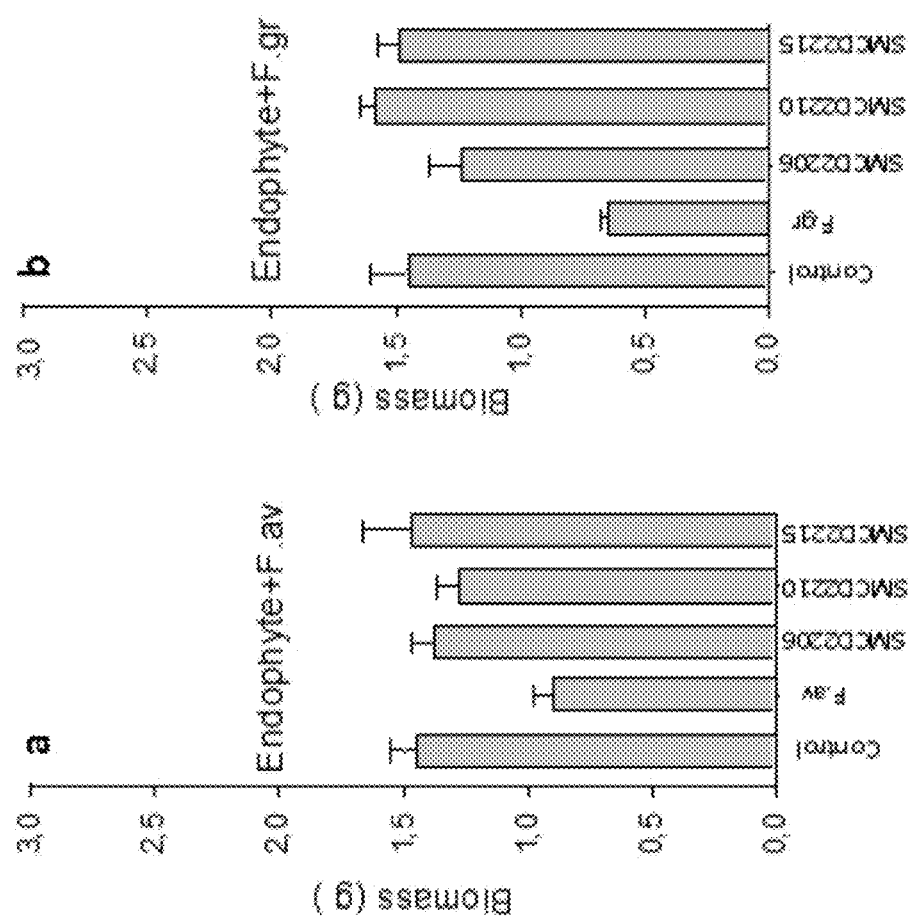
FIG. 41 shows dry weight of kernels/plant (TEAL cultivar) in wheat using the double pre-inoculation approach: a) SMCD endophyte+*Fusarium avenaceum* (F.av), and b) SMCD endophyte+*Fusarium graminearum* (F.gr). Vertical error bars on data points represent the standard error of the mean.

The histograms in FIG. 41 illustrate the performance of endophytes in improving the biomass or dry weight of wheat spikes after double inoculation (SMCD endophyte and *Fusarium* pathogen).

The yield of wheat in the presence of an endophyte and *Fusarium* significantly improves using all endophytic strains compared with treatment infected with *F. graminearum* and *F. avenaceum* but without an endophyte (E−) (FIG. 42). Plants treated with the pathogen alone show a significantly lower size of spikes compared to control plants and plants with endophytes (E+) (FIG. 42).

Example 11

Endophyte-Mediated Abiotic Stress Resistance Gene Expression in Pulses

Figure 43:
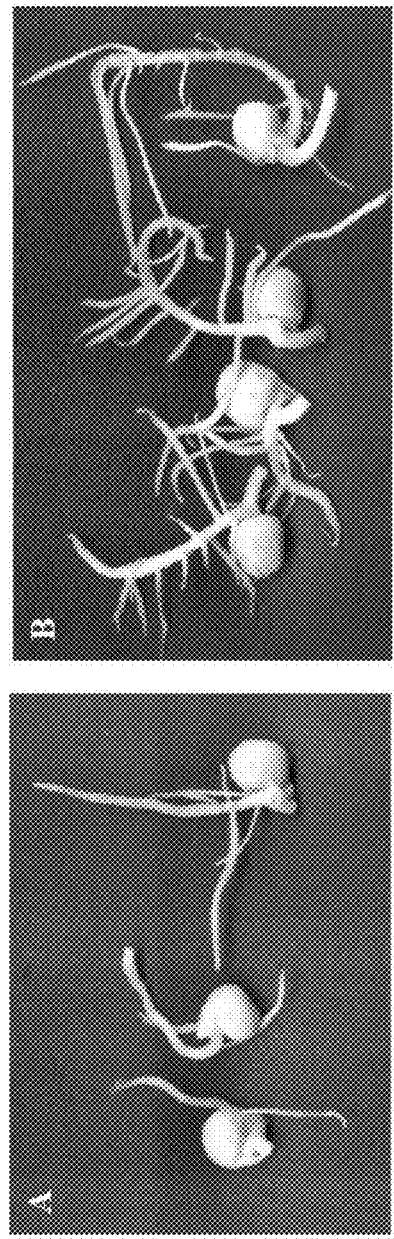
FIG. 43 shows the effect of SMCD 2215 on Handel (pea) on 10% PEG after 7 days at 21 degrees C. in darkness. (A) shows the control seeds, and (B) shows the SMCD 2215-treated seeds.

Abstract:
The genomic and proteomic mechanisms of plant endophytes beneficial effects on host plant resistance to abiotic stressors are poorly understood. One of the contemporary theories suggests that the symbiotic plants are protected from oxidative stress produced by heat, drought and salt stressors by the production of antioxidant molecules. The aim of this study is to shed more light on defensive symbiosis of pea, chickpea and lentil genotypes assessing the Pro, SOD, and MnSOD gene expressions triggered by the association between host genotypes and endophytes. The results of this study demonstrated endophyte-mediated gene expression in endophyte-inoculated plants. These genes play an important role and provide the host protection through an enhanced stress tolerance to the tested abiotic stressors.
Materials and Methods Leaves were collected for this analysis from normal and stressed 6 seed varieties (Amit, Vanguard [chick pea] (FIG. 43), Golden, Handel [peas] and Glamis, Sedley [lentils]) with or without endophytes.

Real-Time PCR was used to amplify genes such as Proline (Pro), SOD and Mn SOD using primers as shown in SEQ ID NOs: 8-15 (Table 6), stress proteins generally found to play special roles in protecting cytoplasm from dehydration and in protecting plants by palliating the toxicity produced by the high concentrations of ions. PCR was conducted under the following conditions: 3 min at 95° C. (enzyme activation), 40 cycles each of 30 sec at 95° C. (denaturation) and 30 s at 60° C. (anneal/extend). Finally, a melting curve analysis was performed from 65° to 95° C. in increments of 0.5° C., each lasting 5 s, to confirm the presence of a single product and absence of primer-dimer. Quantitation is relative to the control gene by subtracting the CT of the control gene from the CT of the gene of interest (ΔCT). The resulting difference in cycle number is then divided by the calibrator normalized target value, and the value obtained (ΔΔCT) is the exponent of base 2 (due to the doubling function of PCR) to generate the relative expression levels.

Results

Different gene expressions during drought stress were analyzed. Table 6 shows the genes that were tested. Some of the results obtained from Handel variety when exposed to 6% PEG.

SOD and MnSOD

Figure 44:
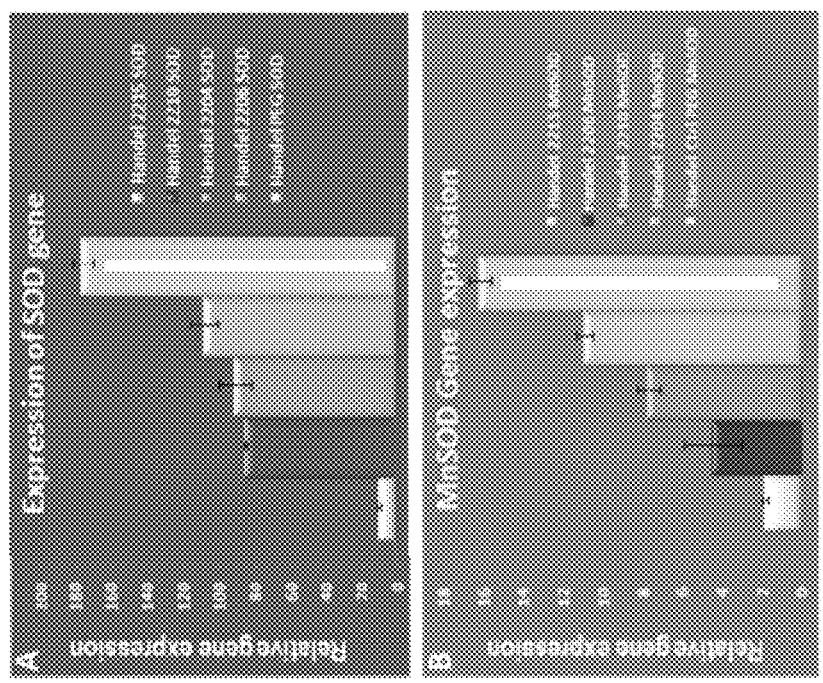
FIG. 44 shows (A) SOD and (B) MnSOD relative gene expressions in pea (Handel) exposed to PEG with and without endophytes.

In general, SODs play a major role in antioxidant defense mechanisms. In the present study very high levels of SOD expression were observed in normal (E−, control) leaves exposed to 6% PEG, an almost 200 fold increase. Endophytes played a very significant role in decreasing this stress. Especially, SMCD 2215, followed by and SMCD 2210, SMCD 2204 and SMCD 2206. These symbionts drastically reduced the stress with only a 9 and 24 fold increased expression observed (FIG. 44A).

MnSOD is one of the SOD forms. Control leaves showed a 16 fold increase in the gene expression, whereas SMCD 2215 suppressed the stress and decreased the fold change from 16 fold to 2 fold, followed by SMCD 2206, SMCD 2210 and SMCD 2204 (FIG. 44B).

Proline

Figure 45:
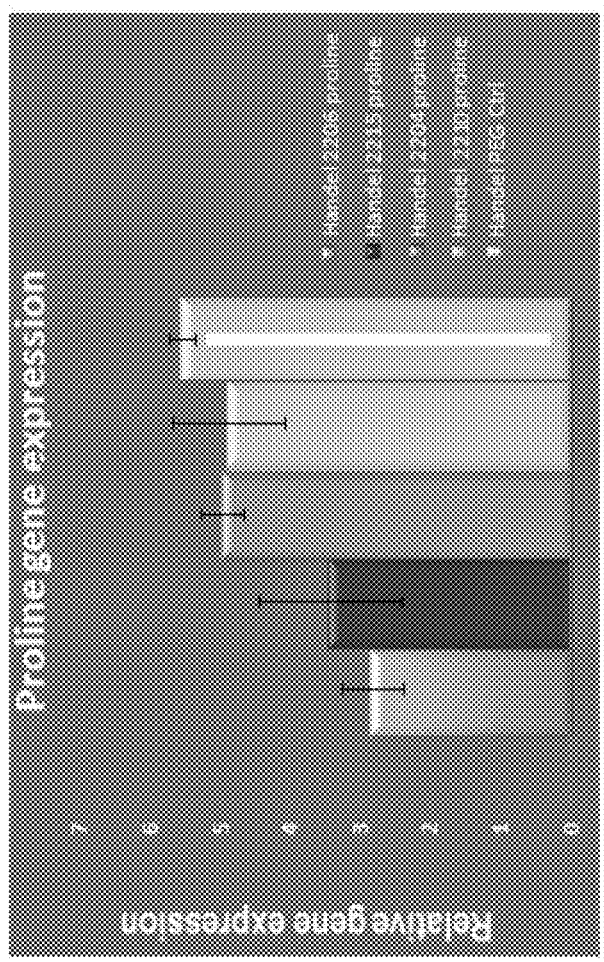
FIG. 45 shows Proline relative gene expression in pea (Handel) exposed to PEG with and without endophytes.

Proline is essential for primary metabolism. Proline biosynthesis is controlled by the activity of two P5CS genes in plants. This gene was assessed in Pea variety Handel with endophytes under drought condition. As expected P5CS gene was upregulated and increased expression by 5 fold in the leaves collected from PEG exposed plants. Whereas the leaves collected from seeds associated with SMCD 2206 expressed 2.8 fold followed by SMCD 2215 at 3.4 fold expressed proline coding gene (FIG. 45). These results confirmed that endophytes play major role in stress resistance modifying proline gene expression compared to uninoculated stressed plants.

Example 12

Gene Expression Patterns in Wheat Coleorhiza Under Cold and Biological Stratification Abstract:
Wheat is one of the widely used major crops in the world. However, global wheat production has decreased about 5.5% in last two decades and a further decline has been predicted due to pervasive global warming Thus, elucidating conditions and techniques that enhance seed germination is of great importance. Cold stratification is a long-known method of releasing seed dormancy and promoting germination. Biological stratification through fungal endophytes can also stimulate seed germination in many cereal crops. Coleorhiza is one of the most active tissues in seed and it is also the first part to emerge out of germinating seeds. To evaluate the efficiency of the stratification methods, germination percentage of wheat seeds was assessed under cold and biological stratification and the expression level of gibberellin and abscisic acid genes in coleorhiza were determined Both cold and biological stratification treatments significantly ($P<0.05$) enhanced the rate and efficacy of germination. Spatial distance between the fungal endophyte and seeds is a determining factor of biological stratification as seeds in direct contact with fungal endophyte showed highest germination percentage (up to 86%). High expression of GA3ox2 gene in wheat coleorhiza was found throughout the germination period revealing consistent production of the bioactive GA3 molecule. The 14-3-3 gene expression was lowest under endophyte-direct treatment. The expression of abscisic acid-ABA biosynthesis gene, TaNCED2, was considerably high in cold stratification seeds reflecting the role of abscisic acid as a stress-adaptation hormone. High expression of TaABA8'OH1 gene was also found in coleorhiza. Overall, this study provides molecular evidence of the importance of coleorhiza in germinating wheat seeds. By comparing cold and biological stratification methods, seed germinability can be markedly enhanced through application of fungal endophytes, and the spatial distance between seed and endophyte is a factor driving mycovitality.

Materials and Methods
Wheat Seeds

Seeds of the *durum* wheat cultivar AC Avonlea with low resistance to environmental stress conditions were used in this study. These seeds were produced by Agriculture and Agri-Food Canada Seed Increase Unit Research Farm in 2006 under greenhouse conditions, and were recommended as free of microbes. Seeds were kept in sterile ziplock bags and stored in 4° C. cold room until further use.

Comparison of Seed Sterilization Protocols

Various methods have been proposed for surface sterilization of wheat seeds. Here four widely acknowledged seed-sterilization methods were compared to identify the best suitable protocol that efficiently sterilize seed-surface without affecting seed quality and vitality in this variety of wheat. In the first method, seeds were surface sterilized with 95% ethanol for 10 s, followed by rinsing in sterile distilled water three times for 1 min [Zhang et al., 2007. BMC Genetics 8]. Second protocol was bleach-sterilization where seeds were surface sterilized in 5% sodium hypochlorite for 3 min followed by thorough rinsing in sterile distilled water three times for 1 min. In the third protocol, seeds were surface sterilized with 95% ethanol for 10 s, rinsed in sterile distilled water, then submerged for 3 min in 5% sodium hypochlorite, rinsed three times in sterile distilled water and placed on potato dextrose agar (PDA) for germination [Abdellatif et al. 2009]. The fourth method was vapour phase sterilization of seeds with chlorine gas [Desfeux et al., 2000]. In fume hood chamber, a small beaker with 20 ml bleach is placed in a 5 liter snaptite box. Wheat seeds were placed in a 96 well-plate and kept in the snaptite box. Then 3 ml of concentrated hydrochloric acid was added into the small beaker to create chlorine gas. Lid was kept closed for 4 hours to retain seeds in contact with chlorine gas. After sterilization, the 96 well-plate was placed for 1 hour in a laminar flow hood to disperse trace chlorine gas. Sterilized seeds were then rinsed three times in sterile distilled water and were plated out on PDA plates. Comparison of these sterilization methods suggests that chlorine gas sterilization protocol was the most effective method showing 80% germination without contamination while control seeds had highest percentage of contamination (Table 7). Although bleach and ethyl methods successfully inhibited contamination, seed germination was affected considerably. Therefore, chlorine gas protocol is a highly efficient method of sterilization of wheat seeds and it was selected to sterilize the seeds required for experiments conducted in this study.

Cold and Biological Stratification

For cold stratification, surface sterilized seeds were kept on moist filter paper at 4° C. cold-room for 48 hours [Mukhopadhyay et al., 2004; Wu et al., 2008]. After 2 days, cold stratified seeds were taken to room temperature where they were quickly rinsed in sterilized distilled water and placed on potato dextrose agar (PDA) plates. For biological stratification, sterilized seeds were incubated in presence of SMCD 2206. Fungal endophyte was grown on PDA at room temperature in darkness for at least three days before use. To assess this efficiency, wheat seeds were germinated in direct contact and at a certain distance from the fungal endophyte. An agar plug (5 mm$^2$) of the endophyte dissected from the margins of a parent colony was placed in the centre of a 90 cm petri dish with PDA. Then 10 surface sterilized seeds were placed at the periphery of the petri dish encircling the fungal agar plug at approximately 4 cm distance. All petri dishes were sealed with 5 layers of Parafilm® (Pechiny Plastic Packaging) to avoid any biological contamination and diffusion of volatile/gaseous compounds. The impact of direct-contact of the fungal endophyte was elucidated by placing a 3 mm$^2$ agar plug between two adjacent surface sterilized wheat seeds and 5 mm$^2$ plug in the centre of the PDA plates. All treatments were carried out with three replicates of PDA plates with ten surface sterilized seeds on each plate. Petri dishes were incubated in a bench-top incubator at room temperature (–20° C.) in darkness. Incubation time was recorded and data collection and coleorhiza isolation were carried out after 24, 48, and 72-hours.

Germination Percentage

Emergence of early radicles was carefully monitored. Percentage of germination was calculated by estimating the number of seeds germinated out of 10 wheat seeds on each PDA plate. The 50% germination rate was assumed as the energy of germination. The efficacy of germination in different treatments was calculated by following equation:

$$\text{Efficacy} = \% \text{ germination in a treatment} - \% \text{ germination in control} \quad \text{[Eqn. 1]}$$

Rate of germination was observed for all treated samples and replicates. For Day 2 and Day 3 samples, germination rate was monitored from Day 1 to assess the overall vitality. The PDA plates were kept sealed throughout the data collection period.

Isolation of Coleorhiza

After observing the rate of germination, PDA plates were immediately transferred to a sterile biosafety hood chamber for coleorhiza isolation. Wheat seeds were carefully dissected under compound microscope and layers of coleorhiza were cleaved off using sterilized needle and scalpel. Isolated coleorhizas were stored in an RNase-free sterilized microcentrifuge tube. Seeds from all biological replicates of a treatment were combined and approximately 20 to 30 coleorhizas were isolated to obtain optimum amount plant material for RNA extraction.

RNA Extraction and cDNA Synthesis

To avoid any degradation in plant material, RNA extraction was carried out forthwith after coleorhiza isolation on each day. Approximately 20 mg of coleorhiza samples were taken for RNA extraction. Total RNA was extracted using Aurum™ Total RNA Mini Kit according to manufacturer's instructions (Bio-Rad Laboratories). RNA concentration was spectrophotometrically measured by Nanodrop (Thermo Scientific) Immediately after RNA extraction, cDNA synthesis was performed using iScript cDNA Synthesis Kit following manufacturer's instructions (Bio-Rad Laboratories). A 600 ng aliquot of RNA was taken for cDNA synthesis. Reverse transcription was carried out at 42° C. for 30 minutes with a final denaturation at 85° C. for 5 minutes.

Quantitative Real-Time PCR

Expression of gibberellin and abscisic acid functional genes was estimated by relative quantification using quantitative real-time PCR (QRT-PCR). Various catabolic and biosynthetic genes were selected to assess their respective roles in cold and biological stratification. Wheat actin gene of 131 bp length fragment was used as the internal control [Nakamura et al., 2010]. QRT-PCR was performed using a MJ-Mini Gradient Thermal Cycler (Bio-Rad Laboratories) following manufacturer's instructions. The PCR condition was 1 cycle of 95° C. for 1 minute and 40 cycles of 94° C. for 20 s, 60° C. for 30 s, and 72° C. for 1 min. For real-time PCR, cDNA samples from the treatments were used and all reactions were carried out in three replicates and two negative controls. Each 25 µl reaction contained 18 µl of iQ™ SYBR® Green supermix (Bio-Rad Laboratories), 10 pmol of the appropriate forward and reverse primers, 2.5 µl bovine serum albumin, and 25 ng template cDNA. Relative quantification was performed according to Zhang et al. [2007]. Expression levels were calculated using cycle threshold (Ct) value determined according to manually adjusted baseline. The difference between the Ct values of target gene and actin ($Ct^{target}-Ct^{actin}$) was estimated as Ct and then the expression level was calculated as $2^{-ct}$. The mean values of $2^{-ct}$ were used to assess difference in expression between control and stratification treatments. To ensure the specificity and consistency of amplicons, melting curve analysis and agarose gel electrophoresis were performed after each QRT-PCR run.

Sequencing

Amplicons of Actin and various GA and ABA genes were purified using BioBasic PCR Purification Kit (Bio Basic Inc.). For each treatment, purified amplicons were sent for sequencing at Plant Biotechnology Institute (NRC-PBI). Gene sequences were identified by Basic Local Alignment Search Tool (BLAST) analyses (http://blast.ncbi.nlm.nih.gov).

Statistical Analysis

One way analysis of variance of germination percentage and gene expression data was performed using IBM SPSS Statistics software version 19. Differences between control and stratification treatments were examined with the Duncan's post-hoc test.

Results and Discussion

Percentage and Efficacy of Germination

Figure 46:
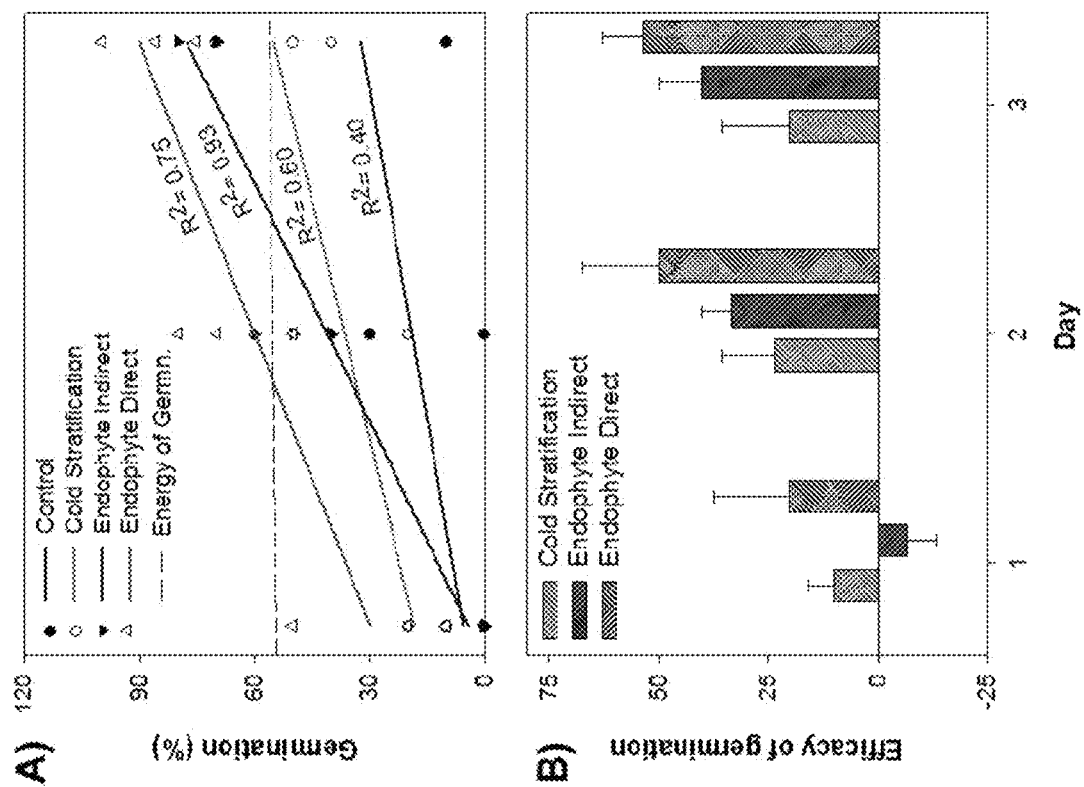
FIG. 46 shows germination of wheat seeds in vitro after three days on potato dextrose agar (PDA). Cold stratification was imposed by keeping seeds at 4° C. cold-room for 48 hours. For endophyte-indirect and endophyte-direct treatments, using SMCD 2206, seeds were germinated at approximately 4 cm distance and in direct contact respectively. A) Percentage of germination in comparison with energy of germination (50% germination). B) Efficacy of germination of wheat seeds subjected to cold and biological stratification. Efficacy was calculated by subtracting the germination percentage of control from treated seeds.

Both cold stratification and biological stratification treatments significantly enhanced the rate of germination with all three treatments exhibiting higher germination percentage than control (FIG. 46A; Table 8). Endophyte-direct showed highest germination percentage after each day and increased 60% from Day 1 to Day 3. Throughout the germination period (3 days) it demonstrated significantly (P<0.05) higher germinability than the other three treatments. Only biological stratification treatments produced more than 50% germination after Day 2. Interestingly, endophyte-indirect treatments showed no germination after Day 1 but produced a remarkable 50% germination after Day 2. Cold stratification treatment demonstrated no significant difference from control after Day 1, and then steadily increased showing significant difference after Day 2 and Day 3. Pattern of increase in germination is also reflected in $R^2$ values. Whereas control showed an $R^2$ value of 0.40, cold stratification and endophyte-direct treatment showed 0.60 and 0.75 respectively. On the other hand, owing to its 50% increase from Day 1 to Day 2, endophyte-indirect treatment had the highest $R^2$ value of 0.93, which is about 2.5 times higher than control. Energy of germination is a critical parameter determining the capacity of seeds to break dormancy and start germination. Energy of germination is assumed as the percentage of seed germination after certain time or the number of days necessary to achieve 50% germination. Endophyte-direct showed highest efficacy followed by endophyte-indirect and cold stratification (FIG. 46B). As there was no germination in endophyte-indirect seeds after Day 1, the efficacy of germination was negative. Overall, the stratification treatments showed tremendously positive result by reaching 50% germination after 48 hours.

Stratification plays an important ecological role in the release of primary dormancy and enhancement of seed germination [Bewley and Black 1982; Probert et al., 1989]. Alleviation of seed dormancy and improvement of germination through cold stratification have been achieved in many species including grasses [Schutz and Rave 1999], mulberry [Koyuncu 2005], pine [Carpita et al., 1983], tobacco [Wu et al., 2008], rice [Mukhopadhyay et al. 2004], and apple [Bogatek and Lewak 1988]. Germination was also increased by cold stratification in 33 annual weed species and stratification has been proposed to even be capable of nullifying differences in seed germinability between populations [Milberg and Andersson 1998]. However, little information is available on the impact of cold stratification on wheat seed germination. This study found that the effect of cold stratification requires an initial period and thus seed germination was not significantly different from the control on Day 1. However, it demonstrated considerable impact on germination from Day 2 and the percentage of germination increased as much as 20% higher than the control. The time period of cold stratification in this study was selected from previous reports that showed a period of 48 hours is effective for cold stratification in tobacco [Wu et al., 2008] and rice [Mukhopadhyay et al. 2004]. Earlier studies have shown that the impact of cold stratification is proportional to its time-length [Baskin et al. 1992; Cavieres and Arroyo, 2000]. The findings support this and further extend the notion to envisage that a slightly longer stratification period (~4 days) may be required for wheat to attain maximum germinability.

Several reports have shown the enhancement of seed germination through the application of fungal endophytes [Vujanovic 2007b; Hubbard et al. 2012; Vujanovic and Vujanovic 2007]. The present study supports the concept of "mycovitalism", which is the increase of vitality through fungal colonization. Fungal endophytes are well known to produce volatile compounds that affect plant phenophases [Mitchell et al., 2009; Strobel et al., 2004]. Thus, endophytes may be capable of affecting seed germination even when they are not in direct contact with seeds, and this attribute is particularly useful in field conditions. Here it was also tested how physical distance may influence seed germination under biological stratification. These findings suggest that seeds in direct contact with fungal endophyte are undoubtedly more benefitted than their counterparts. Endophyte-direct produced highest percentage and efficacy of seed germination on each day of the germination period. Similar to endophyte-direct contact, seeds placed at 4 cm from the endophyte also germinated at a significantly higher rate than control. However, the germination percentage and efficacy were indeed affected by the distance and indirect-contact seeds have between 14% and 27% less germination than direct-contact ones. Furthermore, no germination activity was observed on Day 1 which was followed by a sharp rise (50%) on Day 2. Seed germination is an extremely complex process and its underlying mechanisms are relatively less understood [Nonogaki et al., 2010]. Thus it is not clear how fungal endophytes facilitate the release of dormancy and onset seed germination. Considering fungi are capable of producing a range of plant-growth promoting substances, it is possible these substances are more effective in close vicinity. Consequently, endophyte-direct seeds have significantly higher germination rate than other treatments. On the contrary, endophyte-indirect seeds showed high efficacy of germination after 48 hours, this period may have allowed enough accumulation of growth promoting substances. There is a difference in germination percentage (6.6%) between the control and endophyte-indirect treatments on Day 1, however, it is not substantial.

Expression Level of Gibberellin and Abscisic Acid Genes in Coleorhiza

Figure 47:
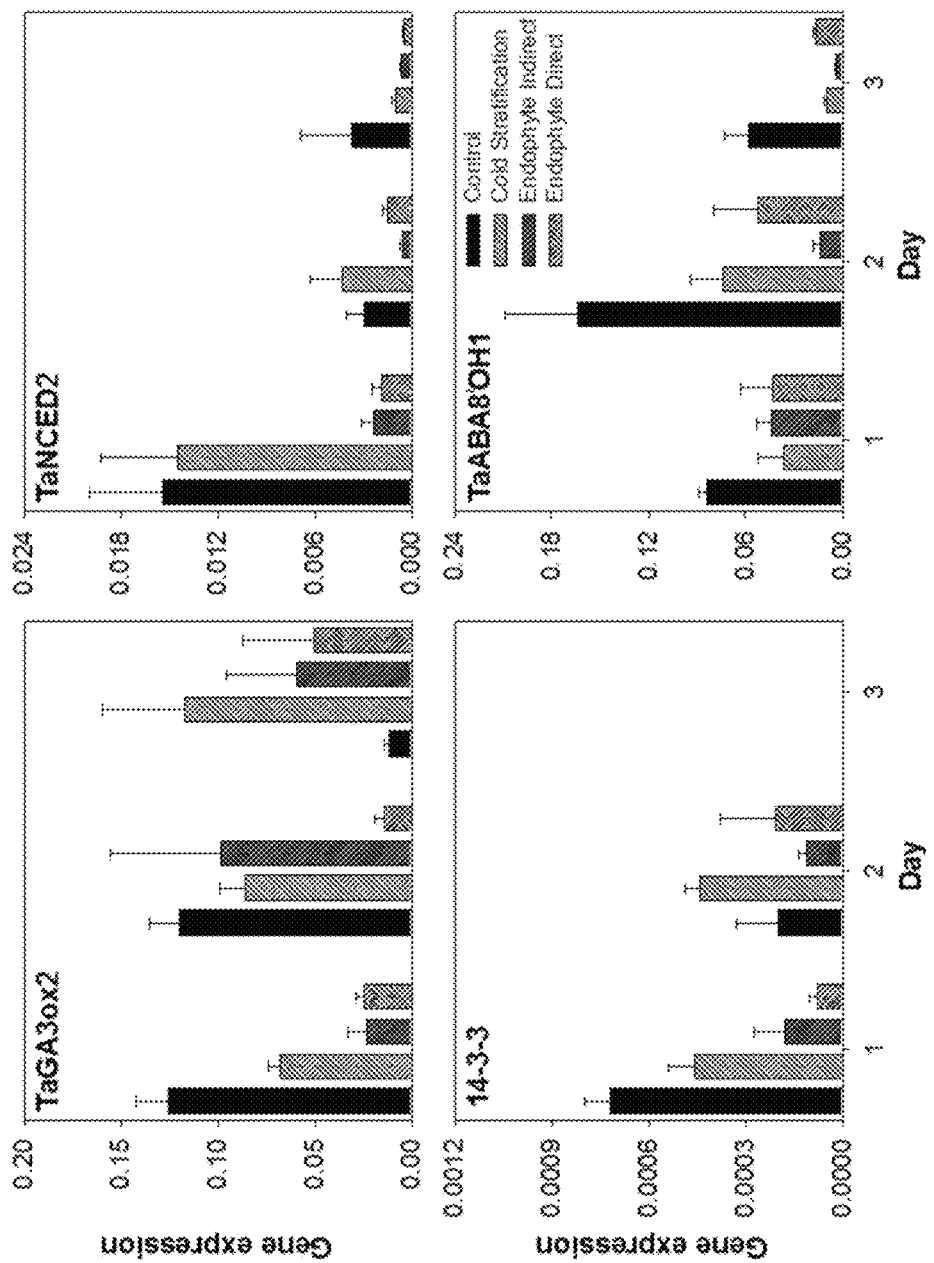
FIG. 47 shows differential expression patterns of gibberellin (TaGA3ox2 and 14-3-3) and ABA (TaNCED2 and TaABA8′OH1) genes in coleorhiza of germinating wheat seeds for three days under cold and biological stratification. Gene expression was calculated as $2^{-CT}$.

The GA3-oxidase 2 and 14-3-3 genes were selected as GA biosynthetic gene and negative regulator of the GA biosynthesis pathway respectively [Ji et al., 2011; Zhang et al., 2007]. The NCED gene is well known for its role in ABA biosynthesis pathway whereas ABA 8'-hydroxylase gene is involved in ABA catabolic pathway [Ji et al., 2011]. Real-time quantitative PCR analysis indicated that the differential (FIG. 47) and ratio expression (FIG. 48) values of distinct functional genes varied significantly (P<0.05) among the treatments. Except for the 14-3-3 gene on Day 3, detectable expression was observed for all four genes on each day. On Day 1, all genes were down-regulated in comparison with control. Expression of GA biosynthesis gene, TaGA3ox2, was considerably higher in cold stratification treatment than that of biological stratification. On the other hand, 14-3-3 expression did not vary significantly among cold and endophyte treatments although the expression of cold stratification was slightly higher than endophytic ones. The transcript level of ABA biosynthesis gene, TaNCED2, did not vary between control and cold stratification, and was significantly up-regulated than endophytic treatments. The ABA 8'-hydroxylase gene, TaABA8'OH1, showed significant down-regulation in all three stratification treatments, with lowest expression observed under cold stratification. The expression pattern did not vary between endophyte-indirect and endophyte-direct treatments. On Day 2, TaGA3ox2 expression was significantly down-regulated in all stratification treatments than control. Expression did not vary between cold stratification and endophyte-indirect treatments, and lowest expression was detected in endophyte-direct coleorhizas. No significant difference was observed for 14-3-3 transcript level among all four treatments, although expression was somewhat higher under cold stratification. The expression of TaNCED2 gene was significantly lower in endophytic treatments than control and cold stratification. Similarly, TaABA8'OH1 gene demonstrated considerable down-regulation in stratification treatments than control. The lowest expression was detected in endophyte-indirect treatment. The transcript level of TaGA3ox2 gene also varied significantly among the treatments on Day 3. Cold stratification showed about ten times higher expression than control while two endophytic treatments did not vary significantly. Conversely, TaNCED2 and TaABA8'OH1 genes were significantly down-regulated in all stratification treatments with lowest expression in endophyte-direct and endophyte-indirect treatments respectively. No detectable expression was observed for the 14-3-3 gene on Day 3.

Figure 48:
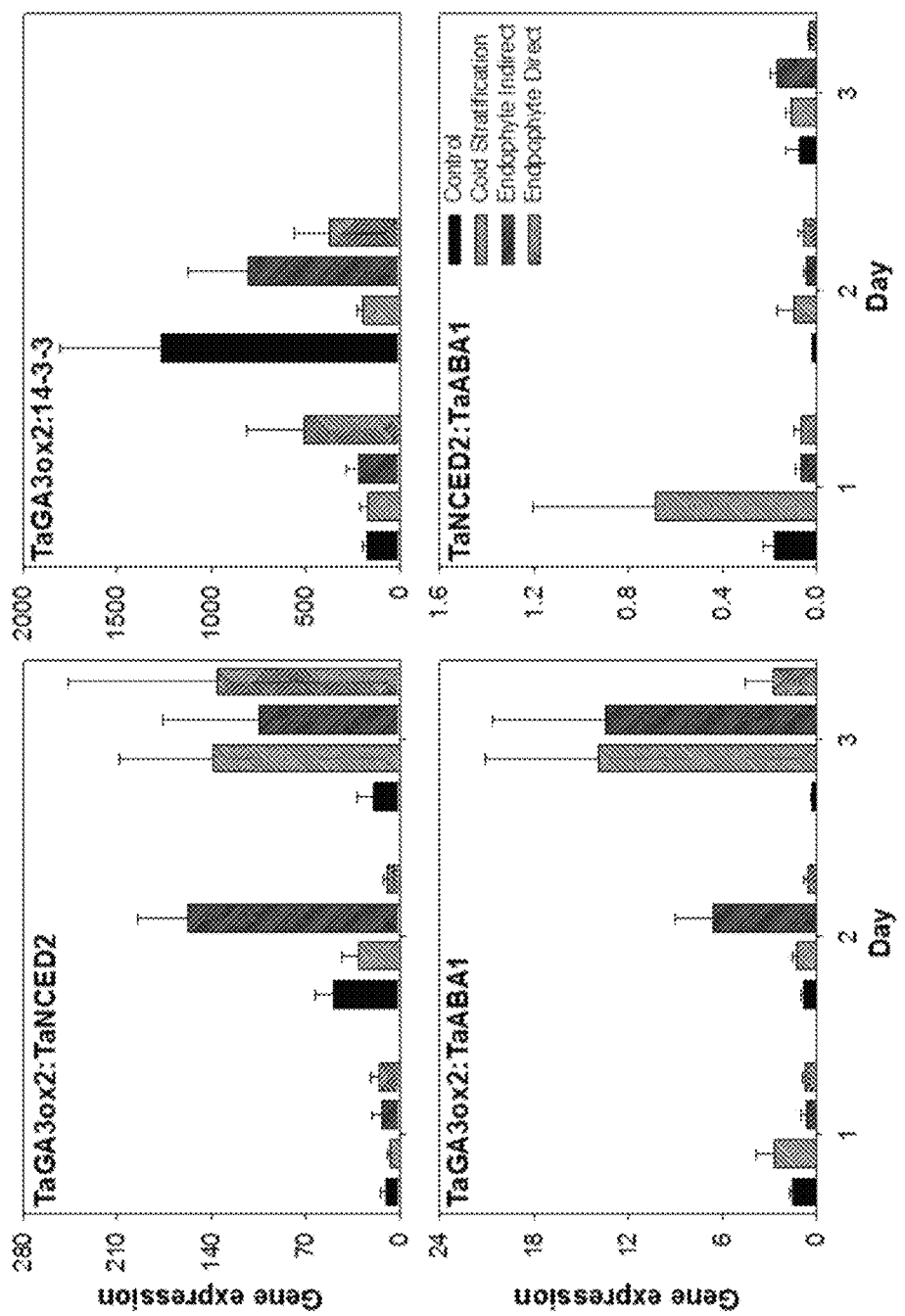
FIG. 48 shows the ratio of expression levels ($2^{-CT}$) of gibberellin (TaGA3ox2 and 14-3-3) and ABA (TaNCED2 and TaABA8′OH1) genes in coleorhiza of germinating wheat seeds for three days under cold and biological stratification.

The ratio of GA and ABA biosynthesis gene expression, TaGA3ox2:TaNCED2, shows no considerable difference among the treatments on Day 1 but steadily increased thereafter (FIG. 48). Endophyte-indirect exhibited highest value on Day 2, which is about 5-10 times higher than the other treatments; however, all three stratification treatments demonstrated similar values on Day 3. Conversely, for the ratio of GA biosynthesis and catabolic genes (TaGA3ox2: 14-3-3), endophyte-direct showed highest value on Day 1 followed by endophyte-indirect, cold stratification, and control, which is fairly similar to their germination percentage. The ratio of GA biosynthesis and ABA catabolic genes, TaGA3ox2:TaABA1, exhibited similar patterns for all treatments on Day 1, however, endophyte-indirect was considerably higher than others on Day 2. On Day 3, cold stratification and endophyte-indirect demonstrated similar expression level and control was negligible. The ratio between ABA biosynthesis and catabolic genes (TaNCED2:TaABA1) did not vary among the treatments throughout the germination period although cold stratification showed slightly higher expression level on Day 1.

Genes encoding GA and ABA biosynthesis and catabolism enzymes show differential expression patterns depending on the accumulation of transcript [Hedden and Phillips, 2000]. Expression patterns of GA3ox1 genes have been studied in plethora of plant species including *Arabidopsis* [Phillips et al., 1995], rice [Oikawa et al., 2004], and wheat [Zhang et al., 2007]. Whereas other GA biosynthesis genes such as GA-20ox are associated with growing vegetative tissues, and flowers, GA3ox (GA3ox2 or GA4H) is exclusively expressed in during seed germination and supposedly plays a crucial role [Phillips et al., 1995; Yamaguchi et al., 1998; Hedden and Phillips, 2000]. Similar to previous reports, this study also demonstrated high expression of GA3ox2 gene in wheat coleorhiza throughout the germination period. Potentially, without wishing to be bound by theory, this reflects consistent production of the bioactive GA molecule GA3 in wheat coleorhiza during germination. On the other hand, the low expression of 14-3-3 gene, a negative regulator of GA biosynthesis, was also detected in coleorhiza. With gradual seedling growth and increase in endogenous GA content, the transcript level of 14-3-3 also declined and finally diminished after Day 2. Interestingly, control had highest 14-3-3 level followed by cold stratification, endophyte-indirect, and endophyte-direct, which was somewhat reflected in their germinability. These results were in accordance with previous report by Zhang et al. [2007] who showed GA biosynthesis and catabolic genes closely linked to GA content and shoot growth.

Expression patterns of the ABA pathway genes have been studied in a wide range of cereals and pulses including rice [Oliver et al., 2007], wheat [Ji et al., 2011; Nakamura et al., 2010], bean [Qin and Zeevart, 1999]. The present results show that except control and cold stratification on Day 1, expression of TaNCED2 gene did not vary among treatments. Abscisic acid plays a pivotal role in plant stress-adaptation pathways [Nakamura et al., 2010]. Since the cold stratification seeds were kept at 4° C. for 48 hours prior to their incubation at room temperature, the abscisic acid content may have been higher. On the other hand, high TaNCED2 expression in control may have resulted in higher ABA synthesis and thereby in slower germination rate. Recent reports suggest that the catabolism of ABA mainly occurs in coleorhiza [Millar et al., 2006; Okamoto et al., 2006]. Furthermore, Barrero et al. [2009] reported up-regulation and highest expression of ABA8'OH-1 in barley coleorhiza. Similar to these reports, here high expression pattern of TaABA8'OH1 gene was found in wheat coleorhiza. The ratio of GA and ABA biosynthesis genes was fairly linked to percentage of germination. Although, TaGA3ox2:TaNCED2 did not vary remarkably on Day 1, it was highest in endophyte-indirect on Day 2 owing to its significant increase. On the other hand, all three stratification treatments showed considerable up-regulation of TaGA3ox2:TaNCED2 on Day 3, which may have reflected in their germination.

The underlying mechanisms of biological stratification are still relatively unknown but they could reveal how plant-fungus or plant-bacterial interactions take place in the early stages of germination. The role of fungal endophytes as bioenhancers is widely acknowledged [Arnold et al., 2001; Hubbard et al. 2011; Saikkonen et al., 1998; Khan et al. 2012]. In this study, we demonstrated that fungal endophytes can stimulate seed germination significantly, and this mycovitality is proportional to the physical distance between the seed and fungal endophyte. Moreover, the effect of biological stratification mediated by fungal endophyte is considerably higher than cold pre-treatment. Previous studies have shown that initiation of germination is proportional to the time of cold stratification [Cavieres and Arroyo, 2000b] considering this, future study may extend cold stratification period (>48 hours) to increase seed germinability in wheat. Although, cold stratification increased the transcript level of ABA biosynthesis gene, fungal endophytes did not directly stimulate the expression of phytohormone genes in coleorhiza. However, this study specifically assessed the expression of four genes in coleorhiza.

No study has compared germination patterns under cold and biological stratification, and elucidated GA and ABA biosynthesis and catabolic gene expression in wheat coleorhiza. Coleorhiza has recently been shown as a highly active component of germinating seed [Barrero et al., 2009]. In accordance with this Example, high expression of various functional genes in coleorhiza of germinating wheat seeds was also demonstrated. Seed germinability can be substantially enhanced through the application of fungal endophytes: 1) via indirect mycovitality or without the endophyte-seed contact on tested distance (for example, the 4 cm distance was used in this Example) and 2) via direct mycovitality or once the endophyte reaches seed.

Example 13

Figure 49:
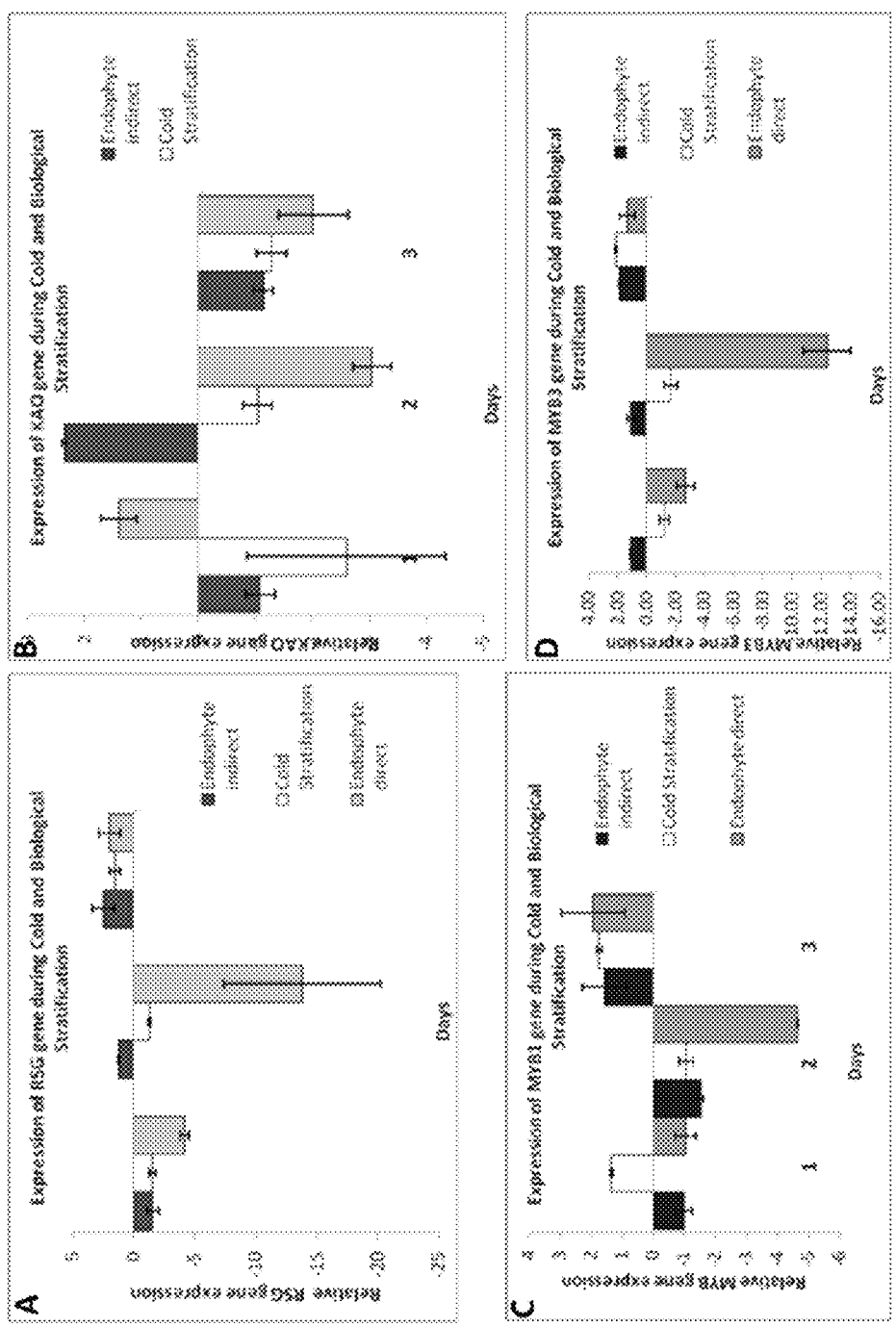
FIG. 49 shows relative expression patterns of hormonal RSG and KAO regulator genes and MYB 1 and MYB 2 resistance genes in coleorhiza of germinating wheat seeds for three days under cold and biological stratification. Gene expression was calculated as $2^{-\Delta CT}$.
Figure 50:
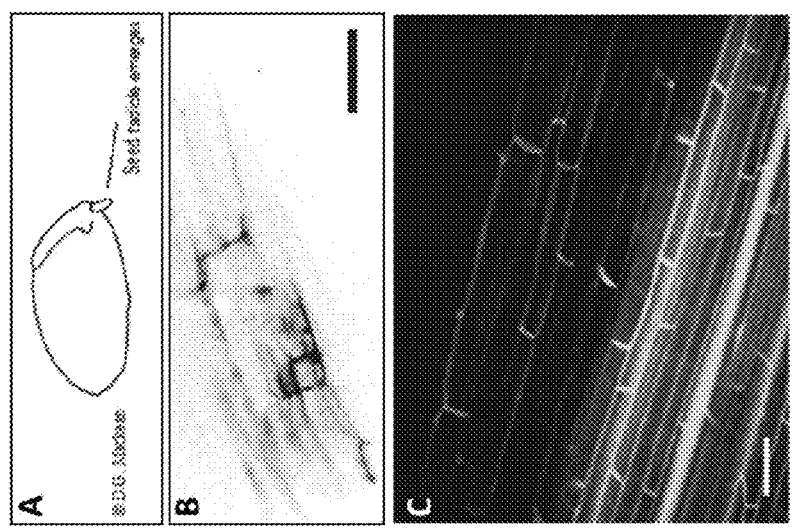
FIG. 50 shows emerging radicle from wheat geminating seed (A) Inverted fluorescence (B) and fluorescence imaging of DAF-2DA fluorescence upon reaction with NO in radicle cells (C) of AC Avonlea germinant at 5 min after treatment [Nakatsubo et al. 1998] with the fungal SMCD 2206 exudate. No fluorescence reaction observed in control radicle cells. Bar=25 mm; Bar=50 mm.

Endophytic Stratification Effects on Hormonal Regulators (RSG and KAO) and Resistance MYBs Genes Stratification is the exposure of seeds to cold and moist conditions in order to break dormancy, or enhance seed germination. As stratification is presently limited to the role of abiotic factors, this study aims to render the definition more inclusive by recognizing the role of biotic factors using mycovitality or bactovitality, or a seed-fungus or seed-bacteria symbiosis as a model. This acknowledges the existence of both cold and biological stratifications. Germination of wheat seeds subjected to cold stratification at 4° C. was compared to that of inoculated wheat seeds at room temperature. Seeds were inoculated with endophytic SMCD2206 strain. Changes in the seed's expression pattern of plant growth promoting genes—regulators (RSG and KAO) and phytohormonal gibberellins (GAs); and acquired resistance genes (MYBs) in abiotic conditions, during the early breakage of seed dormancy and germination, were assessed. Measurements were made in the coleorhiza cells using qRT-PCR (as described under Example 12). The results indicate that the RSG and KAO genes (FIG. 49), coding for enzymes promoting biosynthesis of GAs, and the MYBs resistance genes (FIG. 49) are up-regulated in inoculated seeds. Mycovitality, thus, demonstrates a reprogramming effect in pre- and post-germination events of wheat seed towards enhanced dormancy breakage and germination, effectively contributing to the prenatal care of cereal crops.

Material and Methods

RNA samples

This study is the continuation of Example 12. The same material (wheat and SMCD 2206) and in vitro methods as well as the extracted RNA samples were used to assess phytohormone RSG and KAO regulators and resistance MYB gene expresssion by qRT-PCR.

Before RNA extraction started, tubes carried with coleorhiza tissues were stored in liquid nitrogen immediately as soon as coleorhiza tissues were isolated to preserve the cells and prevent denaturation of RNA. Aurum™ Total RNA Mini Kit (Bio-Rad Laboratories) was used in total RNA extraction from plant tissues, and it suggested a minimum 20 mg of plant tissues were suitable for each sample. The extraction steps were done rapidly and the entire process was kept either in ice, as RNA, were easily denatured at room temperature. Fresh extracted total RNA, were directly loaded with premixed cDNA synthesis agents obtained from iScript cDNA Synthesis Kit (Bio-Rad Laboratories). Reverse transcription was carried out at 42° C. for 30 minutes with a final denaturation at 85° C. for 5 minutes in a Thermo cycler. cDNA concentration was measured by Nanodrop spectroscopy (Thermo Scientific) and diluted or concentrated to 100 ng/µl.

Quantitative RT-PCR and Statistical Analysis

The quantitative real-time PCR (QRT-PCR) was performed on a MiniOpticon™ Real-Time PCR Detection System (Bio-Rad Laboratories) with iQ™ SYBR® Green supermix kit (Bio-Rad Laboratories). In order to normalize QRT-PCR data, actin gene (131 bp length fragment) was selected as a reference gene and served as internal control to avoid fluctuation bias of gene expression under low cDNA concentration [Zhang et al. 2007; Nicot 2005]. KAO and RSG gene's primer according to Zhang et al. [2007] were tested in this experiment, whereas original primers were designed for MYB1 and MYB2 based on *Triticum aestivum* sequences publicly available (http://compbio.dfci.harvard-.edu/cgi-bin/tgi/geneprod_search.pl) in Computational Biology and Functional Genomics Laboratory (Harvard University). The MBY newly designed primers (Table 9):

Transcription factor Myb2 mRNA (158 bp) which comprises the sequences as shown in SEQ ID NO:16 and SEQ ID NO:17 and transcription factor Myb1 mRNA (152 bp) which comprises the sequences as shown in SEQ ID NO:18 and SEQ ID NO: 19 (Table 9).

100 ng/µl cDNA samples were further diluted to 10 ng/µl and 2 µl cDNA were used for each 25 µl reaction. In addition, 12.5 µl of iQ™ SYBR® Green supermix, 8.5 µl sterile milli-Q water, 1 µl of each forward and reverse primer (10 pmol) were made up to 25 µl reaction mix. The protocol of thermo-cycle was suggested as 95° C. for 10 minutes and 40 cycles of 94° C. for 20 s, 60° C. for 30 s, and 72° C. for 1 min. All the cDNA samples from the treatments were carried out in three replicates and two negative controls in QRT-PCR. The gene expression levels referred to quantitative curves were carried out by CFX Manager™ Software (Bio-Rad Laboratories). Cycle quantification (Cq) value from the recorded fluorescence measurements were adjusted manually with baseline. Relative quantitation is the statistical method chosen in this study [Gizinger 2002]. Gene of interest relative to the endogenous control gene was used to compare with different treatments. The quantification (ΔCT) was done relative to the subtraction from Cq value of the gene of interest to Cq value of the control gene. ΔCT was further subtracted by calibrator value and generated corresponding ΔΔCT values which were transformed to log 2 (doubling function of PCR) to synthesize relative gene expression levels [Jurado et al., 2010]. Amplified, RSG, KAO and MYB genes were purified by using BioBasic PCR Purification Kit (Bio Basic Inc.) and sent for sequence job at Plant Biotechnology Institute (NRC-PBI). Gene sequences were identified by Basic Local Alignment Search Tool (BLAST) analyses (http://blast.ncbi.nlm.nih.gov). High identity or similar genes corresponding to different homologous organisms were assembled and aligned by software MEGAS (Molecular Evolutionary Genetics Analysis). A phylogeny tree was made with the statistical method of Neighbor-joining based on the aligned genes.

Example 14

Nitric Oxide (NO) Showed the Regulatory Effect on Mycovitalism During Early Seed Germination Events Nitric oxide (NO) is a highly reactive signal molecule common to fungal, animal and plant systems. NO is also known as a signaling molecule involved in eukaryotic cell hormonal signaling [Guo et al. 2003] and plant response to abiotic and biotic stresses [Hayat et al. 2010]. While there is evidence for NO accumulation, increased activation of SOD and proline contributing to the delay of $O^{2-}$ and $H_2O_2$ accumulation in wheat leaves under salt stress, almost no information exists for fungal endophytes and there interaction with seed germination (mycovitalism). Here, the occurrence of NO in the early stages of germinating wheat AC Avonlea seeds was investigated for three days—endophyte SMCD 2206 on PDA, focusing on the radicle response to fungal diffusible molecules. NO was visualized in radicle (early root organ) in culture germinants by fluorescence microscopy using the specific probe 4,5-diaminofluoresce in diacetate; the assessment was conducted after five-minute of exposition to the fungal exudate, as sufficient to induce significant NO accumulation [Calcagno et al. 2012]. Since, SMCD 2206 exudate induced a significant production of NO in the wheat's root tissues; without wishing to be bound by theory, it is possible that this production is regulated by a molecular dialogue occurring in the wheat symbiosis.

Material and Methods

The accumulation of NO in radicle tissues was analyzed in wheat AC Avonlea germinating seed (in vitro approach presented under Example 12) using the cell permeable NO-specific probe DAF-2DA according to Calcagno et al. [2012] which is converted into its fluorescent triazole derivate DAF-2T upon reaction with NO. The formation of DAF-2T was visualized by fluorescence (Carl Zeiss Axioscop 2) microscopy. AC Avonlea germinant was assessed at 5 min after treatment with the fungal SMCD 2206 exudate following procedure proposed by Nakatsubo et al. [1998]

The specificity of this response to endophytic SMCD 2206 was confirmed by the lack of response in the non-inoculated radical cells. The analyses were repeated in three independent biological replicates.

Results and Discussion

Seed treatment with the fungal exudate can mimic—to some extent—the approach of endophytic hyphae during the presymbiotic phase of the interaction, as suggested for AM mycorrhiza in co-culture with *Arabidopsis* roots [Calcagno et al. 2010]. The fungal exudate could, therefore, be confidently used to test whether diffusible fungal signals elicit NO accumulation in the host wheat tissues (FIG. 51) during the early germination events enhancing mycovitality.

Figure 51:
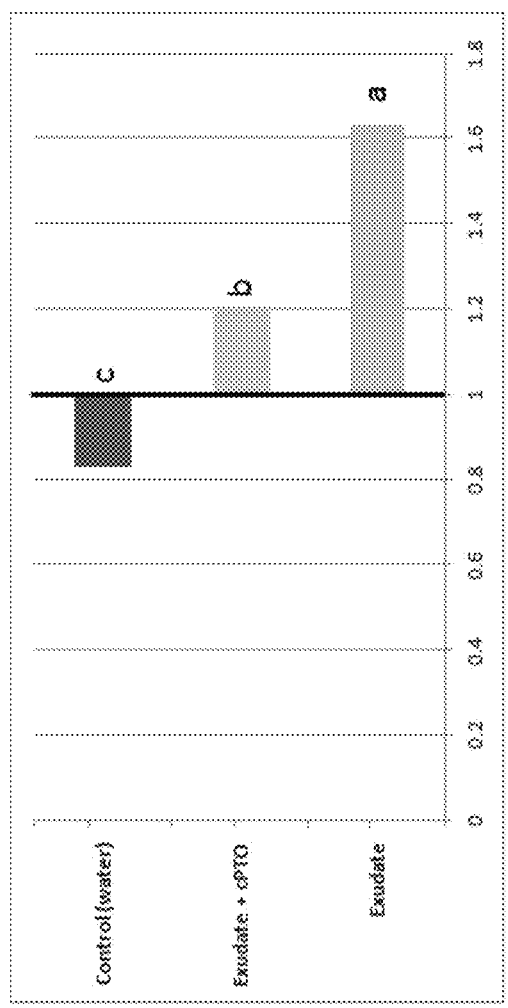
FIG. 51 shows DAF-2T fluorescence intensity values at 5 min after treatment of wheat radicle from AC Avonlea germinants with the SMCD 2206 fungal exudate, fungal exudate together with the NO scavenger cPTIO, and sterile water. Radicle segments were incubated for 30 min in 2 ml of detection buffer (10 mM Tris-Hcl, pH 7.4, 10 mM KCl) containing 15 μM DAF-2DA (Sigma-Aldrich) with or without 1 mM 2-(4-carboxyphenyl)-4,4,5,5-tetramethylimidazoline-1-oxyl-3-oxide (cPTIO) as an NO scavenger. Average fluorescence values are reported as a ratio of the fluorescence intensity at 5 min to the fluorescence intensity at time 0. Different letters indicate statistically significant differences between samples (p≤0.05, Kruskal-Wallis test).

Cellular evidence, therefore, suggests that NO accumulation is a novel component in the signaling pathway that leads to mycosymbiosis related with mycovitalism of wheat seed (FIG. 51). This finding has both theoretical and practical values in attempts to improve plant prenatal-care using endophytic symbionts.

Example 15

Study of the Effects of Endophytes on Phytoremediation and Phytoreclamation

Phytoremediation is a promising environmental technique. It has been shown to be cost-effective for reclamation of hydrocarbon/petroleum, salt, heavy metal and radioisotope-contaminated soils. In this study, the effects of coniferous (*Picea* or *Pinus*) and deciduous (*Salix* or *Populus*) trees, shrubs (*Caragana* or *Krascheninnikovia*), and grasses (*Festuca* or *Elymus*) infected (E+) and non-infected (E−) by endophytic organisms (via plant propagation material, seed or root infection and colonization) (SMCD 2204, 2206, 2208, 2210 and 2215) on the decomposition, transformation or degradation of petroleum hydrocarbons in petroleum contaminated soil will be investigated. Plants will be grown in pots containing petroleum contaminated and non-contaminated soils. Plants will be inoculated and incubated for 6 months using the greenhouse method suggested by Soleimani et al. (2010). Unplanted pots will be used as control. At the end of the experiment, plant-root colonization (Abdellatif et al. 2009), soil hydrophobicity (Chau 2012), total petroleum hydrocarbons (TPHs), and polycyclic aromatic hydrocarbons (PAHs) contents will be analysed (Germida et al. 2010). The difference in E+vs. E− plants root and shoot biomass and leaf photosynthesis will be compared (Hubbard et al. 2012) with PAH and TPH removal in the rhizosphere of the plants. Unplanted pots will be used as control to calculate the efficacy of symbiotic (E+) plants on degradation of petroleum hydrocarbons (Soleimani et al. 2010). The infected plants will decompose, transform or degrade hydrocarbons and salts, uptake and accumulate and clean up or eliminate the heavy metals and radioisotopes in the contaminated site, soil or environment.

Example 16

Seed Coating and Preparation for Field Trials

Fungal strains SMCD 2204, 2204F, 2206, 2208, and 2210, as well as bacterial strain SMCD 2215, were plated from a cryopreserved aliquot onto PDA plates and incubated in the dark at room temperature for 5-10 days.

From there, approximately 10 agar plugs of 1 cm² area were inoculated into 1 liter of the medium in a 2.8 liter Fernbach flask, and cultivated for 10 days at room temperature and 130 rpm. Media were as follows: molasses broth (30 g/l molasses and 5 g/l brewer's yeast) for SMCD 2204, 2206, 2208, and 2210; YEP broth (10 g/l peptone, 10 g/l yeast extract, and 5 g/l sodium chloride) for SMCD 2215, and PD broth (30 g/l dextrose and 4 g/l infusion from potato solids) for SMCD 2204F. Typical final biomass titers for 10 days of growth were 6-12 g-dry cell weight per liter of culture broth (g-DCW/l).

Fungal biomass containing conidia, chlamydospores, and mycelial fragments was filtered through filter paper using a Buchner funnel under vacuum pressure and washed with sterile water. Biomass was then dried over night at room temperature in a biosafety hood, and ground in a Wiley mill through a 425 μm (40 mesh) screen.

For SMCD 2204, 2204F, 2206, 2208, and 2210, wheat seeds were coated with sodium alginate (2%) (1 g of wheat with seeds 37.5 uL of sodium alginate) followed by coating with a mixture of fungal ground biomass with talc (1:12 ratio). For SMCD 2215, sonicated liquid culture was mixed with 2% sodium alginate in a 1:1 ratio followed by coating with talc.

Example 17

Field-Trial Preparation and Planting

The effects of the previously described microbial hosts (SMCD 2204, 2204F, 2206, 2208, 2210, and 2215) were analyzed on 9 different crops: corn, spring wheat, soybean, *durum*, barley, canola, pea, chickpea, and lentil. Field trials were conducted at the following locations: 1) three sites at University of Saskatchewan (Saskatoon, Stewart Valley, and Vanguard, Saskatchewan, Canada) for the following crops: spring wheat, *durum* wheat, barley, canola, pea, chickpea, and lentil; 2) one site in Brookings, S. Dak., USA for spring wheat and corn; and 3) one site in York, Nebr., USA for corn.

The size of the test plots were 10 m by 1.5 m at Stewart Walley and Vangard, and 2.5 m×2.5 m at Saskatoon (University of Saskatchewan), Saskatchewan Canada, and 5 feet by 50 feet (for wheat), 5 feet by 40 feet (for corn) at Brookings, S. Dak., and 5 feet by 40 feet for corn at York, Nebr., USA.

The varieties shown in Table 10 were used across these test sites. Anhydrous urea was used as fertilizer at Brookings, S. Dak. and York, Nebr. No fertilizer was applied in Saskatchewan, Canada.

Water was applied by using center pivot irrigation three times over the cultivation period at Brookings, S. Dak., and line irrigation was used in York, Nebr. In Saskatoon, Saskatchewan, Canada, water was provided once per week with 50% of field capacity until spike formation. Vanguard, Saskatchewan, Canada was a naturally dryland site (brown soil, semi-arid), while Stewart Valley, Saskatchewan, Canada was a naturally moist site (dark brown soil).

The targeted seeding density, planting date, and harvesting date for each crop and location are listed in Table 11. Plants were harvested using a 5 foot research combine.

Example 18

Quantification of Traits in Field Trials

Figure 52:
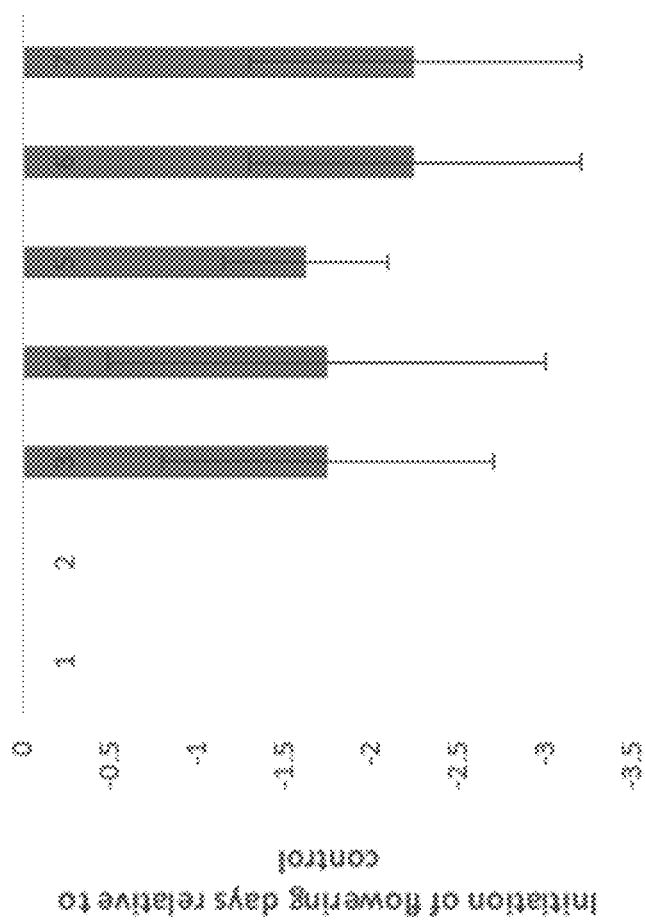
FIG. 52 shows the change (in days) in the initial flowering time of canola crops treated with the microbial compositions described. Data shown is from n=4 independent replicate plots±one standard deviation. 1=Abiotic formulation control, 2=SMCD 2204, 3=SMCD 2204F, 4=SMCD 2206, 5=SMCD 2208, 6=SMCD 2210, 7=SMCD 2215.

Flowering time was assessed by visually scoring the plots on the date of the first flower opening (bud burst). Data presented shows the change in flowering time (in days) relative to the abiotic formulation control. FIG. 52 shows the early flowering of canola plants treated with the microbial formulations, as compared to the abiotic formulation control.

Figure 53:
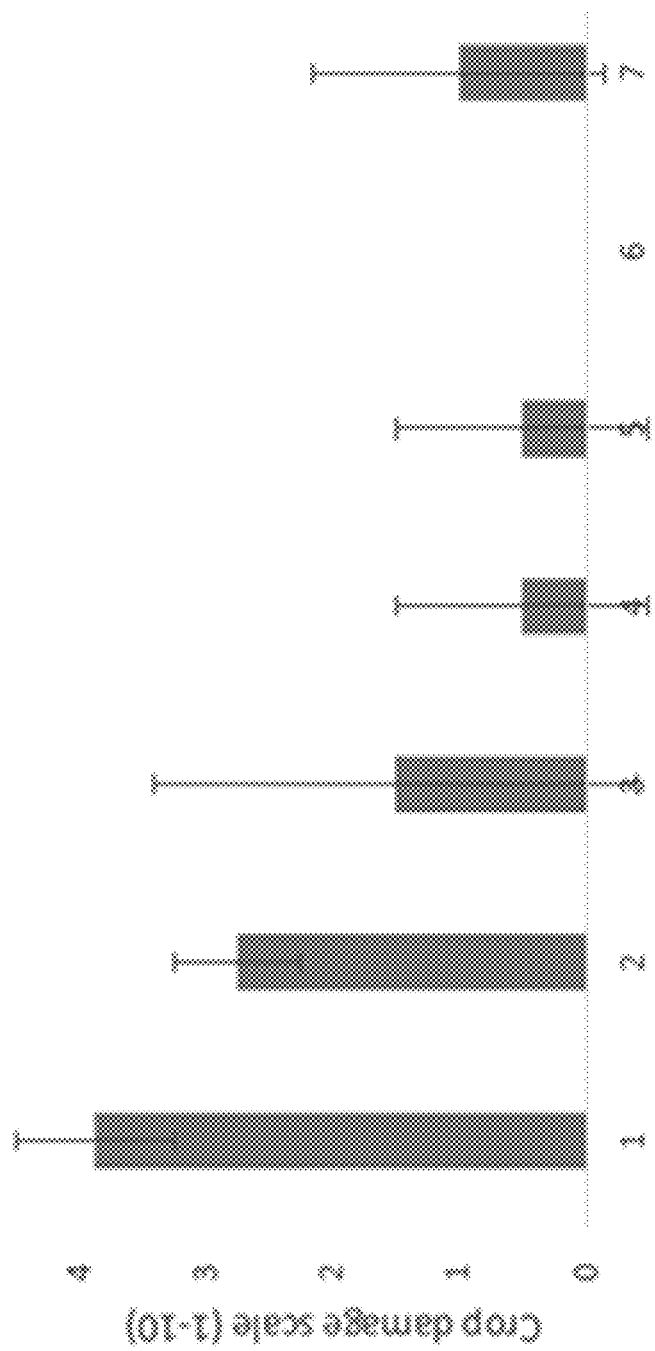
FIG. 53 shows the damage score due to pests of canola crops treated with the microbial compositions described. Data shown is from n=4 independent replicate plots±one standard deviation. 1=Abiotic formulation control, 2=SMCD 2204, 3=SMCD 2204F, 4=SMCD 2206, 5=SMCD 2208, 6=SMCD 2210, 7=SMCD 2215.

Damage resulting from pests (grasshopper, in this case) was assessed by visually scoring the loss of crop flowers (for canola). FIG. 53 shows the reduced canola crop damage in plants treated with the microbial formulations, as compared to the abiotic formulation control.

Figure 54:
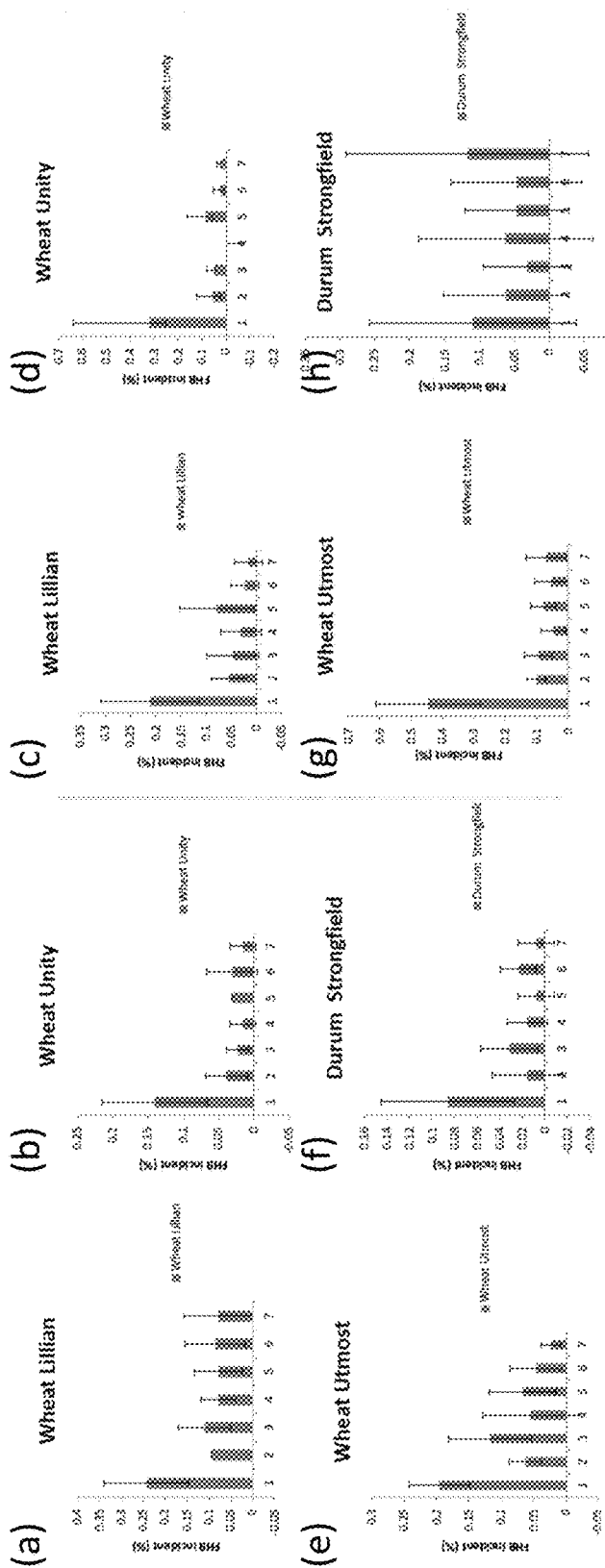
FIG. 54 shows the *Fusarium* Head Blight (FHB) incidence percentage for three spring wheat (Lillian, Unity, and Utmost) and one *durum* wheat (Strongfield) varieties. Subplots (a), (b), (e), and (f) refer to the Vanguard, Saskatchewan, Canada test site, while subplots (c), (d), (g), and (h) refer to the Stewart Valley, Saskatchewan, Canada test site. Data shown is from n=4 independent replicate plots±one standard deviation. 1=Abiotic formulation control, 2=SMCD 2204, 3=SMCD 2204F, 4=SMCD 2206, 5=SMCD 2208, 6=SMCD 2210, 7=SMCD 2215.

*Fusarium* head blight (FHB) is caused largely by the *Fusarium graminearum* species in North America. Infection was assessed visually, where symptoms of disease in wheat include tan or brown colored lesions that may include single spikelets or large sections of the head. FIG. 54 shows the reduced incidence of FHB for three spring wheat and one *durum* wheat varieties, across two sites.

Figure 55:
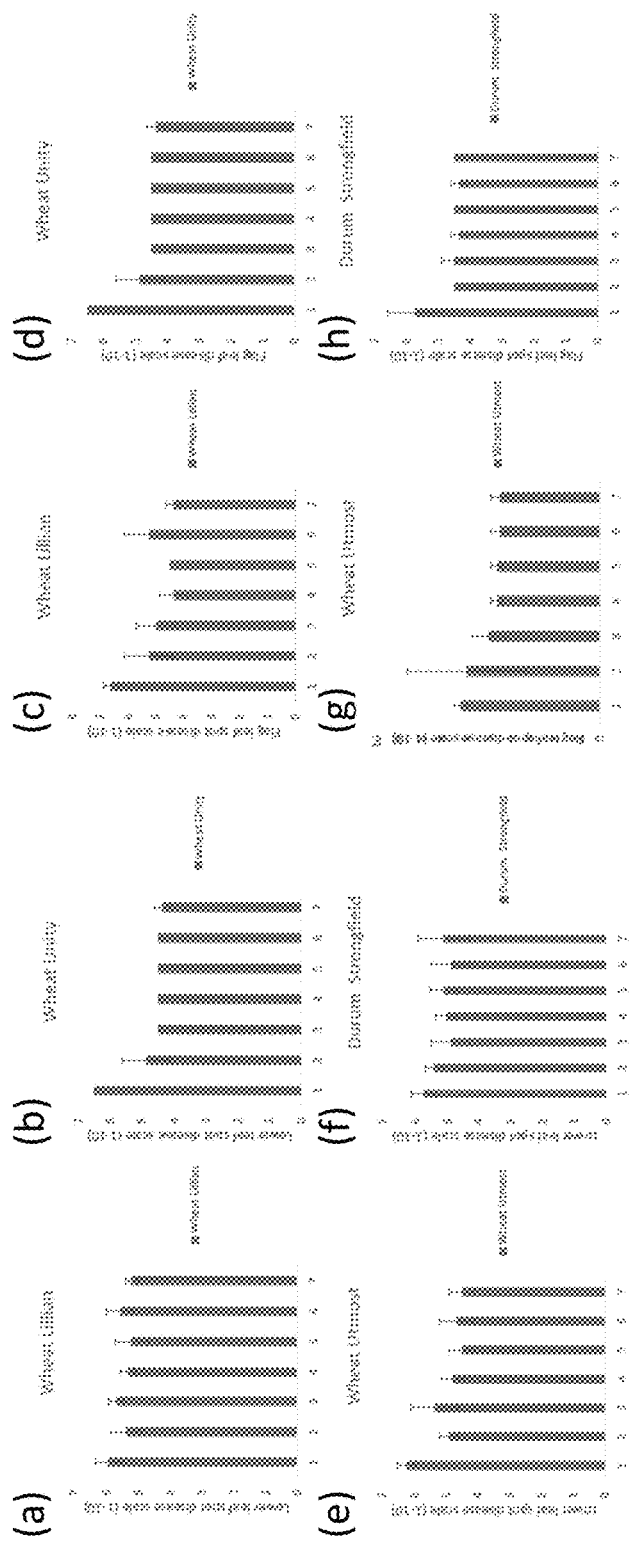
FIG. 55 shows the leaf spot disease rating for three spring wheat (Lillian, Unity, and Utmost) and one *durum* wheat (Strongfield) varieties. A rating of 1 is most healthy and a rating of 10 is most diseased. Subplots (a), (b), (e), and (f) refers to the leaf spot disease rating on the lower leaf, while subplots (c), (d), (g), and (h) refer to the leaf spot disease rating on the flag leaf. Data shown is from n=4 independent replicate plots±one standard deviation. 1=Abiotic formulation control, 2=SMCD 2204, 3=SMCD 2204F, 4=SMCD 2206, 5=SMCD 2208, 6=SMCD 2210, 7=SMCD 2215.

Lower leaf spot and flag leap spot diseases are largely caused by *Pyrenophora tritici-repentis* (tan spot), *Stagonospora nodorum* (*Stagonospora* blotch), *Septoria tritici* (*Septoria* blotch). This was assessed visually for wheat and scored on a scale of 1-10 (low to high infection). FIG. 55 shows the reduced spot disease rating of three spring wheat varieties and one *durum* wheat variety when inoculated with the described microbial compositions. These have greener leaves as compared to the abiotic formulation control, indication protecting from leaf spot diseases, delayed senescence, or both.

Figure 56:
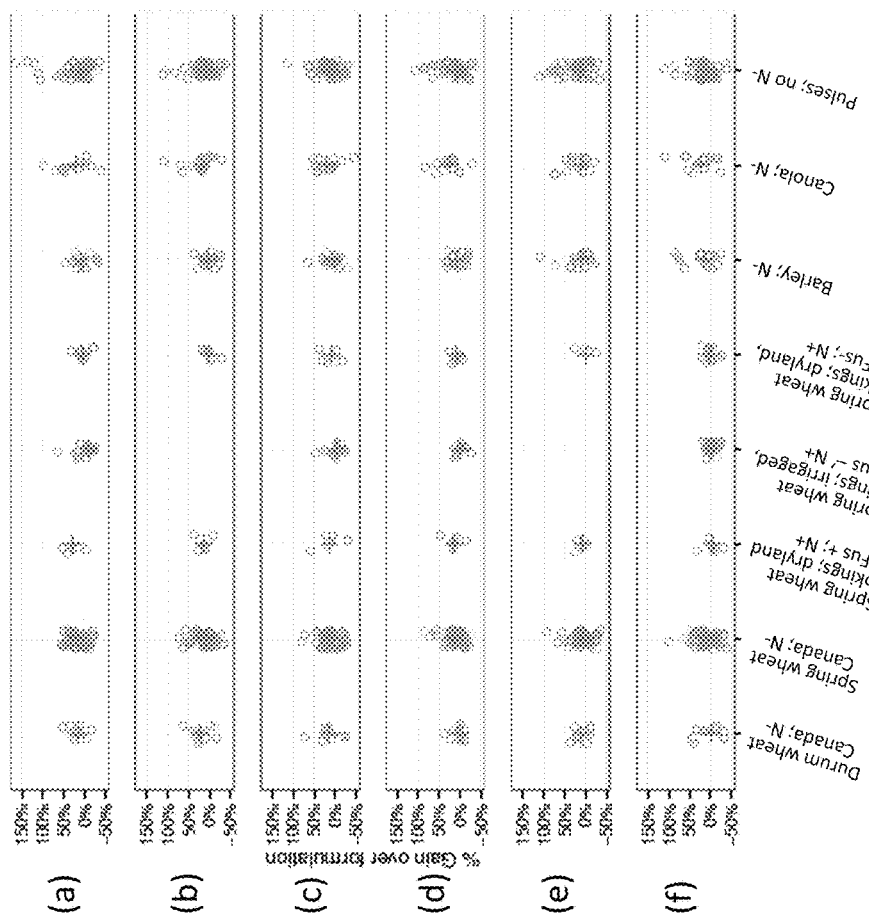
FIG. 56 shows aggregated yield data for *durum* wheat, spring wheat, barley, canola, and pulses (chickpea, pea, and lentil). Each dot refers to a single plot. The "+" refers to the group mean. The data are presented as percentage gain over the abiotic formulation control for each combination of crop, location and condition (irrigated or dryland). (a) refers to SMCD 2215, (b) refers to SMCD 2210, (c) refers to SMCD 2204, (d) refers to SMCD 2206, (e) refers to SMCD 2208, and (f) refers to SMCD 2204F. Data shown are from n=4 independent replicate plots for all Canadian sites and n=6 plots for Brookings, S. Dak. sites. While no fields were experimentally inoculated with a pathogen, the notation "Fus−" indicates that there was no visible occurrence of *Fusarium* Head Blight (*Fusarium graminearum*) in that specific field and "Fus+" indicates that there was clear evidence of *Fusarium* Head Blight (*Fusarium graminearum*) occurrence. N− indicates that there was no nitrogen applied to the field and N+indicates that nitrogen was applied at agriculturally relevant rates.

Grain yield (for wheat and corn), in dry bushels per acre, was calculated by using the weight harvested per plot, the test weight, the percent moisture, and shrinkage factor. Pod weight was measured for canola, and total biomass was measured for lentil, chickpea, and pea. FIG. 56 and FIG. 57 show the percentage change in yield (represented by grain or seed weight, pod weight, or total biomass) of the crops treated with the described microbial compositions relative to the abiotic formulation control in their corresponding field condition. FIG. 58 shows the percentage increase in corn ear weight of the crop treated with the described microbial compositions relative to the abiotic formulation control in their corresponding field condition.

Example 19

Greenhouse Trials with Additional Crops

A variety of other corn crops were grown with the applied microbial compositions to assess their ability to affect a variety of plant traits. Tomato, alfalfa, corn, sweet corn, organic corn, swiss chard, radish, and cabbage were all grown in the greenhouse under normal water and/or drought conditions. For normal water conditions, the plants received water three times per week over the course of two months. For drought conditions, the plants received watering three times per week for two weeks and no water for the next two months. FIG. 59 shows the effect of SMCD 2204F, 2206, and 2215 on tomato in shoot length and weight, root length and weight, total plant biomass, and fruit weight. FIG. 60 shows the effect of SMCD 2204, 2206, and 2215 on alfalfa in shoot length and weight, root length and weight, and total plant biomass. FIG. 61 shows the effects of the described microbial compositions in the form of total plant biomass under normal water and drought conditions for corn, sweet corn, organic corn, swiss chard, radish, and cabbage.

Example 20

Mycovitalism Modulates Phytohormone Production in Wheat Seed Treatment and Plant Growth Phytohormone quantification was undertaken on wheat (CDC Avonlea) plants in a greenhouse scenario, treated with SMCD 2206 and an untreated control group. Germination and plant growth was undertaken at 21 C. The first leaves were collected at 7 days post-germination. Green leaf samples were treated with liquid nitrogen, freeze dried, and stored at −80 C until analysis described below.

Tables 12 through 14 describe the phytohormones analyzed in this study. Analysis was performed on a UPLC-ESI-MS/MS utilizing a Waters ACQUITY UPLC system, equipped with a binary solvent delivery manager and a sample manager coupled to a Waters Micromass Quattro Premier XE quadrupole tandem mass spectrometer via a Z-spray interface. MassLynx™ and QuanLynx™ (Micromass, Manchester, UK) were used for data acquisition and data analysis.

Extraction and Purification

An aliquot (100 ul) containing all the internal standards, each a concentration of 0.2 ng/ul, was added to homogenized sample (approximately 50 mg). 3 ml isopropanol: water:glacial acetic acid (80:19:1, v/v/v) were further added, and the samples were agitated in the dark for 24 hr at 4 C. Samples were then centrifuged and the supernatant was isolated and dried on a Buchi Syncore Polyvap (Buchi, Switzerland). Further, they were reconstituted in 100 ul acidifed methanol, adjusted to 1 ml with acidified water, and then partitioned against 2 ml hexane. After 30 min, the aqueous layer was isolated and dried as above. Dry samples were reconstituted in 800 ul acidied methanol and adjusted to 1 ml with acidied water. The reconstituted samples were passed through an equilibrated Sep-Pak C18 cartridges (Waters, Mississauga, ON, Canada), the final eluate was split in two equal portions.

Hormone Quantification by HPLC-ESI-MS/MS

The procedure for quantification for abscisic acid and its metabolites, cytokinins, and gibberellins has been described in detail previously (Chiwocha 2003 2005). Samples were injected onto an ACQUITY UPLC HSS C18 SB column (2.1×100 mm, 1.8 um) with an in-line filter and separate db a gradient elution of water containing 0.02% formic acid against an increasing percentage of a mixture of acetonitrile: methanol (50:50, v/v).

Briefly, the analysis using the Multiple Reaction Monitoring (MRM) function of the MassLynx 4.1 control software. The resulting chromatographic traces are quantified off-line by the software wherein each trace is integrated and the resulting ratio of signals (non-deuterated/internal standard) is compared with a previously constructed calibration curve to yield the amount of analyze present (ng per sample). Results are expressed in nanograms per gram of dry weight.

Results

Induction of increased levels of ABA and its related metabolites by seed age is sufficient to prevent seed germination. FIG. 62 shows the increase of gibberellin production, concomitant with the decreased production of ABA and its related metabolites (shown in FIG. 63), by direct and indirect application of SMCD 2206 in wheat. Germination suppression can be prevented by endophytes acting as inhibitors of ABA biosynthesis, natural agents responsible for ABA degradation and inducers of gibberellin production. Further, lower cytokinin production in the SMCD 2206 treatments (FIG. 64) is consistent with this mechanism. IAA-Asp concentration was higher in direct and indirect application of SMCD 2206 as compared to the control (FIG. 65).

Example 21

Growth and Scale-Up of Microbes for Inoculation

Growth and Scale-Up of Bacteria for Inoculation on Solid Media

The bacterial isolates are grown by loop-inoculation of a single colony into R2A broth (supplemented with appropriate antibiotics) in 100 mL flasks. The bacterial culture is incubated at 30±2° C. for 2 days at 180 rpm in a shaking incubator (or under varying temperatures and shaking speeds as appropriate). This liquid suspension is then used to inoculate heat sterilized vermiculite powder that is premixed with sterile R2A broth (without antibiotics), resulting in a soil like mixture of particles and liquid. This microbial powder is then incubated for an additional couple of days at 30±2° C. with daily handshaking to aerate the moist powder and allow bacterial growth. Microbially inoculated vermiculite powder is now ready for spreading on to soil or onto plant parts. Alternatively, the R2A broth is used to inoculate Petri dishes containing R2A or another appropriate nutrient agar where lawns of bacteria are grown under standard conditions and the solid colonies scraped off, resuspended in liquid and applied to plants as desired.

Growth and Scale-Up of Fungi for Inoculation on Solid Media

Once a fungal isolate has been characterized, conditions are optimized for growth in the lab and scaled-up to provide sufficient material for assays. For example, the medium used to isolate the fungus is supplemented with nutrients, vitamins, co-factors, plant-extracts, and other supplements that can decrease the time required to grow the fungal isolate or increase the yield of mycelia and/or spores the fungal isolate produces. These supplements can be found in the literature or through screening of different known media additives that promote the growth of all fungi or of the particular fungal taxa.

To scale up the growth of fungal isolates, isolates are grown from a frozen stock on several Petri dishes containing media that promotes the growth of the particular fungal isolate and the plates are incubated under optimal environmental conditions (temperature, atmosphere, light). After mycelia and spore development, the fungal growth is scraped and resuspended in 0.05 M Phosphate buffer (pH 7.2, 10 mL $plate^{-1}$). Disposable polystyrene Bioassay dishes (500 $cm^2$, Thermo Scientific Nunc UX-01929-00) are prepared with 225 mL of autoclaved media with any required supplements added to the media, and allowed to solidify. Plates are stored at room temperature for 2-5 days prior to inoculation to confirm sterility. Five mL of the fungal suspension is spread over the surface of the agar in the Bioassay plate in a biosafety cabinet, plates are allowed to dry for 1 h, and they are then incubated for 2-5 days, or until mycelia and/or spores have developed.

A liquid fungal suspension is then created via the following. Fungal growth on the surface of the agar in the Bioassay plates are then scraped and resuspended in 0.05 M Phosphate buffer (pH 7.2). $OD_{600}$ readings are taken using a spectrometer and correlated to previously established OD$_{600}$/CFU counts to estimate fungal population densities, and the volume adjusted with additional sodium phosphate buffer to result in 100 mL aliquots of fungi at a density of approximately $10^6$-$10^{11}$ spores mL$^{-1}$. This suspension may or may not be filtered to remove mycelia and can be used to create a liquid microbial formulation as described herein to apply the fungal isolate onto a plant, plant part, or seed.

Growth and Scale-Up of Bacteria for Inoculation in Liquid Media

Bacterial strains are grown by loop-inoculation of one single colony into R2A broth (amended with the appropriate antibiotics) in 100 mL flasks. The bacterial culture is incubated at 28±2° C. for 1 day at 180 rpm in a shaking incubator (or under varying temperatures and shaking speeds as appropriate). The bacteria are pelleted by centrifugation and resuspended in sterile 0.1 M sodium phosphate. OD$_{600}$ readings are taken using a spectrometer and correlated to previously established OD$_{600}$/CFU counts to estimate bacterial population densities, and the volume adjusted with additional sodium phosphate buffer to result in 100 mL aliquots of bacteria at a density of $1 \times 10^8$ cells/mL. To help break surface tension, aid bacterial entry into plants and provide microbes for some energy for growth, 10 μL of Silwet L-77 surfactant and 1 g of sucrose is added to each 100 mL aliquot (resulting in 0.01% v/v and 1% v/v concentrations, respectively) in a similar way as in the protocol for *Agrobacterium*-mediated genetic transformation of *Arabidopsis thaliana* seed [Clough, S., Bent, A. (1999) The Plant Journal 16(6): 735-743].

Growth and Scale-Up of Fungi for Inoculation in Liquid Media

Once a fungal isolate has been characterized, conditions are optimized for growth in the lab and scaled-up to provide enough material for assays. For example, the medium used to isolate the fungi is supplemented with nutrients, vitamins, co-factors, plant-extracts, and/or other supplements that can decrease the time required to grow the fungal isolate and/or increase the yield of mycelia and/or spores the fungal isolate produces. These supplements can be found in the literature or through screening of different known media additives that promote the growth of all fungi or of the particular fungal taxa.

To scale up the growth of fungal isolates, isolates are grown from a frozen stock on Petri dishes containing media that promotes the growth of the particular fungal isolate and the plates are incubated under optimal environmental conditions (temperature, atmosphere, light). After mycelia and spore development, the fungal culture is scraped and resuspended in 0.05M Phosphate buffer (pH 7.2, 10 mL/plate). 1 liter of liquid media selected to grow the fungal culture is prepared in 2 L glass flasks and autoclaved and any required supplements added to the media. These are stored at room temperature for 2-5 days prior to inoculation to confirm sterility. 1 mL of the fungal suspension is added aseptically to the media flask, which is then incubated for 2-5 days, or until growth in the liquid media has reached saturation. Spore counts were determined using hemacytometer and correlated to previously established CFU counts to estimate fungal population densities, and the volume adjusted with additional sodium phosphate buffer to result in 100 mL aliquots of fungi at a density of approximately $10^6$-$10^{11}$ spores/mL. This suspension may or may not be filtered to remove mycelia and can be used to create a liquid microbial formulation as described herein to apply the fungal isolate onto a plant, plant part, or seed.

Creation of Liquid Microbial Formulations or Preparations for the Application of Microbes to Plants Bacterial or fungal cells are cultured in liquid nutrient broth medium to between $10^2$-$10^{12}$ CFU mL$^{-1}$. The cells are separated from the medium and suspended in another liquid medium if desired. The microbial formulation may contain one or more bacterial or fungal isolates. The resulting formulation contains living cells, lyophilized cells, or spores of the bacterial or fungal isolates. The formulation may also contain water, nutrients, polymers and binding agents, surfactants or polysaccharides such as gums, carboxymethyl-cellulose and polyalcohol derivatives. Suitable carriers and adjuvants can be solid or liquid and include natural or regenerated mineral substances, solvents, dispersants, wetting agents, tackifiers, thickeners, binders or fertilizers. Compositions can take the form of aqueous solutions, oil-in-water emulsions, or water-in-oil emulsions. Small amounts of insoluble material can optionally be present, for example in suspension in the medium, but it is generally preferred to minimize the presence of such insoluble material.

Inoculation of Plants by Coating Microbes Directly onto Seed

Seed is treated by coating it with a liquid microbial formulation (prepared as described herein) including microbial cells and other formulation components, directly onto the seed surface at the rate of $10^2$-$10^8$ microbial CFU per seed. Seeds are soaked in liquid microbial formulation for 1, 2, 3, 5, 10, 12, 18 or 24 hours or 2, 3, or 5 days. After soaking in microbial formulation, seeds are planted in growing containers or in an outdoor field. Seeds may also be coated with liquid microbial formulation by using an auger or a commercial batch treater. One or more microbial formulations or other seed treatments are applied concurrently or in sequence. Treatment is applied to the seeds using a variety of conventional treatment techniques and machines, such as fluidized bed techniques, augers, the roller mill method, rotostatic seed treaters, and drum coaters. Other methods, such as spouted beds may also be useful. The seeds are pre-sized before coating. Optionally the microbial formulation is combined with an amount of insecticide, herbicide, fungicide, bactericide, or plant growth regulator, or plant micro- or macro-nutrient prior to or during the coating process. After coating, the seeds are typically dried and then transferred to a sizing machine for grading before planting. Following inoculation, colonization of the plants or seeds produced therefrom is confirmed via any of the various methods described herein. Growth promotion or stress resilience benefits to the plant are tested via any of the plant growth testing methods described herein.

Inoculation of Plants with a Combination of Two or More Microbes

Seeds can be coated with bacterial or fungal endophytes. This method describes the coating of seeds with two or more bacterial or fungal isolates. The concept presented here involves simultaneous seed coating of two microbes (e.g., both a gram negative endophytic bacterium *Burkholderia phytofirmans* and a gram positive endophytic bacterium *Bacillus mojavensis*). Optionally, both microbes are genetically transformed by stable chromosomal integration as follows. *Bacillus mojavensis* are transformed with a construct with a constitutive promoter driving expression of a synthetic operon of GFPuv and spectinomycin resistance genes, while *Burkholderia* phytofirmans are transformed with a construct with a constitutive promoter driving expression of the lac operon with an appended spectinomycin resistance gene. Seeds are coated with a prepared liquid formulation of the two microbes the various methods described herein. Various concentrations of each endophyte in the formulation are applied, from $10^2$ seed$^{-1}$ to about $10^8$ seed$^{-1}$. Following inoculation, colonization of the plants or seeds produced therefrom may be confirmed via any of the various methods described herein. Growth promotion or stress resilience benefits to the plant are tested via any of the plant growth testing methods described herein.

Example 22

In-Vitro Characterization of Endophytes

Endophytes may be characterized by their ability to produce certain substances. The following assays allow for the characterization of endophytes.

Assay for Growth on Nitrogen Free LGI Media

All glassware is cleaned with 6 M HCl before media preparation. A new 96 deep-well plate (2 mL well volume) is filled with 1 mL/well of sterile LGI broth (per L, 50 g Sucrose, 0.01 g FeCl$_3$-6H$_2$O, 0.8 g K$_3$PO$_4$, 0.2 g MgSO$_4$-7H$_2$O, 0.002 g Na$_2$MoO$_4$-2H$_2$O, pH 7.5). Bacteria are inoculated with a flame-sterilized 96-pin replicator. The plate is sealed with a breathable membrane, incubated at 25° C. with gentle shaking for 5 days, and OD$_{600}$, measurements are taken daily.

ACC Deaminase Activity Assay

Microbes are assayed for growth with ACC as their sole source of nitrogen. Prior to media preparation all glassware is cleaned with 6 M HCl. A 2 M filter sterilized solution of ACC (#1373A, Research Organics, USA) is prepared in water. 1 μl/mL, of this is added to autoclaved LGI broth (see above), and 1 mL aliquots are placed in a new 96 well plate. The plate is sealed with a breathable membrane, incubated at 25° C. with gentle shaking for 5 days, and OD$_{600nm}$ readings are taken daily. Only wells that are significantly more turbid than their corresponding nitrogen free LOT wells are considered to display ACC deaminase activity.

Mineral Phosphate Solubilization Assay

Microbes are plated on tricalcium phosphate media. This is prepared as follows: 10 g/l. glucose, 0.373 g/L NH$_4$NO$_3$, 0.41 g/L MgSO$_4$, 0.295 g/L NaCl, 0.003 FeCl$_3$, 0.7 g/L Ca$_3$HPO$_4$ and 20 g/L Agar, pH 6, then autoclaved and poured into 150 mm plates. After 3 days of growth at 25° C. in darkness, clear halos are measured around colonies able to solubilize the tricalcium phosphate.

RNAse Activity Assay 1.5 g of torula yeast RNA (#R6625, Sigma) is dissolved in 1 mL of 0.1 M Na$_2$HPO$_4$ at pH 8, filter sterilized and added to 250 mL of autoclaved R2A agar media which is poured into 150 mm plates. The bacteria from a glycerol stock plate are inoculated using a flame-sterilized 96 pin replicator, and incubated at 25° C. for 3 days. On day three, plates are flooded with 70% perchloric acid (#311421, Sigma) for 15 minutes and scored for clear halo production around colonies.

Acetoin and Diacetyl Production Assay 1 mL of autoclaved R2A broth supplemented with 0.5% glucose is aliquoted into a 96 deep well plate (#07-200-700. Fisher). The bacteria from a glycerol stock plate are inoculated using a flame-sterilized 96 pin replicator, sealed with a breathable membrane, then incubated for 5 days with shaking (200 rpm) at 25° C. At day 5, 100 μl aliquots of culture are removed and placed into a 96 well white fluorometer plate, along with 100 μl/well of Barritt's Reagents A and B which are prepared by mixing 5 g/L creatine mixed 3:1 (v/v) with freshly prepared alpha-naphthol (75 g/L in 2.5 M sodium hydroxide). After 15 minutes, plates are scored for red or pink colouration against a copper coloured negative control.

Auxin Production Assay

R2A agar media (Reasoner's 2A agar) supplemented with 5 mM L-tryptophan is autoclaved and poured into 150 mm plates. Using a 96 pin plate replicator, all microbes are inoculated onto the fresh plate from a 96 well plate glycerol stock. The plate is incubated at 25° C. for 3 days, then overlaid with a nitrocellulose membrane, and put in a fridge at 4° C. overnight, allowing bacteria and their metabolites to infiltrate into the paper. The next day, the nitrocellulose membrane is removed and placed for 30 min on Whatman #2 filter papers saturated with Salkowski reagent (0.01 M ferric chloride in 35% perchloric acid, #311421, Sigma). Absorbance at 535 nm is measured using spectrophotometer. Auxin concentration produced by bacterial isolates is determined using standard curves for IAA prepared from serial dilutions of 10-100 μg mL$^{-1}$.

Enzyme Production Assays

Oxidase and catalase activities are tested with 1% (w/v) tetramethyl-p-phenylene diamine and 3% (v/v) hydrogen peroxide solution, respectively. Gelatin and casein hydrolytic properties are analyzed by streaking bacterial strains onto TSA plates from the stock culture. After incubation, trichloroacetic acid (TCA) is applied to the plates and an observation is made immediately for a period of at least 4 min (Medina and Baresi 2007, J Microbiol Methods 69:391-393). Chitinase activity of the isolates is determined as zones of clearing around colonies following the method of Chernin et al. (1998) J Bacteriol 180:4435-4441 (incorporated herein by rereference). Hemolytic activity is determined by streaking bacterial isolates onto Columbia 5% sheep blood agar plates. Protease activity is determined using 1% skimmed milk agar plates, while lipase activity is determined on peptone agar medium. Formation of halo zone around colonies was used as indication of activity (Smibert and Krieg 1994, In: Gerhardt P, Murray R, Wood W, Krieg N (Eds) Methods for General and Molecular Bacteriology, ASM Press, Washington, D.C., pp 615-640, incorporated herein by reference). Pectinase activity is determined on nutrient agar supplemented with 5 g L$^{-1}$ pectin. After 1 week of incubation, plates are flooded with 2% hexadecyl trimethyl ammonium bromide solution for 30 min. The plates are washed with 1M NaCl to visualize the halo zone around the bacterial growth (Mateos et al. 1992, Appl Environ Microbiol 58:1816-1822, incorporated herein by reference).

Siderophore Production Assay

To ensure no contaminating iron is carried over from previous experiments, all glassware is deferrated with 6 M HCl and water prior to media preparation. In this cleaned glassware, R2A agar media, which is iron limited, is prepared and poured into 150 mm Petri dishes and inoculated with bacteria using a 96 pin plate replicator. After 3 days of incubation at 25° C., plates are overlaid with O-CAS overlay. 1 liter of O-CAS overlay is made by mixing 60.5 mg of Chrome azurol S (CAS), 72.9 mg of hexadecyltrimethyl ammonium bromide (HDTMA), 30.24 g of finely crushed Piperazine-1,4-bis-2-ethanesulfonic acid (PIPES) with 10 mL of 1 mM FeCl$_3$.6H$_2$O in 10 mM HC solvent. The PIPES is finely powdered and mixed gently with stirring (not shaking) to avoid producing bubbles, until a dark blue colour is achieved. Melted 1% agarose is then added to pre-warmed O-CAS just prior pouring the overlay in a proportion of 1:3 (v/v). After 15 minutes, colour change is scored by looking for purple halos (catechol type siderophores) or orange colonies (hydroxamate siderophores).

Cellulase Activity Assay X

Adapting a previous protocol, 0.2% carboxymethylcellulose (CMC) sodium salt (#C5678, Sigma) and 0.1% triton X-100 (are added to R2A media, autoclaved and poured into 150 mm plates. Bacteria are inoculated using a 96 pin plate replicator. After 3 days of culturing in the darkness at 25° C., cellulose activity is visualized by flooding the plate with Gram's iodine. Positive colonies are surrounded by clear halos.

Antibiosis Assay

Bacteria are inoculated using a 96 pin plate replicator onto 150 mm Petri dishes containing R2A agar, then grown for 3 days at 25° C. At this time, colonies of either *E. coli* DH5α (gram negative tester), *Bacillus subtillus* ssp. *Subtilis* (gram positive tester), or yeast strain AH 109 (fungal tester) are resuspended in 1 mL of 50 mM $Na_2HPO_4$ buffer to an $OD_{600}$ of 0.2, and 30 µl of this is mixed with 30 mL of warm LB agar. This is quickly poured completely over a microbe array plate, allowed to solidify and incubated at 37° C. for 16 hours. Antibiosis is scored by looking for clear halos around microbial colonies.

Assays for Exopolysaccharide, $NH_3$ and HCN Production

For exopolysaccharide (EPS) activity (qualitative), strains are grown on Weaver mineral media enriched with glucose and production of EPS is assessed visually (modified from Weaver et al. 1975, Arch Microbiol 105:207-216). The EPS production is monitored as floc formation (fluffy material) on the plates after 48 h of incubation at 28° C. Strains are tested for the production of ammonia ($NH_3$) in peptone water as described by Cappuccino and Sherman (1992), Biochemical activities of microorganisms. In: Microbiology, A Laboratory Manual. The Benjamin/Cummings Publishing Co. California, USA, pp 125-178, incorporated herein by reference. The bacterial isolates are screened for the production of hydrogen cyanide (HCN) by inoculating King's B agar plates amended with 4.4 g $L^{-1}$ glycine (Lorck 1948, Physiol Plant 1:142-146, incorporated herein by reference). Filter paper (Whatman no. 1) saturated with picrate solution (2% $Na_2CO_3$ in 0.5% picric acid) is placed in the lid of a petri plate inoculated with bacterial isolates. The plates are incubated at 28±2° C. for 5 days. HCN production is assessed by the colour change of yellow filter paper to reddish brown.

Assays for Poly-Hydroxybutyrate (PHB) and n-Acyl-Homoserine Lactone (AHL) Production The bacterial isolates are tested for PHB production (qualitative) following the viable colony staining methods using Nile red and Sudan black B (Juan et al. 1998 Appl Environ Microbiol 64:4600-4602; Spiekermann et al. 1999, Arch Microbiol 171:73-80, each of which is incorporated by reference). The LB plates with overnight bacterial growth are flooded with 0.02% Sudan black B for 30 min and then washed with ethanol (96%) to remove excess strains from the colonies. The dark blue coloured colonies are taken as positive for PHB production. Similarly, LB plates amended with Nile red (0.5 µL $mL^{-1}$) were exposed to UV light (312 nm) after appropriate bacterial growth to detect PHB production. Colonies of PHA-accumulating strains show fluoresce under ultraviolet light. The bacterial strains were tested for AHL production following the method modified from Cha et al. (1998), Mol Plant-Microbe Interact 11:1119-1129. The LB plates containing 40 µg $ml^{-1}$ X-Gal are plated with reporter strains (*A. tumefaciens* NTL4.pZLR4). The LB plates are spot inoculated with 10 µL of bacterial culture and incubated at 28±2° C. for 24 h. Production of AHL activity is indicated by a diffuse blue zone surrounding the test spot of culture. *Agrobacterium tumefaciens* NTL1 (pTiC58AaccR) is used as positive control and plate without reporter strain is considered as a negative control.

Antagonistic Activities Against Plant Pathogenic Bacteria, Fungi and Oomycetes

The antagonistic activities of bacterial isolates are screened against plant pathogenic bacteria (*Agrobacterium tumefaciens, Pseudomonas syringae, Streptococcus pneumoniae*), fungi (*Fusarium caulimons, Fusarium graminarium, Fusarium oxysporum, Fusarium solani, Rhizoctonia solani, Thielaviopsis basicola*) and oomycetes (*Phytophthora infestans, Phytophthora citricola, Phytophthora cominarum*). For antibacterial assays, the bacterial isolates and pathogen are cultivated in tryptic soy broth at 30° C. for 24 h. The bacterial isolates are spot-inoculated (10 µL aliquots) on TSA plates pre-seeded with 100 µL tested pathogen. The plates are incubated at 28° C. for 48 h and clear zones of inhibition are recorded.

Antagonistic activity of the bacterial isolates against fungi and oomycetes is tasted by the dual culture technique on potato dextrose agar (PDA) and yeast malt agar (YMA) media (Dennis and Webster 1971, Trans Brit Mycol Soc 57:25-39, incorporated herein by reference). A small disk (5 mm) of target fungus/oomycetes is placed in the center of petri dishes of both media. Aliquots of 10 µL of overnight bacterial cultures grown in tryptic soy broth are spotted 2 cm away from the center. Plates are incubated for 14 days at 24° C. and zones of inhibition are scored.

Antagonistic activity of the fungal isolates against pathogenic fungi and oomycetes is tested by the dual culture technique on potato dextrose agar (PDA) and yeast malt agar (YMA) media (Dennis and Webster 1971, Trans Brit Mycol Soc 57:25-39, incorporated herein by reference). A small agar plug (5 mm in diameter) of target fungus/oomycetes is placed near the edge of petri dishes of both media, adjacent to an agar plug of the isolated fungus (as close as possible without touching). Plates are incubated for 14 days at 24° C. and radial growth or inhibition of it is measured.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Sequences

2204 ITS rDNA
CCTATAGCTGACTGCGGAGGGACATTACAAGTGACCCCGGTCTAACCACCGGGATGTTCATA
ACCCTTTGTTGTCCGACTCTGTTGCCTCCGGGGCGACCCTGCCTTCGGGCGGGGGCTCCGGG

TABLE 1-continued

Sequences

TGGACACTTCAAACTCTTGCGTAACTTTGCAGTCTGAGTAAACTTAATTAATAAATTAAAAC
TTTTAACAACGGATCTCTTGGTTCTGGCATCGATGAAGAACGCAGCGAAATGCGATAAGTAA
TGTGAATTGCAGAATTCAGTGAATCATCGAATCTTTGAACGCACATTGCGCCCCTGGTATT
CCGGGGGGCATGCCTGTTCGAGCGTCATTTCACCACTCAAGCCTCGCTTGGTATTGGGCAAC
GCGGTCCGCCGCGTGCCTCAAATCGACCGGCTGGGTCTTCTGTCCCCTAAGCGTTGTGGAAA
CTATTCGCTAAAGGGTGTTCGGGAGGCTACGCCGTAAAACAACCCCATTTCTAAGGTTGACC
TCGGATCAGGTAGGGATACCCGCTGAACTTAAGCATATCAATAAGCGGAGGAAAAGAAACCA
ACAGGGATTGCCCCAGTAACGAA (SEQ ID NO: 1)

>*Sarocladium* sp. SMCD 2204F LSU rRNA
CAATGGGGAGTGTCGTCTTCTAAGCTAAATACCGGCTCAGAGACCGATAGCGCACAAGTAGAG
TGATCGAAAGATGAAAAGCACTTTGAAAAGAGGGTTAAAAAGTACGTGAAATTGTTGAAAGG
GAAGCATTCATGACCAGACTTGGGCTTGGTTGAACATCCGGCGTTCTCGCCGGTGCACTCTG
CCAGTCCAGGCCAGCATCAGTTTGCCCCGGGGGACAAAGGCGGTGGGAATGTGGCTCCCTTC
GGGGAGTGTTATAGCCCGCCGTGTAATGCCCTGGGGCGGACTGAGGAACGCGCTTCGGCACG
GATGCTGGCGTAATGGTCATCAATGACCCGTCTTGAAACACGGACCAAGGAGTCTAACATCA
(SEQ ID NO: 2)

>2206 ITS rDNA
TCGACGGCGTATCCTAGTGACTGCGGAGGATCATTACCGAGTGAGGGCCCTCTGGGTCCAAC
CTCCCACCCGTGTTTAATTTACCTTGTTGCTTCGGCGGGCCCGCCTTAACTGGCCGCCGGGG
GGCTTACGCCCCCGGGCCCGCGCCCGCCGAAGACACCCTCGAACTCTGTCTGAAGATTGTAG
TCTGAGTGAAAATATAAATTATTTAAAACTTTCAACAACGGATCTCTTGGTTCCGGCATCGA
TGAAGAACGCAGCGAAATGCGATACGTAATGTGAATTGCAAATTCAGTGAATCATCGAGTCT
TTGAACGCACATTGCGCCCCTGGTATTCCGGGGGGCATGCCTGTCCGAGCGTCATTGCTGC
CCTCAAGCACGGCTTGTGTGTTGGGCCCCGTCCTCCGATCCCGGGGACGGGCCCGAAAGGC
AGCGGCGGCACCGCGTCCGGTCCTCGAGCGTATGGGCTTTGTCACCCGCTCTGTAGGCCCG
GCCGGCGCTTGCCGATCAACCCAAATTTTTATCCAGGTTGACCTCGGATCAGGTAGGGATAC
CCGCTGAACTTAAGCATATCAATAAGCGGAGGAA (SEQ ID NO: 3)

>2208 ITS rDNA
TAACTGATTTGGCGGACTGGCGGAAGGACATTAAAGAGACGTTGCCCTTCGGGGTATACCTC
CCACCCTTTGTTTACCTTTTCCTTTGTTGCTTTGGCGGGCCCGTCCTCGGACCACCGGTTTC
GGCTGGTCAGTGCCCGCCAGAGGACCTAAAACTCTGTTTGTTCATATTGTCTGAGTACTATA
TAATAGTTAAAACTTTCAACAACGGATCTCTTGGTTCTGGCATCGATGAAGAACGCAGCGAA
ATGCGATAAGTAATGTGAATTGCAGAATTCAGTGAATCATCGAATCTTTGAACGCACATTGC
GCCCCCTGGTATTCCGGGGGGCATGCCTGTTCGAGCGTCATTACAACCCTCAAGCTCTGCTT
GGTATTGGGCTCTGCCGGTCCCGGCAGGCCTTAAAATCATTGGCGGTGCCATTCGGCTTCAA
GCGTAGTAATTCTTCTCGCTTTGGAGACCCGGGTGCGTGCTTGCCATCAACCCCCAATTTTT
TCAGGTTGACCTCGGATCAGGTAGGGATACCCGCTGAACTTAAGCATATCAATAAGCGGAGG
AAAAGAAACCAACAGGGATTGTCCCAATAACGAATTTATAAATAATA (SEQ ID NO: 4)

>2210 ITS rDNA
TCGAGAGTTCGGACTAAGTGCCTGATCCGAGGTCAAGACGGTAATGTTGCTTCGTGGACGCG
GGCCACGCCCCCCGCAGACGCAATTGTGCTGCGCGAGAGGAGGCAAGGACCGCTGCCAATG
AATTTGGGGCGAGTCCGCGCGCGAAGGCGGGACAGACGCCCAACACCAAGCAGAGCTTGAGG
GTGTAGATGACGCTCGAACAGGCATGCCCCATGGAATACCAAGGGGCGCAATGTGCGTTCAA
AGATTCGATGATTCACTGAATTCTGCAATTCACACTACTTATCGCATTTCGCTGCGTTCTTC
ATCGATGCCAGAGCCAAGAGATCCATTGTTGAAAGTTGTAACGATTGTTTGTATCAGAACAG
GTAATGCTAGATGCAAAAAAGGTTTTGTTAAGTTCCAGCGGCAGGTTGCCCCGCCGAAGGAG
AACGAAAGGTGCTCGTAAAAAAAGGATGCAGGAATGCGGCGCGTGAGGGTGTTACCCCTACC
ACCCGGGAGAGAACCCCCGAGGGCCGCGACCGCACCTGGTTGAGATGGATAATGATCCTTCC
GCAGGTTCACCTACGGAAACC (SEQ ID NO: 5)

>2215 16S rDNA
CCGGGGGCACTCCACTGCGTATGTGTGACGAGTAGACCGCTGCGCTTAGCTGAGGTCTGATG
AAATGTAGAACACTTAACAAAAATATGCCCGGATGGATATACTTTTCAACGACAGGGCTGCG
ATTGGATGATCTCCTTTGAAACACAGAACTAGTCACGGCGACGAATACTCAACTTCGACCCC
CCCCCTTTCTGGAGGCGCGTCTTAGTCCCCTCCTTGATGGAGCTGCCCCGTGCTCGGCGGCC
GGAGTCGGCGGTGTTTTCCGCTGTACCTGAGACGCTGGACCAACTCCTTCGGGAGGCAGCAG
TGGGGAATATTGCACAATGGGCGCAAGCCTGATGCAGCGACGCCGCGTGAGGGATGACGGCC
TTCGGGTTGTAAACCTCTTTCAGCAGGGAAGAAGCGCAAGTGACGGTACCTGCAGAAGAAGC
GCCGGCTAACTACGTGCCAGCAGCCGCGGTAATACGTAGGGCGCAAGCGTTGTCCGGAATTA
TTGGGCGTAAAGAGCTCGTAGGCGGCTTGTCACGTCGATTGTGAAAGCCCGAGGCTTAACCT
CGGGTCTGCAGTCGATACGGGCAGGCTAGAGTGTGGTAGGGGAGATCGGAATTCCTGGTGTA
GCGGTGAAATGCGCAGATATCAGGAGGAACACCGGTGGCGAAGGCGGATCTCTGGGCCATTA
CTGACGCTGAGGAGCGAAAGCGTGGGGAGCGAACAGGATTAGATACCCTGGTAGTCCACGCC
GTAAACGGTGGGAACTAGGTGTTGGCGACATTCCACGTCGTCGGTGCCGCAGCTAACGCATT
AAGTTCCCCGCCTGGGGAGTACGGCCGCAAGGCTAAAACTCAAAGGAATTGACGGGGGCCCG
CACAAGCGGCGGAGCATGTGGCTTAATTCGACGCAACGCGAAGAACCTTACCAAGGCTTGAC
ATACACCGGAAACATCCAGAGATGGGTGCCCCCTTGTGGTCGGCGTACAGGTCGTGCATGGC

TABLE 1 -continued

Sequences

TGTCGTCAGCTCGTGTCGTGAGATGTTGGGTAAGTCCCGCAACGAGCGCAACCTTGTTCTGG
TGCTGCCAGCATGCCCTTCGGGTGATGGGACTTCACCACGGAGACCGCGGCTCCACTCCGAC
GAGGTGGGGACGACGTCAGTCATCATGCCCTAATGTCTGGCTG (SEQ ID NO: 6)

TABLE 2

SMCD endophytic root colonization frequency assessed in 3D wheat germinant radicles.

| Endophytes | SMCD2204 | SMCD2206 | SMCD2210 | SMCD2215 |
|---|---|---|---|---|
| % colonization | 43 | 40 | 49 | 48 |

TABLE 3

Energy of germination (EG) and hydrothermal time (HTT) of wheat seeds grown under heat (36° C.), drought (potato dextrose agar (PDA) media plus 8% polyethylene glycol (PEG) 8000), heat and drought combined and control in vitro conditions.

1.

| | Heat | | Drought | | Heat and Drought | | Control | |
|---|---|---|---|---|---|---|---|---|
| Endophyte | EG (days) | HTT to 50% germination (MPa ° C. days) | EG (days) | HTT to 50% germination (MPa ° C. days) | EG (days) | HTT to 50% germination (MPa ° C. days) | EG (days) | HTT to 50% germination (MPa ° C. days) |
| SMCD 2204 | 3.7 ± 0.3 | 91 ± 7 | 2.9 ± 0.3 | 52 ± 5 | 2.0 ± 0.8 | 22 ± 8 | 1.6 ± 0.2 | 65 ± 8 |
| SMCD 2206 | 2.5 ± 0.3 | 62 ± 7 | 1.9 ± 0.1 * | 34 ± 2 * | 2.0 ± 0.8 | 22 ± 8 | 1.5 ± 0.2 | 61 ± 8 |
| SMCD 2208 | 3.7 ± 0.3 | 91 ± 7 | 3.0 ± 0.3 | 53 ± 5 | 4.0 ± 1.0 | 43 ± 10 | 1.6 ± 0.2 | 65 ± 8 |
| SMCD 2210 | 1.8 ± 0.2 * | 44 ± 5 * | 2.2 ± 0.2 * | 39 ± 3 * | 1.0 ± 0.5 | 11 ± 5 | 1.6 ± 0.2 | 65 ± 8 |
| SMCD 2215 | 2.5 ± 0.3 | 62 ± 7 | 2.3 ± 0.2 * | 41 ± 3 * | 1.3 ± 0.2 | 14 ± 2 | 1.5 ± 0.2 | 61 ± 8 |
| No Endo | 3.8 ± 0.5 | 94 ± 11 | 4.5 ± 0.5 | 80 ± 8 | 3.0 ± 1.5 | 32 ± 15 | 1.6 ± 0.2 | 65 ± 8 |

Within a column, data followed by an asterisk (*) are significantly different from the no endophyte control (p ≤ 0.05; ANOVA, followed by a post-hoc LSD test).
Note:
The seeds used in EG and HTT determination were from the second round of experiments, and hence subjected to sterilization in 5% sodium hypochlorite for one minute, rather than three;
SMCD—Saskatchewan Microbial Collection and Database

TABLE 4

Endophytes increase drought tolerance efficiency (DTE) and yield in barley and wheat under stress conditions.

| | | | Control conditions | | | Drought Stress | | |
|---|---|---|---|---|---|---|---|---|
| | | | Average YIELD spikes g (3plants/pot) | | | Average YIELD spikes g (3plants/pot) | | |
| Crop | Genotypes | DTE‡ (%) | E− | E+ | Increased % | E− | E+ | Increased % |
| WHEAT | AC Avonlea (Cont) | 16.1 | 18.27 | 25.52 | 28.41 | 2.94 | 10.62 | 72.32 |
| | PT 580 Control | 57.3 | 23.42 | 32.60 | 28.16 | 13.38 | 21.53 | 37.85 |
| | CDC Utmost VB | 72.3 | 20.55 | 35.4 | 41.95 | 16.67 | 29.8 | 44.06 |
| | Strongfield | 75.6 | 13.54 | 16.77* | 19.26 | 10.23 | 14.98 | 31.71 |
| | Unity VB | 75.3 | 20.72 | 26.6 | 22.11 | 15.61 | 23.2 | 32.72 |
| | CDC Teal | 76.9 | 19.51 | 30.37 | 35.76 | 14.90 | 25.1 | 40.64 |
| | Carberry | 83.8 | 17.31 | 33.07 | 47.66 | 14.52 | 22.9 | 36.59 |
| | BW 423 | 85.0 | 13.26 | 25.83 | 48.66 | 12.28 | 21.41 | 42.64 |

TABLE 4-continued

Endophytes increase drought tolerance efficiency (DTE) and yield in barley and wheat under stress conditions.

| | | | Control conditions | | | Drought Stress | | |
| | | | Average YIELD spikes g (3plants/pot) | | Increased | Average YIELD spikes g (3plants/pot) | | Increased |
| Crop | Genotypes | DTE‡ (%) | E− | E+ | % | E− | E+ | % |
|---|---|---|---|---|---|---|---|---|
| | CDC Veronna | 87.8 | 15.35 | 22.58 | 32.02 | 13.49 | 20.16 | 33.09 |
| | Lillian | 87.8 | 20.50 | 28.3 | 27.56 | 18.1 | 23.6 | 23.31 |
| | Two row barley | | | | | | | |
| | CDC Copeland | 4.9 | 6.01 | 10.78 | 44.25 | 2.91 | 6.95 | 58.13 |
| | CDC Kendall | 13.2 | 9.93 | 24.19 | 58.95 | 0.32 | 1.03 | 68.93 |
| BARLEY | AC Metcalfe | 43.2 | 16.5 | 22.4* | 26.34 | 7.3 | 14.05 | 48.04 |
| | New Dale | 72.1 | 9.55 | 26.88 | 64.47 | 6.89 | 12.17 | 43.39 |
| | Six row barley | | | | | | | |
| | Legacy | 1.1 | 20.42 | 26.87* | 24.00 | 2.26. | 2.38* | 5.04 |
| | CDC Bold | 57.0 | 9.16 | 19.9 | 53.97 | 5.22 | 7.5 | 30.40 |

‡Drought tolerance efficiency (DTE) = (Yield under stress/Yield under non-stress) × 100; presented in increasing order within the Table. Genotypes with high DTE are considered as drought resistant; whereas genotypes with low DTE are considered as drought susceptible.
Note:
Effect of the endophyte's absence (E−) or presence (E+) on genotype yield was calculated as an average of all three tested SMCD 2206, SMCD 2210, and SMCD 2215 strains.
*Within the rows, a mean is not statistically significant at $p \geq 0.05$.

TABLE 5

Rhizobium sequence maximum identity against GenBank database

| Accession | Description | Max score | Total score | Query coverage | E value | Max ident |
|---|---|---|---|---|---|---|
| EF549401.1 | *Rhizobium* sp. CCBAU 83431 16S ribosomal DNA gene, partial sequence | 1007 | 1007 | 46% | 0.0 | 99% |

**Native *Rhizobium* Nodulator in Interaction with *Streptomyces* SMCD2215**

16S F (Golden) *Rhizobium* sp.
(SEQ ID NO: 7)

```
GGAAGGGGGCGGCTTACCATGCAAGTCGAGCGCCCCGCAAGGGGAGCGG
CAGACGGGTGAGTAACGCGTGGGAATCTACCCTTGACTACGGAATAACGC
AGGGAAACTTGTGCTAATACCGTATGTGTCCTTCGGGAGAAAGATTTATC
GGTCAAGGATGAGCCCGCGTTGGATTAGCTAGTTGGTGGGGTAAAGGCCT
ACCAAGGCGACGATCCATAGCTGGTCTGAGAGGATGATCAGCCACATTGG
GACTGAGACACGGCCCAAACTCCTACGGGAGGCAGCAGTGGGGAATATTG
GACAATGGGCGCAAGCCTGATCCAGCCATGCCGCGTGAGTGATGAAGGCC
CTAGGGTTGTAAAGCTCTTTCACCGGAGAAGATAATGACGGTATCCGGAG
AAGAAGCCCCGGCTAACTTCGTGCCAGCAGCCGCGGTAATACGAAGGGGG
CTAGCGTTGTTCGGAATTACTGGCCGTAAAGCGCACGTAGGCGGATCGAT
CAGTCAGGGGTGAAATCCCAGGGCTCAACCCTGGAACTGTCTTTGATACT
AGCACCGGCACCCCGTTTCGACATGCAAAAAATGATGCCCAGGCTTATGT
GTCGATCTGGAGAACTTCCTGCTCGAGTGATTTACCCACATGGCGTTGAA
CCTGGCTGCTACGGCTCTCTTCGGCGTGGACCCCGGCCTCCTATCCCCGG
GATGCCACCCATGGACGCCGCAGTCTCCATGGATATATCATGGAGGTGGG
TTTTCTCCGACTCATGATGCCGGCTTCTTGCTGGAAGTTGATGAAGCAAC
TAAACATCAGCCCTGAGAGAAAGCTTCGCATGCCGCGCAGGGTGCTCCGA
GTGTTCGTCTGGAGATGATGAAATAGACGAAGATCATCTCATGTCATGTT
GGTAACGACGAGAACAAGATGGTGTGGATTTTGTGTCTTCCATCCTCCAT
GACCCTGACGATGCTGATGATGACGTGGTTCATGCTATGATGACTCGATA
CTGGTCGCTGCAAGCGGATACAGTTGGGACCTACCGCTAACATGGTTCTT
TCTACAACCTCCCCCCAAACCGCATAGGATCGTGGTCAATCATTCGGCAC
GAACCTCTTCCCCCATTGCCTCCAACTAGTTTATCGCTCTAGAGTTGGGG
AGCCCTGTGTGACCTTTCGTACGCGA
```

TABLE 6

Set of SOD, MnSOD and Pro primers used to assess pea [Handel] genes expression exposed to PEG drought/osmotic stress by qPCR

| Gene Name | Primer | Reference |
|---|---|---|
| PP2A internal control | CCACATTACCTGTATCGGATGACA (F) (SEQ ID NO: 8)<br>GAGCCCAGAACAGGAGCTAACA (R) (SEQ ID NO: 9) | Die et. al, Planta (2010) 232:145-153 |
| MnSOD salt and drought | gcagaaaaaccctatcctccgtgct (F) (SEQ ID NO: 10)<br>gctccaaagctccgtagtcg (R) (SEQ ID NO: 11) | Wong Vega et. al., Plant Mol. Biol. 17 (6), 1271-1274 (1991) |
| Pea SOD | ctgtactcgctgttggggtg (F) (SEQ ID NO: 12)<br>gcatggatatggaagccgtg (R) (SEQ ID NO: 13) | Nakamura et. al., Plant Biotechnol. 20, 247-253 (2003) |
| Proline (Pro) | aatggccgaaagcattgcca (F) (SEQ ID NO: 14)<br>aaggacggtgatgccgatggactc (R) (SEQ ID NO: 15) | Williamson, C.L. and Slocum, R.D., Plant Physiol. 100, 1464-1470 (1992) |

TABLE 7

Evaluation of the efficiency of seed sterilization methods. Seeds were germinated on potato dextrose agar for 4 days at ambient temperature (20° C.). Each petri dish had 10 wheat seeds.

| Sterilization type | Potato dextrose agar (PDA) | |
|---|---|---|
| | Contamination | Germination |
| Control | 50% | 80% |
| 50% Bleach | 0 | 50% |
| 95% Ethyl alcohol | 0 | 70% |
| 50% Bleach + 95% Ethyl alcohol | 0 | 50% |
| Chlorine gas | 0 | 80% |

TABLE 8

Average germination of wheat seeds under cold and biological stratification treatments

| Day | Control | Cold Stratification | Endophyte-indirect | Endophyte direct |
|---|---|---|---|---|
| 1 | $6.66 \pm 6.66^{ab}$ | $16.6 \pm 3.33^{ab}$ | $0.00 \pm 0.00^{a}$ | $26.6 \pm 12.02^{b}$ |
| 2 | $16.6 \pm 8.81^{p}$ | $40.0 \pm 11.5^{pq}$ | $50.0 \pm 5.77^{q}$ | $66.6 \pm 8.81^{q}$ |
| 3 | $33.3 \pm 12.01^{x}$ | $53.3 \pm 8.81^{xy}$ | $73.3 \pm 3.33^{yz}$ | $86.9 \pm 7.24^{z}$ |

* Duncan test was performed to test significant difference among the treatments (Control, Cold Stratification, Endophyte-indirect, and Endophyte direct) on Day 1 (a, b, c), Day 2 (p, q), and Day 3 (x, y, z)
** Different letters indicate significant difference at $P < 0.05$

TABLE 9

Transcription factor Myb2 mRNA (158 bp)

TaMyb2 1F  acatcaagcgcggcaacttca (SEQ ID NO: 16)
TaMyb2 1R  gagccgcttcttgaggtgggtgt (SEQ ID NO: 17)

Transcription factor Myb1 mRNA (152 bp)

TaMyb1 1F  ccagggaggacggacaacga (SEQ ID NO: 18)
TaMyb1 1R  ctctgcgccgtctcgaagga (SEQ ID NO: 19)

TABLE 10

Summary of the crops tested in the field and their respective varieties

| Crop | Varieties Tested |
|---|---|
| Corn | 39A16, 40R73 |
| Spring Wheat | Lillian, Unity, Utmost, Briggs, Prosper, Select |
| Durum Wheat | Strongfield |
| Barley | Bold, Kendal |
| Canola | Victory 1, Victory 2 |
| Pea | Meadow (green), Striker (yellow) |
| Chickpea | Counsul, Frontier |
| Lentil | Dazil, Impower |

TABLE 11

Summary of the targeted seeding density, planting date, and harvesting date for each crop and location.

| Location | Crop | Targeted Seeding Density | Planting Date* | Harvesting Date* |
|---|---|---|---|---|
| Saskatchewan, Canada | Spring Wheat | 4200 seeds/15 m³ | Jun 24/ June 25 | Sep 18/ Sep 24 |
| | Durum | 4200 seeds/15 m³ | Jun 24/ June 25 | Sep 18/ Sep 24 |
| | Barley | 5400 seeds/15 m³ | Jun 24/ June 25 | Sep 18/ Sep 24 |
| | Canola | 1600 seeds/15 m³ | Jun 23/ Jul 4 | Sep 18/ Sep 24 |
| | Pea | 3200 seeds/15 m³ | Jun 23/ Jul 4 | Sep 18/ Sep 24 |
| | Chickpea | 6500 seeds/15 m³ | Jun 24/ Jul 4 | Sep 18/ Sep 24 |
| | Lentil | 2000 seeds/15 m³ | Jun 24/ Jul 3 | Sep 18/ Sep 24 |
| Brookings, South Dakota | Spring Wheat | 65 lb-seed/acre | May 14 | Sep 9 |
| | Corn | 32,500 seeds/acre | Jun 5 | Nov 14 |
| York, Nebraska | Corn | 32,500 seeds/acre | Jun 19 | Nov 14 |

*indicates first planting and harvesting dates were for Vanguard and second were for Stewart Valley.

TABLE 12

The abbreviation and full name of the Gibberellin derivatives

| | |
|---|---|
| GA1 | Gibberellin 1 |
| GA19 | Gibberellin 19 |
| GA44 | Gibberellin 44 |
| GA53 | Gibberellin 53 |

TABLE 13

The abbreviation and full name of abscisic acid and its related metabolites

| | |
|---|---|
| ABA | cis-Abscisic acid |
| ABAGE | Abscisic acid glucose ester |
| PA | Phaseic acid |
| 7'OH-ABA | 7'-Hydroxy-abscisic acid |
| t-ABA | trans-Abscisic acid |

TABLE 14

The abbreviation and full name of the cytokinins and its related metabolites

| | |
|---|---|
| c-ZOG | trans-Zeatin-O-glucoside |
| c-Z | cis-Zeatin |
| C-ZR | czs-Zeatin riboside |

REFERENCES

Abdellatif et al. 2009. Mycological Research, 113:782-791.
Abdellatif et al. 2010. Can J Plant Pathol, 32: 468-480.
Adriaensen et al. 2006. Mycorrhiza, 16: 553-558.
Agius et al. 2006. PNAS, 103: 11796-11801.
Ali et al. 1994. Annals of Applied Biology, 125: 367-375.
Allen 1958. Forest Chron, 34: 266-298.
Armas et al. 2004. Ecology, 85: 2682-2686.
Arnold et al. 2001. Mycological Research, 105: 1502-1507.
Bacon and White 2000. In: Bacon C W and White J F J (Eds), *Microbial endophytes*. Marcel Dekker Inc; New York, N.Y., USA. 237-263.
Bae et al. 2009. J Exp Bot 60: 32793295.
Baird et al. 2010. Mycorrhiza. 20: 541-549.
Barrero et al. 2009. Plant Physiology, 150: 1006-1021.
Baskin et al. 1992. International Journal of Plant Sciences, 153: 239-243.
Baskin and Baskin 2004. Sci. Res., 14: 1-16.
Bewley and Black 1982. Physiology and Biochemistry of Seeds. 2. Viability, Dormancy, and Environmental Control. Springer-Verlag, Berlin.
Bloom and Richard 2002. ASAE Paper No 027010. ASAE, St. Joseph, Mich.
Bogatek and Lewak 1988. Physiologia Plantarum, 73: 406-411.
Boyko and Kovalchuk 2008. Environmental and Molecular Mutagenesis, 49: 61-72.
Bradford 2002. In: J. Kigel J, Galili G (eds), *Seed Develop and Germin*. Marcel Dekker Inc, New York, pp. 351-396.
Calcagno et al. 2012. Mycorrhiza, 22:259-69.
Cao and Moss. 1989. Crop Sci, 29: 1018-1021.
Carpita et al. 1983. Physiologia Plantarum 59: 601-606.
Cavieres and Arroyo, 2000. Plant Ecology 149: 1-8.
Cavieres and Arroyo, 2000b. Gayana Botanica 64: 40-45.
Charlton et. al. 2008. Metabolomics, 4: 312-327.
Chau et al. 2012. Fungal Biology, 116:1212-1218.
Chipanshi et al. 2006. Clim Res, 30: 175-187.
Chiwocha et al. 2003. Plant J., 3:405-417.
Chiwocha et al. 2005. Plant J., 42:35-48.
Choi and Sano, 2007. Molecular Genetics and Genomics, 277: 589-600.
Davitt et al. 2010. New Phytol, 188: 824-834. de Bary 1866. Vol. II. Hofmeister's Handbook of Physiological Botany. Leipzig, Germany.
Desfeux et al., 2000. Plant Physiology, 123: 895-904.
Dong-dong et al. 2009. J Zhejiang Univ-Sci B, 9: 964-968.
Farquhar and Richards 1984. Australian Journal Plant Physiology 11: 539-552.
Farquhar et al. 1989 In: Jones H G, Flowers T J and Jones M B (Eds) Plants under stress. Cambridge University Press, Cambridge, pp 47-69.
Farquhar et al. 1989b. Annual Review of Plant Physiology and Plant Molecular Biology. 40: 503-537.
Finnegan et al. 1998. Plant Molecular Biology 95: 5824-5829.
Freeman 1904. Philosophical Transactions of the Royal Society London (Biology) 196: 1-27.
Friend et al. 1962. Can J Bot, 40: 1299-1311.
Gan et al. 2004. Can. J Plant Sci, 84: 697-704.
Germida et al. 2010. Field-scale assessment of phytoremediation at a former oil tank battery in Bruderheim, Alberta. World Congress of Soil Science, Soil Solutions for a Changing World, 1-6 Aug. 2010. Brisbane, Australia. Available on-line at: http://www.iuss.org/19th%20WCSS/Symposium/pdf/0694.pdf
Gizinger 2002. Experimental Hematology, 30: 503-512.
Gornall et al. 2010. Phil. Trans. R. Soc. B, 365, 2973-2989.
Grant et al. 2009. Tree Physiology, 29: 1-17.
Gummerson 1986. J Exp Bot, 37: 729-741.
Gundel et al. 2010. Evol Appi, 3: 538-546.
Guo et al. 2003. Science, 302: 100-103.
Hayat et al. 2010. Nitric Oxide in Plant Physiology, Issue 58, Willey-VCH Verlag, Germany.
Hedden and Phillips, 2000. Trends in Plant Science, 5: 523-530.
Hubbard et al. 2011. In: Wheat: Genetics, Crops and Food Production. Nova Science Publishers Hauppauge, N.Y., USA. pp. 333-345.
Hubbard et al. 2012. Botany, 90(2): 137-149.
Jame et al. 1998. Agric Forest Meteorol 92: 241-249.
Ji et al., 2011. Plant Physiology, 156: 647-662.
Johannes et al. 2009. Plos Genetics 5: e1000530.
Johannes et al. 2011. Genetics, 188: 215-227.
Johnson et al. 1990. Crop Science, 30: 338-343.
Jost et al. 2001. Nucleic Acids Research, 29: 4452-4461.
Jumpponen and Trappe 1998. New Phytologist, 140: 295-310.
Jurado et al., 2010. Food Microbiology, 27: 50-57.
Kane 2011. Environmental and Experimental Botany, 71: 337-344.
Kang et al. 2008. International Journal of Sustainable Development and World Ecology, 15: 440-447.
Karavata & Manetas 1999. Photosynthetica, 36: 41-49.
Khan et al. 2010. Pakistan Journal of Botany, 42: 259-267.
Khan et al. 2012. BMC Microbiol, 12; 12:3.
Kiffer and Morelet 2000. Science Publisher Inc, Enfield, N.H., Plymouth.
Kochy and Tielborger 2007. Basic Appl Ecol 8: 171-182.
Koyuncu 2005. Acta Biologica Cracoviensia Series Botanica, 47: 23-26.
Labeda et al 2012. Antonie van Leeuwenhoek, 101:73-104.
Lang-Mladek et al. 2010. Molecular Plant, 3: 594-602.
Larran et al. 2002. World Journal of Microbial Biotechnology, 18: 683-686.

Leone et al. 1994. Physiol Plantarum, 92: 21-30.
Li et al. 2008. Ecological Research, 23: 927-930.
Li et al. 2011. Agronomy Journal, 103: 1619-1628.
Lu et al. 2007. Plant Biology, 49: 1599-1607.
Lucht et al. 2002. Nature Genetics, 30: 311-314.
Madsood et al. 2005. Engineering Applications of Artificial Intelligence, 18: 115-125.
Margulis, 1991. In Symbiosis as a Source of Evolutionary Innovation, L. Margulis and R. Fester, ed. The MIT Press: Cambridge. pp. 1-14.
Marquez et al. 2007. Science, 315: 513-515.
McCormick M C, Siegel (eds.) 1999. Prenatal Care: Effectiveness and implementation. Cambridge University Press UK.
McDonald 2009. Handbook of biological statistics. 2nd ed. Sparky House Publishing, Baltimore, Md.
McMaster 2009. In: Carver B F (ed), Wheat, science and trade, Wiley-Blackwell, Iowa, USA, pp. 31-55.
Milberg and Andersson 1998. Plant Ecology, 134: 225-234.
Millar et al., 2006. Plant Journal, 45: 942-954.
Miransari et al. 2011. Applied Microbiology and Biotechnology, 92: 875-885.
Mitchell et al., 2009. Microbiology-SGM, 156: 270-277.
Mühlmann and Peintner 2000. Mycorrhiza, 18: 171-180.
Mukhopadhyay et al., 2004. PNAS, 101: 6309-6314.
Nakatsubo et al. 1998. FEBS Lett, 427:263-266.
Nakamura et al., 2010. Euphytica, 171: 111-120.
Nelson, 2004. Annu Rev Phytopathol, 42: 271-309.
Nicot 2005. Journal of Experimental Botany, 56: 2907-2914.
Nonogaki et al., 2010. Plant Science, 179: 574-581.
Oikawa et al., 2004. Plant Molecular Biology, 55: 687-700.
Okamoto et al., 2006. Plant Physiology, 141:97-107.
Oliver et al., 2007. Plant and Cell Physiology, 48: 1319-1330.
Penterman et al. 2007. PNAS, 104: 6752-6757.
Phillips et al., 1995. Plant Physiology, 108: 1049-1057.
Probert et al., 1989. Journal of Experimental Botany, 40: 293-301.
Qin and Zeevart, 1999. PNAS, 96: 15354-15361.
Reynolds et al. 2007 Journal of Experimental Botany, 58: 177-186.
Richards et al. 2002. Crop Science, 42: 111-121.
Ries et al. 2000. Nature, 406: 98-101.
Rivero et al. 2011. International Conference on *Arabidopsis* Research. June 22-25, Madison USA.
Ruan et al. 2002. Seed Sci Technol, 30: 61-67.
Ryan et al. 2008. FEMS Microbiol Lett, 278: 1-9.
Saikkonen et al., 1998. Annual Review of Ecology and Systematics, 29: 319-343.
Saze 2008. Seminars in Cell and Developmental Biology, 19: 527-536.
Schrey and Tarkka 2008. Antonie van Leeuwenhoek, 94:11-19.
Schutz and Rave 1999. Ecology, 144: 215-230.
Semenov and Shewry 2011. Scientific Reports, 1: 66-71.
Sinclair et al. 1984. BioScience, 34: 36-40.
Singh et al. 2011. Plant Signal Behav, 6: 175-191.
Smith and Read 2008. Mycorrhizal symbiosis, Third Edition. Elsevier Ltd. Mycorrhizas in acholorophyllous plants (mycoheterotrophs). Chapter 13: 458-507.
Solaiman et al. 2010. Australian Journal of Soil Research, 48: 546-554.
Soleimani et al. 2010. Chemosphere, 81: 1084-1090.
Stone et al., 2000. In: Bacon, C. W. and White, J. F. eds., Microbial Endophytes, Marcel Dekker: New York Chap. 1: 3-29.
Strobel et al., 2004. Journal of Natural Products, 67: 257-268.
Sun et al. 2010. Journal of Plant Physiolog, 167: 1009-1017.
Tan and Zou, 2001. Nat Prod Rep, 18: 448-45.
Tokala et al. 2002. Appl Environ Microbiol, 68:2161-2171.
Vaughn et al. 2007. PloS Biology, 5: 1617-1629.
Verhoeven et al. 2010. New Phytologis, 185: 1108-1118.
Vujanovic et al. 2000. Annals of Botany, 86: 79-86.
Vujanovic and Brisson 2002. Mycological Progress. 1: 147-154.
Vujanovic and Vujanovic 2006. Floriculture, Ornamental and Plant Biotech, 63: 563-569.
Vujanovic and Vujanovic 2007. Symbiosis, 44: 93-99.
Vujanovic 2007b. Can J Plant Pathol, 29: 451-451.
Vujanovic 2008. 19th International Conference on *Arabidopsis*. Research Proceedings—ICAR13, July 23-27, Montreal, QC, Canada.
Waller et al. 2005. PNAS, 102: 13386-13391.
Wallin 1927. Symbionticism and the Origin of Species. London: Baillière, Tindall and Cox.
Wang et al. 2011. Journal of Experimental Botany, 62: 1951-1960.
Whalley et al. 2006. Plant and Soil, 280: 279-290.
White and Torres 2010. Physiol. Plant, 138: 440-446.
Wu et al. 2008. Plant Physiology, 148: 1953-1963.
Wu and Sardo 2010. Lichtfouse E. (Ed.), Sociology, Organic Farming, Climate Change and Soil Science. Sustainable Agriculture Reviews. 3: DOI 10.1007/978-90-481-3333-8_3.
Yamaguchi et al. 1998. Plant Cell, 10: 2115-2126
Yang et al., 2002. Planta, 215: 645-652.
Zadoks et al. 1974. Weed Research, 14:415-421.
Zhang et al., 2007. BMC Genet, 2007, 8: 40.
Zhang et al. 2010. Journal of Cereal Science, 52: 263-269.
Zhang et al. 2011. African Journal of Microbiology Research, 5: 5540-5547.
Zhao et al. 2007. Journal of Plant Nutrition, 30: 947-963.
Zhong et al. 2009. African Journal of Biotechnology, 8: 6201-6207.
Zhu et al. 2007. Current Biology, 17: 54-59.
Foresight. The future of food and farming: challenges and choices for global sustainability. Final Project Report. London: The Government Office for Science, UK, 2011.
IPCC Climate Change 2007. In: Solomon S, Qin D, Manning M, Chen Z, Marquis M, Averyt K B, Tignor M and Miller H L (Eds). Cambridge University Press, Cambridge, UK.
Saskatchewan Ministry of Agriculture 2008. Varieties of Grain Crops. SaskSeed guide. Regina, SK, Canada

The invention claimed is:

1. A method of reducing the effects of drought stress in wheat, said method comprising manually or mechanically inoculating a wheat seed with a composition comprising at least one endophyte and a carrier, wherein the at least one endophyte is of genus *Streptomyces* and comprises a 16S rDNA sequence with 100% sequence identity to SEQ ID NO:6 or is deposited as IDAC 081111-06 and is capable of causing populations of inoculated seeds from both cereal and pulse crops to reach 50% germination earlier under drought stress conditions compared to control seeds.

2. The method of claim 1, wherein the endophyte is deposited as IDAC 081111-06.

3. The method of claim 1, wherein the endophyte comprises a 16S rDNA sequence with 100% sequence identity to SEQ ID NO:6.

4. The method of claim 1, wherein the drought stress conditions are germinating seeds on potato dextrose agar (PDA) comprising 8% polyethylene glycol.

5. The method of claim 1, wherein the effects of drought stress are reduced by at least 10%.

6. The method of claim 1, wherein manually or mechanically inoculating the seed comprises coating the seed with the endophyte.

7. The method of claim 1, wherein the carrier is a liquid carrier.

8. The method of claim 1, wherein the endophyte colonizes at least 1% of the cortical cells of an agricultural plant grown from the inoculated seed.

9. The method of claim 1, wherein the endophyte is a spore.

10. The method of claim 1, wherein the inoculated seed is coated with at least 100 CFU endophytes per seed.

11. The method of claim 1, wherein the wheat seed is a durum wheat cultivar AC Avonlea.

12. The method of claim 1, further comprising cultivating the inoculated seed into a first generation wheat plant.

* * * * *

SEQUENCE LISTING

<160> NUMBER OF SEQ ID NOS: 19

<210> SEQ ID NO 1
<211> LENGTH: 581
<212> TYPE: DNA

<213> ORGANISM: Cladosporium sp.

<400> SEQUENCE: 1

```
cctatagctg actgcggagg acattacaa gtgaccccgg tctaaccacc gggatgttca      60
taaccctttg ttgtccgact ctgttgcctc cggggcgacc ctgccttcgg gcggggggctc   120
cgggtggaca cttcaaactc ttgcgtaact ttgcagtctg agtaaactta attaataaat    180
taaaacttt  aacaacggat ctcttggttc tggcatcgat gaagaacgca gcgaaatgcg    240
ataagtaatg tgaattgcag aattcagtga atcatcgaat ctttgaacgc acattgcgcc    300
ccctggtatt ccgggggggca tgcctgttcg agcgtcattt caccactcaa gcctcgcttg   360
gtattgggca acgcggtccg ccgcgtgcct caaatcgacc ggctgggtct tctgtcccct    420
aagcgttgtg gaaactattc gctaaagggt gttcgggagg ctacgccgta aaacaacccc    480
atttctaagg ttgacctcgg atcaggtagg gatacccgct gaacttaagc atatcaataa    540
gcggaggaaa agaaaccaac agggattgcc ccagtaacga a                        581
```

<210> SEQ ID NO 2
<211> LENGTH: 372
<212> TYPE: DNA
<213> ORGANISM: Sarocladium sp.

<400> SEQUENCE: 2

```
caatggggag tgtcgtcttc taagctaaat accggccaga gaccgatagc gcacaagtag    60
agtgatcgaa agatgaaaag cactttgaaa agagggttaa aaagtacgtg aaattgttga   120
aagggaagca ttcatgacca gacttgggct tggttgaaca tccggcgttc tcgccggtgc   180
actctgccag tccaggccag catcagtttg ccccggggga caaaggcggt gggaatgtgg   240
ctcccttcgg ggagtgttat agcccgccgt gtaatgccct ggggcggact gaggaacgcg   300
cttcggcacg gatgctggcg taatggtcat caatgacccg tcttgaaaca cggaccaagg   360
agtctaacat ca                                                        372
```

<210> SEQ ID NO 3
<211> LENGTH: 592
<212> TYPE: DNA
<213> ORGANISM: Penicillium sp.

<400> SEQUENCE: 3

```
tcgacggcgt atcctagtga ctgcggagga tcattaccga gtgagggccc tctgggtcca    60
acctcccacc cgtgtttaat ttaccttgtt gcttcggcgg gccgccttaa ctggccgcc   120
ggggggctta cgcccccggg cccgcgcccg ccgaagacac cctcgaactc tgtctgaaga   180
ttgtagtctg agtgaaaata taattattt aaaactttca acaacggatc tcttggttcc    240
ggcatcgatg aagaacgcag cgaaatgcga tacgtaatgt gaattgcaaa ttcagtgaat   300
catcgagtct ttgaacgcac attgcgcccc ctggtattcc ggggggcatg cctgtccgag   360
cgtcattgct gccctcaagc acggcttgtg tgttgggccc cgtcctccga tcccggggga   420
cgggcccgaa aggcagcggc ggcaccgcgt ccggtcctcg agcgtatggg gctttgtcac   480
ccgctctgta ggcccggccg gcgcttgccg atcaacccaa attttatcc aggttgacct    540
cggatcaggt agggataccc gctgaactta agcatatcaa taagcggagg aa            592
```

<210> SEQ ID NO 4
<211> LENGTH: 605
<212> TYPE: DNA
<213> ORGANISM: Pseudeurotium sp.

<400> SEQUENCE: 4

```
taactgattt ggcggactgg cggaaggaca ttaaagagac gttgcccttc ggggtatacc      60
tcccacccct tgtttacctt ttcctttgtt gctttggcgg gcccgtcctc ggaccaccgg    120
tttcggctgg tcagtgcccg ccagaggacc taaaactctg tttgttcata ttgtctgagt    180
actatataat agttaaaact ttcaacaacg gatctcttgg ttctggcatc gatgaagaac    240
gcagcgaaat gcgataagta atgtgaattg cagaattcag tgaatcatcg aatctttgaa    300
cgcacattgc gccccctggt attccggggg gcatgcctgt tcgagcgtca ttacaaccct    360
caagctctgc ttggtattgg gctctgccgg tcccggcagg ccttaaaatc attggcggtg    420
ccattcggct tcaagcgtag taattcttct cgctttggag acccgggtgc gtgcttgcca    480
tcaacccca atttttcag gttgacctcg gatcaggtag ggatacccgc tgaacttaag    540
catatcaata agcggaggaa aagaaaccaa cagggattgt cccaataacg aatttataaa    600
taata                                                                605
```

<210> SEQ ID NO 5
<211> LENGTH: 579
<212> TYPE: DNA
<213> ORGANISM: Paraconyothirium sp.

<400> SEQUENCE: 5

```
tcgagagttc ggactaagtg cctgatccga ggtcaagacg gtaatgttgc ttcgtggacg     60
cgggccacgc ccccccgcag acgcaattgt gctgcgcgag aggaggcaag gaccgctgcc   120
aatgaatttg gggcgagtcc gcgcgcgaag gcgggacaga cgcccaacac caagcagagc   180
ttgagggtgt agatgacgct cgaacaggca tgccccatgg aataccaagg ggcgcaatgt   240
gcgttcaaag attcgatgat tcactgaatt ctgcaattca cactacttat cgcatttcgc   300
tgcgttcttc atcgatgcca gagccaagag atccattgtt gaaagttgta acgattgttt   360
gtatcagaac aggtaatgct agatgcaaaa aaggttttgt taagttccag cggcaggttg   420
ccccgccgaa ggagaacgaa aggtgctcgt aaaaaaagga tgcaggaatg cggcgcgtga   480
gggtgttacc cctaccaccc gggagagaac ccccgagggc cgcgaccgca cctggttgag   540
atggataatg atccttccgc aggttcacct acggaaacc                           579
```

<210> SEQ ID NO 6
<211> LENGTH: 1160
<212> TYPE: DNA
<213> ORGANISM: Streptomyces sp.

<400> SEQUENCE: 6

```
ccggggcac tccactgcgt atgtgtgacg agtagaccgc tgcgcttagc tgaggtctga      60
tgaaatgtag aacacttaac aaaaatatgc ccggatggat atacttttca acgacagggc    120
tgcgattgga tgatctcctt tgaaacacag aactagtcac ggcgacgaat actcaacttc    180
gacccccccc ctttctggag gcgcgtctta gtcccctcct tgatggagct gccccgtgct    240
cggcggccgg agtcggcggt gttttccgct gtacctgaga cgctggacca actccttcgg    300
gaggcagcag tggggaatat tgcacaatgg gcgcaagcct gatgcagcga cgccgcgtga    360
gggatgacgg ccttcgggtt gtaaacctct ttcagcaggg aagaagcgca agtgacggta    420
cctgcagaag aagcgccggc taactacgtg ccagcagccg cggtaatacg tagggcgcaa    480
gcgttgtccg gaattattgg gcgtaaagag ctcgtaggcg gcttgtcacg tcgattgtga    540
```

```
aagcccgagg cttaacctcg ggtctgcagt cgatacgggc aggctagagt gtggtagggg      600
agatcggaat tcctggtgta gcggtgaaat gcgcagatat caggaggaac accggtggcg      660
aaggcggatc tctgggccat tactgacgct gaggagcgaa agcgtgggga gcgaacagga      720
ttagataccc tggtagtcca cgccgtaaac ggtgggaact aggtgttggc gacattccac      780
gtcgtcggtg ccgcagctaa cgcattaagt tccccgcctg gggagtacgg ccgcaaggct      840
aaaactcaaa ggaattgacg ggggcccgca caagcggcgg agcatgtggc ttaattcgac      900
gcaacgcgaa gaaccttacc aaggcttgac atacaccgga acatccaga  gatgggtgcc      960 cccttgtggt cggcgtacag gtcgtgcatg gctgtcgtca gctcgtgtcg tgagatgttg     1020
ggtaagtccc gcaacgagcg caaccttgtt ctggtgctgc cagcatgccc ttcgggtgat     1080
gggacttcac cacggagacc gcggctccac tccgacgagg tgggggacga cgtcagtcat     1140
catgccctaa tgtctggctg                                                 1160

<210> SEQ ID NO 7
<211> LENGTH: 1176
<212> TYPE: DNA
<213> ORGANISM: Rhizobium sp.

<400> SEQUENCE: 7 ggaaggggggg cggcttacca tgcaagtcga gcgccccgca aggggagcgg cagacgggtg      60
agtaacgcgt gggaatctac ccttgactac ggaataacgc agggaaactt gtgctaatac     120
cgtatgtgtc cttcgggaga aagatttatc ggtcaaggat gagcccgcgt tggattagct     180
agttggtggg gtaaaggcct accaaggcga cgatccatag ctggtctgag aggatgatca     240
gccacattgg gactgagaca cggcccaaac tcctacggga ggcagcagtg gggaatattg     300
gacaatgggc gcaagcctga tccagccatg ccgcgtgagt gatgaaggcc ctagggttgt     360
aaagctcttt caccggagaa gataatgacg gtatccggag aagaagcccc ggctaacttc     420
gtgccagcag ccgcggtaat acgaaggggg ctagcgttgt tcggaattac tgggcgtaaa     480
gcgcacgtag gcggatcgat cagtcagggg tgaaatccca gggctcaacc ctggaactgt     540
ctttgatact gtcgatctgg agaacttcct gctcgagtga tttacccaca tggcgagcac     600
cggcaccccg tttcgacatg caaaaaatga tgcccaggct tatgtttgac ctggctgcta     660
cggctctctt cggcgtggac cccggcctcc tatccccgga gatgccaccc atggacgccg     720
cagtctccat ggatatatca tggaggtggg ttttctccga ctcatgatgc cggcttcttg     780
ctggaagttg atgaagcaac taaacatcag ccctgagaga aagcttcgca tgccgcgcag     840
ggtgctccga gtgttcgtct ggagatgatg aaatagacga agatcatctc atgtcatgtt     900
ggtaacgacg agaacaagat ggtgtggatt ttgtgtcttc catcctccat gacccctgacg     960 atgctgatga tgacgtggtt catgctatga tgactcgata ctggtcgctg caagcggata    1020
cagttgggac ctaccgctaa catggttctt tctacaacct cccccaaac cgcataggat     1080 cgtggtcaat cattcggcac gaacctcttc ccccattgcc tccaactagt ttatcgctct    1140
agagttgggg agccctgtgt gacctttcgt acgcga                              1176

<210> SEQ ID NO 8
<211> LENGTH: 24
<212> TYPE: DNA
<213> ORGANISM: Pisum sativum

<400> SEQUENCE: 8
ccacattacc tgtatcggat gaca                                              24
```

```
<210> SEQ ID NO 9
<211> LENGTH: 22
<212> TYPE: DNA
<213> ORGANISM: Pisum sativum

<400> SEQUENCE: 9
gagcccagaa caggagctaa ca                                             22

<210> SEQ ID NO 10
<211> LENGTH: 25
<212> TYPE: DNA
<213> ORGANISM: Pisum sativum

<400> SEQUENCE: 10
gcagaaaaac cctatcctcc gtgct                                          25

<210> SEQ ID NO 11
<211> LENGTH: 20
<212> TYPE: DNA
<213> ORGANISM: Pisum sativum

<400> SEQUENCE: 11
gctccaaagc tccgtagtcg                                                20

<210> SEQ ID NO 12
<211> LENGTH: 20
<212> TYPE: DNA
<213> ORGANISM: Pisum sativum

<400> SEQUENCE: 12
ctgtactcgc tgttggggtg                                                20

<210> SEQ ID NO 13
<211> LENGTH: 20
<212> TYPE: DNA
<213> ORGANISM: Pisum sativum

<400> SEQUENCE: 13
gcatggatat ggaagccgtg                                                20

<210> SEQ ID NO 14
<211> LENGTH: 20
<212> TYPE: DNA
<213> ORGANISM: Pisum sativum

<400> SEQUENCE: 14
aatggccgaa agcattgcca                                                20

<210> SEQ ID NO 15
<211> LENGTH: 24
<212> TYPE: DNA
<213> ORGANISM: Pisum sativum

<400> SEQUENCE: 15
aaggacggtg atgccgatgg actc                                           24

<210> SEQ ID NO 16
<211> LENGTH: 21
<212> TYPE: DNA
<213> ORGANISM: Triticum aestivum

<400> SEQUENCE: 16
```

```
acatcaagcg cggcaacttc a                                              21

<210> SEQ ID NO 17
<211> LENGTH: 23
<212> TYPE: DNA
<213> ORGANISM: Triticum aestivum

<400> SEQUENCE: 17
gagccgcttc ttgaggtggg tgt                                            23

<210> SEQ ID NO 18
<211> LENGTH: 20
<212> TYPE: DNA
<213> ORGANISM: Triticum aestivum

<400> SEQUENCE: 18
ccagggagga cggacaacga                                                20

<210> SEQ ID NO 19
<211> LENGTH: 20
<212> TYPE: DNA
<213> ORGANISM: Triticum aestivum

<400> SEQUENCE: 19
ctctgcgccg tctcgaagga                                                20
```